(12) United States Patent
Mi et al.

US008058406B2

(10) Patent No.: US 8,058,406 B2
(45) Date of Patent: Nov. 15, 2011

(54) COMPOSITION COMPRISING ANTIBODIES TO LINGO OR FRAGMENTS THEREOF

(75) Inventors: Sha Mi, Belmont, MA (US); R. Blake Pepinsky, Arlington, MA (US); Christilyn Graff, Cambridge, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 144 days.

(21) Appl. No.: 12/500,472

(22) Filed: Jul. 9, 2009

(65) Prior Publication Data

US 2010/0015131 A1 Jan. 21, 2010

Related U.S. Application Data

(60) Provisional application No. 61/079,355, filed on Jul. 9, 2008.

(51) Int. Cl.
*C07K 16/28* (2006.01)
*A61K 39/395* (2006.01)
*C12P 21/08* (2006.01)

(52) U.S. Cl. ............ 530/388.85; 424/178.1; 424/181.1; 435/69.6

(58) Field of Classification Search .................. None
See application file for complete search history.

(56) References Cited

U.S. PATENT DOCUMENTS

| | | |
|---|---|---|
| 4,399,216 A | 8/1983 | Axel et al. |
| 4,444,887 A | 4/1984 | Hoffmann |
| 4,510,245 A | 4/1985 | Cousens et al. |
| 4,634,665 A | 1/1987 | Axel et al. |
| 4,694,778 A | 9/1987 | Learn et al. |
| 4,716,111 A | 12/1987 | Osband et al. |
| 4,816,397 A | 3/1989 | Boss et al. |
| 4,816,567 A | 3/1989 | Cabilly et al. |
| 4,946,778 A | 8/1990 | Ladner et al. |
| 4,968,615 A | 11/1990 | Koszinowski et al. |
| 5,122,464 A | 6/1992 | Wilson et al. |
| 5,168,062 A | 12/1992 | Stinski |
| 5,179,017 A | 1/1993 | Axel et al. |
| 5,223,409 A | 6/1993 | Ladner et al. |
| 5,225,539 A | 7/1993 | Winter |
| 5,252,714 A | 10/1993 | Harris et al. |
| 5,258,498 A | 11/1993 | Huston et al. |
| 5,314,995 A | 5/1994 | Fell, Jr. et al. |
| 5,403,484 A | 4/1995 | Ladner et al. |
| 5,413,923 A | 5/1995 | Kucherlapati et al. |
| 5,427,908 A | 6/1995 | Dower et al. |
| 5,428,130 A | 6/1995 | Capon et al. |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,565,335 A | 10/1996 | Capon et al. |
| 5,569,825 A | 10/1996 | Lonberg et al. |
| 5,571,698 A | 11/1996 | Ladner et al. |
| 5,574,009 A | 11/1996 | Cohen et al. |
| 5,580,717 A | 12/1996 | Dower et al. |
| 5,585,089 A | 12/1996 | Queen et al. |
| 5,589,369 A | 12/1996 | Seidman et al. |
| 5,625,126 A | 4/1997 | Lonberg et al. |
| 5,633,425 A | 5/1997 | Lonberg et al. |
| 5,658,570 A | 8/1997 | Newman et al. |
| 5,658,727 A | 8/1997 | Barbas et al. |
| 5,661,016 A | 8/1997 | Lonberg et al. |
| 5,693,761 A | 12/1997 | Queen et al. |
| 5,693,762 A | 12/1997 | Queen et al. |
| 5,693,780 A | 12/1997 | Newman et al. |
| 5,698,426 A | 12/1997 | Huse |
| 5,725,859 A | 3/1998 | Omer |
| 5,733,743 A | 3/1998 | Johnson et al. |
| 5,750,753 A | 5/1998 | Kimae et al. |
| 5,756,096 A | 5/1998 | Newman et al. |
| 5,772,997 A | 6/1998 | Hudziak et al. |
| 5,780,225 A | 7/1998 | Wigler et al. |
| 5,807,715 A | 9/1998 | Morrison et al. |
| 5,811,524 A | 9/1998 | Brams et al. |
| 5,814,318 A | 9/1998 | Lonberg et al. |

(Continued)

FOREIGN PATENT DOCUMENTS

EP 0 154 316 B1 9/1989

(Continued)

OTHER PUBLICATIONS

Paul, WE, ed. Fundamental Immunology, Third Edition. Raven Press, New York, 1993, pp. 292-295, under the heading "Fv Structure and Diversity in Three Dimensions".*
Rudikoff S et al. Single amino acid substitution altering antigen-binding specificity. Proc Natl Acad Sci USA, 1982; 79(6):1979-1983.*
Battaglia, G., et al., "Protective role of group-II metabotropic glutamate receptors against nigro-striatal degeneration induced by 1-methyl-4-phenyl-1,2,3,6-tetrahydropyridine in mice," *Neuropharmacol.* 45:155-166, Elsevier Science Ltd. (2003).
Baulida, J., et al., "All ErbB Receptors Other Than the Epidermal Growth Factor Receptor Are Endocytosis Impaired," *J. Biol. Chem.* 271:5251-5257, The American Society for Biochemistry and Molecular Biology, Inc. (1996).

(Continued)

*Primary Examiner* — Elizabeth C Kemmerer
*Assistant Examiner* — Kimberly A Ballard
(74) *Attorney, Agent, or Firm* — Sterne, Kessler, Goldstein & Fox P.L.L.C.

(57) ABSTRACT

Endogenous LINGO-1 is a negative regulator for neuronal survival, axon regeneration, oligodendrocyte differentiation and myelination. Molecules that block endogenous LINGO-1 function, such anti-LINGO-1 antibodies can be used as therapeutics for the treatment of neuron and oligodendrocyte dysfunction. The present invention provides antibodies specific for LINGO-1, and methods of using such antibodies as antagonists of endogenous LINGO-1 function. The invention further provides specific hybridoma and phage library-derived monoclonal antibodies, nucleic acids encoding these antibodies, and vectors and host cells comprising these antibodies. The invention further provides methods of promoting oligodendrocyte survival and myelination in a vertebrate, comprising administering to a vertebrate in need of such treatment an effective amount of an anti-LINGO-1 antibody.

15 Claims, 24 Drawing Sheets

U.S. PATENT DOCUMENTS

Figure 1:
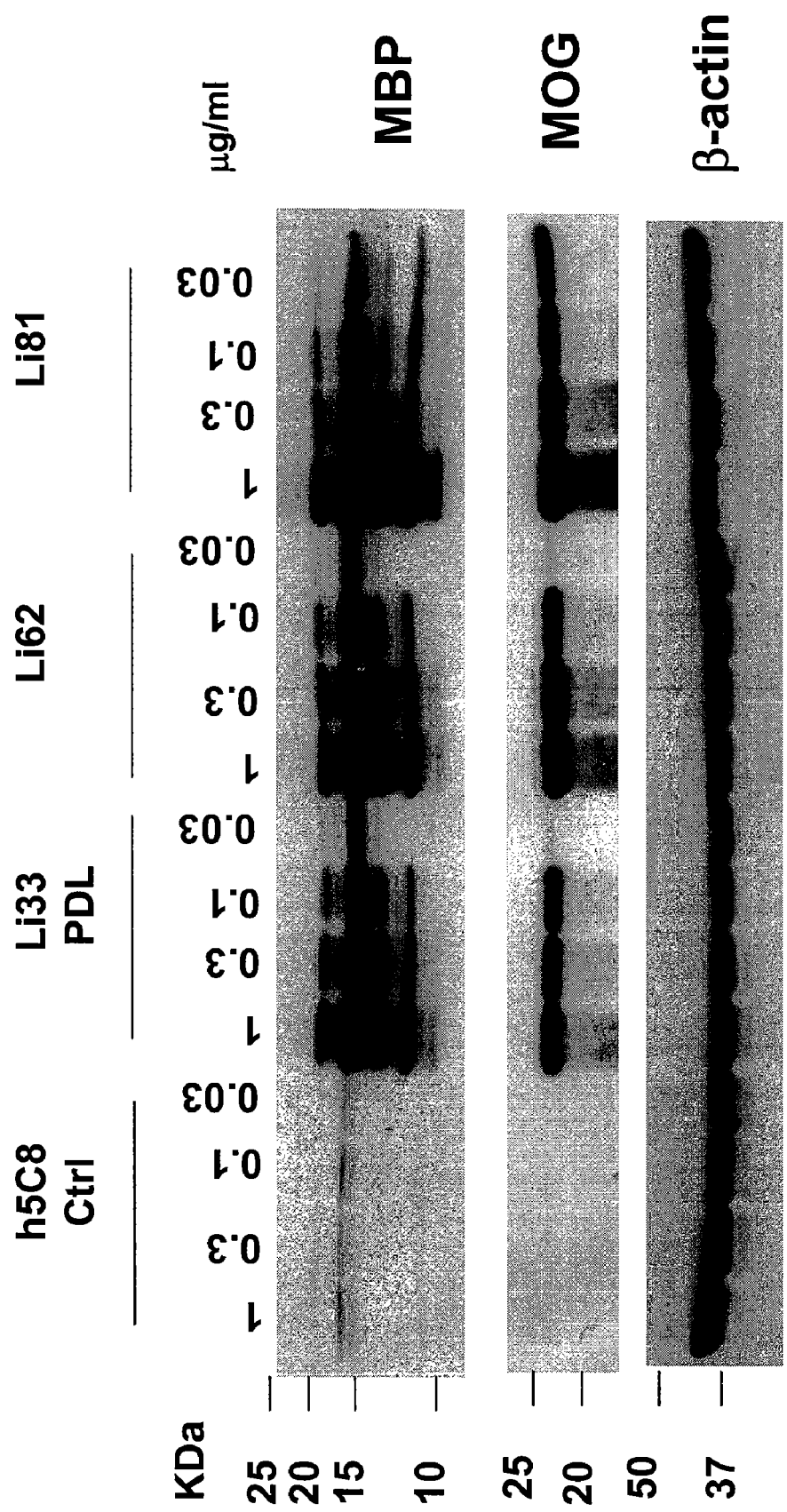

| | | | |
|---|---|---|---|
| 5,821,047 | A | 10/1998 | Garrard et al. |
| 5,837,821 | A | 11/1998 | Wu |
| 5,892,019 | A | 4/1999 | Schlom et al. |
| 5,914,237 | A | 6/1999 | Godowski et al. |
| 5,939,598 | A | 8/1999 | Kucherlapati et al. |
| 5,969,108 | A | 10/1999 | McCafferty et al. |
| 6,025,145 | A | 2/2000 | Godowski et al. |
| 6,054,561 | A | 4/2000 | Ring |
| 6,075,181 | A | 6/2000 | Kucherlapati et al. |
| 6,150,584 | A | 11/2000 | Kucherlapati et al. |
| 6,159,730 | A | 12/2000 | Reff |
| 6,180,370 | B1 | 1/2001 | Queen et al. |
| 6,190,887 | B1 | 2/2001 | Boyce et al. |
| 6,280,964 | B1 | 8/2001 | Kavanaugh et al. |
| 6,333,169 | B1 | 12/2001 | Hudziak et al. |
| 6,338,953 | B1 | 1/2002 | Boyce et al. |
| 6,387,371 | B1 | 5/2002 | Hudziak et al. |
| 6,399,063 | B1 | 6/2002 | Hudziak et al. |
| 6,413,777 | B1 | 7/2002 | Reff et al. |
| 6,420,140 | B1 | 7/2002 | Hori et al. |
| 6,458,592 | B1 | 10/2002 | Jakobovits et al. |
| 6,656,465 | B2 | 12/2003 | Clary et al. |
| 6,686,451 | B1 | 2/2004 | Desnoyers et al. |
| 6,696,290 | B2 | 2/2004 | Fitzpatrick et al. |
| 6,949,245 | B1 | 9/2005 | Sliwkowski |
| 6,974,689 | B1 | 12/2005 | Ashkenazi et al. |
| 6,987,088 | B2 | 1/2006 | Dennis |
| 7,098,302 | B2 | 8/2006 | Krag et al. |
| 7,223,558 | B2 | 5/2007 | Wu et al. |
| 2002/0004587 | A1 | 1/2002 | Miller et al. |
| 2002/0123057 | A1 | 9/2002 | Zauderer et al. |
| 2002/0182671 | A1 | 12/2002 | Lal et al. |
| 2003/0195163 | A1 | 10/2003 | Wu et al. |
| 2004/0005579 | A1 | 1/2004 | Birse et al. |
| 2004/0067490 | A1 | 4/2004 | Zhong et al. |
| 2004/0253605 | A1 | 12/2004 | McCarthy et al. |
| 2005/0123990 | A1 | 6/2005 | Lal et al. |
| 2005/0153396 | A1 | 7/2005 | Baker et al. |
| 2005/0214288 | A1 | 9/2005 | Bell et al. |
| 2005/0215770 | A1 | 9/2005 | Bell et al. |
| 2006/0009288 | A1 | 1/2006 | deVos et al. |
| 2006/0009388 | A1 | 1/2006 | Mi et al. |
| 2006/0034840 | A1 | 2/2006 | Agus et al. |
| 2006/0088523 | A1 | 4/2006 | Andya et al. |
| 2007/0059793 | A1 | 3/2007 | Mi et al. |
| 2007/0071675 | A1 | 3/2007 | Wu et al. |
| 2007/0083334 | A1 | 4/2007 | Mintz et al. |
| 2007/0105122 | A1 | 5/2007 | Ota et al. |
| 2007/0274918 | A1 | 11/2007 | Mosyak et al. |
| 2009/0017039 | A1 | 1/2009 | Mi et al. |
| 2009/0175872 | A1 | 7/2009 | Mi et al. |
| 2009/0246189 | A1 | 10/2009 | Mi et al. |
| 2009/0252748 | A1 | 10/2009 | Mi et al. |
| 2010/0074907 | A1 | 3/2010 | Mi et al. |
| 2010/0297121 | A1 | 11/2010 | Mi et al. |

FOREIGN PATENT DOCUMENTS

| | | | |
|---|---|---|---|
| EP | 0 401 384 A1 | 12/1990 | |
| EP | 0 256 055 B1 | 8/1991 | |
| EP | 0 323 997 B1 | 4/1993 | |
| EP | 0 396 387 B1 | 12/1993 | |
| EP | 0 368 684 B1 | 3/1994 | |
| EP | 0 239 400 B1 | 8/1994 | |
| EP | 0 338 841 B1 | 3/1995 | |
| EP | 0 401 384 B1 | 3/1996 | |
| EP | 1 074 617 A2 | 2/2001 | |
| EP | 0 058 481 B2 | 5/2003 | |
| EP | 0 592 106 B1 | 11/2004 | |
| EP | 0 519 596 B1 | 2/2005 | |
| EP | 1 574 520 A2 | 9/2005 | |
| WO | WO 86/05807 A1 | 10/1986 | |
| WO | WO 89/01036 A1 | 2/1989 | |
| WO | WO 89/10134 A1 | 11/1989 | |
| WO | WO 89/12624 A2 | 12/1989 | |
| WO | WO 90/02809 A1 | 3/1990 | |
| WO | WO 90/11364 A1 | 10/1990 | |
| WO | WO 91/09967 A1 | 7/1991 | |
| WO | WO 91/10737 A1 | 7/1991 | |
| WO | WO 91/10741 A1 | 7/1991 | |
| WO | WO 91/14438 A1 | 10/1991 | |
| WO | WO 92/01047 A1 | 1/1992 | |
| WO | WO 92/08495 A1 | 5/1992 | |
| WO | WO 92/18619 A1 | 10/1992 | |
| WO | WO 92/22324 A1 | 12/1992 | |
| WO | WO 93/11236 A1 | 6/1993 | |
| WO | WO 94/09817 A1 | 5/1994 | |
| WO | WO 95/15982 A2 | 6/1995 | |
| WO | WO 95/20401 A1 | 8/1995 | |
| WO | WO 96/33735 A1 | 10/1996 | |
| WO | WO 96/34096 A1 | 10/1996 | |
| WO | WO 97/00271 A1 | 1/1997 | |
| WO | WO 98/16654 A1 | 4/1998 | |
| WO | WO 98/24893 A2 | 6/1998 | |
| WO | WO 98/46645 A2 | 10/1998 | |
| WO | WO 98/50433 A2 | 11/1998 | |
| WO | WO 98/52976 A1 | 11/1998 | |
| WO | WO 88/09810 A1 | 12/1998 | |
| WO | WO 99/06427 A1 | 2/1999 | |
| WO | WO 99/14328 A2 | 3/1999 | |
| WO | WO 00/15796 A2 | 3/2000 | |
| WO | WO 00/34317 A2 | 6/2000 | |
| WO | WO 00/58473 A2 | 10/2000 | |
| WO | WO 01/04311 A1 | 1/2001 | |
| WO | WO 01/12662 A2 | 2/2001 | |
| WO | WO 01/33042 A1 | 5/2001 | |
| WO | WO 01/40466 A2 | 6/2001 | |
| WO | WO 01/55317 A2 | 8/2001 | |
| WO | WO 01/55333 A2 | 8/2001 | |
| WO | WO 01/57262 A1 | 8/2001 | |
| WO | WO 01/59063 A2 | 8/2001 | |
| WO | WO 02/14368 A2 | 2/2002 | |
| WO | WO 02/29058 A2 | 4/2002 | |
| WO | WO 02/060955 A2 | 8/2002 | |
| WO | WO 02/068579 A2 | 9/2002 | |
| WO | WO 02/096948 A2 | 12/2002 | |
| WO | WO 03/023008 A2 | 3/2003 | |
| WO | WO 03/035833 A2 | 5/2003 | |
| WO | WO 03/061559 A2 | 7/2003 | |
| WO | WO 03/083047 A2 | 10/2003 | |
| WO | WO 2004/022718 A2 | 3/2004 | |
| WO | WO 2004/085648 A2 | 10/2004 | |
| WO | WO 2005/035584 A1 | 4/2005 | |
| WO | WO 2005/063819 A2 | 7/2005 | |
| WO | WO 2005/079566 A2 | 9/2005 | |
| WO | WO 2006/002437 A2 | 1/2006 | |
| WO | WO 2006/119016 A2 | 11/2006 | |
| WO | WO 2006/136006 A1 | 12/2006 | |
| WO | WO 2007/008547 A2 | 1/2007 | |
| WO | WO 2007/056161 A1 | 5/2007 | |
| WO | WO 2007/064882 A2 | 6/2007 | |
| WO | WO 2007/098283 A2 | 8/2007 | |
| WO | WO 2008/013782 A2 | 1/2008 | |
| WO | WO 2008/086006 A2 | 7/2008 | |
| WO | WO 2009/048605 A1 | 4/2009 | |
| WO | WO 2009/061500 A1 | 5/2009 | |
| WO | WO 2010/003108 A2 * | 1/2010 | |

OTHER PUBLICATIONS

Baulida, J. and Carpenter, G., "Heregulin Degradation in the Absence of Rapid Receptor-Mediated Internalization," *Exp. Cell Res.* 232:167-172, Academic Press (1997).

Baumann, N., et al., "Biology of Oligodendrocyte and Myelin in the Mammalian Central Nervous System," *J. Physiol. Rev.* 81:871-927, American Physiological Society (2001).

Blum, M., "A null mutation in TGF-α leads to a reduction in midbrain dopaminergic neurons in the substantia nigra," *Nat. Neurosci.* 1:374-377, Nature Publishing Group (1998).

Brittis, P.A., et al., Nogo Domains and a Nogo Receptor: Implications for Axon Regeneration, *Neuron* 30:11-14 Cell Press (2001).

Brundin, P., et al., "The rotating 6-hydroxydopamine-lesioned mouse as a model for assessing functional effects of neuronal grafting," *Brain Res.* 366:346-349, Elsevier Publishers B.V. (1986).

Carim-Todd, L., et al., "LRRN6A/LERN1 (leucine-rich repeat neuronal protein 1), a novel gene with enriched expression in limbic system and neocortex," *Eur. J. Neurosci.* 18:3167-3182, Federation of European Neuroscience Societies (2003).

Chang, A., et al., "Premyelinating Oligodendrocytes in Chronic Lesions of Multiple Sclerosis," *N. Engl. J. Med.* 346:165-173, Massachusetts Medical Society (2002).

Chen, M.S., et al., "Nogo-A is a Myelin-Associated Neurite Outgrowth Inhibitor and an Antigen for Monoclonal Antibody IN-1," *Nature* 403:434-439, Macmillan Magazines Ltd. (2000).

Chen, Y., et al., "AMIGO and friends: An emerging family of brain-enriched, neuronal growth modulating, type 1 transmembrane proteins with leucine-rich repeats (LRR) and cell adhesion molecule motifs," *Brain Res. Rev.* 51:265-74, Elsevier B.V. (Electronically available Jan. 2006).

Citri, A., et al., "The deaf and the dumb: The biology of ErbB-2 and ErbB-3," *Exp. Cell Res.* 284:54-65, Elsevier Science (2003).

Cohen, S., et al., "Nonchromosomal Antibiotic Resistance in Bacteria: Genetic Transformation of *Escherichia coli* by R-Factor DNA," *Proc. Natl. Acad. Sci. USA* 69:2110-2114 (1972).

Csordás, G., et al,. "Sustained Down-regulation of the Epidermal Growth Factor Receptor by Decorin," *J. Biol. Chem.* 275:32879-32887, The American Society for Biochemistry and Molecular Biology, Inc. (2000).

Domeniconi M., et al., "Myelin-Associated Glycoprotein Interacts with the Nogo66 Receptor to Inhibit Neurite Outgrowth," *Neuron* 35:283-290, Cell Press (2002).

Eby, M.T., et al., "TAJ, a Novel Member of the Tumor Necrosis Factor Receptor Family, Activates the c-Jun N-terminal Kinase Pathway and Mediates Caspase-independent Cell Death," *J. Biol. Chem.* 275:15336-15342, The American Society for Biochemistry and Molecular Biology, Inc. (2000).

Fendly, B.M., et al., "The Extracellular Domain of HER2/neu Is a Potential Immunogen for Active Specific Immunotherapy of Breast Cancer," *J. Biol. Resp. Mod.* 9:449-455, Raven Press Ltd. (1990).

Fournier, A.E., et al., "Identification of a Receptor Mediating Nogo-66 Inhibition of Axonal Regeneration," *Nature* 409:341-346, Nature Publishing Group (2001).

Fu, Q.-L., et al., "Blocking LINGO-1 Function Promotes Retinal Ganglion Cell Survival Following Ocular Hypertension and Optic Nerve Transection," *Invest. Ophthal. Vis. Sci.* 49:975-985, Association for Research in Vision and Ophthalmology (Mar. 2008).

Fuxe, K. and Ungerstedt, U., "Antiparkinsonian Drugs and Dopaminergic Neostriatal Mechanisms: Studies in Rats with Unilateral 6-Hydroxydopamine (=6-OH-DA)-Induced Degeneration of the Nigro-Neostriatal DA Pathway and Quantitative Recording of Rotational Behaviour," *Pharmac. Ther.* B:41-47, Pergamon Press (1976).

Ghiglione, C., et al., "The Transmembrane Molecule Kekkon 1 Acts in a Feedback Loop to Negatively Regulate the Activity of the *Drosophila* EGF Receptor during Oogenesis," *Cell* 96:847-856, Cell Press (1999).

Gill, S.S., et al., "Direct brain infusion of glial cell line-derived neurotrophic factor in Parkinson disease," *Nat. Med.* 9:589-595, Nature Publishing Company (2003).

Gill, S.S., et al., "Addendum: Direct brain infusion of glial cell line-derived neurotrophic factor in Parkinson disease," *Nat. Med.* 12:479, Nature Publishing Company (Apr. 2006).

Gille, G., et al., "Oxidative Stress to Dopaminergic Neurons as Models of Parkinson's Disease," *Ann. N.Y. Acad. Sci.* 1018:533-540, New York Academy of Sciences (Jun. 2004).

GrandPr, T., et al., "Identification of the Nogo Inhibitor of Axon Regeneration as a Reticulon Protein," *Nature* 403:439-444, Macmillan Magazines Ltd. (2000).

Grimpe, B., et al., "The Critical Role of Basement Membrane-Independent Laminin γ1 Chain During Axon Regeneration in the CNS," *J. Neurosci.* 22:3144-3160, Society for Neuroscience (2002).

Gur, G., et al., "LRIG1 restricts growth factor signaling by enhancing receptor ubiquitylation and degradation," *EMBO J.* 23:3270-3281, Oxford University Press (Aug. 2004).

Ha, H., et al., "Membrane Rafts Play a Crucial Role in Receptor Activator of Nuclear Factor κB Signaling and Oteoclast Function," *J. Biol. Chem.* 278:18573-18580, The American Society for Biochemistry and Molecular Biology, Inc. (2003).

Harwerth, I.-M., et al., "Monoclonal Antibodies against the Extracellular Domain of the erbB-2 Receptor Function as Partial Ligand Agonists," *J. Biol. Chem.* 267:15160-15167, The American Society for Biochemistry and Molecular Biology, Inc. (1992).

Hoet, R.M., et al., "Generation of high-affinity human antibodies by combining donor-derived and synthetic complementarity-determining-region diversity," *Nat. Biotechnol.* 23:344-348, Nature America Publishing (Mar. 2005).

Huang, J., et al., "Glial Membranes at the Node of Ranvier Prevent Neurite Outgrowth," *Science* 310:1813-7, American Association for the Advancement of Science (Dec. 2005).

Isacson, O., "Problems and Solutions for Circuits and Synapses in Parkinson's Disease," *Neuron* 43:165-168, Cell Press (Jul. 2004).

Jones, L.L., et al., "NG2 Is a Major Chondroitin Sulfate Proteoglycan Produced after Spinal Cord Injury and Is Expressed by Macrophages and Oligodendrocyte Progenitors," *J. Neurosci.* 22:2792-2803, Society for Neuroscience (2002).

Kasper, C., et al, "Structural Basis of Cell—Cell Adhesion by NCAM," *Nat. Struct. Biol.* 7:389-393, Nature American Inc. (2000).

Kim, J.Y., et al., "The Role of ErbB2 Signaling in the Onset of Terminal Differentiation of Oligodendrocytes In Vivo," *J. Neurosci.* 23:5561-5571, Society of Neuroscience (2003).

Klapper, L.N., et al., "A subclass of tumor-inhibitory monoclonal antibodies to ErbB-2/HER2 blocks crosstalk with growth factor receptors," *Oncogene* 14:2099-2109, Nature Publishing Company (1997).

Knappik, A., et al., "Fully Synthetic Human Combinatorial Antibody Libraries (HuCAL) Based on Modular Consensus Frameworks and CDRs Randomized with Trinucloetides," *J. Mol. Biol.* 296:57-86, Academic Press (2000).

Kolodny, E.H., "Dysmyelinating and demyelinating comditions in infancy," *Curr. Opin. Neurol. Neurosurg.* 6:379-386, Current Science (1993).

Kornilova, E., et al., "Lysosomal Targeting of Epidermal Growth Factor Receptors via a Kinase-dependent Pathway Is Mediated by the Receptor Carboxyl-terminal Residues 1022-1123," *J. Biol. Chem.* 271:30340-30346, The American Society for Biochemistry and Molecular Biology, Inc. (1996).

Laederich, M.B., et al., "The Leucine-rich Repeat Protein LRIG1 Is a Negative Regulator of ErbB Family Receptor Tyrosine Kinases," *J. Biol.Chem.* 279:47050-47056, The American Society for Biochemistry and Molecular Biology, Inc. (Nov. 2004).

Laederich, M.B., et al., "The Leucine-rich Repeat Protein LRIG1 Is a Negative Regulator of ErbB Family Receptor Tyrosine Kinases," *J. Biol. Chem.* 279:52806, The American Society for Biochemistry and Molecular Biology, Inc. (Dec. 2004).

Li, W., et al., "Neutralization of Myelin-Associated NOGO-A by a NOGO Receptor-FC Fusion Protein," *Society for Neuroscience Abstracts* ABS3332, Society for Neuroscience (2002).

Li, S., et al., "Blockade of Nogo-66, Myelin-Associated Glycoprotein, and Oligodendrocyte Myelin Glycoprotein by Soluble Nogo-66 Receptor Promotes Axonal Sprouting and Recovery after Spinal Injury," *J. Neurosci.* 24:10511-10520, Society of Neuroscience (Nov. 2004).

Lin, L., et al., "Netrin-1 and slit-2 regulate and direct neurite growth of ventral midbrain dopaminergic neurons," *Molec. Cell. Neurosci.* 28:547-555, Elsevier Inc. (Mar. 2005).

Ma, L., et al., "Ligand-Dependent Recruitment of the ErbB4 Signaling Complex into Neuronal Lipid Rafts," *J. Neurosci.* 23:3164-3175, Society of Neuroscience (2003).

McKerracher, L., et al., "Identification of Myelin-Associated Glycoprotein as a Major Myelin-Derived Inhibitor of Neurite Growth," *Neuron* 13:805-811, Cell Press (1994).

Messier, C., et al., "New Techniques in Stereotaxic Surgery and Anesthesia in the Mouse," *Pharmacol. Biochem. Behav.* 63:313-318, Elsevier Science Inc. (1999).

Mi, S., et al., "A Novel CNS-Specific Protein Promotes Axonal Elongation by Modulating RHOA Signaling," *Society for Neuroscience* Abstracts, Abstract No. 891.5, Society for Neuroscience (2003).

Mi, S., et al., "LINGO-1 is a component of the Nogo-66 receptor/p75 signaling complex," *Nat. Neurosci.* 7:221-8, Nature Publishing Group (Mar. 2004).

Mi, S., et al., "LINGO-1 negatively regulates myelination by oligodendrocytes," *Nat. Neurosci.* 8:745-51, Nature Publishing Group (Electronically available May 2005).

Mi, S., et al., "LINGO-1 antagonist promotes spinal cord remyelination and axonal integrity in MOG-induced experimental autoimmune encephalomyelitis," *Nat. Med.* 13:1228-1233, Nature Publishing Group (Oct. 2007).

Mikol D.D. et al., "A Phosphatidylinositol-Linked Peanut Agglutinin-Binding Glycoprotein in Central Nervous System Myelin and on Oligodendrocytes," *J. Cell. Biol.* 106:1273-1279, The Rockefeller University Press (1988).

Morell, P., et al., "Gene Expression in Brain during Cuprizone-Induced Demyelination and Remyelination," *Molec. Cell. Neurosci.* 12:220-227, Academic Press (1998).

Mukhopadhyay, G., et al., "A Novel Role for Myelin-Associated Glycoprotein as an Inhibitor of Axonal Regeneration," *Neuron* 13:757-767, Cell Press (1994).

Nagy, P., et al., "Lipid rafts and the local density of ErbB proteins influence the biological role of homo- and heteroassociations of ErbB2," *J. Cell Sci.* 115:4251-4262, The Company of Biologists Ltd. (2002).

Nagy, Z.A., et al., "Fully human, HLA-DR-specific monoclonal antibodies efficiently induce programmed death of malignant lymphoid cells," *Nat. Med.* 8:801-807, Nature Publishing Group (2002).

Okafuji, T., et al., "Expression pattern of LINGO-1 in the developing nervous system of the chick embryo," *Gene Expr. Patterns* 6:57-62, Elsevier (Electronically available Jul. 2005).

Orlandi, R., et al., "Cloning immunoglobulin variable domains for expression by the polymerase chain reaction," *Proc. Natl. Acad. Sci. USA* 86:3833-3837, National Academy of Sciences (1989).

Park, S.-K., et al., "The erbB2 gene is required for the development of terminally differentiated spinal cord oligodendrocytes," *J. Cell Biol.* 154:1245-1258, The Rockefeller University Press (2001).

Park, J.B., et al., A TNF Receptor Family Member, TROY, is a Coreceptor with Nogo Receptor in Mediating the Inhibitory Activity of Myelin Inhibitors, *Neuron* 3:345-351, Elsevier Inc. (Feb. 2005).

Park, J.B., et al., A TNF Receptor Family Member, TROY, is a Coreceptor with Nogo Receptor in Mediating the Inhibitory Activity of Myelin Inhibitors, Erratum in *Neuron* 3:815, Elsevier Inc. (Mar. 2005).

Pinkas-Kramarski, R., et al., "Neu Differentiation Factor/Neuregulin Isoforms Activate Distinct Receptor Combinations," *J. Biol. Chem.* 271:19029-19032, The American Society for Biochemistry and Molecular Biology, Inc. (1996).

Plant, G.W., et al., "Purified Adult Ensheathing Glia Fail to Myelinate Axons under Culture Conditions that Enable Schwann Cells to Form Myelin," *J. Neurosci.* 22:6083-6091, Society for Neuroscience (2002).

Qiu, X.-B. And Goldberg, A.L., "Nrdp1/FLRF is a ubiquitin ligase promoting ubiquitination and degradation of the epidermal growth factor receptor family member, ErbB3," *Proc. Natl. Acad. Sci. USA* 99:14843-14848, National Academy of Sciences (2002).

Rauchenberger, R., et al., "Human Combinatorial Fab Library Yielding Specific and Functional Antibodies against the Human Fibroblast Growth Factor Receptor 3," *J. Biol. Chem.* 278:38194-38205, The American Society for Biochemistry and Molecular Biology, Inc. (2003).

Rubinson, D.A., et al., "A lentivirus-based system to functionally silence genes in primary mammalian cells, stem cells and transgenic mice by RNA interference," *Nat. Genet.* 33:401-406, Nature Publishing Group (2003).

Rutishauser, U. et al., "Cell Adhesion Molecules in Vertebrate Neural Develeopment," *Physiol. Rev.* 68:819-857, American Physiological Society (1988).

Schmucker, J., et al.,"erbB3 Is Dispensable for Oligodendrocyte Development In Vitro and In Vivo," *Glia* 44:67-75, Wiley-Liss, Inc. (2003).

Shah, B.H., et al., "Role of EGF Receptor Transactivation in Phosphoinositide 3-Kinase-Dependent Activation of MAP Kinase by GPCRs," *J. Cell. Physiol.* 206:47-57, Wiley-Liss Inc. (Jan. 2006).

Shao, Z., et al., "TAJ/TROY, an Orphan TNF Receptor Family Member, Binds Nogo-66 Receptor 1 and Regulates Axonal Regeneration," *Neuron* 45:353-9, Elsevier Inc. (Feb. 2005).

Stolt, C.C., et al., "Terminal differentiation of myelin-forming oligodendrocytes depends on the transcription factor Sox10," *Genes & Dev.* 16:165-170, Cold Spring Harbor Laboratory Press (2002).

Sussman, C.R., et al., "The ErbB4 Neuregulin Receptor Mediates Suppression of Oligodendrocyte Maturation," *J. Neurosci.* 25:5757-5762, Society for Neuroscience (Jun. 2005).

Trapp, B.D., et al., "Pathogenesis of tissue injury in MS lesions," *J. Neuroimmunol.* 98:49-56, Elsevier Science B.V. (1999).

Trapp, B.D., et al., "Axonal pathology in multiple sclerosis: relationship to neurologic disability," *Curr. Opin. Neurol.* 12:295-302, Lippincott Williams & Wilkins (1999).

Trifunovski, A. et al. "Neuronal activity-induced regulation of LINGO-1," *Neuroreport* 15:2397-2400, Lippincott, Williams & Wilkins (Oct. 2004).

Tzahar, E., et al., "Bivalence of EGF-like ligands drives the ErbB signaling network," *EMBO J.* 16:4938-4950, Oxford University Press (1997).

Vartanian, T., et al., "Failure of spinal cord oligodendrocyte development in mice lacking neuregulin," *Proc. Natl. Acad. Sci. USA* 96:731-735, National Academy of Sciences (1999).

Wang, K.C., et al., "Oligodendrocyte-Myelin Glycoprotein is a Nogo Receptor Ligand That Inhibits Neurite Outgrowth," *Nature* 417:941-944, Nature Publishing Group (2002).

Williams, E.-J. and Doherty, P., "Evidence for and against a Pivotal Role of PI 3-Kinase in a Neuronal Cell Survival Pathway," *Molec. Cell. Neurosci.* 13:272-280, Academic Press (1999).

Xu, W., et al., "Chaperone-dependent E3 ubiquitin ligase CHIP mediates a degradative pathway for c-ErbB2/Neu," *Proc. Natl. Acad. Sci. USA* 99:12847-12852, National Academy of Sciences (2002).

Yang, L., et al., "A novel azulenyl nitrone antioxidant protects against MPTP and 3-nitropropionic acid neurotoxicities," *Exp. Neurol.* 191:86-93, Elsevier Inc. (Jan. 2005).

Yu, W., et al., "Segregation of Nogo66 receptors into lipid rafts in rat brain and inhibition of Nogo66 signaling by cholesterol depletion," *FEBS Lett.* 577:87-92, Elsevier B.V. (Nov. 2004).

Zhou, P., et al., "ErbB2 Degradation Mediated by the Co-chaperone Protein CHIP," *J. Biol. Chem.* 278:13829-13837, The American Society for Biochemistry and Molecular Biology, Inc. (2003).

NCBI Entrez, Accession No. BC011057, (first available Jul. 30, 2001; last updated Feb. 8, 2007).

NCBI Entrez, Accession No. BC068558, (first available Apr. 6, 2004; last updated Feb. 8, 2007).

NCBI Entrez, Accession No. NM_152570, (first available Sep. 6, 2002; last updated Feb. 11, 2008).

NCBI Entrez, Accession No. NM_032808, (first available May 31, 2001; last updated Feb. 11, 2008).

NCBI Entrez, Accession No. DR000281, (first available May 17, 2005; last updated May 17, 2005).

NCBI Entrez, Accession No. AY324320, (first available May 4, 2004; last updated May 4, 2004).

NCBI Entrez, Accession No. AY324322, (first available May 4, 2004; last updated May 4, 2004).

NCBI Entrez, Accession No. AY324323, (first available May 4, 2004; last updated May 4, 2004).

Brummell, D.A., et al., "Probing the combining site of an anti-carbohydrate antibody by saturation-mutagenesis: role of the heavy-chain CDR3 residues," *Biochemistry* 32(4):1180-7, American Chemical Society, United States (Feb. 1993).

Burks, E.A., et al., "In vitro scanning saturation mutagenesis of an antibody binding pocket," *Proc. Natl. Acad. Sci. U.S.A.* 94(2):412-7 National Academy of Sciences, United States (Jan. 1997).

Casset, F., et al., "A peptide mimetic of an anti-CD4 monoclonal antibody by rational design," *Biochem. Biophys. Res. Commun.* 307(1):198-205, Academic Press, United States (Jul. 2003).

Chen, Y., et al., "Selection and analysis of an optimized anti-VEGF antibody: crystal structure of an affinity-matured Fab in complex with antigen," *J. Mol. Biol.* 293(4):865-81, Academic Press, England (Nov. 1999).

Colman, P.M., "Effects of amino acid sequence changes on antibody-antigen interactions," *Res. Immunol.* 145(1):33-6, Elsevier, France (Jan. 1994).

De Pascalis, R., et al., "Grafting of 'abbreviated' complementarity-determining regions containing specificity-determining residues essential for ligand contact to engineer a less immunogenic humanized monoclonal antibody," *J. Immunol.* 169(6):3076-84, American Association of Immunologists, United States (Sep. 2002).

Holm, P., et al., "Functional mapping and single chain construction of the anti-cytokeratin 8 monoclonal antibody TS1," *Mol. Immunol.* 44(6):1075-84, Pergamon Press, England (Feb. 2007; Epub Sep. 20 2006).

Kobayashi, H., et al., "Tryptophan H33 plays an important role in pyrimidine (6-4) pyrimidone photoproduct binding by a high-affinity antibody," *Protein Eng.* 12(10):879-84, Oxford University Press, England (Oct. 1999).

MacCallum, R.M., et al., "Antibody-antigen interactions: contact analysis and binding site topography," *J. Mol. Biol.* 262(5):732-45, Academic Press, England (Oct. 1996).

Vajdos, F.F., et al., "Comprehensive functional maps of the antigen-binding site of an anti-ErbB2 antibody obtained with shotgun scanning mutagenesis," *J. Mol. Biol.* 320(2):415-28, Academic Press, England (Jul. 2002).

Wu, H., et al., "Humanization of a murine monoclonal antibody by simultaneous optimization of framework and CDR residues," *J. Mol. Biol.* 294(1):151-62, Academic Press, England (Nov. 1999).

International Search Report mailed Oct. 31, 2006 in Patent Cooperation Treaty Application No. PCT/US05/22881, filed Jun. 24, 2005.

International Preliminary Report on Patentability issued Dec. 28, 2006 in Patent Cooperation Treaty Application No. PCT/US05/22881, filed Jun. 24, 2005.

International Search Report mailed Sep. 16, 2008 in Patent Cooperation Treaty Application No. PCT/US08/00316, filed Jan. 9, 2008.

International Preliminary Report on Patentability issued Jul. 14, 2009 in Patent Cooperation Treaty Application No. PCT/US08/00316, filed Jan. 9, 2008.

International Search Report mailed Aug. 3, 2010 in Patent Cooperation Treaty Application No. PCT/US2009/003999, filed Jul. 9, 2009.

International Preliminary Report on Patentability issued Jan. 11, 2011 in Patent Cooperation Treaty Application No. PCT/US2009/003999, filed Jul. 9, 2009.

U.S. Appl. No. 12/741,957, inventor Mi, S., et al., filed Dec. 21, 2010 (Unpublished).

Damle, N.K. and Frost, P., "Antibody-targeted chemotherapy with immunoconjugates of calicheamicin," *Curr. Opin. Pharmacol.* 3:386-390, Elsevier Science Ltd. (2003).

Declaration of Robert H. Miller filed in copending U.S. Appl. No. 11/165,576 on May 8, 2008.

Declaration of Robert B. Pepinsky filed in copending U.S. Appl. No. 11/165,576 on Feb. 5, 2009.

Declaration of Sha Mi filed in copending U.S. Appl. No. 11/165,576 on May 8, 2008.

International Search Report and Written Opinion of the International Searching Authority for International Application No. PCT/US06/26271, mailed on Jan. 27, 2009, ISA/US, Virginia, U.S.A.

Office Action mailed Feb. 17, 2001, in U.S. Appl. No. 11/892,036, Mi, et al., filed Aug. 17, 2007.

* cited by examiner

Li81: RTP-RO8-0-02, BP 12359-103, Isotype control: BiogenJF 042899
* unilateral severe hind limb paresis,  complete tail paralysis, * distal tail paralysis. treatment
➤ Treatment

COMPOSITION COMPRISING ANTIBODIES TO LINGO OR FRAGMENTS THEREOF

CROSS REFERENCE TO RELATED APPLICATIONS

The present application claims the benefit of the filing date of U.S. Provisional Application No. 61/079,355, filed Jul. 9, 2008, which is incorporated herein by reference in its entirety.

REFERENCE TO A SEQUENCE LISTING SUBMITTED ELECTRONICALLY VIA EFS-WEB

The content of the electronically submitted sequence listing (Name: sequence listing.ascii.txt, Size: 258 kilobytes; and Date of Creation: Jul. 9, 2009) filed with the application is incorporated by reference in its entirety.

BACKGROUND OF THE INVENTION

1. Field of the Invention

This invention relates to neurology, neurobiology and molecular biology. More particularly, this invention relates to molecules and methods for treatment of neurological diseases, disorders and injuries such as spinal cord injury.

2. Background of the Invention

Axons and dendrites extend from neurons. The distal tip of an extending axon or neurite includes a specialized region, known as the growth cone. Growth cones sense the local environment and guide axonal growth toward a neuron's target cell. Growth cones respond to environmental cues, for example, surface adhesiveness, growth factors, neurotransmitters and electric fields. The growth cones generally advance at a rate of one to two millimeters per day. The growth cone explores the area ahead of it and on either side, by means of elongations classified as lamellipodia and filopodia. When an elongation contacts an unfavorable surface, it withdraws. When an elongation contacts a favorable growth surface, it continues to extend and guides the growth cone in that direction. When the growth cone reaches an appropriate target cell a synaptic connection is created.

Nerve cell function is influenced by contact between neurons and other cells in their immediate environment (Rutishauser, et al., 1988, *Physiol. Rev.* 68:819). These cells include specialized glial cells, oligodendrocytes in the central nervous system (CNS), and Schwann cells in the peripheral nervous system (PNS), which sheathe the neuronal axon with myelin (Lemke, 1992, in *An Introduction to Molecular Neurobiology*, Z. Hall, Ed., p. 281, Sinauer).

CNS neurons have the inherent potential to regenerate after injury, but they are inhibited from doing so by inhibitory proteins present in myelin (Brittis et al., 2001, *Neuron* 30:11-14; Jones et al., 2002, *J. Neurosci.* 22:2792-2803; Grimpe et al., 2002, *J. Neurosci.*:22:3144-3160).

Several myelin inhibitory proteins found on oligodendrocytes have been characterized. Known examples of myelin inhibitory proteins include NogoA (Chen et al., Nature, 2000, 403, 434-439; Grandpre et al., *Nature* 2000, 403, 439-444), myelin associated glycoprotein (MAG) (McKerracher et al., 1994, *Neuron* 13:805-811; Mukhopadhyay et al., 1994, *Neuron* 13:757-767) and oligodendrocyte glycoprotein (OM-gp), Mikol et al., 1988, *J. Cell. Biol.* 106:1273-1279). Each of these proteins has been separately shown to be a ligand for the neuronal Nogo receptor-1 (NgR1 (Wang et al., *Nature* 2002, 417, 941-944; Grandpre et al., *Nature* 2000, 403, 439-444; Chen et al., *Nature*, 2000, 403, 434-439; Domeniconi et al., *Neuron* 2002, published online Jun. 28, 2002).

Nogo receptor-1 (NgR1) is a GPI-anchored membrane protein that contains 8 leucine rich repeats (Fournier et al., 2001, *Nature* 409:341-346). Upon interaction with inhibitory proteins (e.g., NogoA, MAG and OM-gp), the NgR1 complex transduces signals that lead to growth cone collapse and inhibition of neurite outgrowth.

There is an unmet need for molecules and methods for inhibiting NgR1-mediated growth cone collapse and the resulting inhibition of neurite outgrowth. Additionally there is a need for molecules which increase neuronal survival and axon regeneration. Particularly for the treatment of disease, disorders or injuries which involve axonal injury, neuronal or oligodendrocyte cell death, demyelination or dymyelination or generally relate to the nervous system.

Such diseases, disorders or injuries include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy. Among these diseases, MS is the most widespread, affecting approximately 2.5 million people worldwide.

MS generally begins with a relapsing-remitting pattern of neurologic involvement, which then progresses to a chronic phase with increasing neurological damage. MS is associated with the destruction of myelin, oligodendrocytes and axons localized to chronic lesions. The demyelination observed in MS is not always permanent and remyelination has been documented in early stages of the disease. Remyelination of neurons requires oligodendrocytes.

Various disease-modifying treatments are available for MS, including the use of corticosteroids and immunomodulators such as interferon beta and Tysabri®. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., *N. Engl. J. Med.* 346: 165-73 (2002). However, there remains an urgent need to devise additional therapies for MS and other demyelination and dismyelination disorders.

BRIEF SUMMARY OF THE INVENTION

The present invention is based on the discovery that certain LINGO-1 antibodies promote survival, proliferation and differentiation of oligodendrocytes and neuronal cells, as well as myelination of neurons. LINGO-1, previously called Sp35, has been described in detail in International Applications PCT/US2006/026271, filed Jul. 7, 2006, PCT/US2004/008323, filed Mar. 17, 2004, PCT/US2005/022881, filed Jun. 24, 2005 and PCT/US2008/000316, filed Jan. 9, 2008, each of which is incorporated by reference in its entirety herein. Based on these discoveries, the invention relates generally to antibodies, antigen binding fragments or derivatives thereof which can be used as an antagonist of LINGO-1. Additionally, the invention generally relates to methods for treating various diseases, disorders or injuries associated with demyelination, dysmyelination, oligodendrocyte/neuronal cell death or axonal injury by the administration of a LINGO-1 antagonist antibody or antigen binding fragment.

In certain embodiments, the invention includes an isolated antibody or antigen binding fragment thereof which specifically binds to the same LINGO-1 epitope as the reference monoclonal antibody Li62 or Li81.

Certain embodiments of the invention include an isolated polypeptide comprising an immunoglobulin heavy chain variable region (VH) wherein the CDR1, CDR2 and CDR3 regions are selected from the polypeptide sequences shown in Table 3 or at least 80%, 85%, 90% or 95% identical to the polypeptide sequences shown in Table 3 or at least 80%, 85%, 90, 95% or 100% identical to the VH CDR1, CDR2 and CDR3 regions of the immunoglobulin heavy chain of Li62 or Li81. In some embodiments, the VH comprises the polypeptide sequence of SEQ ID NO: 4 or SEQ ID NO:8 or any one of SEQ ID NOs: 17 to 49.

Certain embodiments of the invention include an isolated polypeptide comprising an immunoglobulin light chain variable region (VL) wherein the CDR 1, CDR2 and CDR3 regions are selected from the polypeptide sequences shown in Table 4 or at least 80%, 85%, 90% or 95% identical to the polypeptide sequences shown in Table 4 or at least 80%, 85%, 90%, 95% or 100% identical to the VL CDR1, CDR2 and CDR3 regions of the immunoglobulin light chain of Li62 or Li81.

Certain embodiments of the invention include an isolated polypeptide comprising an immunoglobulin heavy chain variable region (VH) selected from the group consisting of SEQ ID NOs: 1, 5, and 53-85 or at least 80%, 85%, 90% or 95% identical to said SEQ ID NOs: 1, 5 and 53-85.

Certain embodiments of the invention include an isolated polypeptide comprising an immunoglobulin light chain variable region (VL) selected from the group consisting of SEQ ID NOs: 9 and 13, as shown in Table 4, or at least 80%, 85%, 90% or 95% identical to said SEQ ID NOs: 9 and 13, as shown in Table 4.

Other embodiments of the invention include an isolated polynucleotide comprising a nucleic acid encoding an immunoglobulin heavy chain variable region (VH) selected from the group consisting of SEQ ID NOs: 1, 5 and 53-85, or at least 80%, 85%, 90% or 95% identical to said SEQ ID NOs: 1, 5 and 53-85. In some embodiments, the polynucleotide comprises a nucleic acid encoding the polypeptide sequence of SEQ ID NO: 4 or SEQ ID NO:8 or any one of SEQ ID NOs: 17 to 49.

Other embodiments of the invention include an isolated polynucleotide comprising a nucleic acid encoding an immunoglobulin light chain variable region (VL) selected from the group consisting of SEQ ID NOs: 9 and 13, as shown in Table 4, or at least 80%, 85%, 90% or 95% identical to said SEQ ID NOs: 9 and 13, as shown in Table 4.

In certain embodiments, the invention includes compositions comprising the antibodies or antigen binding fragments described herein.

In additional embodiments, the invention includes methods for treating CNS injury, ALS, Huntington's disease, Alzheimer's disease, Parkinson's disease, diabetic neuropathy and stroke comprising administering to an animal in need of said treatment an effective amount of an agent selected from the group consisting of an isolated LINGO-1 antibody or fragment thereof or compositions comprising said antibody or fragment thereof.

In other embodiments, the invention includes methods for treating diseases or disorders associated with inhibition of oligodendrocyte growth or differentiation; demyelination or dysmyelination of CNS neurons including multiple sclerosis (MS), progressive multifocal leukoencephalopathy (PML), encephalomyelitis (EPL), central pontine myelolysis (CPM), Wallerian Degeneration, adrenoleukodystrophy, Alexander's disease, and Pelizaeus Merzbacher disease (PMZ) by administering to an animal in need of said treatment an effective amount of an agent selected from the group consisting of an isolated LINGO-1 antibody or fragment thereof or compositions comprising said antibody or fragment thereof.

Other embodiments of the present invention include a method of inhibiting signal transduction by Nogo receptor 1 (NgR1), comprising contacting the NgR1 with an effective amount of an agent selected from the group consisting of the isolated LINGO-1 antibody or fragment thereof or compositions comprising said antibody or fragment thereof.

Additional embodiments of the present invention include a method of decreasing inhibition of axonal growth of a central nervous system (CNS) neuron, comprising contacting the neuron with an effective amount of an agent selected from the group consisting of the isolated LINGO-1 antibody or fragment thereof or of or compositions comprising said antibody or fragment thereof.

Other embodiments of the present invention include a method of inhibiting growth cone collapse of a CNS neuron, comprising contacting the neuron with an effective amount of an agent selected from the group consisting of the isolated LINGO-1 antibody or fragment thereof or compositions comprising said antibody or fragment thereof.

BRIEF DESCRIPTION OF THE DRAWINGS/FIGURES

FIG. 1: Western blot of co-cultured oligodendrocyte precursor cells and DRGs after incubation with anti-LINGO-1 antibodies (Li33 PDL, Li62 (agly) and Li81 (agly)) and control antibody (h5C8) as described in Example 2.

Figure 2:
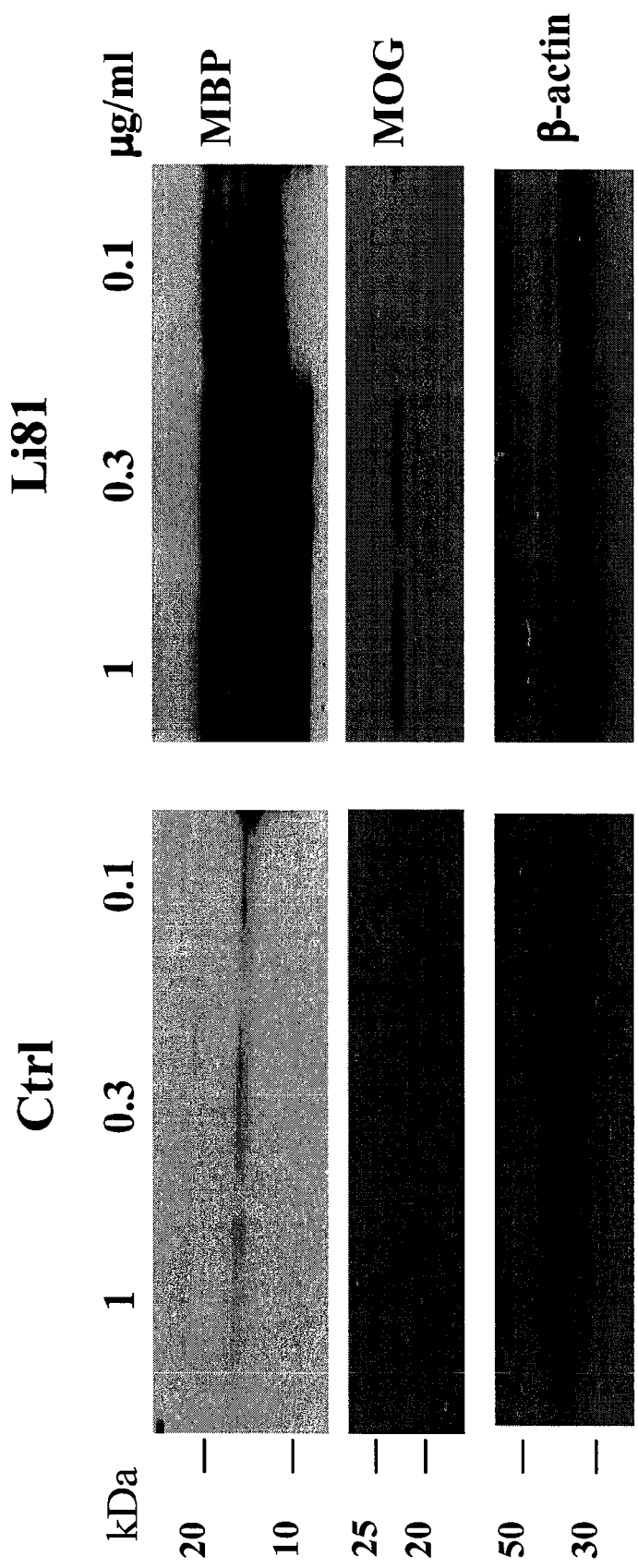

FIG. 2: Western blot of MBP, MOG and β-actin in rat A2B5+ progenitor cells treated with anti-LINGO-1 antibody (Li81 (agly)) or control antibody (Ctrl) as described in Example 4.

Figure 3:
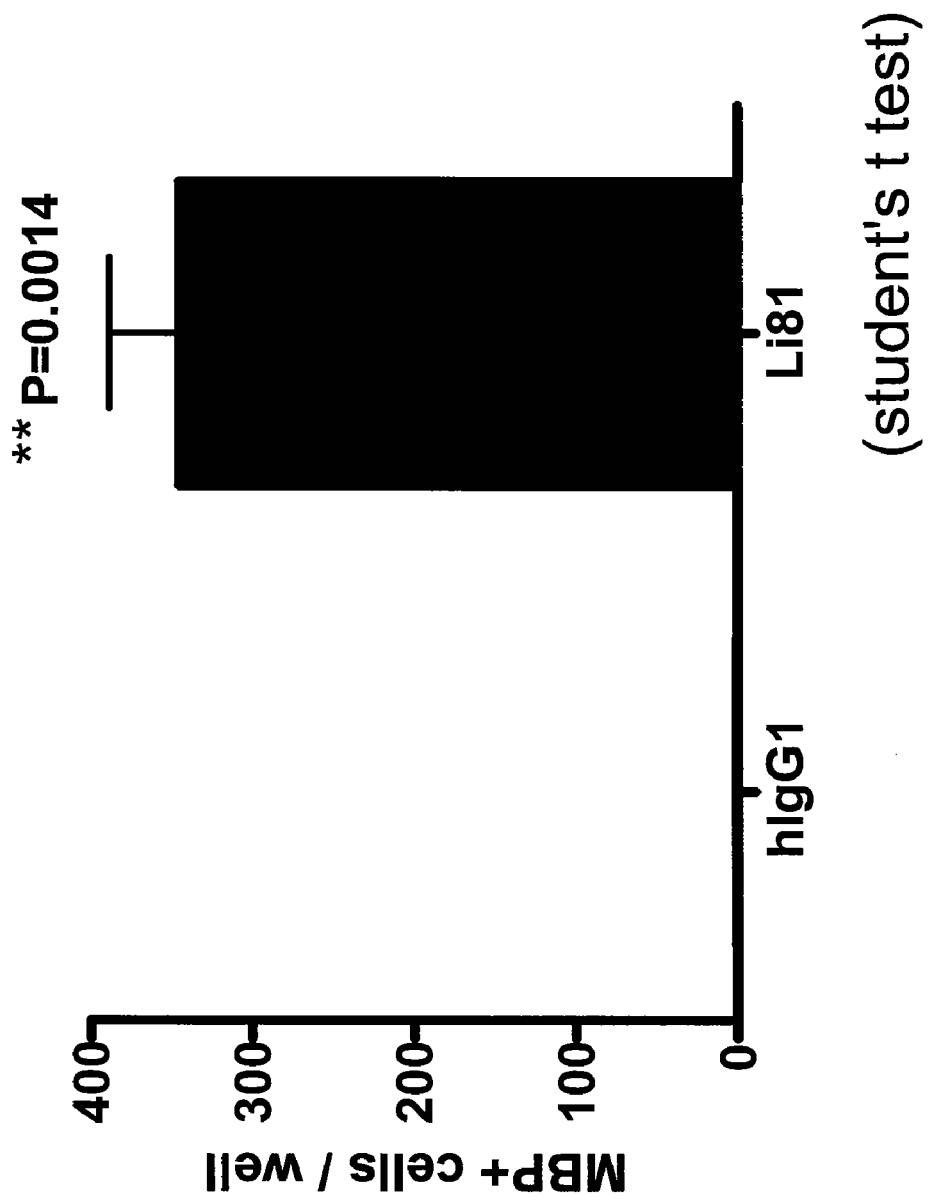

FIG. 3: Bar graph showing the number of MBP-positive cells in human oligodendrocyte precursor cell cultures treated with anti-LINGO-1 antibody (Li81 (agly)) or a control antibody (hIgG1) as described in Example 5.

Figure 4:
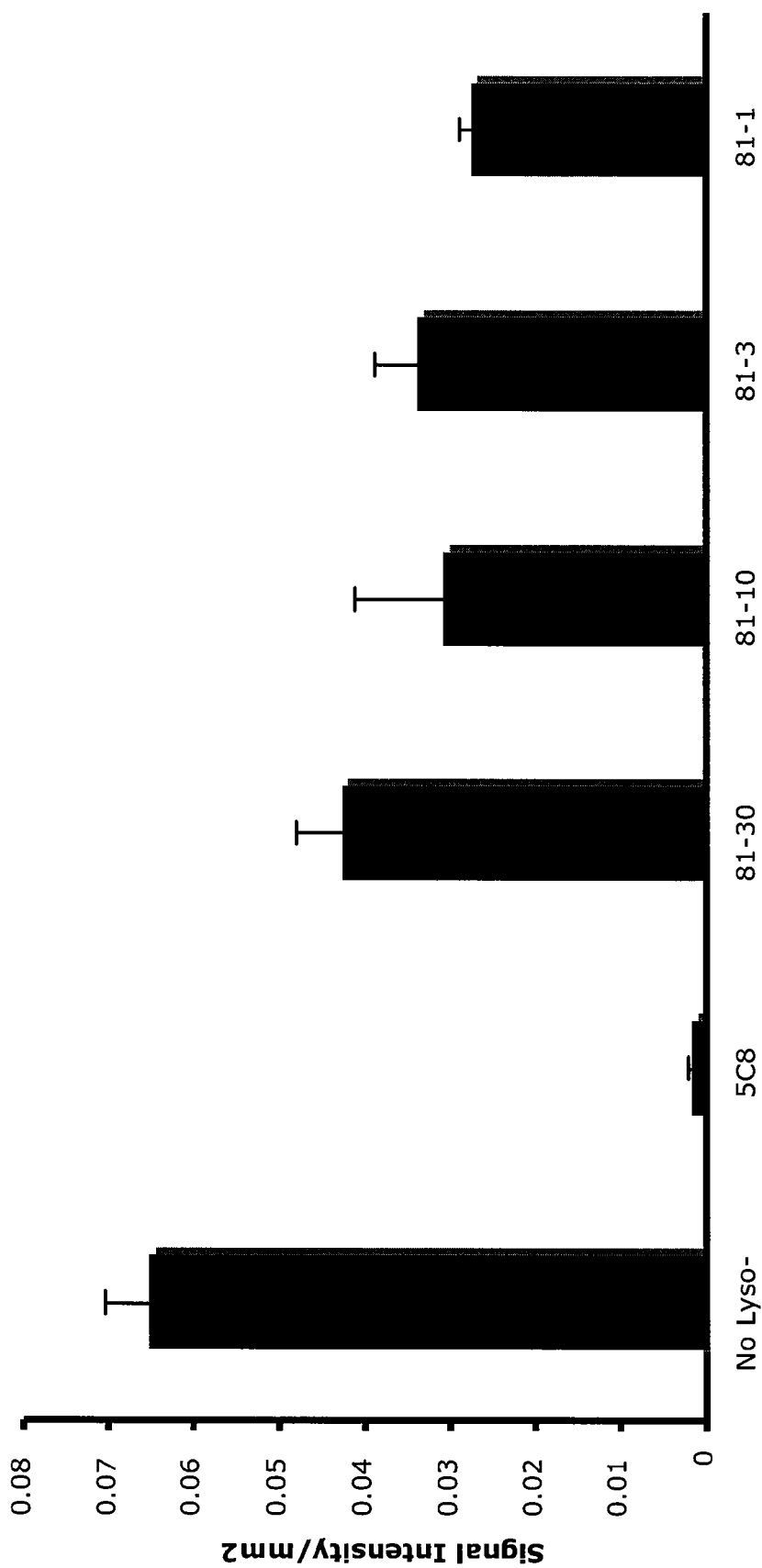

FIG. 4: Bar graph showing intensity of black gold immunostaining to mark myelination in lysolecithin ("Lyso")-treated brain slices exposed to control antibody (5C8) or anti-LINGO-1 antibody (Li81 (agly)) at concentrations of 30 µg/ml (81-30), 10 µg/ml (81-10), 3 µg/ml (81-3), or 1 µg/ml (81-1). Experiments were performed as described in Example 6.

Figure 5:
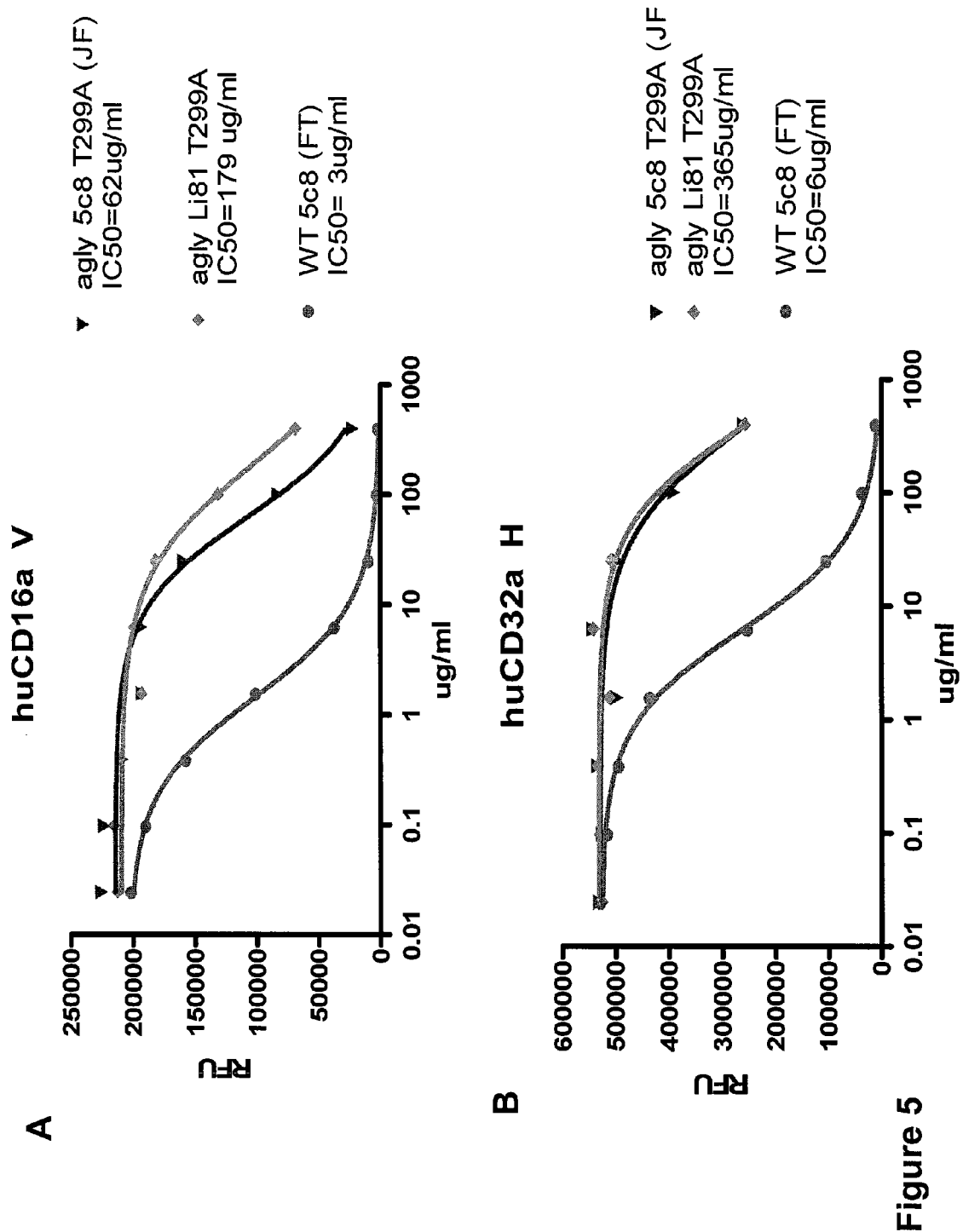
Figure 5:
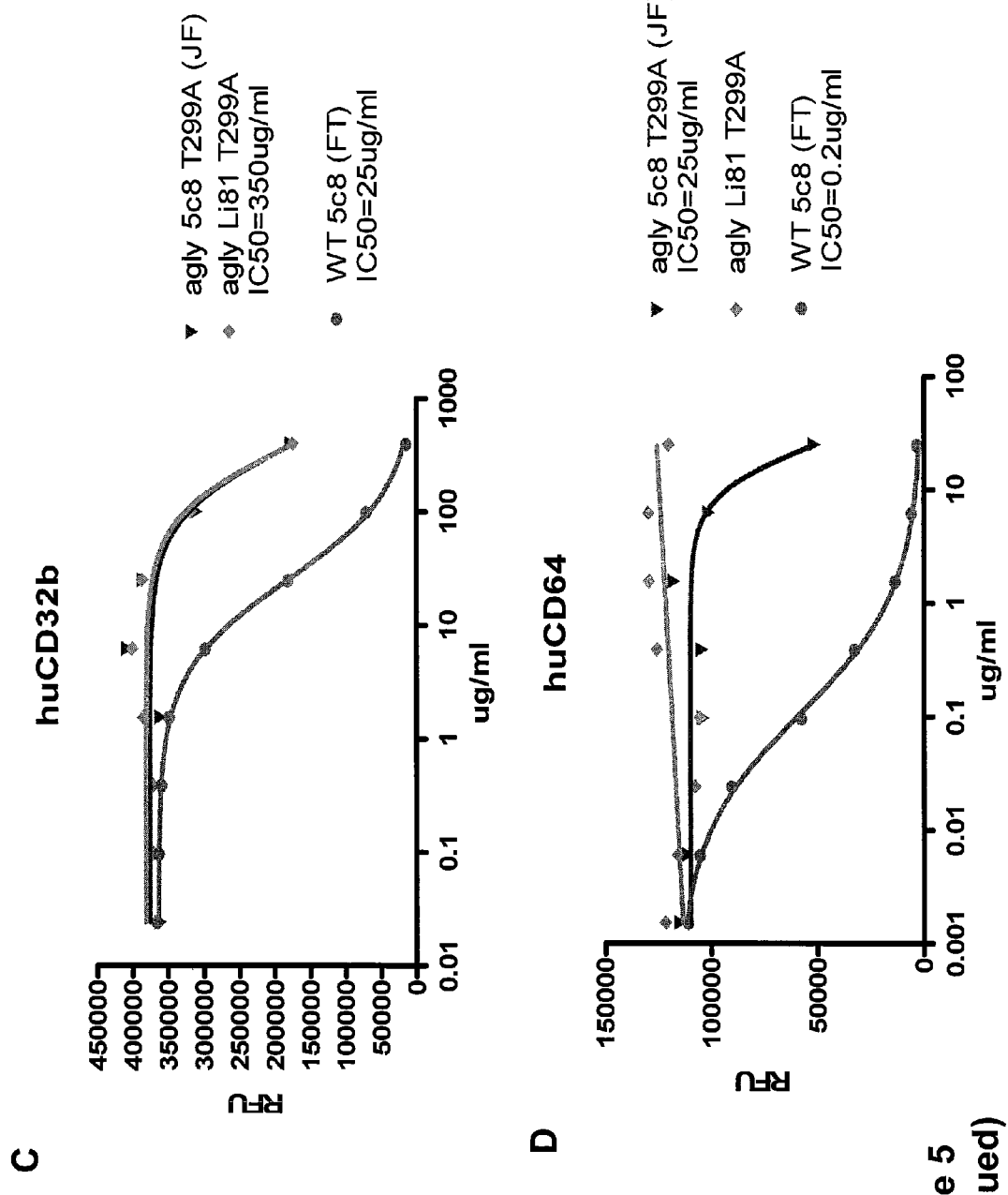

FIG. 5: Graphs depicting IC50 values of an aglycosylated anti-LINGO-1 antibody (Li81 (agly)), a control antibody (WT 5c8) and an aglycosylated control antibody (agly 5c8) for human Fc receptors CD16 (A), CD32a (B), CD32b (C) and CD64 (D). Experiments were performed as described in Example 7.

Figure 6:
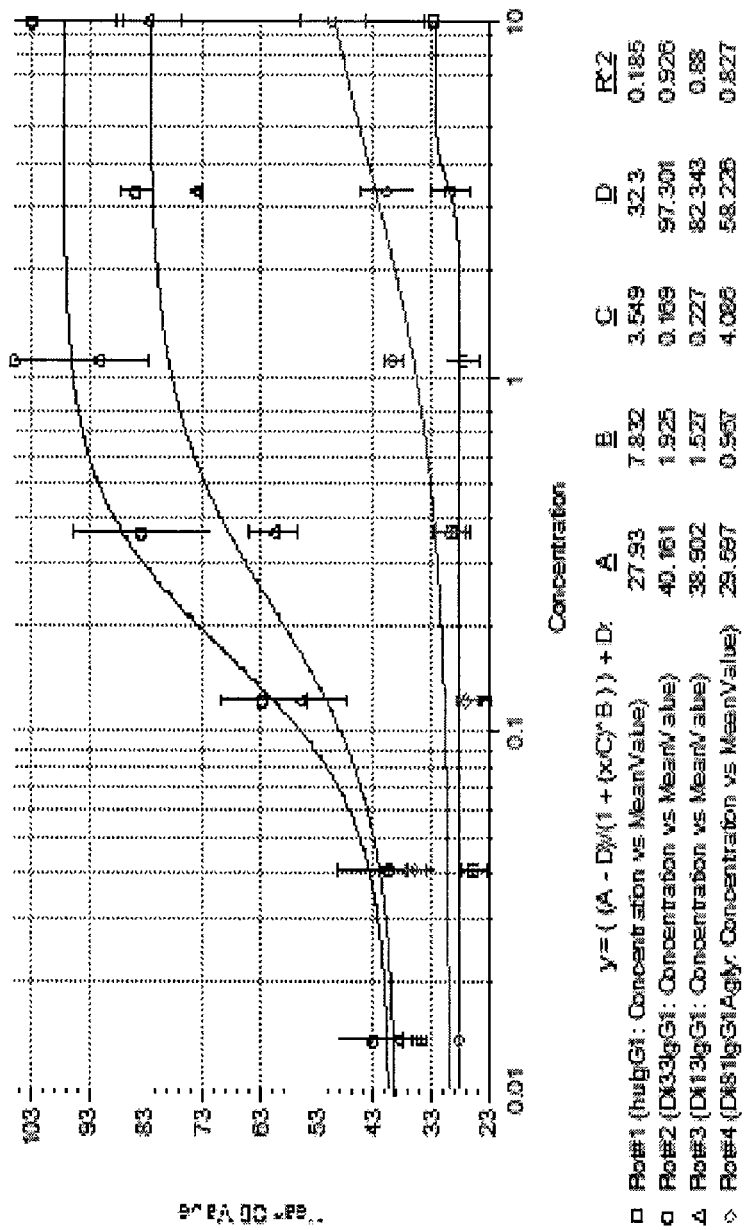

FIG. 6: Graph depicting binding of anti-LINGO-1 antibodies (Li33 ("Di33IgG1") and Li13 "Di13IgG1")), aglycosylated anti-LINGO-1 antibody (Li81 (agly) ("Di81IgG1Agly"), and a control antibody (huIgG1) to CD64 and CD32 as measured by the cell bridging assay described in Example 7.

Figure 7:
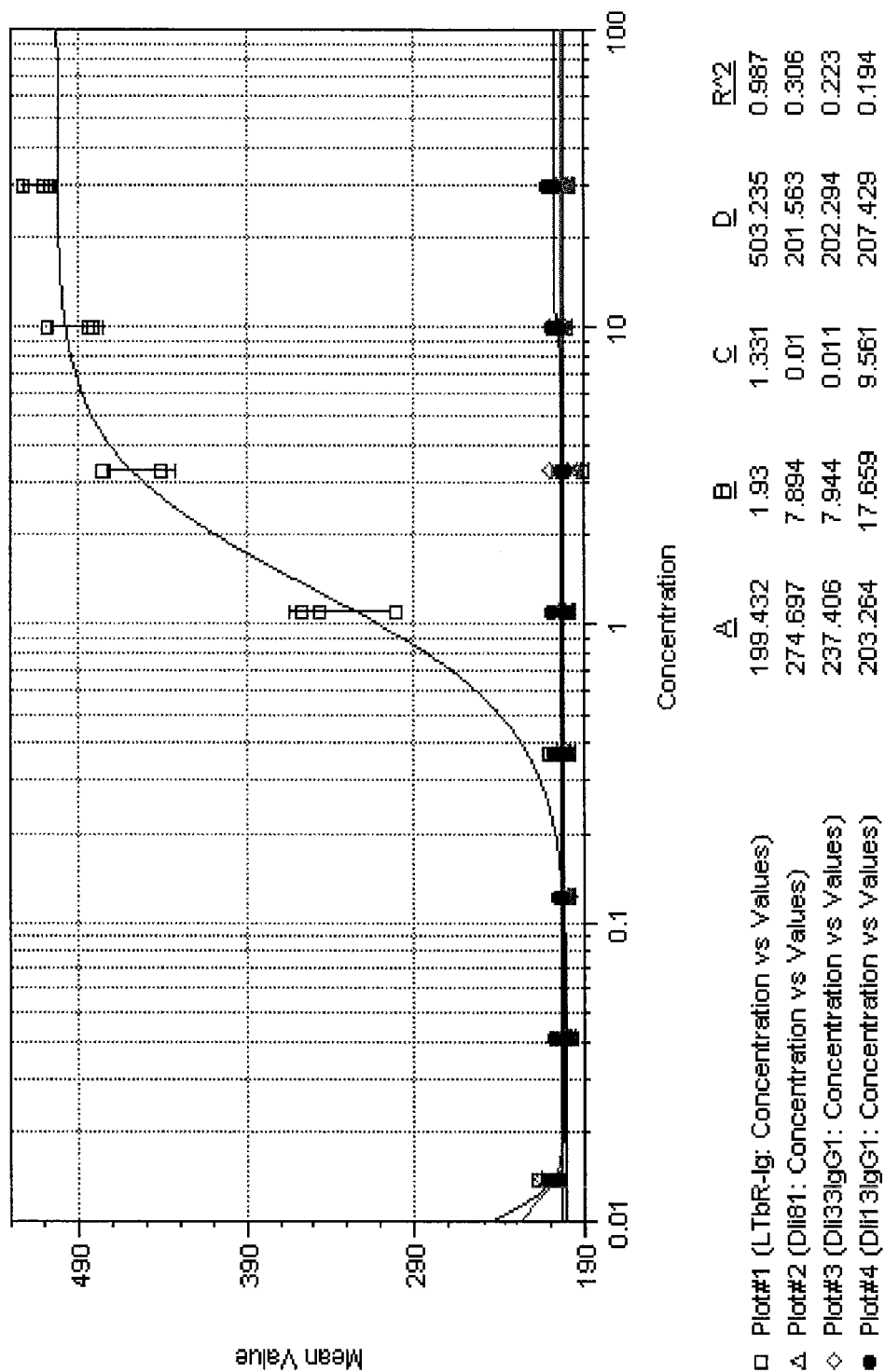

FIG. 7: Graph depicting complement activation in CHO cells expressing LINGO-1 incubated with anti-LINGO-1 antibodies (Li81 (agly) ("Dli81"), Li33 ("Dli13IgG1"), Li13 ("Dli13IgG1")) and a positive control antibody (LTbetaR-Ig). Experiments were performed as described in Example 8.

Figure 8:
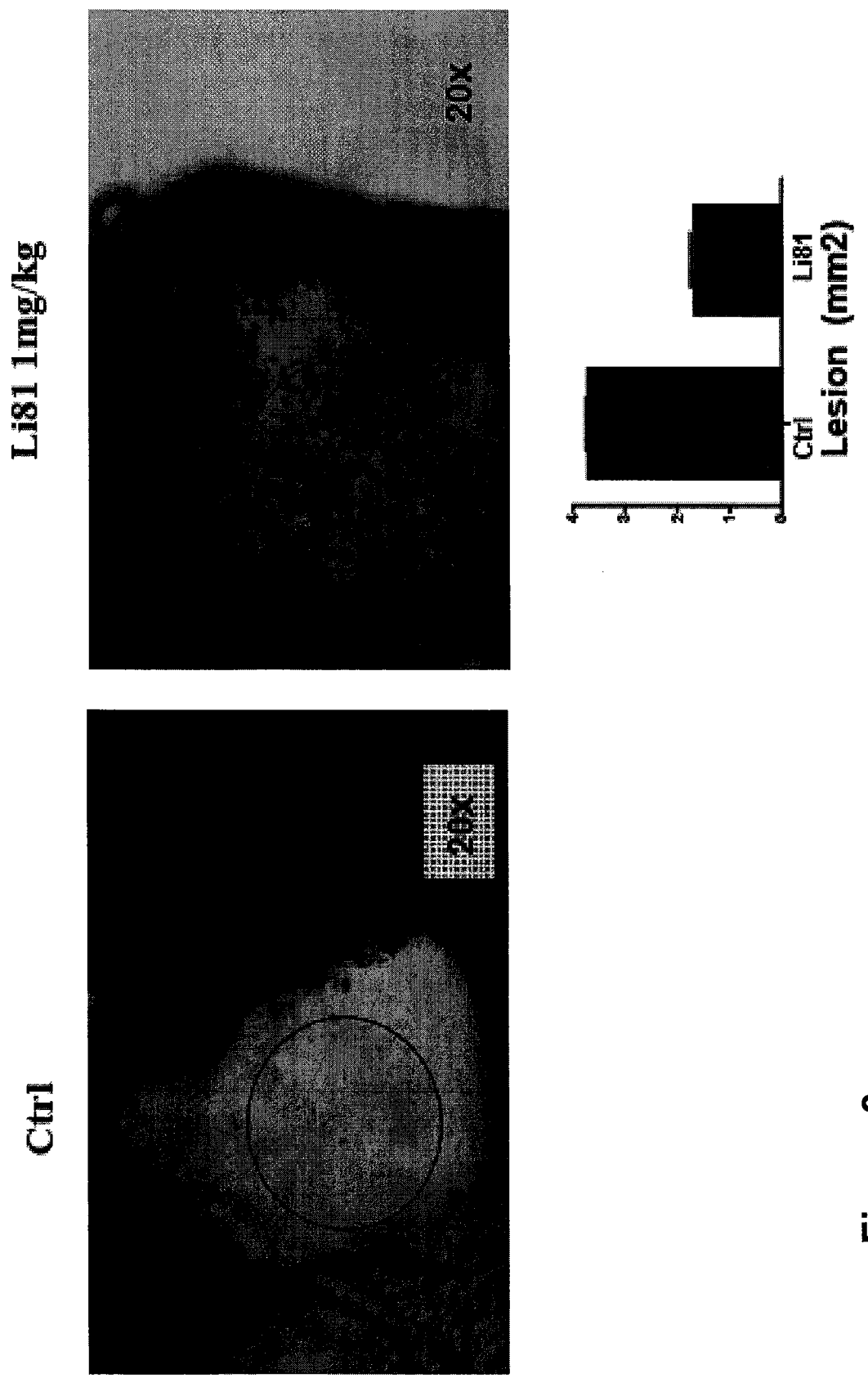

FIG. 8: Images showing lesions in lysolecithin-treated animals administered a control antibody ("Ctrl") or an anti-LINGO-1 antibody (Li81 (agly)) and a bar graph depicting the size of demyelinated lesions in rats treated with lysolecithin and administered control antibody or anti-LINGO-1 antibody (Li81 (agly)). Experiments were performed as described in Example 9.

Figure 9:
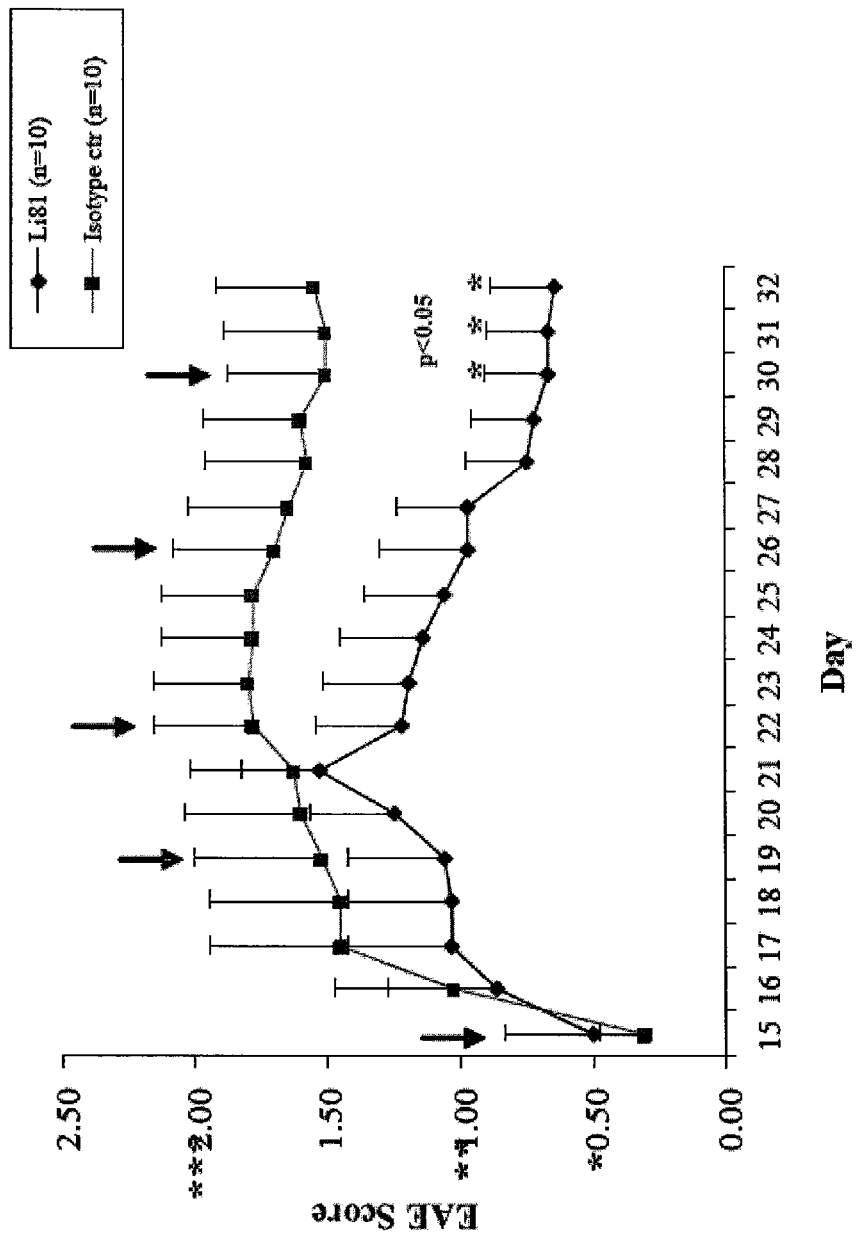

FIG. 9: Graph depicting EAE score to assess paralysis in rats administered recombinant myelin oligodendrocyte glycoprotein and treated with control antibody ("Isotype ctr") or anti-LINGO-1 antibody (Li81). Downward arrows indicate timepoints at which antibody treatment was administered. Experiments were performed as described in Example 10.

Figure 10:
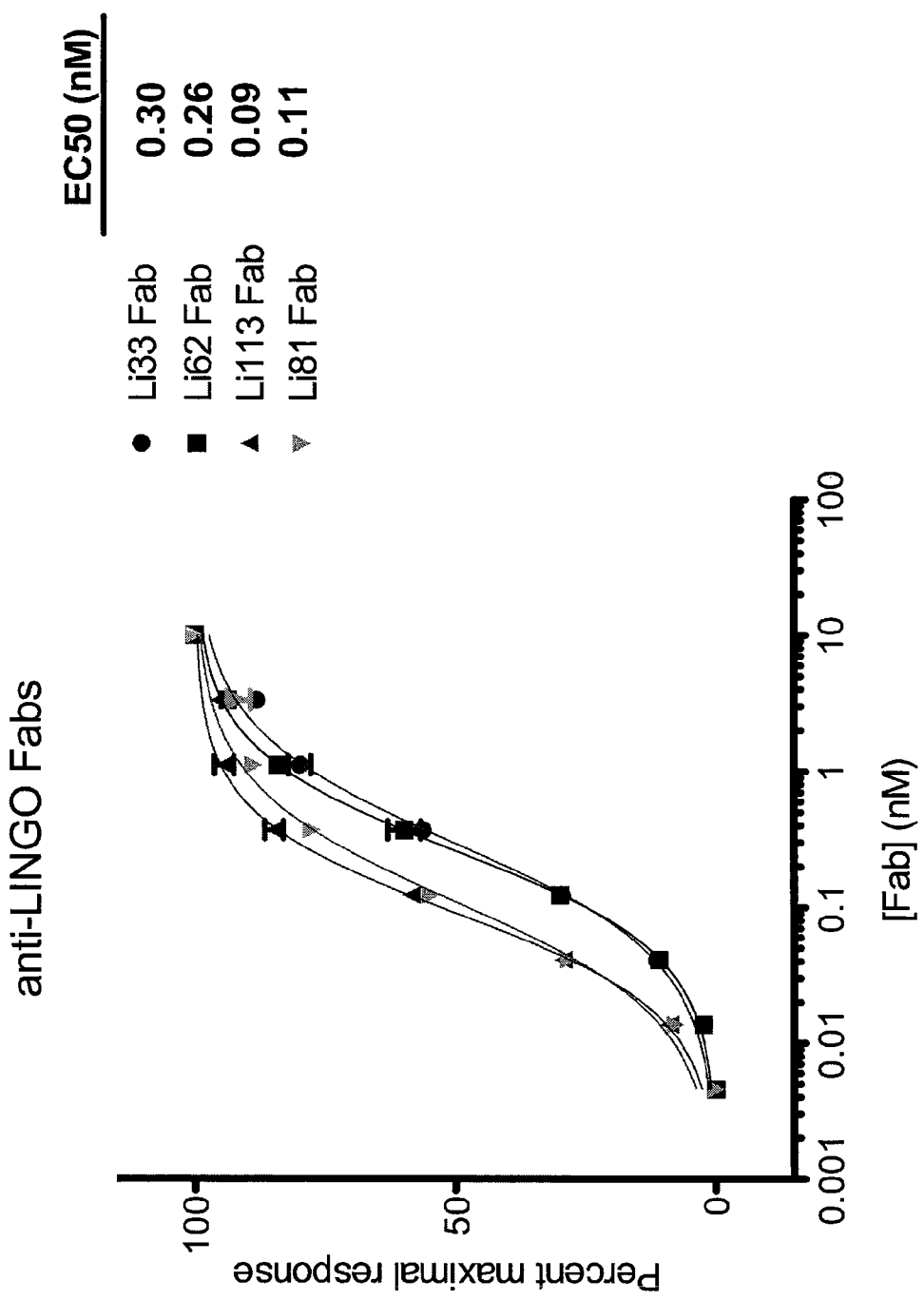

FIG. 10: Graph showing the binding of Li113 Fab to LINGO-1 as measured by ELISA assay.

Figure 11:
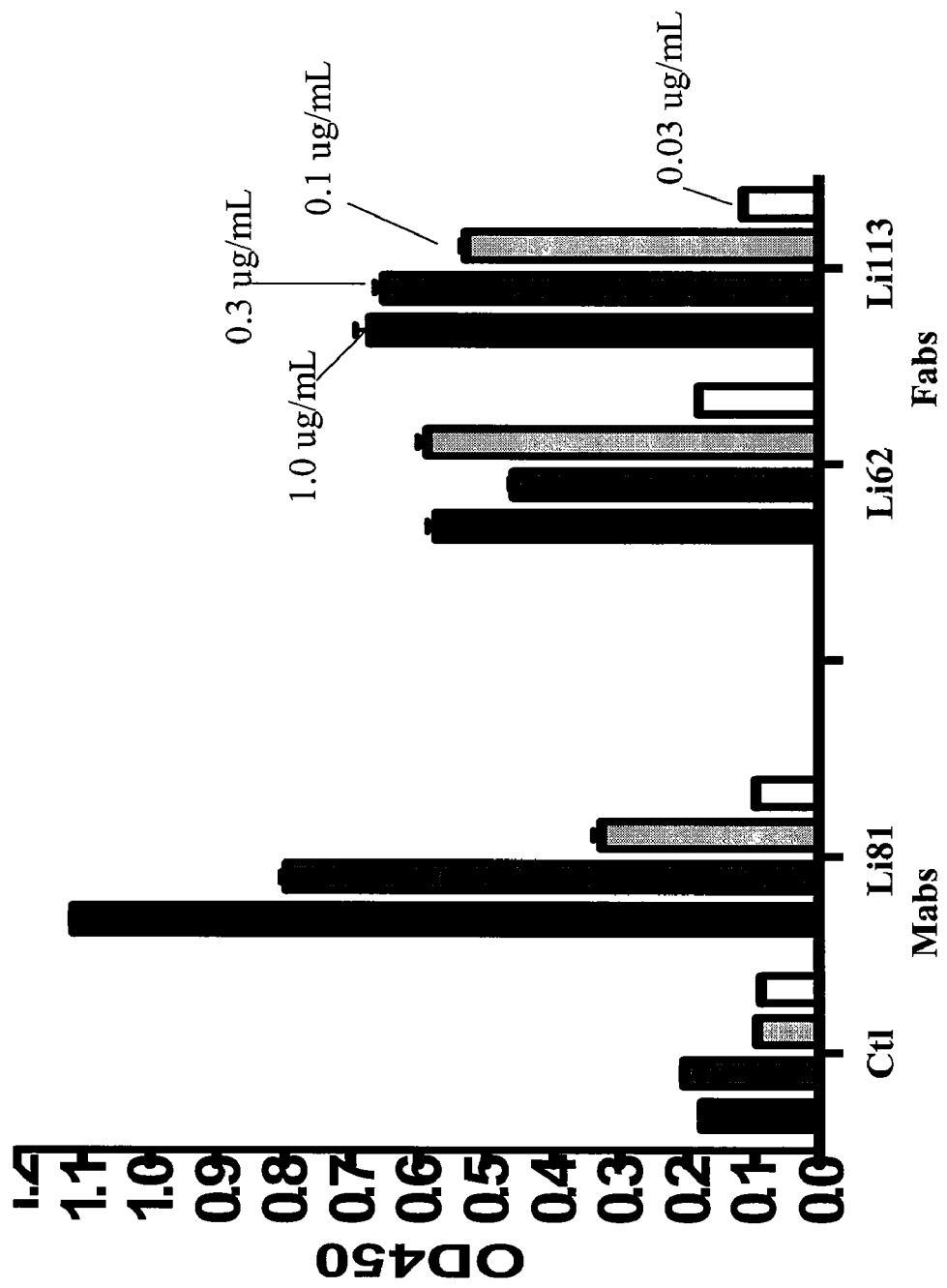

FIG. 11: Graph depicting efficacy of LINGO-1 monoclonal antibodies and Fabs in an oligodendrocye differentiation assay. Bar height represents the concentration of MBP as measured by ELISA. Antibodies were tested at concentrations of 1 µg/ml (black), 0.3 µg/ml (dark grey), 0.1 µg/ml (light grey) and 0.03 µg/ml (white).

Figure 12:
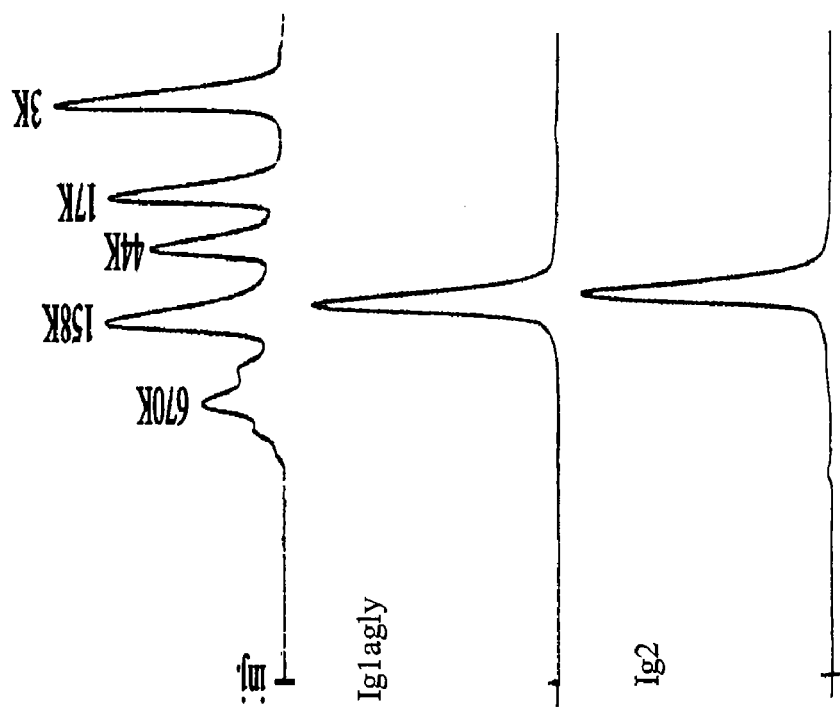

FIG. 12: Image showing the size exclusion chromatography profiles for Li33 Ig1 (agly) and Ig2. Top panel shows the elution profile of BIO RAD gel filtration markers and shows molecular masses.

Figure 13:
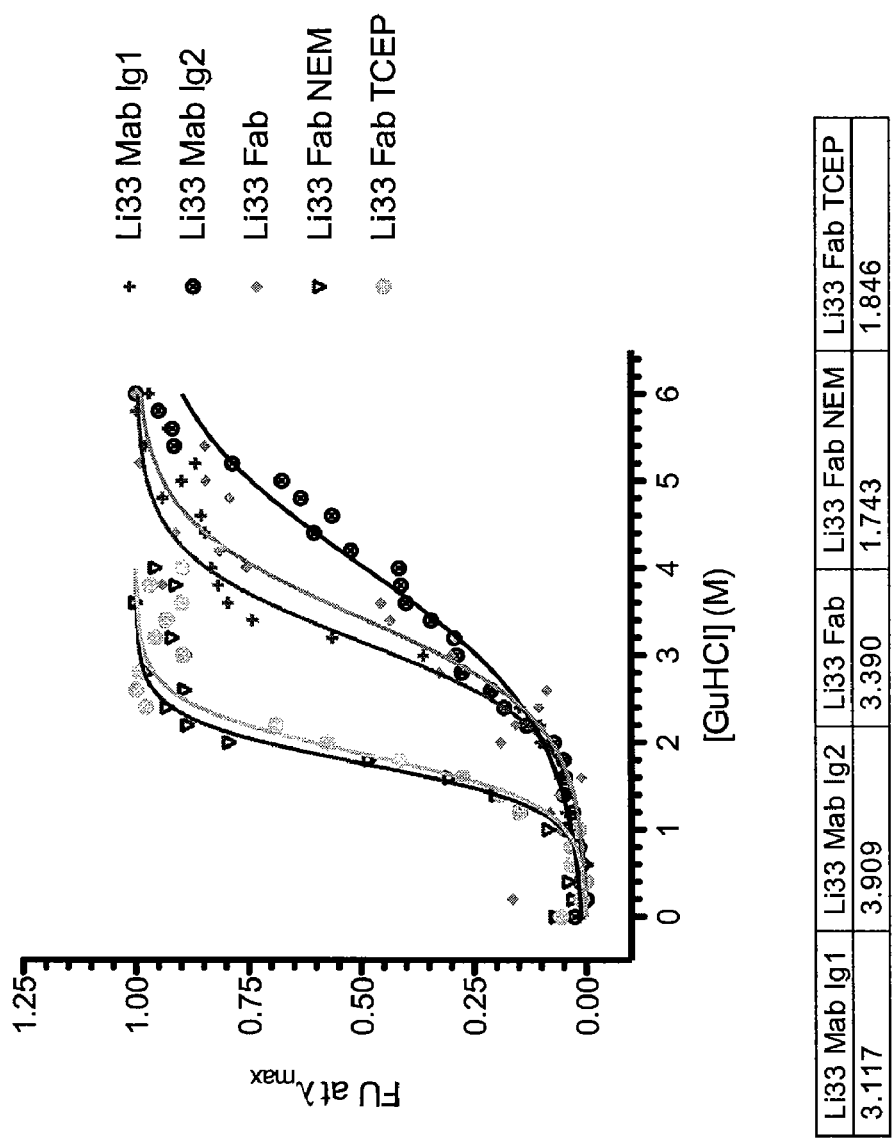

FIG. 13: Graph depicting the denaturation of Li33 Ig1 and Ig2 by guanidine hydrochloride. Flourescence data from the emission spectra at 350 nm are plotted as a function of the guanidine hydrochloride concentration and standardized using the change in flourecence from maximum for each test condition. NEM refers to N-ethylmaleimide and TCEP refers to Tris(2-carboxyethyl)phosphine.

Figure 14:
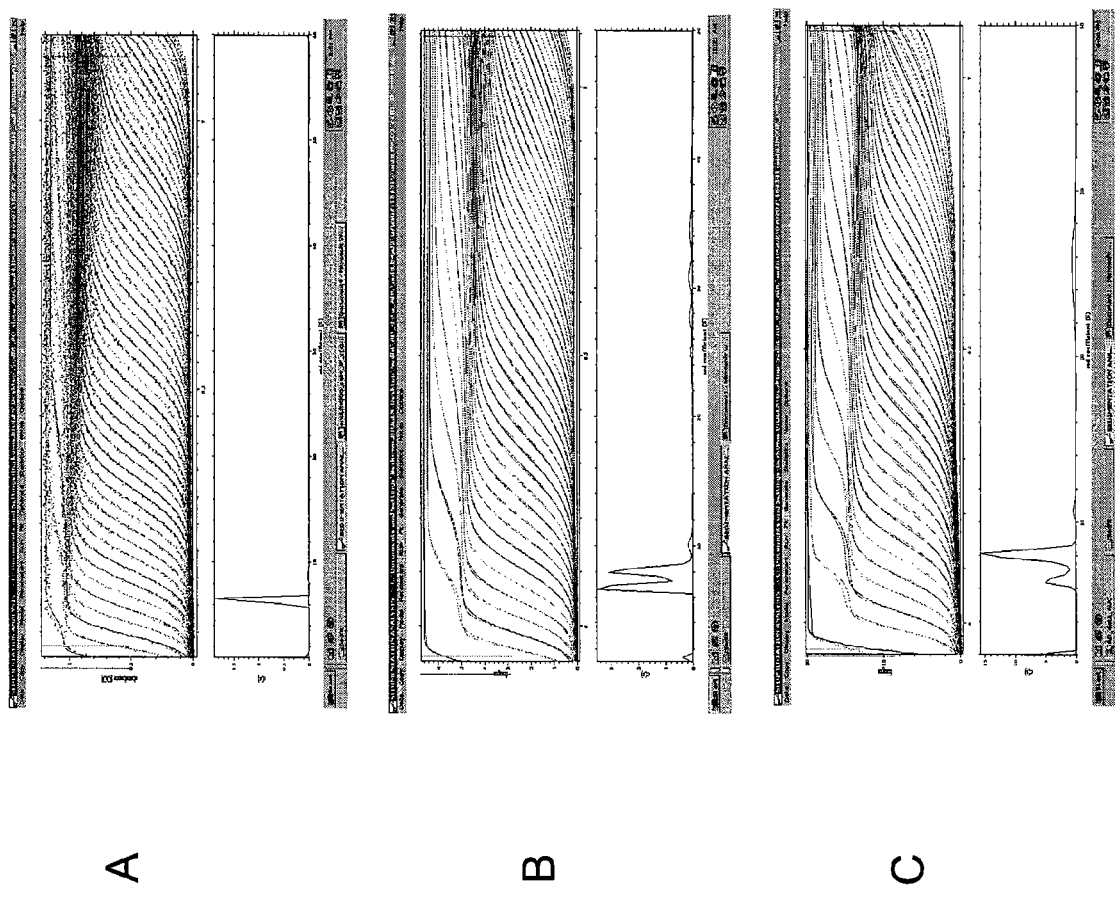

FIG. 14: Image showing the results of an analytical ultracentrifugation evaluating the aggregation state of Li33 Ig2. Absorbance scan data from velocity sedimentation centrifugation studies with Li33 Ig2 Mab at 0.4 mg/ml (A), 7 mg/ml (B) and 27 mg/ml (C) are shown. Top panels show raw absorbance data as a function of time. Bottom panels show relative concentrations as a function of sedimentation coefficient.

Figure 15:
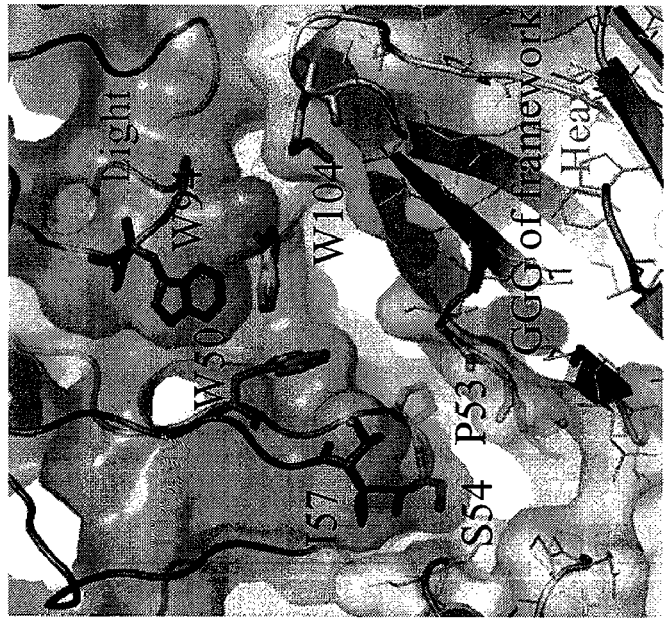
Figure 15:
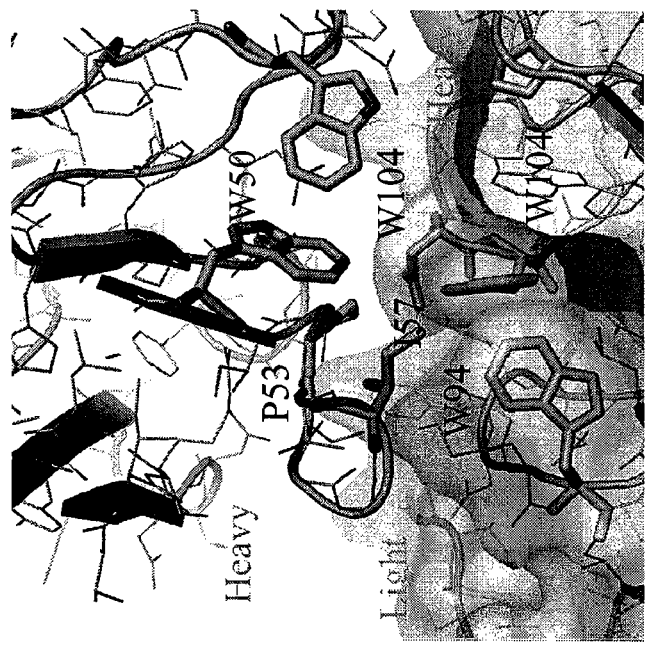

FIG. 15: Image showing protein-protein interactions in the Li33 Fab structure.

Figure 16:
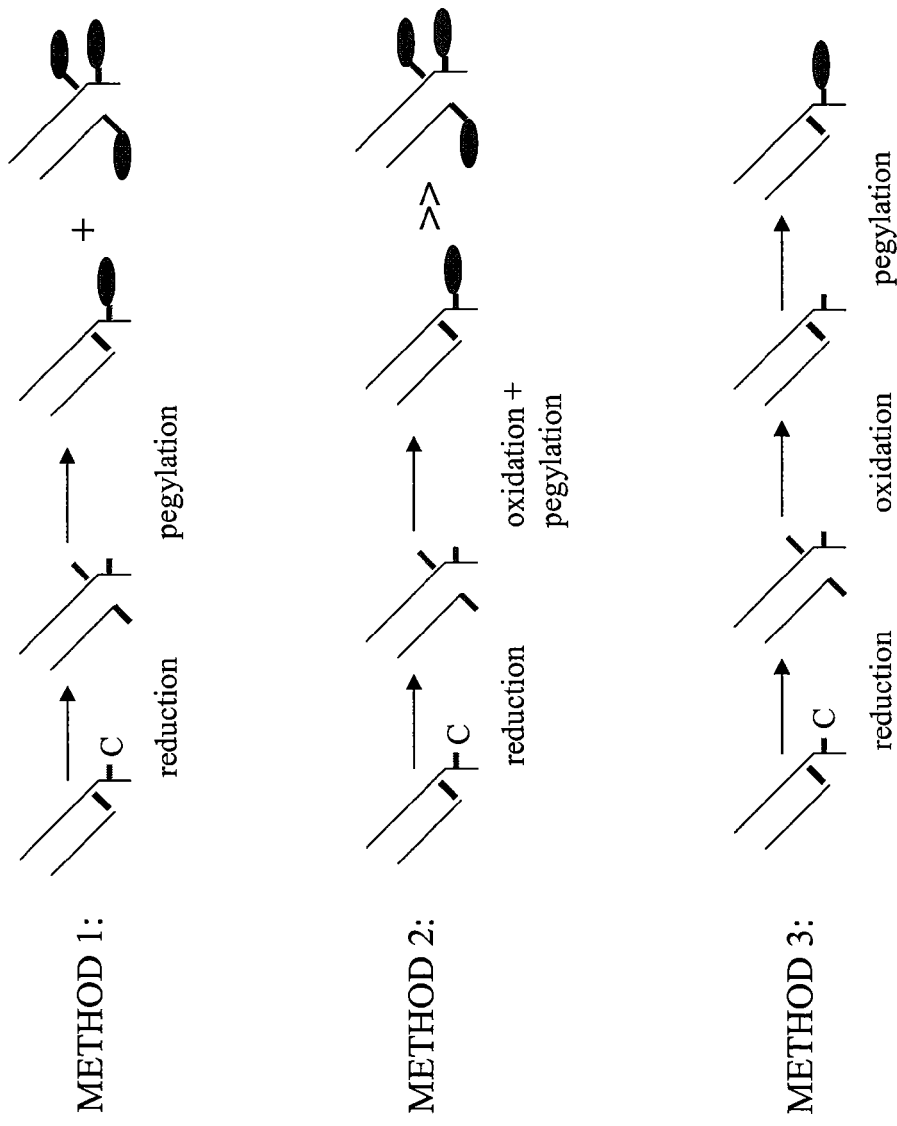

FIG. 16: Image depicting methods of generating PEGylated Fabs through direct expression.

Figure 17:
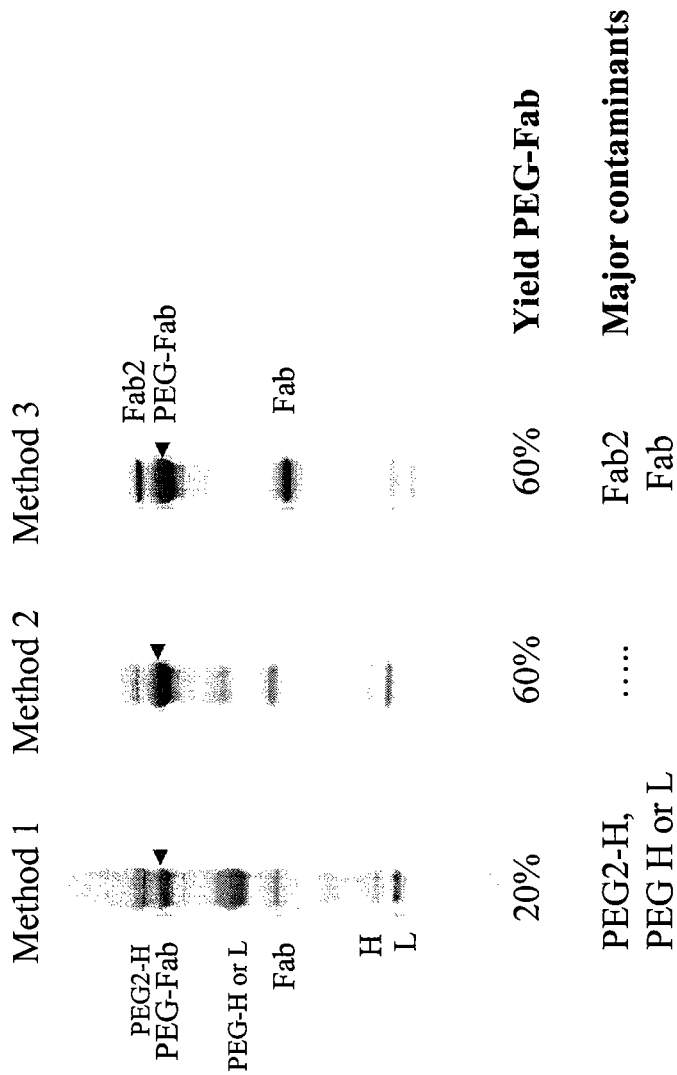

FIG. 17: Image displaying an SDS-PAGE gel under non-reducing conditions showing the results of PEGylated Fab direct expression studies using the methods shown in FIG. 16. Arrowhead indicates PEGylated Fab.

Figure 18:
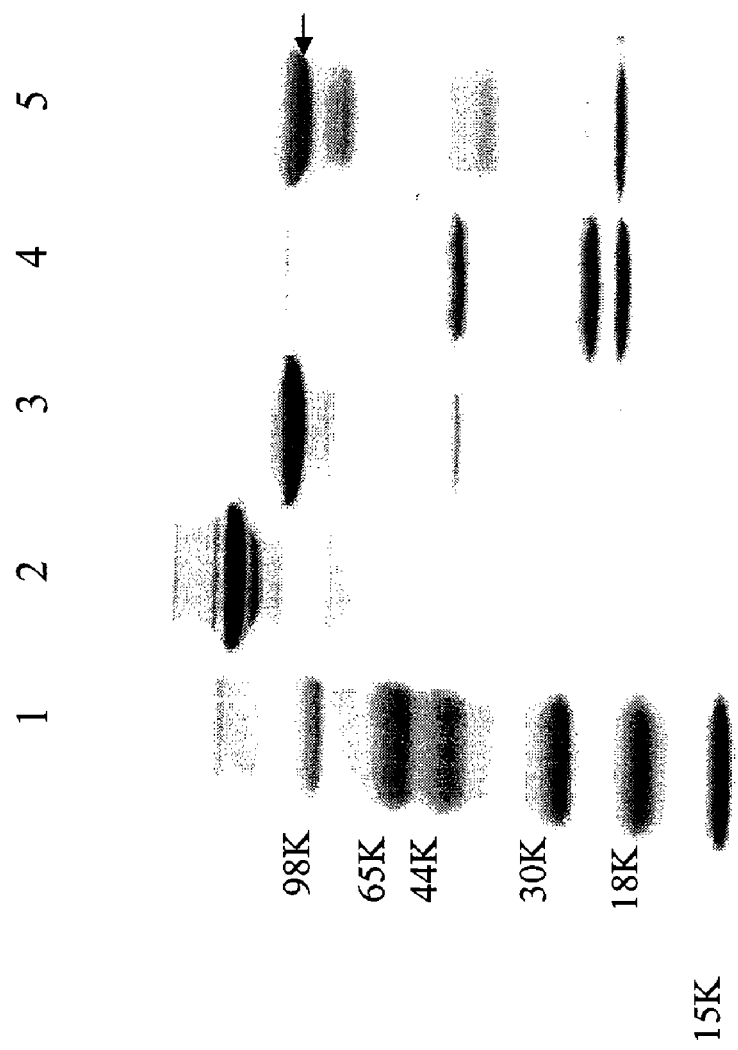

FIG. 18: Image displaying an SDS-PAGE gel under non-reducing conditions showing the results of PEGylated Fab enzymatic digestion studies. Lane 1 shows molecular mass markers. Lane 2 shows Li33 Ig1 Mab. Lane 3 shows Li33 Ig1 Fab2. Lane 4 shows Li33 Ig1 Fab2 treated with TCEP, and lane 5 shows Li33 Ig1 Fab2 treated with TCEP and then with PEG. Arrow indicates PEGylated Li33 Fab' product.

Figure 19:
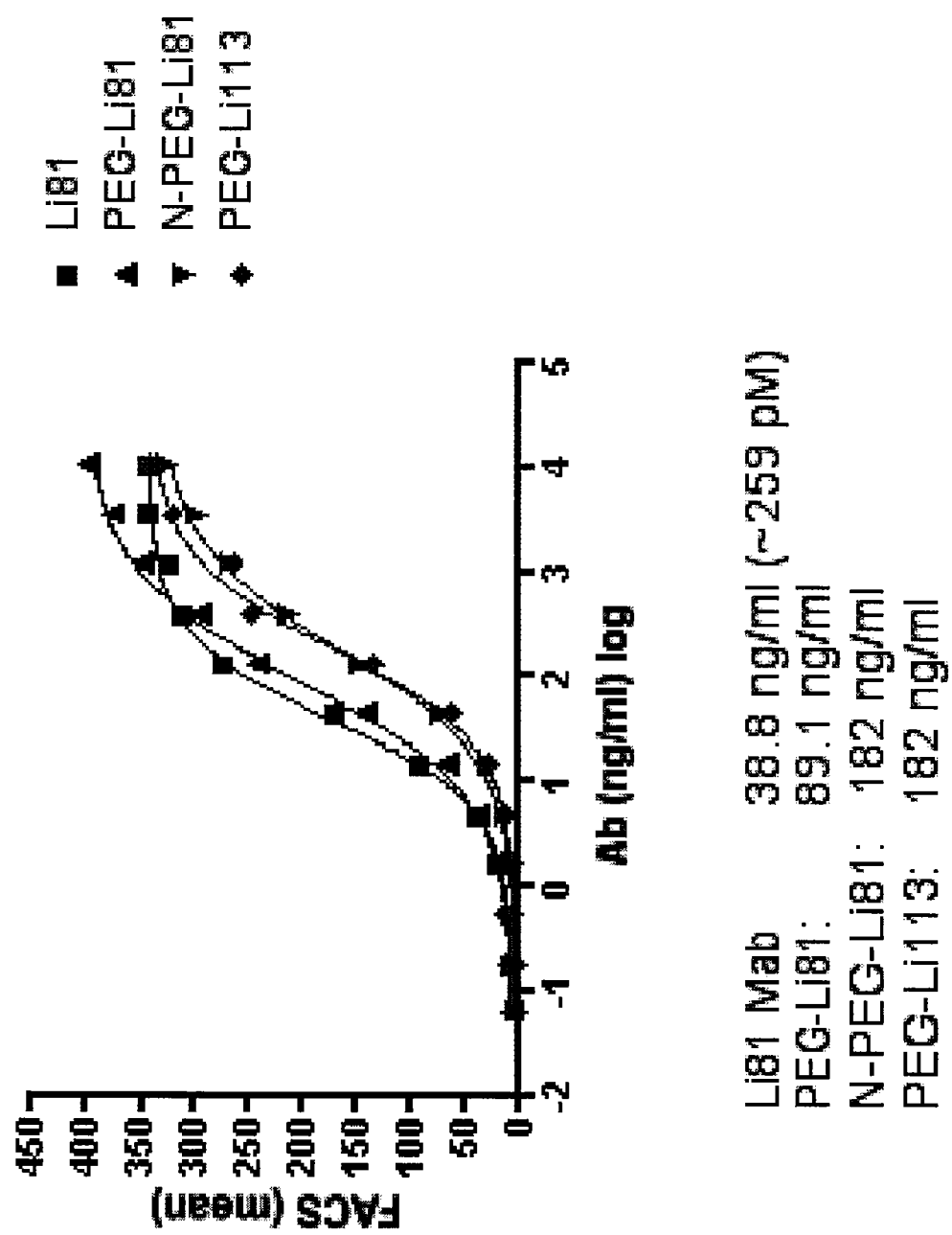

FIG. 19: Graph depicting the results of a FACS assay to assess binding of PEGylated LINGO-1 antibodies to LINGO-1.

Figure 20:
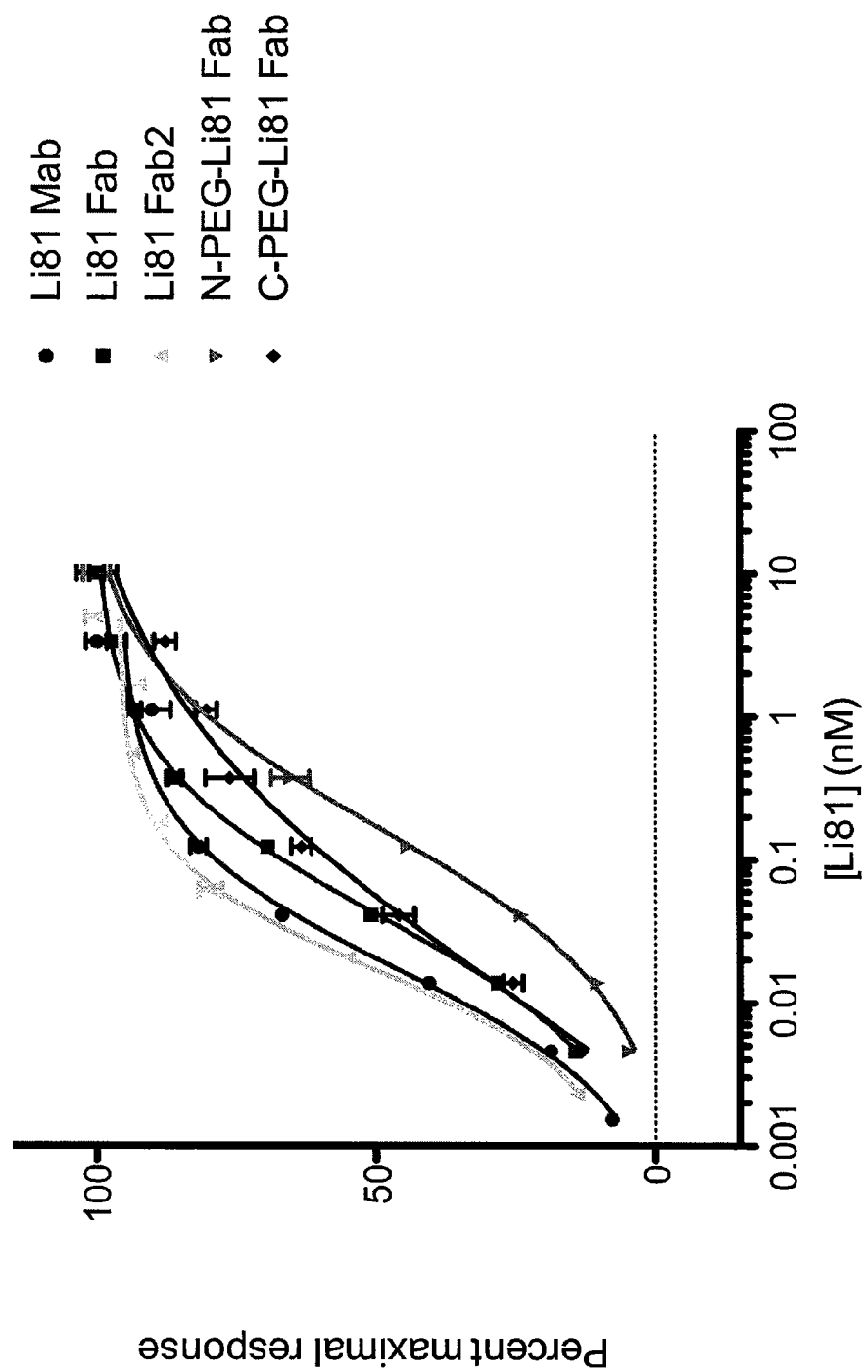

FIG. 20: Graph depicting the results of Li81 binding measured in a direct binding ELISA assay using LINGO-1 coated plates.

Figure 21:
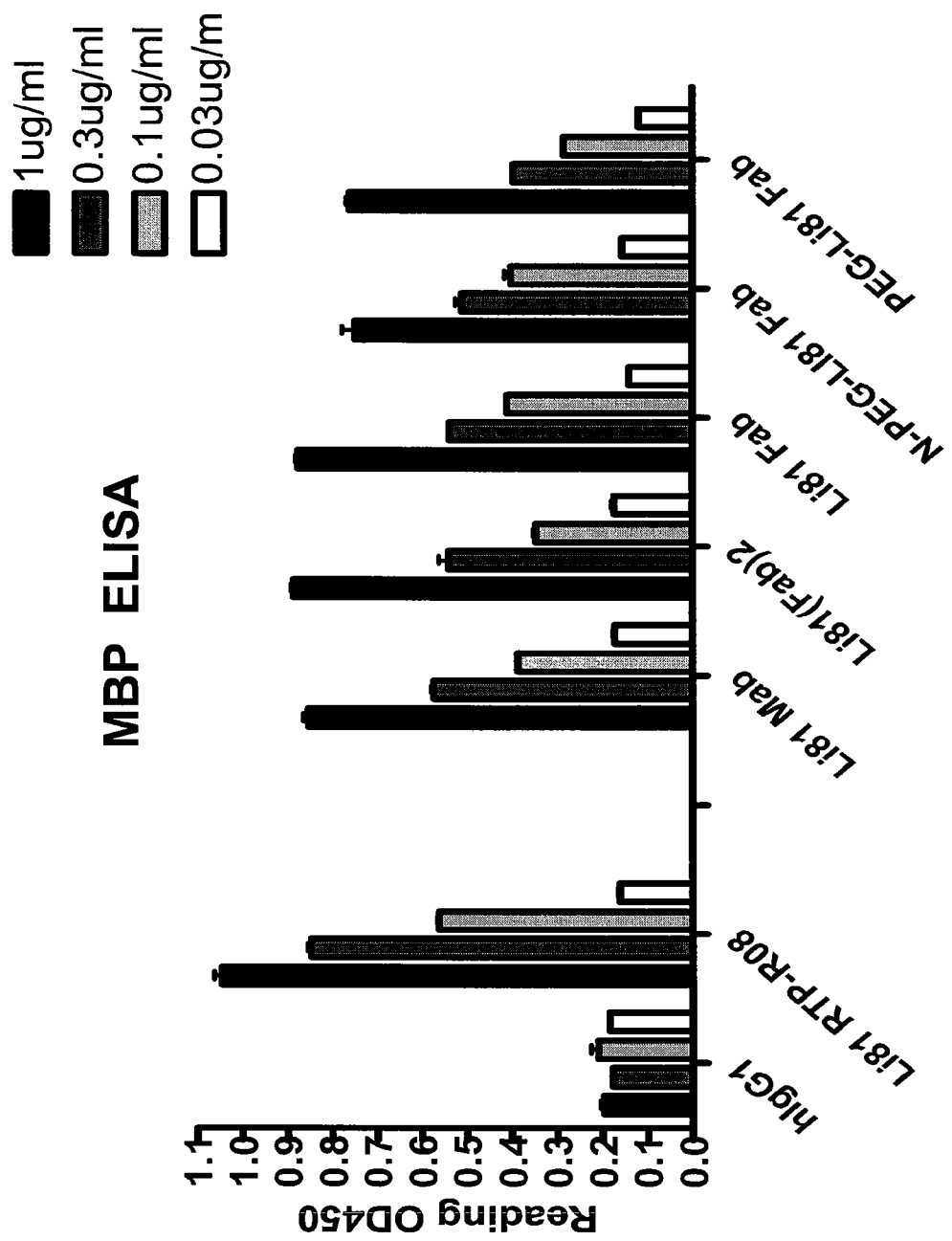

FIG. 21: Graph depicting results of an oligodendrocyte differentiation assay using Li81. Bar height indicates the concentration of MBP as measured by ELISA. Li81 RTP-RO8 indicates an Li81 (agly) reference standard.

Figure 22:
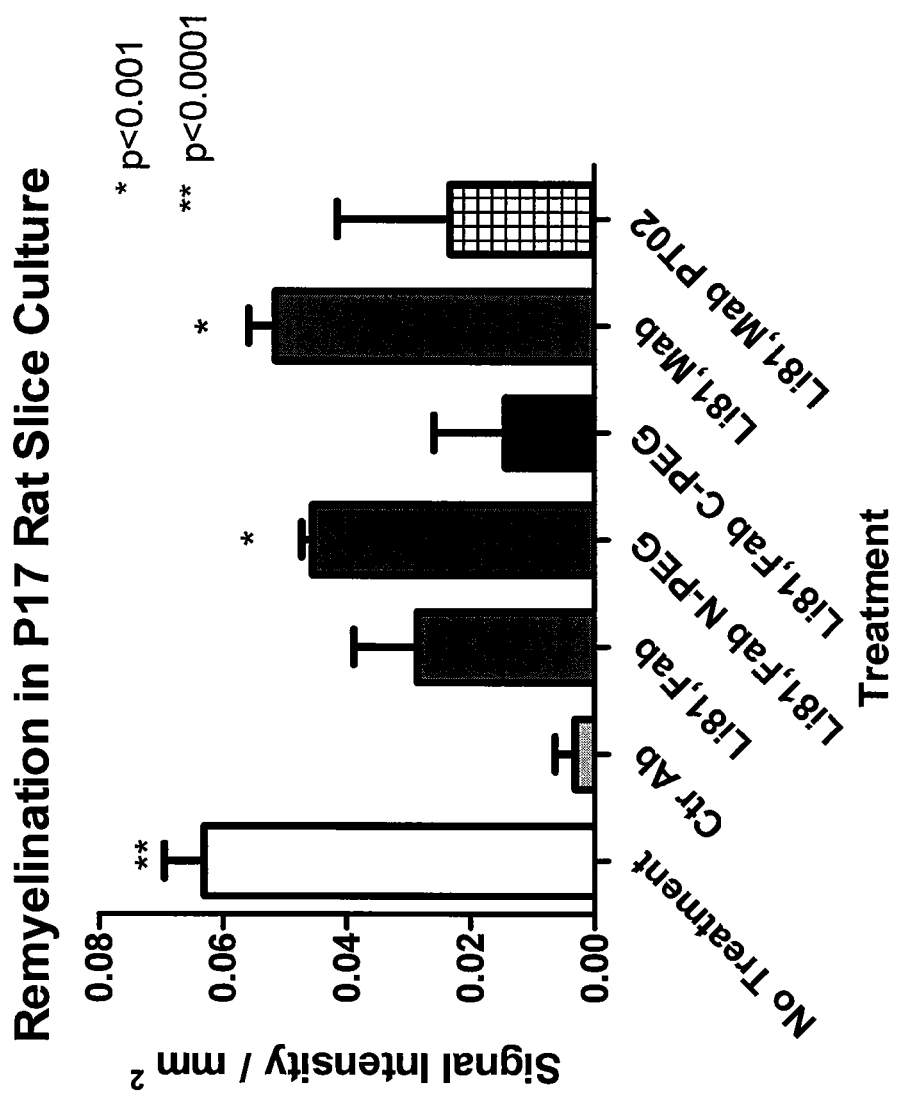

FIG. 22: Graph depicting results of remyelination assay using Li81 antibody and antibody fragments. Bar height represents the intensity of black gold signal.

Figure 23:
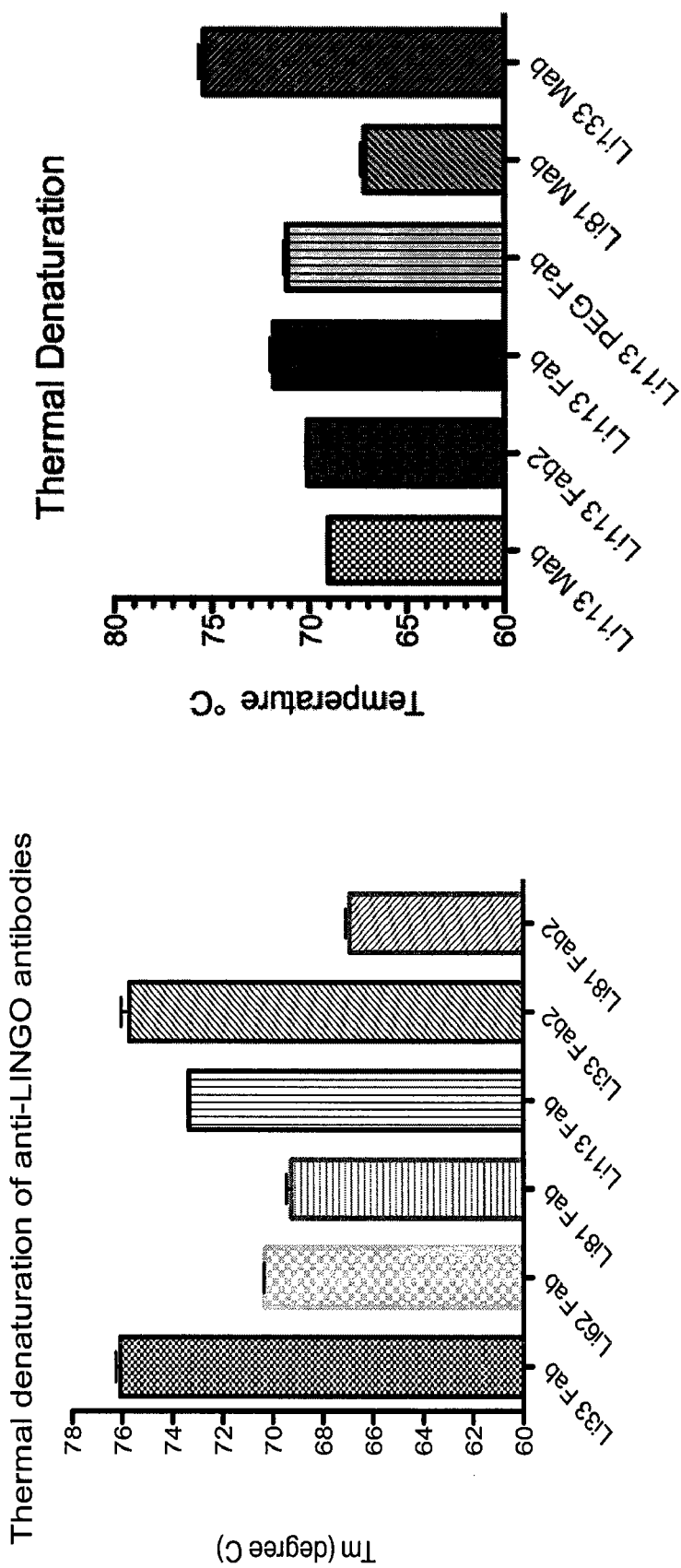

FIG. 23: Graphs depicting results of thermal denaturation studies of LINGO-1 antibodies and antibody fragments. Bar height indicates TM.

DETAILED DESCRIPTION OF THE INVENTION

I. Definitions

It is to be noted that the term "a" or "an" entity refers to one or more of that entity; for example, "a LINGO-1 antibody," is understood to represent one or more LINGO-1 antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to LINGO-1 antibodies or antibody polypeptides of the present invention include any polypeptides which retain at least some of the antigen-binding properties of the corresponding native antibody or polypeptide. Fragments of polypeptides of the present invention include proteolytic fragments, as well as deletion fragments, in addition to specific antibody fragments discussed elsewhere herein. Variants of LINGO-1 antibodies and antibody polypeptides of the present invention include fragments as described above, and also polypeptides with altered amino acid sequences due to amino acid substitutions, deletions, or insertions. Variants may occur naturally or be non-naturally occurring Non-naturally occurring variants may be produced using art-known mutagenesis techniques. Variant polypeptides may comprise conservative or non-conservative amino acid substitutions, deletions or additions. Derivatives of LINGO-1 antibodies and antibody polypeptides of the present invention, are polypeptides which have been altered so as to exhibit additional features not found on the native polypeptide. Examples include fusion proteins. Variant polypeptides may also be referred to herein as "polypeptide analogs." As used herein a "derivative" of a LINGO-1 antibody or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refer to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a LINGO-1 antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a LINGO-1 antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

The present invention is directed to certain LINGO-1 antibodies, or antigen-binding fragments, variants, or derivatives thereof. Unless specifically referring to full-sized antibodies such as naturally-occurring antibodies, the term "LINGO-1 antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$ or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H3$ and $C_L$ domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen binding site. This quaternary antibody structure forms the antigen binding site present at the end of each arm of the Y. More specifically, the antigen binding site is defined by three CDRs on each of the $V_H$ and $V_L$ chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196: 901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-

917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
|---|---|---|
| $V_H$ CDR1 | 31-35 | 26-32 |
| $V_H$ CDR2 | 50-65 | 52-58 |
| $V_H$ CDR3 | 95-102 | 95-102 |
| $V_L$ CDR1 | 24-34 | 26-32 |
| $V_L$ CDR2 | 50-56 | 50-52 |
| $V_L$ CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambigously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in a LINGO-1 antibody or antigen-binding fragment, variant, or derivative thereof of the present invention are according to the Kabat numbering system.

In camelid species, the heavy chain variable region, referred to as $V_H H$, forms the entire antigen-binding domain. The main differences between camelid $V_H H$ variable regions and those derived from conventional antibodies ($V_H$) include (a) more hydrophobic amino acids in the light chain contact surface of $V_H$ as compared to the corresponding region in $V_H H$, (b) a longer CDR3 in $V_H H$, and (c) the frequent occurrence of a disulfide bond between CDR1 and CDR3 in $V_H H$.

Antibodies or antigen-binding fragments, variants, or derivatives thereof of the invention include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to LINGO-1 antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody fragments, including single-chain antibodies, may comprise the variable region(s) alone or in combination with the entirety or a portion of the following: hinge region, $C_H 1$, $C_H 2$, and $C_H 3$ domains. Also included in the invention are antigen-binding fragments also comprising any combination of variable region(s) with a hinge region, $C_H 1$, $C_H 2$, and $C_H 3$ domains. Antibodies or immunospecific fragments thereof for use in the diagnostic and therapeutic methods disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a $C_H 1$ domain, a hinge (e.g., upper, middle, and/or lower hinge region) domain, a $C_H 2$ domain, a $C_H 3$ domain, or a variant or fragment thereof. For example, a binding polypeptide for use in the invention may comprise a polypeptide chain comprising a $C_H 1$ domain; a polypeptide chain comprising a $C_H 1$ domain, at least a portion of a hinge domain, and a $C_H 2$ domain; a polypeptide chain comprising a $C_H 1$ domain and a $C_H^3$ domain; a polypeptide chain comprising a $C_H 1$ domain, at least a portion of a hinge domain, and a $C_H^3$ domain, or a polypeptide chain comprising a $C_H 1$ domain, at least a portion of a hinge domain, a $C_H 2$ domain, and a $C_H 3$ domain. In another embodiment, a polypeptide of the invention comprises a polypeptide chain comprising a $C_H 3$ domain. Further, a binding polypeptide for use in the invention may lack at least a portion of a $C_H 2$ domain (e.g., all or part of a $C_H 2$ domain). As set forth above, it will be understood by one of ordinary skill in the art that these domains (e.g., the heavy chain portions) may be modified such that they vary in amino acid sequence from the naturally occurring immunoglobulin molecule.

In certain LINGO-1 antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding polypeptide for use in the diagnostic and treatment methods disclosed herein may be derived from different immunoglobulin molecules. For example, a heavy chain portion of a polypeptide may comprise a $C_H 1$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or $C_L$ domain.

LINGO-1 antibodies, or antigen-binding fragments, variants, or derivatives thereof disclosed herein may be described or specified in terms of the epitope(s) or portion(s) of an antigen, e.g., a target polypeptide (LINGO-1) that they recognize or specifically bind. The portion of a target polypeptide which specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an "epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide epitope recognized by LINGO-1 antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of LINGO-1.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody or antigen-binding fragment, variant, or derivative disclosed herein may be said to bind a target polypeptide disclosed herein or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind a target polypeptide disclosed herein or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or antigen-binding fragment, variant, or derivative disclosed herein may be said to bind a target polypeptide disclosed herein or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said to bind a target polypeptide disclosed herein or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

LINGO-1 antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

LINGO-1 antibodies or antigen-binding fragments, variants or derivatives thereof of the invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

LINGO-1 antibodies or antigen-binding fragments, variants or derivatives thereof of the invention may be "multispecific," e.g., bispecific, trispecific or of greater multispecificity, meaning that it recognizes and binds to two or more different epitopes present on one or more different antigens (e.g., proteins) at the same time. Thus, whether a LINGO-1 antibody is "monospecfic" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in a LINGO-1 antibody, binding polypeptide or antibody. Each binding domain specifically binds one epitope. When a LINGO-1 antibody, binding polypeptide or antibody comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Appl. Publ. Nos. 2003/020734 and 2002/0155537, the disclosures of all of which are incoporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

As previously indicated, the subunit structures and three dimensional configuration of the constant regions of the various immunoglobulin classes are well known. As used herein, the term "$V^H$ domain" includes the amino terminal variable domain of an immunoglobulin heavy chain and the term "$C_H1$ domain" includes the first (most amino terminal) constant region domain of an immunoglobulin heavy chain. The $C_H1$ domain is adjacent to the $V_H$ domain and is amino terminal to the hinge region of an immunoglobulin heavy chain molecule.

As used herein the term "$C_H2$ domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The $C_H2$ domain is unique in that it is not closely paired with another domain. Rather, two N-linked branched carbohydrate chains are interposed between the two $C_H2$ domains of an intact native IgG molecule. It is also well documented that the $C_H3$ domain extends from the $C_H2$ domain to the C-terminal of the IgG molecule and comprises approximately 108 residues.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the $C_H1$ and $C_L$ regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "properly folded polypeptide" includes polypeptides (e.g., LINGO-1 antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of a LINGO-1 antibody" and "an animal in need of treatment" includes subjects, such as mammalian subjects, that would benefit from administration of a LINGO-1 antibody used, e.g., for detection of a LINGO-1 polypeptide (e.g., for a diagnostic procedure) and/or from treatment, i.e., palliation or prevention of a disease such as MS, with a LINGO-1 antibody. As described in more detail herein, the LINGO-1 antibody can be used in unconjugated form or can be conjugated, e.g., to a drug, prodrug, or an isotope.

II. LINGO-1

Naturally occurring humanLINGO-1 (LINGO-1) is a glycosylated central nervous system-specific protein which is predicted to have 614 amino acids (SEQ ID NO: 51), including a 33 amino acid signal sequence. As used herein, the term "LINGO-1" is used interchangeably with the term "Sp35" as described in International Applications PCT/US2006/026271, filed Jul. 7, 2006, PCT/US2004/008323, filed Mar. 17, 2004, PCT/US2005/022881, filed Jun. 24, 2005 and PCT/US2008/000316, filed Jan. 9, 2008, each of which is incorporated herein by reference in its entirety. LINGO-1 is also known in the art by the names LRRN6, LRRN6A, FLJ14594, LERN1, MGC17422 and UNQ201. The human, full-length wild-type LINGO-1 polypeptide contains an LRR domain consisting of 14 leucine-rich repeats (including N- and C-terminal caps), an Ig domain, a transmembrane region, and a cytoplasmic domain. The cytoplasmic domain contains a canonical tyrosine phosphorylation site. In addition, the naturally occurring LINGO-1 protein contains a signal sequence, a short basic region between the LRRCT and Ig domain, and a transmembrane region between the Ig domain and the cytoplasmic domain. The human LINGO-1 gene (SEQ ID NO:52) contains alternative translation start codons, so that six additional amino acids, i.e., MQVSKR (SEQ ID NO:87) may or may not be present at the N-terminus of the LINGO-1 signal sequence. Table 2 lists the LINGO-1 domains and other regions, according to amino acid residue number, based on the LINGO-1 amino acid sequence presented herein as SEQ ID NO: 51. The LINGO-1 polypeptide is characterized in more detail in PCT Publication No. WO 2004/085648, which is incorporated herein by reference in its entirety.

TABLE 2

| LINGO-1 Domains | | |
| --- | --- | --- |
| Domain or Region | Beginning Residue | Ending Residue |
| Signal Sequence | 1 | 33 or 35 |
| LRRNT | 34 or 36 | 64 |
| LRR | 66 | 89 |
| LRR | 90 | 113 |
| LRR | 114 | 137 |
| LRR | 138 | 161 |

TABLE 2-continued

LINGO-1 Domains

| Domain or Region | Beginning Residue | Ending Residue |
|---|---|---|
| LRR | 162 | 185 |
| LRR | 186 | 209 |
| LRR | 210 | 233 |
| LRR | 234 | 257 |
| LRR | 258 | 281 |
| LRR | 282 | 305 |
| LRR | 306 | 329 |
| LRR | 330 | 353 |
| LRRCT | 363 | 414 or 416 |
| Basic | 415 or 417 | 424 |
| Ig | 419 | 493 |
| Connecting sequence | 494 | 551 |
| Transmembrane | 552 | 576 |
| Cytoplasmic | 577 | 614 |

Tissue distribution and developmental expression of LINGO-1 has been studied in humans and rats. LINGO-1 biology has been studied in an experimental animal (rat) model. Expression of rat LINGO-1 is localized to neurons and oligodendrocytes, as determined by northern blot and immuno-histochemical staining. Rat LINGO-1 mRNA expression level is regulated developmentally, peaking shortly after birth, i.e., ca. postnatal day one. In a rat spinal cord transection injury model, LINGO-1 is up-regulated at the injury site, as determined by RT-PCR. See Mi et al. *Nature Neurosci.* 7:221-228 (2004).

In the context of the amino acids comprising the various structural and functional domains of a LINGO-1 polypeptide, the term "about" includes the particularly recited value and values larger or smaller by several (e.g., 10, 9, 8, 7, 6, 5, 4, 3, 2, or 1) amino acids. Since the location of these domains as listed in Table 2 have been predicted by computer graphics, one of ordinary skill would appreciate that the amino acid residues constituting the domains may vary slightly (e.g., by about 1 to 15 residues) depending on the criteria used to define the domain.

The inventors have discovered that full-length, wild-type LINGO-1 binds to NgR1. See PCT Publication No. WO 2004/085648. The inventors have also discovered that LINGO-1 is expressed in oligodendrocytes and that the LINGO-1 protein is involved in the regulation of oligodendrocyte-mediated myelination of axons. See U.S Patent Publication No. 2006/0009388 A1, which is incorporated herein by reference in its entirety.

The nucleotide sequence for the full-length LINGO-1 molecule is as follows:

(SEQ ID NO: 52)
ATGCTGGCGGGGGGCGTGAGGAGCATGCCCAGCCCCCTCCTGGCCTGCTG

GCAGCCCATCCTCCTGCTGGTGCTGGGCTCAGTGCTGTCAGGCTCGGCCA

CGGGCTGCCCGCCCCGCTGCGAGTGCTCCGCCCAGGACCGCGCTGTGCTG

TGCCACCGCAAGCGCTTTGTGGCAGTCCCCGAGGGCATCCCCACCGAGAC

GCGCCTGCTGGACCTAGGCAAGAACCGCATCAAAACGCTCAACCAGGACG

AGTTCGCCAGCTTCCCGCACCTGGAGGAGCTGGAGCTCAACGAGAACATC

GTGAGCGCCGTGGAGCCCGGCGCCTTCAACAACCTCTTCAACCTCCGGAC

GCTGGGTCTCCGCAGCAACCGCCTGAAGCTCATCCCGCTAGGCGTCTTCA

CTGGCCTCAGCAACCTGACCAAGCTGGACATCAGCGAGAACAAGATTGTT

ATCCTGCTGGACTACATGTTTCAGGACCTGTACAACCTCAAGTCACTGGA

GGTTGGCGACAATGACCTCGTCTACATCTCTCACCGCGCCTTCAGCGGCC

TCAACAGCCTGGAGCAGCTGACGCTGGAGAAATGCAACCTGACCTCCATC

CCCACCGAGGCGCTGTCCCACCTGCACGGCCTCATCGTCCTGAGGCTCCG

GCACCTCAACATCAATGCCATCCGGGACTACTCCTTCAAGAGGCTCTACC

GACTCAAGGTCTTGGAGATCTCCCACTGGCCCTACTTGGACACCATGACA

CCCAACTGCCTCTACGGCCTCAACCTGACGTCCCTGTCCATCACACACTG

CAATCTGACCGCTGTGCCCTACCTGGCCGTCCGCCACCTAGTCTATCTCC

GCTTCCTCAACCTCTCCTACAACCCCATCAGCACCATTGAGGGCTCCATG

TTGCATGAGCTGCTCCGGCTGCAGGAGATCCAGCTGGTGGGCGGGCAGCT

GGCCGTGGTGGAGCCCTATGCCTTCCGCGGCCTCAACTACCTGCGCGTGC

TCAATGTCTCTGGCAACCAGCTGACCACACTGGAGGAATCAGTCTTCCAC

TCGGTGGGCAACCTGGAGACACTCATCCTGGACTCCAACCCGCTGGCCTG

CGACTGTCGGCTCCTGTGGGTGTTCCGGCGCCGCTGGCGGCTCAACTTCA

ACCGGCAGCAGCCCACGTGCGCCACGCCCGAGTTTGTCCAGGGCAAGGAG

TTCAAGGACTTCCCTGATGTGCTACTGCCCAACTACTTCACCTGCCGCCG

CGCCCGCATCCGGGACCGCAAGGCCCAGCAGGTGTTTGTGGACGAGGGCC

ACACGGTGCAGTTTGTGTGCCGGGCCGATGGCGACCCGCCGCCCGCCATC

CTCTGGCTCTCACCCCGAAAGCACCTGGTCTCAGCCAAGAGCAATGGGCG

GCTCACAGTCTTCCCTGATGGCACGCTGGAGGTGCGCTACGCCCAGGTAC

AGGACAACGGCACGTACCTGTGCATCGCGGCCAACGCGGGCGGCAACGAC

TCCATGCCCGCCCACCTGCATGTGCGCAGCTACTCGCCCGACTGGCCCCA

TCAGCCCAACAAGACCTTCGCTTTCATCTCCAACCAGCCGGGCGAGGGAG

AGGCCAACAGCACCCGCGCCACTGTGCCTTTCCCCTTCGACATCAAGACC

CTCATCATCGCCACCACCATGGGCTTCATCTCTTTCCTGGGCGTCGTCCT

CTTCTGCCTGGTGCTGCTGTTTCTCTGGAGCCGGGGCAAGGGCAACACAA

AGCACAACATCGAGATCGAGTATGTGCCCCGAAAGTCGGACGCAGGCATC

AGCTCCGCCGACGCGCCCCGCAAGTTCAACATGAAGATGATATGA.

The polypeptide sequence for the full-length LINGO-1 polypeptide is as follows:

(SEQ ID NO: 51)
MLAGGVRSMPSPLLACWQPILLLVLGSVLSGSATGCPPRCECSAQDRAVL

CHRKRFVAVPEGIPTETRLLDLGKNRIKTLNQDEFASFPHLEELELNENI

VSAVEPGAFNNLFNLRTLGLRSNRLKLIPLGVFTGLSNLTKLDISENKIV

ILLDYMFQDLYNLKSLEVGDNDLVYISHRAFSGLNSLEQLTLEKCNLTSI

PTEALSHLHGLIVLRLRHLNINAIRDYSFKRLYRLKVLEISHWPYLDTMT

PNCLYGLNLTSLSITHCNLTAVPYLAVRHLVYLRFLNLSYNPISTIEGSM

LHELLRLQEIQLVGGQLAVVEPYAFRGLNYLRVLNVSGNQLTTLEESVFH

SVGNLETLILDSNPLACDCRLLWVFRRRWRLNFNRQQPTCATPEFVQGKE

FKDFPDVLLPNYFTCRRARIRDRKAQQVFVDEGHTVQFVCRADGDPPPAI

LWLSPRKHLVSAKSNGRLTVFPDGTLEVRYAQVQDNGTYLCIAANAGGND

-continued

SMPAHLHVRSYSPDWPHQPNKTFAFISNQPGEGEANSTRATVPFPFDIKT

LIIATTMGFISFLGVVLFCLVLLFLWSRGKGNTKHNIEIEYVPRKSDAGI

SSADAPRKFNMKMI.

III. LINGO-1 Antibodies

In one embodiment, the present invention is directed to LINGO-1 antibodies, or antigen-binding fragments, variants, or derivatives thereof. For example, the present invention includes at least the antigen-binding domains of Li62, Li81 and fragments, variants, and derivatives thereof. As used herein, the term "antigen binding domain" includes a site that specifically binds an epitope on an antigen (e.g., an epitope of LINGO-1). The antigen binding domain of an antibody typically includes at least a portion of an immunoglobulin heavy chain variable region and at least a portion of an immunoglobulin light chain variable region. The binding site formed by these variable regions determines the specificity of the antibody.

The present invention is more specifically directed to a LINGO-1 antibody, or antigen-binding fragment, variant or derivatives thereof, where the LINGO-1 antibody binds to the same epitope as Li62 or Li81.

The invention is further drawn to a LINGO-1 antibody, or antigen-binding fragment, variant or derivatives thereof, where the LINGO-1 antibody competitively inhibits Li62 or Li81 from binding to LINGO-1.

The invention is also drawn to a LINGO-1 antibody, or antigen-binding fragment, variant or derivatives thereof, where the LINGO-1 antibody comprises at least the antigen binding region of Li62 or Li81.

In certain embodiments, the present invention is directed to an antibody, or antigen-binding fragment, variant, or derivative thereof which specifically or preferentially binds to a particular LINGO-1 polypeptide fragment or domain. Such LINGO-1 polypeptide fragments include, but are not limited to, a LINGO-1 polypeptide comprising, consisting essentially of, or consisting of amino acids 34 to 532; 34 to 417; 34 to 425; 34 to 493; 66 to 532; 66 to 417; 66 to 426; 66 to 493; 66 to 532; 417 to 532; 417 to 425 (the LINGO-1 basic region); 417 to 493; 417 to 532; 419 to 493 (the LINGO-11 g region); or 425 to 532 of SEQ ID NO:51; or a LINGO-1 variant polypeptide at least 70%, 75%, 80%, 85%, 90%, or 95% identical to amino acids 34 to 532; 34 to 417; 34 to 425; 34 to 493; 66 to 532; 66 to 417; 66 to 426; 66 to 493; 66 to 532; 417 to 532; 417 to 425 (the LINGO-1 basic region); 417 to 493; 417 to 532; 419 to 493 (the LINGO-11 g region); or 425 to 532 of SEQ ID NO:51.

Additional LINGO-1 peptide fragments to which certain antibodies, or antigen-binding fragments, variants, or derivatives thereof of the present invention bind include, but are not limited to those fragments comprising, consisting essentially of, or consisting of one or more leucine-rich-repeats (LRR) of LINGO-1. Such fragments, include, for example, fragments comprising, consisting essentially of, or consisting of amino acids 66 to 89; 66 to 113; 66 to 137; 90 to 113; 114 to 137; 138 to 161; 162 to 185; 186 to 209; 210 to 233; 234 to 257; 258 to 281; 282 to 305; 306 to 329; or 330 to 353 of SEQ ID NO:51. Corresponding fragments of a variant LINGO-1 polypeptide at least 70%, 75%, 80%, 85%, 90%, or 95% identical to amino acids 66 to 89; 66 to 113; 90 to 113; 114 to 137; 138 to 161; 162 to 185; 186 to 209; 210 to 233; 234 to 257; 258 to 281; 282 to 305; 306 to 329; or 330 to 353 of SEQ ID NO:51 are also contemplated.

Additional LINGO-1 peptide fragments to which certain antibodies, or antigen-binding fragments, variants, or derivatives thereof of the present invention bind include, but are not limited to those fragments comprising, consisting essentially of, or consisting of one or more cysteine rich regions flanking the LRR of LINGO-1. Such fragments, include, for example, a fragment comprising, consisting essentially of, or consisting of amino acids 34 to 64 of SEQ ID NO:51 (the N-terminal LRR flanking region (LRRNT)), or a fragment comprising, consisting essentially of, or consisting of amino acids 363 to 416 of SEQ ID NO:51 (the C-terminal LRR flanking region (LRRCT)), amino acids Corresponding fragments of a variant LINGO-1 polypeptide at least 70%, 75%, 80%, 85%, 90%, or 95% identical to amino acids 34 to 64 and 363 to 416 of SEQ ID NO:51 are also contemplated.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, *Advances in Applied Mathematics* 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

Additional LINGO-1 peptide fragments to which certain antibodies, or antigen-binding fragments, variants, or derivatives thereof of the present invention bind include, but are not limited to those fragments comprising, consisting essentially of, or consisting of amino acids 41 to 525 of SEQ ID NO:51; 40 to 526 of SEQ ID NO:51; 39 to 527 of SEQ ID NO:51; 38 to 528 of SEQ ID NO:51; 37 to 529 of SEQ ID NO:51; 36 to 530 of SEQ ID NO:51; 35 to 531 of SEQ ID NO:51; 34 to 531 of SEQ ID NO:51; 46 to 520 of SEQ ID NO:51; 45 to 521 of SEQ ID NO:51; 44 to 522 of SEQ ID NO:51; 43 to 523 of SEQ ID NO:51; and 42 to 524 of SEQ ID NO:51.

Still additional LINGO-1 peptide fragments to which certain antibodies, or antigen-binding fragments, variants, or derivatives thereof of the present invention bind include, but are not limited to those fragments comprising, consisting essentially of, or consisting of amino acids 1 to 33 of SEQ ID NO:51; 1 to 35 of SEQ ID NO:51; 34 to 64 of SEQ ID NO:51; 36 to 64 of SEQ ID NO:51; 66 to 89 of SEQ ID NO:51; 90 to 113 of SEQ ID NO:51; 114 to 137 of SEQ ID NO:51; 138 to 161 of SEQ ID NO:51; 162 to 185 of SEQ ID NO:51; 186 to 209 of SEQ ID NO:51; 210 to 233 of SEQ ID NO:51; 234 to 257 of SEQ ID NO:51; 258 to 281 of SEQ ID NO:51; 282 to 305 of SEQ ID NO:51; 306 to 329 of SEQ ID NO:51; 330 to 353 of SEQ ID NO:51; 363 to 416 of SEQ ID NO:51; 417 to 424 of SEQ ID NO:51; 419 to 493 of SEQ ID NO:51; and 494 to 551 of SEQ ID NO:51.

Further still, LINGO-1 peptide fragments to which certain antibodies, or antigen-binding fragments, variants, or derivatives thereof of the present invention bind include, but are not limited to those fragments comprising, consisting essentially of, or consisting of amino acids 1 to 33 of SEQ ID NO:51; 1 to 35 of SEQ ID NO:51; 1 to 64 of SEQ ID NO:51; 1 to 89 of SEQ ID NO:51; 1 to 113 of SEQ ID NO:51; 1 to 137 of SEQ ID NO:51; 1 to 161 of SEQ ID NO:51; 1 to 185 of SEQ ID NO:51; 1 to 209 of SEQ ID NO:51; 1 to 233 of SEQ ID NO:51; 1 to 257 of SEQ ID NO:51; 1 to 281 of SEQ ID NO:51; 1 to 305 of SEQ ID NO:51; 1 to 329 of SEQ ID NO:51; 1 to 353 of SEQ ID NO:51; 1 to 416 of SEQ ID NO:51; 1 to 424 of SEQ ID NO:51; 1 to 493 of SEQ ID NO:51; 1 to 551 of SEQ ID NO:51; 1 to 531 of SEQ ID NO:51 and 1 to 532 of SEQ ID NO:51.

Additional LINGO-1 peptide fragments to which certain antibodies, or antigen-binding fragments, variants, or derivatives thereof of the present invention bind include, but are not limited to those fragments comprising, consisting essentially of, or consisting of amino acids 34 to 64 of SEQ ID NO:51; 34 to 89 of SEQ ID NO:51; 34 to 113 of SEQ ID NO:51; 34 to 137 of SEQ ID NO:51; 34 to 161 of SEQ ID NO:51; 34 to 185 of SEQ ID NO:51; 34 to 209 of SEQ ID NO:51; 34 to 233 of SEQ ID NO:51; 34 to 257 of SEQ ID NO:51; 34 to 281 of SEQ ID NO:51; 34 to 305 of SEQ ID NO:51; 34 to 329 of SEQ ID NO:51; 34 to 353 of SEQ ID NO:51; 34 to 416 of SEQ ID NO:51; 34 to 424 of SEQ ID NO:51; 34 to 493 of SEQ ID NO:51; and 34 to 551 of SEQ ID NO:51.

More additional LINGO-1 peptide fragments to which certain antibodies, or antigen-binding fragments, variants, or derivatives thereof of the present invention bind include, but are not limited to those fragments comprising, consisting essentially of, or consisting of amino acids 34 to 530 of SEQ ID NO:51; 34 to 531 of SEQ ID NO:51; 34 to 532 of SEQ ID NO:51; 34 to 533 of SEQ ID NO:51; 34 to 534 of SEQ ID NO:51; 34 to 535 of SEQ ID NO:51; 34 to 536 of SEQ ID NO:51; 34 to 537 of SEQ ID NO:51; 34 to 538 of SEQ ID NO:51; 34 to 539 of SEQ ID NO:51; 30 to 532 of SEQ ID NO:51; 31 to 532 of SEQ ID NO:51; 32 to 532 of SEQ ID NO:51; 33 to 532 of SEQ ID NO:51; 34 to 532 of SEQ ID NO:51; 35 to 532 of SEQ ID NO:51; 36 to 532 of SEQ ID NO:51; 30 to 531 of SEQ ID NO:51; 31 to 531 of SEQ ID NO:51; 32 to 531 of SEQ ID NO:51; 33 to 531 of SEQ ID NO:51; 34 to 531 of SEQ ID NO:51; 35 to 531 of SEQ ID NO:51; and 36 to 531 of SEQ ID NO:51.

Further still, LINGO-1 peptide fragments to which certain antibodies, or antigen-binding fragments, variants, or derivatives thereof of the present invention bind include, but are not limited to those fragments comprising, consisting essentially of, or consisting of amino acids 36 to 64 of SEQ ID NO:51; 36 to 89 of SEQ ID NO:51; 36 to 113 of SEQ ID NO:51; 36 to 137 of SEQ ID NO:51; 36 to 161 of SEQ ID NO:51; 36 to 185 of SEQ ID NO:51; 36 to 209 of SEQ ID NO:51; 36 to 233 of SEQ ID NO:51; 36 to 257 of SEQ ID NO:51; 36 to 281 of SEQ ID NO:51; 36 to 305 of SEQ ID NO:51; 36 to 329 of SEQ ID NO:51; 36 to 353 of SEQ ID NO:51; 36 to 416 of SEQ ID NO:51; 36 to 424 of SEQ ID NO:51; 36 to 493 of SEQ ID NO:51; and 36 to 551 of SEQ ID NO:51.

Additional LINGO-1 peptide fragments to which certain antibodies, or antigen-binding fragments, variants, or derivatives thereof of the present invention bind include, but are not limited to those fragments comprising, consisting essentially of, or consisting of amino acids 36 to 530 of SEQ ID NO:51; 36 to 531 of SEQ ID NO:51; 36 to 532 of SEQ ID NO:51; 36 to 533 of SEQ ID NO:51; 36 to 534 of SEQ ID NO:51; 36 to 535 of SEQ ID NO:51; 36 to 536 of SEQ ID NO:51; 36 to 537 of SEQ ID NO:51; 36 to 538 of SEQ ID NO:51; and 36 to 539 of SEQ ID NO:51.

More LINGO-1 peptide fragments to which certain antibodies, or antigen-binding fragments, variants, or derivatives thereof of the present invention bind include, but are not limited to those fragments comprising, consisting essentially of, or consisting of amino acids 417 to 493 of SEQ ID NO:51; 417 to 494 of SEQ ID NO:51; 417 to 495 of SEQ ID NO:51; 417 to 496 of SEQ ID NO:51; 417 to 497 of SEQ ID NO:51; 417 to 498 of SEQ ID NO:51; 417 to 499 of SEQ ID NO:51; 417 to 500 of SEQ ID NO:51; 417 to 492 of SEQ ID NO:51; 417 to 491 of SEQ ID NO:51; 412 to 493 of SEQ ID NO:51; 413 to 493 of SEQ ID NO:51; 414 to 493 of SEQ ID NO:51; 415 to 493 of SEQ ID NO:51; 416 to 493 of SEQ ID NO:51; 411 to 493 of SEQ ID NO:51; 410 to 493 of SEQ ID NO:51; 410 to 494 of SEQ ID NO:51; 411 to 494 of SEQ ID NO:51; 412 to 494 of SEQ ID NO:51; 413 to 494 of SEQ ID NO:51; 414 to 494 of SEQ ID NO:51; 415 to 494 of SEQ ID NO:51; 416 to 494 of SEQ ID NO:51; 417 to 494 of SEQ ID NO:51; and 418 to 494 of SEQ ID NO:51.

In an additional embodiment LINGO-1 peptide fragments to which certain antibodies, or antigen-binding fragments, variants, or derivatives thereof of the present invention bind include, a LINGO-1 polypeptide comprising, consisting essentially of, or consisting of peptides of the Ig domain of LINGO-1 or fragments, variants, or derivatives of such polypeptides. Specifically, polypeptides comprising, consisting essentially of, or consisting of the following polypeptide sequences: ITX$_1$X$_2$X$_3$ (SEQ ID NO:88), ACX$_1$X$_2$X$_3$ (SEQ ID NO:89), VCX$_1$X$_2$X$_3$ (SEQ ID NO:90) and SPX$_1$X$_2$X$_3$ (SEQ ID NO:91) where X$_1$ is lysine, arginine, histidine, glutamine, or asparagine, X$_2$ is lysine, arginine, histidine, glutamine, or asparagine and X$_3$ is lysine, arginine, histidine, glutamine, or asparagine. For example, LINGO-1 peptide fragments to which certain antibodies, or antigen-binding fragments, variants, or derivatives thereof of the present invention bind include, those fragments comprising, consisting essentially of, or consisting of the following polypeptide sequences: SPRKH (SEQ ID NO:92), SPRKK (SEQ ID NO:93), SPRKR (SEQ ID NO:94), SPKKH (SEQ ID NO:95), SPHKH (SEQ ID NO:96), SPRRH (SEQ ID NO:97), SPRHH (SEQ ID NO:98), SPRRR (SEQ ID NO:99), SPHHH (SEQ ID NO:100) SPKKK (SEQ ID NO:101), LSPRKH (SEQ ID NO:102), LSPRKK (SEQ ID NO:103), LSPRKR (SEQ ID NO:104), LSPKKH (SEQ ID NO:105), LSPHKH (SEQ ID NO:106), LSPRRH (SEQ ID NO:107), LSPRHH (SEQ ID NO:108), LSPRRR (SEQ ID NO:109), LSPHHH (SEQ ID NO:110) LSPKKK (SEQ ID NO:111), WLSPRKH (SEQ ID NO:112), WLSPRKK (SEQ ID NO:113), WLSPRKR (SEQ ID NO:114), WLSPKKH (SEQ ID NO:115), WLSPHKH (SEQ ID NO:116), WLSPRRH (SEQ ID NO:117), WLSPRHH (SEQ ID NO:118), WLSPRRR (SEQ ID NO:119), WLSPHHH (SEQ ID NO:120) WLSPKKK (SEQ ID NO:121). These LINGO-1 polypeptides include the basic "RKH loop" (Arginine-Lysine-Histidine amino acids 456-458) in the Ig domain of LINGO-1. Additional LINGO-1 peptides which include a basic tripeptide are ITPKRR (SEQ ID NO:122), ACHHK (SEQ ID NO:123) and VCHHK (SEQ ID NO:124).

Additional LINGO-1 peptide fragments to which certain antibodies, or antigen-binding fragments, variants, or derivatives thereof of the present invention bind include, a LINGO-1 polypeptide comprising, consisting essentially of, or consisting of peptides of the Ig domain of LINGO-1 or fragments, variants, or derivatives of such polypeptides. Specifically, peptides comprising, consisting essentially of, or consisting of the following polypeptide sequences: $X_4X_5RKH$ (SEQ ID NO:125), $X_4X_5RRR$ (SEQ ID NO:126), $X_4X_5KKK$ (SEQ ID NO:127), $X_4X_5HHH$ (SEQ ID NO:128), $X_4X_5RKK$ (SEQ ID NO:129), $X_4X_5RKR$ (SEQ ID NO:130), $X_4X_5KKH$ (SEQ ID NO:131), $X_4X_5HKH$ (SEQ ID NO:132), $X_4X_5RRH$ (SEQ ID NO:133) and $X_4X_5RHH$ (SEQ ID NO:134) where $X_4$ is any amino acid and $X_5$ is any amino acid.

In other embodiments LINGO-1 peptide fragments to which certain antibodies, or antigen-binding fragments, variants, or derivatives thereof of the present invention bind include, a LINGO-1 polypeptide comprising, consisting essentially of, or consisting of peptides of the Ig domain of LINGO-1 or fragments, variants, or derivatives of such polypeptides. Specifically, polypeptides comprising, consisting essentially of, or consisting of the following polypeptide sequences: $ITX_6X_7X_8$ (SEQ ID NO:135), $ACX_6X_7X_8$ (SEQ ID NO:136), $VCX_6X_7X_8$ (SEQ ID NO:137) and $SPX_6X_7X_8$ (SEQ ID NO:138) where $X_6$ is lysine, arginine, histidine, glutamine, or asparagine, $X_7$ is any amino acid and $X_8$ is lysine, arginine, histidine, glutamine, or asparagine. For example, a polypeptide comprising, consisting essentially of, or consisting of the following polypeptide sequence: SPRLH (SEQ ID NO:139).

LINGO-1 peptide fragments to which certain antibodies, or antigen-binding fragments, variants, or derivatives thereof of the present invention bind include, a LINGO-1 polypeptide comprising, consisting essentially of, or consisting of peptides which contain amino acids 452-458 in the Ig domain of LINGO-1, or derivatives thereof, wherein amino acid 452 is a tryptophan or phenylalanine residue.

Additional LINGO-1 peptide fragments to which certain antibodies, or antigen-binding fragments, variants, or derivatives thereof of the present invention bind include, a LINGO-1 polypeptide comprising, consisting essentially of, or consisting of peptides of the basic domain of LINGO-1. Specifically, peptides comprising, consisting essentially of, or consisting of the following polypeptide sequences: RRARIRDRK (SEQ ID NO:140), KKVKVKEKR (SEQ ID NO:141), RRLRLRDRK (SEQ ID NO:142), RRGRGRDRK (SEQ ID NO:143) and RRIRARDRK (SEQ ID NO:144).

Additional exemplary soluble LINGO-1 polypeptides and methods and materials for obtaining these molecules for producing antibodies or antibody fragments of the present invention may be found, e.g., in International Patent Application No. PCT/US2004/008323, incorporated herein by reference in its entirety.

Methods of making antibodies are well known in the art and described herein. Once antibodies to various fragments of, or to the full-length LINGO-1 without the signal sequence, have been produced, determining which amino acids, or epitope, of LINGO-1 to which the antibody or antigen binding fragment binds can be determined by eptiope mapping protocols as described herein as well as methods known in the art (e.g. double antibody-sandwich ELISA as described in "Chapter 11—Immunology," *Current Protocols in Molecular Biology*, Ed. Ausubel et al., v.2, John Wiley & Sons, Inc. (1996)). Additional eiptope mapping protocols may be found in Morris, G. *Epitope Mapping Protocols*, New Jersey: Humana Press (1996), which are both incorporated herein by reference in their entireties. Epitope mapping can also be performed by commercially available means (i.e. ProtoPROBE, Inc. (Milwaukee, Wis.)).

Additionally, antibodies produced which bind to any portion of LINGO-1 can then be screened for their ability to act as an antagonist of LINGO-1 and thus promote neurite outgrowth, neuronal and oligodendrocyte survival, proliferation and differentiation as well as promote myelination. Antibodies can be screened for oligodendrocyte/neuronal survival for example by using the methods described herein such as in Examples 11 or 12 or as described in PCT/US2008/000316, filed Jan. 9, 2008, and PCT/US2006/026271, filed Jul. 7, 2006, which are incorporated herein by reference in their entireties. Additionally, antibodies can be screened for example by their ability to promote myelination by using the methods described herein such as in Examples 2, 6, 9, 10, 11 or 13 or as described in PCT/US2008/000316 and/or PCT/US2006/026271. Finally, antibodies can be screened for their ability to promote oligodendrocyte proliferation and differentiation, as well as neurite outgrowth for example by using the methods described herein such as in Examples 4 or 5 or as described in PCT/US2008/000316 and/or PCT/US2006/026271. Other antagonist functions of antibodies of the present invention can be tested using other assays as described in the Examples herein.

In other embodiments, the present invention includes an antibody, or antigen-binding fragment, variant, or derivative thereof which specifically or preferentially binds to at least one epitope of LINGO-1, where the epitope comprises, consists essentially of, or consists of at least about four to five amino acids of SEQ ID NO:5, at least seven, at least nine, or between at least about 15 to about 30 amino acids of SEQ ID NO:5. The amino acids of a given epitope of SEQ ID NO:51 as described may be, but need not be contiguous or linear. In certain embodiments, the at least one epitope of LINGO-1 comprises, consists essentially of, or consists of a non-linear epitope formed by the extracellular domain of LINGO-1 as expressed on the surface of a cell or as a soluble fragment, e.g., fused to an IgG Fc region. Thus, in certain embodiments the at least one epitope of LINGO-1 comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:51, where the non-contiguous amino acids form an epitope through protein folding.

In other embodiments, the present invention includes an antibody, or antigen-binding fragment, variant, or derivative thereof which specifically or preferentially binds to at least one epitope of LINGO-1, where the epitope comprises, consists essentially of, or consists of, in addition to one, two, three, four, five, six or more contiguous or non-contiguous amino acids of SEQ ID NO:51 as described above, and an additional moiety which modifies the protein, e.g., a carbohydrate moiety may be included such that the LINGO-1 antibody binds with higher affinity to modified target protein than it does to an unmodified version of the protein. Alternatively, the LINGO-1 antibody does not bind the unmodified version of the target protein at all.

In certain aspects, the present invention is directed to an antibody, or antigen-binding fragment, variant, or derivative thereof which specifically binds to a LINGO-1 polypeptide or fragment thereof, or a LINGO-1 variant polypeptide, with an affinity characterized by a dissociation constant ($K_D$) which is less than the $K_D$ for said reference monoclonal antibody.

In certain embodiments, an antibody, or antigen-binding fragment, variant, or derivative thereof of the invention binds specifically to at least one epitope of LINGO-1 or fragment or variant described above, i.e., binds to such an epitope more readily than it would bind to an unrelated, or random epitope; binds preferentially to at least one epitope of LINGO-1 or fragment or variant described above, i.e., binds to such an epitope more readily than it would bind to a related, similar, homologous, or analogous epitope; competitively inhibits binding of a reference antibody which itself binds specifically or preferentially to a certain epitope of LINGO-1 or fragment or variant described above; or binds to at least one epitope of LINGO-1 or fragment or variant described above with an affinity characterized by a dissociation constant $K_D$ of less than about $5\times10^{-2}$ M, about $10^{-2}$ M, about $5\times10^{-3}$ M, about $10^{-3}$ M, about $5\times10^{-4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M. In a particular aspect, the antibody or fragment thereof preferentially binds to a humanLINGO-1 polypeptide or fragment thereof, relative to a murine LINGO-1 polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, an antibody, or antigen-binding fragment, variant, or derivative thereof of the invention binds LINGO-1 polypeptides or fragments or variants thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. Alternatively, an antibody, or antigen-binding fragment, variant, or derivative thereof of the invention binds LINGO-1 polypeptides or fragments or variants thereof with an off rate (k(off)) of less than or equal to $5\times10^{-4}$ sec$^{1}$', $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec or $10^{-7}$ sec$^{-1}$.

In other embodiments, an antibody, or antigen-binding fragment, variant, or derivative thereof of the invention binds LINGO-1 polypeptides or fragments or variants thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. Alternatively, an antibody, or antigen-binding fragment, variant, or derivative thereof of the invention binds LINGO-1 polypeptides or fragments or variants thereof with an on rate (k(on)) greater than or equal to $10^5$ M$^{-1}$ sect, $5\times10^5$ M$^{-1}$ sec$^{-1}$, 10 M$^{-1}$ sec$^{-1}$, or $5\times106$ M$^{-1}$ sec$^{-1}$ or $10^7$ M$^{-1}$ sec$^{-1}$.

In various embodiments, a LINGO-1 antibody, or antigen-binding fragment, variant, or derivative thereof as described herein is an antagonist of LINGO-1 activity. In certain embodiments, for example, binding of an antagonist LINGO-1 antibody to LINGO-1, as expressed on neurons, blocks myelin-associated neurite outgrowth inhibition or neuronal cell death. In other embodiments, binding of the LINGO-1 antibody to LINGO-1, as expressed on oligodendrocytes, blocks inhibition of oligodendrocyte growth or differentiation, or blocks demyelination or dysmyelination of CNS neurons.

Unless it is specifically noted, as used herein a "fragment thereof" in reference to an antibody refers to an antigen-binding fragment, i.e., a portion of the antibody which specifically binds to the antigen. In one embodiment, a LINGO-1 antibody, e.g., an antibody of the invention is a bispecific LINGO-1 antibody, binding polypeptide, or antibody, e.g., a bispecific antibody, minibody, domain deleted antibody, or fusion protein having binding specificity for more than one epitope, e.g., more than one antigen or more than one epitope on the same antigen. In one embodiment, a bispecific LINGO-1 antibody, binding polypeptide, or antibody has at least one binding domain specific for at least one epitope on a target polypeptide disclosed herein, e.g., LINGO-1. In another embodiment, a bispecific LINGO-1 antibody, binding polypeptide, or antibody has at least one binding domain specific for an epitope on a target polypeptide and at least one target binding domain specific for a drug or toxin. In yet another embodiment, a bispecific LINGO-1 antibody, binding polypeptide, or antibody has at least one binding domain specific for an epitope on a target polypeptide disclosed herein, and at least one binding domain specific for a prodrug. A bispecific LINGO-1 antibody, binding polypeptide, or antibody may be a tetravalent antibody that has two target binding domains specific for an epitope of a target polypeptide disclosed herein and two target binding domains specific for a second target. Thus, a tetravalent bispecific LINGO-1 antibody, binding polypeptide, or antibody may be bivalent for each specificity.

LINGO-1 antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the invention include a LINGO-1 antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the $C_H2$ domain will be deleted.

In certain LINGO-1 antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well know immunological techniques without undue experimentation.

Modified forms of LINGO-1 antibodies, or antigen-binding fragments, variants, or derivatives thereof of the invention can be made from whole precursor or parent antibodies using techniques known in the art. Exemplary techniques are discussed in more detail herein.

In certain embodiments both the variable and constant regions of LINGO-1 antibodies, or antigen-binding fragments, variants, or derivatives thereof are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties. Other techniques are known in the art. Fully human antibodies can likewise be produced by various display technologies, e.g., phage display or other viral display systems, as described in more detail elsewhere herein.

LINGO-1 antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

LINGO-1 antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In certain embodiments, LINGO-1 antibodies, or antigen-binding fragments, variants, or derivatives thereof of the invention will not elicit a deleterious immune response in the animal to be treated, e.g., in a human. In one embodiment, LINGO-1 antibodies, or antigen-binding fragments, variants, or derivatives thereof of the invention are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693, 762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, $V_H$ and $V_L$ sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., LINGO-1-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

LINGO-1 antibodies, or antigen-binding fragments, variants, or derivatives thereof of the invention may be generated by any suitable method known in the art. Polyclonal antibodies to an antigen of interest can be produced by various procedures well known in the art. For example, a LINGO-1 antibody, e.g., a binding polypeptide, e.g., a LINGO-1-specific antibody or immunospecific fragment thereof can be administered to various host animals including, but not limited to, rabbits, mice, rats, chickens, hamsters, goats, donkeys, etc., to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using LINGO-1 knockout mice to increase the regions of epitope recognition. Monoclonal antibodies can be prepared using a wide variety of techniques known in the art including the use of hybridoma and recombinant and phage display technology as described elsewhere herein.

Using art recognized protocols, in one example, antibodies are raised in mammals by multiple subcutaneous or intraperitoneal injections of the relevant antigen (e.g., purified tumor associated antigens such as LINGO-1 or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., *Nature* 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, Academic Press, pp 59-103 (1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the $C_H1$ domain of the heavy chain.

Those skilled in the art will also appreciate that DNA encoding antibodies or antibody fragments (e.g., antigen binding sites) may also be derived from antibody libraries, such as phage display libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv OE DAB (individiual Fv region from light or heavy chains) or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243: 211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. For example, DNA sequences encoding $V_H$ and $V_L$ regions are amplified from animal cDNA libraries (e.g., human or murine cDNA libraries of lymphoid tissues) or synthetic cDNA libraries. In certain embodiments, the DNA encoding the $V_H$ and $V_L$ regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the $V_H$ or $V_L$ regions are usually recombinantly fused to either the phage gene III or gene VIII. Phage expressing an antigen binding domain that binds to an antigen of interest (i.e., a LINGO-1 polypeptide or a fragment thereof) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816,397, which are incorporated herein by reference in their entireties. Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988). See also, U.S. Pat. No. 5,565,332, which is incorporated by reference in its entirety.)

Further, antibodies to target polypeptides of the invention can, in turn, be utilized to generate anti-idiotype antibodies that "mimic" target polypeptides using techniques well known to those skilled in the art. (See, e.g., Greenspan & Bona, *FASEB J.* 7(5):437-444 (1989) and Nissinoff, *J. Immunol.* 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a desired target polypeptide and/or to bind its ligands/receptors, and thereby block its biological activity.

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In one embodiment, a LINGO-1 antibody of the invention comprises at least one heavy or light chain CDR of an antibody molecule. In another embodiment, a LINGO-1 antibody of the invention comprises at least two CDRs from one or more antibody molecules. In another embodiment, a LINGO-1 antibody of the invention comprises at least three CDRs from one or more antibody molecules. In another embodiment, a LINGO-1 antibody of the invention comprises at least four CDRs from one or more antibody molecules. In another embodiment, a LINGO-1 antibody of the invention comprises at least five CDRs from one or more antibody molecules. In another embodiment, a LINGO-1 antibody of the invention comprises at least six CDRs from one or more antibody molecules. Exemplary antibody molecules comprising at least one CDR that can be included in the subject LINGO-1 antibodies are described herein.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., LINGO-1. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851-855 (1984); Neuberger et al., *Nature* 312:604-608 (1984); Takeda et al., *Nature* 314:452-454 (1985)) by splicing genes from a mouse antibody molecule of appropriate antigen specificity together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:54-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in *E. coli* may also be used (Skerra et al., *Science* 242: 1038-1041 (1988)).

Yet other embodiments of the present invention comprise the generation of human or substantially human antibodies in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies for use in the diagnostic and therapeutic methods disclosed herein can be produced by any method known in the art for the synthesis of antibodies, in particular, by chemical synthesis or preferably, by recombinant expression techniques as described herein.

In one embodiment, a LINGO-1 antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire $C_H2$ domain has been removed ($\Delta C_H2$ constructs). For other embodiments a short connecting peptide may be substituted for the deleted domain to provide flexibility and freedom of movement for the variable region. Those skilled in the art will appreciate that such constructs are particularly preferred due to the regulatory properties of the $C_H2$ domain on the catabolic rate of the antibody. Domain deleted constructs can be derived using a vector (e.g., from Biogen IDEC Incorporated) encoding an $IgG_1$ human constant domain (see, e.g., WO 02/060955A2 and WO02/096948A2, which are incorporated by reference in their entireties). This exemplary vector was engineered to delete the $C_H2$ domain and provide a synthetic vector expressing a domain deleted $IgG_1$ constant region.

In certain embodiments, LINGO-1 antibodies, or antigen-binding fragments, variants, or derivatives thereof of the invention are minibodies. Minibodies can be made using methods described in the art (see, e.g., see e.g., U.S. Pat. No. 5,837,821 or WO 94/09817A1, which are incorporated by reference in their entireties).

In one embodiment, a LINGO-1 antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the $C_H2$ domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the $V_H$ regions and/or $V_L$ regions) described herein, which antibodies or fragments thereof immunospecifically bind to a LINGO-1 polypeptide or fragment or variant thereof. Standard techniques known to those of skill in the art can be used to introduce mutations in the nucleotide sequence encoding a LINGO-1 antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a LINGO-1 polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a LINGO-1 polypeptide) can be determined using techniques described herein or by routinely modifying techniques known in the art.

IV. Polynucleotides Encoding LINGO-1 Antibodies

The present invention also provides for nucleic acid molecules encoding LINGO-1 antibodies, or antigen-binding fragments, variants, or derivatives thereof of the invention.

In one embodiment, the present invention provides an isolated polynucleotide comprising, consisting essentially of, or consisting of a nucleic acid encoding an immunoglobulin heavy chain variable region (VH), where at least one of the CDRs of the heavy chain variable region or at least two of the CDRs of the heavy chain variable region are at least 80%, 85%, 90% or 95% identical to reference heavy chain CDR1, CDR2, or CDR3 amino acid sequences of Li62 or Li81 or variants thereof as described in Table 3. Alternatively, the CDR1, CDR2, and CDR3 regions of the VH are at least 80%, 85%, 90% or 95% identical to reference heavy chain CDR1, CDR2, and CDR3 amino acid sequences of Li62 or Li81 or variants thereof as described in Table 3. Thus, according to this embodiment a heavy chain variable region of the invention has CDR1, CDR2, or CDR3 polypeptide sequences related to the polypeptide sequences shown in Table 3:

TABLE 3

LINGO-1 Antibody VH Sequences

| Antibody | VH SEQUENCE | VH CDR1 | VH CDR2 | VH CDR3 |
|---|---|---|---|---|
| Li62 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGHNDWTFDLWGRGTLVTVSS (SEQ ID NO: 1) | IYPMF (SEQ ID NO: 2) | WIGPSGGITKYADSVKG (SEQ ID NO: 3) | EGNHDWYGDL (SEQ ID NO: 4) |
| Li62 variant B06 | EVQLLESGGGLQPGGSLRLSCAASGFTFSIYPMFWVRQAPGKGLE WVSWIGPSGGITKYADSVKGRFTISRDNSKNTLYLQMNSLRAEDT ATYYCAREGYYDWYFDQWGRGTLVTVSS (SEQ ID NO: 53) | IYPMF (SEQ ID NO: 2) | WIGPSGGITKYADSVKG (SEQ ID NO: 3) | EGYYDWYFDQ (SEQ ID NO: 17) |
| Li62 variant B12 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGQYDWYFDVWGRGTLVTVSS (SEQ ID NO: 54) | IYPMF (SEQ ID NO: 2) | WIGPSGGITKYADSVKG (SEQ ID NO: 3) | EGQYDWYFDV (SEQ ID NO: 18) |
| Li62 variant F06 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGDYDWYFDLWGRGTLVTVSS (SEQ ID NO: 55) | IYPMF (SEQ ID NO: 2) | WIGPSGGITKYADSVKG (SEQ ID NO: 3) | EGDYDWYFDL (SEQ ID NO: 19) |
| Li62 variant B01 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGQYDWYFELWGRGTLVTVSS (SEQ ID NO: 56) | IYPMF (SEQ ID NO: 2) | WIGPSGGITKYADSVKG (SEQ ID NO: 3) | EGQYDWYFEL (SEQ ID NO: 20) |
| Li62 variant D09 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREADIDWFFDLWGRGTLVTVSS (SEQ ID NO: 57) | IYPMF (SEQ ID NO: 2) | WIGPSGGITKYADSVKG (SEQ ID NO: 3) | EADIDWFFDL (SEQ ID NO: 21) |
| Li62 variant D12 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGHYDWYFDLWGRGTLVTVSS (SEQ ID NO: 58) | IYPMF (SEQ ID NO: 2) | WIGPSGGITKYADSVKG (SEQ ID NO: 3) | EGHYDWYFDL (SEQ ID NO: 22) |
| Li62 variant F01 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGRYDWYFDPWGRGTLVTVSS (SEQ ID NO: 59) | IYPMF (SEQ ID NO: 2) | WIGPSGGITKYADSVKG (SEQ ID NO: 3) | EGRYDWYFDP (SEQ ID NO: 23) |
| Li62 variant F02 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGDYDWYFGLWGRGTLVTVSS (SEQ ID NO: 60) | IYPMF (SEQ ID NO: 2) | WIGPSGGITKYADSVKG (SEQ ID NO: 3) | EGDYDWYFGL (SEQ ID NO: 24) |
| Li62 variant F06 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGRYDWYFDLWGRGTLVTVSS (SEQ ID NO: 61) | IYPMF (SEQ ID NO: 2) | WIGPSGGITKYADSVKG (SEQ ID NO: 3) | EGRYDWYFDL (SEQ ID NO: 25) |
| Li62 variant F10 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCARESHIDRYFDLWGRGTLVTVSS (SEQ ID NO: 62) | IYPMF (SEQ ID NO: 2) | WIGPSGGITKYADSVKG (SEQ ID NO: 3) | ESHIDRYFDL (SEQ ID NO: 26) |
| Li62 variant G08 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGQYDWYGDVWGRGTLVTVSS (SEQ ID NO: 63) | IYPMF (SEQ ID NO: 2) | WIGPSGGITKYADSVKG (SEQ ID NO: 3) | EGQYDWYGDV (SEQ ID NO: 27) |

TABLE 3-continued

LINGO-1 Antibody VH Sequences

| Antibody | VH SEQUENCE | VH CDR1 | VH CDR2 | VH CDR3 |
|---|---|---|---|---|
| Li62 variant H08 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGHYNGYFDLWGRGTLVTSS (SEQ ID NO: 64) | IYPMF (SEQ ID NO: 2) | WIGPSGGITKYADSVKG (SEQ ID NO: 3) | EGHYNGYFDL (SEQ ID NO: 28) |
| Li62 variant C10 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGYYDWYFDLWGRGTLVTSS (SEQ ID NO: 65) | IYPMF (SEQ ID NO: 2) | WIGPSGGITKYADSVKG (SEQ ID NO: 3) | EGYYDWYFDL (SEQ ID NO: 29) |
| Li62 variant C02 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGTYDWYLDLWGRGTLVTSS (SEQ ID NO: 66) | IYPMF (SEQ ID NO: 2) | WIGPSGGITKYADSVKG (SEQ ID NO: 3) | EGTYDWYLDL (SEQ ID NO: 30) |
| Li62 variant D05 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGYYDWYFELWGRGTLVTSS (SEQ ID NO: 67) | IYPMF (SEQ ID NO: 2) | WIGPSGGITKYADSVKG (SEQ ID NO: 3) | EGYYDWYFEL (SEQ ID NO: 31) |
| Li62 variant F02 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGLIDWFFDQWGRGTLVTSS (SEQ ID NO: 68) | IYPMF (SEQ ID NO: 2) | WIGPSGGITKYADSVKG (SEQ ID NO: 3) | EGLIDWFFDQ (SEQ ID NO: 32) |
| Li62 variant C10 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGQFDWYFDLWGRGTLVTSS (SEQ ID NO: 69) | IYPMF (SEQ ID NO: 2) | WIGPSGGITKYADSVKG (SEQ ID NO: 3) | EGQFDWYFDL (SEQ ID NO: 33) |
| Li62 variant H08 | EVQLLESGGGLVQPGGSLRLSCAASGFTFSIYPMFWVRQAPGKGL EWVSWIGPSGGITKYADSVKGRFTISRDNSKNTLYLQMNSLRAED TATYYCAREGTYDWYFDLWGRGTLVTSS (SEQ ID NO: 70) | IYPMF (SEQ ID NO: 2) | WIGPSGGITKYADSVKG (SEQ ID NO: 3) | EGTYDWYFDL (SEQ ID NO: 34) |
| Li81 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGDNDAFDIWGQGTTVTVSS (SEQ ID NO: 5) | AYEMK (SEQ ID NO: 6) | VIGPSGGFTFYADSVKG (SEQ ID NO: 7) | EGDNDAFDI (SEQ ID NO: 8) |
| Li81 variant F09 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGENDAFDVWGQGTTVTVSS (SEQ ID NO: 71) | AYEMK (SEQ ID NO: 6) | VIGPSGGFTFYADSVKG (SEQ ID NO: 7) | EGENDAFDV (SEQ ID NO: 35) |
| Li81 variant G02 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGDNDAYDTWGQGTTVTVSS (SEQ ID NO: 72) | AYEMK (SEQ ID NO: 6) | VIGPSGGFTFYADSVKG (SEQ ID NO: 7) | EGDNDAYDT (SEQ ID NO: 36) |
| Li81 variant H03 | EVQLLESGGGLVQPGGSLRLSCAASGFTFSAYEMKWVRQAPGKGL EWVSVITPSGGFTFYADSVKGRFTISRDNSKNTLYLQMNSLRAED TAVYYCATEGTNDAFDIWGQGTTVTVSS (SEQ ID NO: 73) | AYEMK (SEQ ID NO: 6) | VIGPSGGFTFYADSVKG (SEQ ID NO: 7) | EGTNDAFDI (SEQ ID NO: 37) |
| Li81 variant A12 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGDNDAFDSWGQGTTVTVSS (SEQ ID NO: 74) | AYEMK (SEQ ID NO: 6) | VIGPSGGFTFYADSVKG (SEQ ID NO: 7) | EGNDNAFDS (SEQ ID NO: 38) |
| Li81 variant C02 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGDNDAFDTWGQGTTVTVSS (SEQ ID NO: 75) | AYEMK (SEQ ID NO: 6) | VIGPSGGFTFYADSVKG (SEQ ID NO: 7) | EGDNDAFDT (SEQ ID NO: 39) |
| Li81 variant C11 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGDNDAYDRWGQGTTVTVSS (SEQ ID NO: 76) | AYEMK (SEQ ID NO: 6) | VIGPSGGFTFYADSVKG (SEQ ID NO: 7) | EGDNDAYDR (SEQ ID NO: 40) |
| Li81 variant D11 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGDNDVFDSWGQGTTVTVSS (SEQ ID NO: 77) | AYEMK (SEQ ID NO: 6) | VIGPSGGFTFYADSVKG (SEQ ID NO: 7) | EGDNDVFDS (SEQ ID NO: 41) |

TABLE 3-continued

LINGO-1 Antibody VH Sequences

| Antibody | VH SEQUENCE | VH CDR1 | VH CDR2 | VH CDR3 |
|---|---|---|---|---|
| Li81 variant E05 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGDNDVFDSWGQGTTVTVSS (SEQ ID NO: 78) | AYEMK (SEQ ID NO: 6) | VIGPSGGFTFYADSVKG (SEQ ID NO: 7) | EGDDDVFDM (SEQ ID NO: 42) |
| Li81 variant H04 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGYNDAFDFWGQGTTVTVSS (SEQ ID NO: 79) | AYEMK (SEQ ID NO: 6) | VIGPSGGFTFYADSVKG (SEQ ID NO: 7) | EGYNDAFDF (SEQ ID NO: 43) |
| Li81 variant B04 | EVQLLESGGGLVQPGGSLRLSCAASGFTFSAYEMKWVRQAPKGKL EWVSVIGPSGGFTFYADSVKGRFTISRDNSKNTLYLQMNSLRAED TAVYYCATEGDDDAYDMWGQGTTVTVSS (SEQ ID NO: 80) | AYEMK (SEQ ID NO: 6) | VIGPSGGFTFYADSVKG (SEQ ID NO: 7) | EGDDDAYDM (SEQ ID NO: 44) |
| Li81 variant A02 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEQDYDTYDLWGQGTTVTVSS (SEQ ID NO: 81) | AYEMK (SEQ ID NO: 6) | VIGPSGGFTFYADSVKG (SEQ ID NO: 7) | EQDYDTYDL (SEQ ID NO: 45) |
| Li81 variant B12 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGDDDAFDTWGQGTTVTVSS (SEQ ID NO: 82) | AYEMK (SEQ ID NO: 6) | VIGPSGGFTFYADSVKG (SEQ ID NO: 7) | EGDDDAFDT (SEQ ID NO: 46) |
| Li81 variant H06 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEADDDAFDIWGQGTTVTVSS (SEQ ID NO: 83) | AYEMK (SEQ ID NO: 6) | VIGPSGGFTFYADSVKG (SEQ ID NO: 7) | EADDDAFDI (SEQ ID NO: 47) |
| Li81 variant H08 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGENDAFDMWGQGTTVTVSS (SEQ ID NO: 84) | AYEMK (SEQ ID NO: 6) | VIGPSGGFTFYADSVKG (SEQ ID NO: 7) | EGENDAFDM (SEQ ID NO: 48) |
| Li81 variant E07 | EVQLLESGGGLVQPGGSLRLSCAASGFTFSAYEMKWVRQAPGKGL EWVSVIGPSGGFTFYADSVKGRFTISRDNSKNTLYLQMNSLRAED TAVYYCATEGEYDTYDIWGQGTTVTVSS (SEQ ID NO: 85) | AYEMK (SEQ ID NO: 6) | VIGPSGGFTFYADSVKG (SEQ ID NO: 7) | EGEYDTYDI (SEQ ID NO: 49) |

In certain embodiments, the present invention provides an isolated polynucleotide, comprising, consisting essentially of, or consisting of a nucleic acid encoding an immunoglobulin heavy chain which is identical to the polypeptide of SEQ ID NO:146 except for a replacement of one or more of the following amino acids: W50, P53, I57 and/or W104. In some embodiments, W50 is replaced with an H, F, L, M, G, I, or D residue. In some embodiments, P53 is replaced with an L, S, T, W, or G residue. In some embodiments, I57 is replaced with a G, M, N, H, L, F, W, Y, S, P, V or T residue. In some embodiments, W104 is replaced with a V, H, S, Q, M, L, T, or I residue.

In certain embodiments, the present invention provides an isolated polynucleotide, comprising, consisting essentially of, or consisting of a nucleic acid encoding an immunoglobulin heavy chain variable region which is identical to the polypeptide of SEQ ID NO:5 except for a replacement of amino acid P53. In some embodiments, P53 is replaced with an L, S, T, W, or G residue.

In certain embodiments, the present invention provides an isolated polynucleotide, comprising, consisting essentially of, or consisting of a nucleic acid encoding an immunoglobulin heavy chain varible region which is identical to the polypeptide of SEQ ID NO:1 except for a replacement of one or more of the following amino acids: W50, P53, I57 and/or W104. In some embodiments, W50 is replaced with an H, F, L, M, G, I, or D residue. In some embodiments, P53 is replaced with an L, S, T, W, or G residue. In some embodiments, I57 is replaced with a G, M, N, H, L, F, W, Y, S, P, V or T residue. In some embodiments, W104 is replaced with a V, H, S, Q, M, L, T, or I residue.

In certain embodiments, the present invention provides an isolated polynucleotide, comprising, consisting essentially of, or consisting of a nucleic acid encoding an immunoglobulin heavy chain varible region which is identical to the polypeptide of SEQ ID NO:66 except for a replacement of one or more of the following amino acids: W50, P53, I57 and/or W104. In some embodiments, W50 is replaced with an H, F, L, M, G, I, or D residue. In some embodiments, P53 is replaced with an L, S, T, W, or G residue. In some embodiments, I57 is replaced with a G, M, N, H, L, F, W, Y, S, P, V or T residue. In some embodiments, W104 is replaced with a V, H, S, Q, M, L, T, or I residue.

In certain embodiments, the present invention provides an isolated polynucleotide comprising, consisting essentially of, or consisting of a nucleic acid encoding an immunoglobulin heavy chain variable region (VH) in which the CDR3 region has a polypeptide sequence at least 80%, 85%, 90%, 95% or 100% identical to the CDR3 amino acid sequences selected from the group consisting of SEQ ID NOs: 4, 8 and 17-49. In some embodiments, the CDR1 and CDR2 regions are at least 80%, 85%, 90%, 95% or 100% identical to the CDR1 and CDR2 amino acid sequences of SEQ ID NOs: 2 and 3, respectively, and the CDR3 region is at least 80%, 85%, 90%, 95% or 100% identical to a CDR3 amino acid sequence selected from the group consisting of SEQ ID NOs: 4 and 17-34. In some embodiments, the CDR1 and CDR2 regions are at least 80%, 85%, 90%, 95% or 100% identical to the CDR1 and CDR2 amino acid sequences of SEQ ID NOs: 6 and 7, respectively, and the CDR3 region is at least 80%, 85%, 90%, 95% or 100% identical to a CDR3 amino acid sequence selected from the group consisting of SEQ ID NOs: 8 and 35-49.

In certain embodiments, an antibody or antigen-binding fragment comprising the VH encoded by the polynucleotide specifically or preferentially binds to LINGO-1.

In another embodiment, the present invention provides an isolated polynucleotide comprising, consisting essentially of, or consisting of a nucleic acid encoding an immunoglobulin heavy chain variable region (VH) in which the CDR1, CDR2, and CDR3 regions have polypeptide sequences which are identical to the CDR1, CDR2, and CDR3 groups shown in Table 3. In certain embodiments, an antibody or antigen-binding fragment comprising the VH encoded by the polynucleotide specifically or preferentially binds to LINGO-1.

In certain embodiments, an antibody or antigen-binding fragment thereof comprising, consisting essentially of, or consisting of a VH encoded by one or more of the polynucleotides described above specifically or preferentially binds to the same epitope as a Li62 or Li81 antibody, or will competitively inhibit such a monoclonal antibody from binding to LINGO-1.

In certain embodiments, an antibody or antigen-binding fragment thereof comprising, consisting essentially of, or consisting of a VH encoded by one or more of the polynucleotides described above specifically or preferentially binds to a LINGO-1 polypeptide or fragment thereof, or a LINGO-1 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In a further embodiment, the present invention includes an isolated polynucleotide comprising, consisting essentially of, or consisting of a nucleic acid encoding a VH at least 80%, 85%, 90% or 95% identical to a reference VH polypeptide selected from the group consisting of SEQ ID NOs: 1, 5 and 53-85. In certain embodiments, an antibody or antigen-binding fragment comprising the VH encoded by the polynucleotide specifically or preferentially binds to LINGO-1.

In some embodiments, the isolated polynucleotide comprises, consists essentially of or consists of a nucleic acid encoding an antibody heavy chain as shown below in SEQ ID NO:86.

(SEQ ID NO: 86)
EVQLLESGGGLVQPGGSLRLSCAASGFTFSAYEMKWVRQAPGKGLEWVSV

IGPSGGFTFYADISVKGRFTISRDNSKNTLYLQMNSLRAEDTAVYYCATE

GDNDAFDIWGQGTTVTVSSASTKGPISVFPLAPSSKSTSGGTAALGCLVK

DYFPEPVTVSWNSGALTSGVHTFPAVLQSSGLYSLSSVVTIVPSSSLGTQ

TYICNVNHKPSNTKVDKKVEPKSCDKTHTCPPCPAPELLGGPSVFLFPPK

PKDTLIMISRTPEVTCVVVDVSHEDPEVKFNWYVDGVEVHNAKTKPREEQ

-continued
YNS<u>T</u>YRVVSVLTVLHQDIWLNGKEYKCKVSNKALPAPIEKTISKAKGQPR

EPQVYTLPPSRDELTKNQVSLTCLVKGFYPSIDIAVEWESNGQPENNYKT

TPPVLDSDGSFFLYSKLTVDKSRWQQGNVFSCSVMHEALHNHYTIQKSLS

LSPG

In other embodiments, the isolated polynucleotide comprises, consists essentially of or consists of a nucleic acid encoding an aglycosylated version of an antibody heavy chain. For example, an aglycosylated version of Li81 is described in PCT/US2008/000316, filed Jan. 9, 2008, which is incorporated herein by reference in its entirety. An aglycosylated version of the Li81 antibody was created by changing a single amino acid (T to A) in the Li81 heavy chain sequence. The sequence of an aglycosylated version of Li81 heavy chain (SEQ ID NO:50) is shown below. The single amino acid change is marked in bold and underlined:

(SEQ ID NO: 50)
EVQLLESGGGLVQPGGSLRLSCAASGFTFSAYEMKWVRQAPGKGLEWVSV

IGPSGGFTFYADISVKGRFTISRDNSKNTLYLQMNSLRAEDTAVYYCATE

GDNDAFDIWGQGTTVTVSSASTKGPISVFPLAPSSKSTSGGTAALGCLVK

DYFPEPVTVSWNSGALTSGVHTFPAVLQSSGLYSLSSVVTIVPSSSLGTQ

TYICNVNHKPSNTKVDKKVEPKSCDKTHTCPPCPAPELLGGPSVFLFPPK

PKDTLIMISRTPEVTCVVVDVSHEDPEVKFNWYVDGVEVHNAKTKPREEQ

YNS<b>A</b>YRVVSVLTVLHQDIWLNGKEYKCKVSNKALPAPIEKTISKAKGQPR

EPQVYTLPPSRDELTKNQVSLTCLVKGFYPSIDIAVEWESNGQPENNYKT

TPPVLDSDGSFFLYSKLTVDKSRWQQGNVFSCSVMHEALHNHYTIQKSLS

LSPG.

Therefore, the present invention includes an isolated polynucleotide comprising, consisting essentially of, or consisting of a nucleic acid encoding a heavy chain at least 80%, 85%, 90% or 95% identical to a reference polypeptide comprising the amino acids of SEQ ID NO:50 or 86. In certain embodiments, an antibody or antigen-binding fragment comprising the heavy chain encoded by the polynucleotide specifically or preferentially binds to LINGO-1.

In another aspect, the present invention includes an isolated polynucleotide comprising, consisting essentially of, or consisting of a nucleic acid sequence encoding a VH comprising the amino acids of SEQ ID NO: 1 or SEQ ID NO: 5. In certain embodiments, an antibody or antigen-binding fragment comprising the VH encoded by the polynucleotide specifically or preferentially binds to LINGO-1. In certain embodiments, an antibody or antigen-binding fragment thereof comprising, consisting essentially of, or consisting of a VH encoded by one or more of the polynucleotides described above specifically or preferentially binds to the same epitope as Li62, Li81 or a variant thereof as described in Table 3 or will competitively inhibit such a monoclonal antibody from binding to LINGO-1.

In certain embodiments, an antibody or antigen-binding fragment thereof comprising, consisting essentially of, or consisting of a VH encoded by one or more of the polynucleotides described above specifically or preferentially binds to a LINGO-1 polypeptide or fragment thereof, or a LINGO-1 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $5\times10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

VL Sequences

In another embodiment, the present invention provides an isolated polynucleotide comprising, consisting essentially of, or consisting of a nucleic acid encoding an immunoglobulin light chain variable region (VL), where at least one of the CDRs of the light chain variable region or at least two of the CDRs of the light chain variable region are at least 80%, 85%, 90% or 95% identical to reference light chain CDR1, CDR2, or CDR3 amino acid sequences from monoclonal LINGO-1 antibodies disclosed herein. Alternatively, the CDR1, CDR2, and CDR3 regions of the VL are at least 80%, 85%, 90% or 95% identical to reference light chain CDR1, CDR2, and CDR3 amino acid sequences from monoclonal LINGO-1 antibodies disclosed herein. Thus, according to one embodiment, a light chain variable region of the invention has CDR1, CDR2, or CDR3 polypeptide sequences related to the polypeptide sequences shown in Table 4.

TABLE 4

LINGO-1 Antibody VL Sequences

| Antibody | VL SEQUENCE | VL CDR1 | VL CDR2 | VL CDR3 |
|---|---|---|---|---|
| Li62 | DIQMTQSPSFLSASVGDSVAITCRASQDISRYLAWYQQRPGKAPK LLIYDASNLQTGVPSRFSGSGSGTDFTFTITSLQPEDFGTYYCQQ YDTLHPSFGPGTTDIK (SEQ ID NO: 9) | RASQDISRYLA (SEQ ID NO: 10) | DADNLQT (SEQ ID NO: 11) | QQYDTLHPS (SEQ ID NO: 12) |
| Li81 | DIQMTQSPATLSLSPGERATLSCRASQSVSSYLAWYQQKPGQAPR LLIYDASNRATGIPARFSGSGSGTDFTLTISSLEPEDFAVYYCQQ RSNWPMYTFGQGTKLEIK (SEQ ID NO: 13) | RASQSVSSYLA (SEQ ID NO: 14) | DASNRAT (SEQ ID NO: 15) | QQRSNWPMYT (SEQ ID NO: 16) |

In certain embodiments, an antibody or antigen-binding fragment comprising the VL encoded by the polynucleotide specifically or preferentially binds to LINGO-1.

In certain embodiments, the present invention provides an isolated polynucleotide, comprising, consisting essentially of, or consisting of a nucleic acid encoding an immunoglobulin light chain which is identical to the polypeptide of SEQ ID NO:145 except for a replacement of amino acid W94. In some embodiments, W94 is replaced with an A, D, L, N, G, Q, V, or S residue.

In certain embodiments, the present invention provides an isolated polynucleotide, comprising, consisting essentially of, or consisting of a nucleic acid encoding an immunoglobulin light chain variable region which is identical to the polypeptide of SEQ ID NO:5 except for a replacement of amino acid W94. In some embodiments, W94 is replaced with an A, D, L, N, G, Q, V, or S residue.

In another embodiment, the present invention provides an isolated polynucleotide comprising, consisting essentially of, or consisting of a nucleic acid encoding an immunoglobulin light chain variable region (VL) in which the CDR1, CDR2, and CDR3 regions have polypeptide sequences which are identical to the CDR1, CDR2, and CDR3 groups shown in Table 4. In certain embodiments, an antibody or antigen-binding fragment comprising the VL encoded by the polynucleotide specifically or preferentially binds to LINGO-1.

In certain embodiments, an antibody or antigen-binding fragment thereof comprising, consisting essentially of, or consisting of a VL encoded by one or more of the polynucleotides described above specifically or preferentially binds to the same epitope as Li62 or Li81, or will competitively inhibit such an antibody from binding to LINGO-1.

In certain embodiments, an antibody or antigen-binding fragment thereof comprising, consisting essentially of, or consisting of a VL encoded by one or more of the polynucleotides described above specifically or preferentially binds to a LINGO-1 polypeptide or fragment thereof, or a LINGO-1 variant polypeptide, with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In a further embodiment, the present invention includes an isolated polynucleotide comprising, consisting essentially of, or consisting of a nucleic acid encoding a VL at least 80%, 85%, 90% or 95% identical to a reference VL polypeptide sequence selected from SEQ ID NO: 9 or SEQ ID NO: 13. In certain embodiments, an antibody or antigen-binding fragment comprising the VL encoded by the polynucleotide specifically or preferentially binds to LINGO-1. In another aspect, the present invention includes an isolated polynucleotide comprising, consisting essentially of, or consisting of a nucleic acid sequence encoding a VL of the invention, selected from SEQ ID NO: 9 or SEQ ID NO: 13. In certain embodiments, an antibody or antigen-binding fragment comprising the VL encoded by the polynucleotide specifically or preferentially binds to LINGO-1. In certain embodiments, an antibody or antigen-binding fragment thereof comprising, consisting essentially of, or consisting of a VL encoded by one or more of the polynucleotides described above specifically or preferentially binds to the same epitope as Li62 or Li81, or will competitively inhibit such a monoclonal antibody from binding to LINGO-1.

In certain embodiments, an antibody or antigen-binding fragment thereof comprising, consisting essentially of, or consisting of a VL encoded by one or more of the polynucleotides described above specifically or preferentially binds to a LINGO-1 polypeptide or fragment thereof, or a LINGO-1 variant polypeptide, with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Any of the polynucleotides described above may further include additional nucleic acids, encoding, e.g., a signal peptide to direct secretion of the encoded polypeptide, antibody constant regions as described herein, or other heterologous polypeptides as described herein.

Also, as described in more detail elsewhere herein, the present invention includes compositions comprising the polynucleotides comprising one or more of the polynucleotides described above. In one embodiment, the invention includes compositions comprising a first polynucleotide and second polynucleotide wherein said first polynucleotide encodes a VH polypeptide as described herein and wherein said second polynucleotide encodes a VL polypeptide as described herein.

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding a LINGO-1 antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the antibody or other LINGO-1 antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other LINGO-1 antibody. Amplified nucleic acids generated by PCR may then be cloned into replicable cloning vectors using any method well known in the art.

Once the nucleotide sequence and corresponding amino acid sequence of the LINGO-1 antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual,* 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

A polynucleotide encoding a LINGO-1 antibody, or antigen-binding fragment, variant, or derivative thereof can be composed of any polyribonucleotide or polydeoxyribonucleotide, which may be unmodified RNA or DNA or modified RNA or DNA. For example, a polynucleotide encoding LINGO-1 antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding a LINGO-1 antibody, or antigen-binding fragment, variant, or derivative thereof can be composed of triple-stranded regions comprising RNA or DNA or both RNA and DNA. A polynucleotide encoding a LINGO-1 antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

V. LINGO-1 Antibody Polypeptides

The present invention is further directed to isolated polypeptides which make up LINGO-1 antibodies, antigen binding fragments, variants or derivatives thereof. LINGO-1 antibodies of the present invention comprise polypeptides, e.g., amino acid sequences encoding LINGO-1-specific antigen binding regions derived from immunoglobulin molecules. A polypeptide or amino acid sequence "derived from" a designated protein refers to the origin of the polypeptide. In certain cases, the polypeptide or amino acid sequence which is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at least 30-50 amino acids, or which is otherwise identifiable to one of ordinary skill in the art as having its origin in the starting sequence.

In one embodiment, the present invention provides an isolated polypeptide comprising, consisting essentially of, or consisting of an immunoglobulin heavy chain variable region (VH), where at least one of CDRs of the heavy chain variable region or at least two of the CDRs of the heavy chain variable region are at least 80%, 85%, 90% or 95% identical to reference heavy chain CDR1, CDR2 or CDR3 amino acid sequences from monoclonal LINGO-1 antibodies disclosed herein. Alternatively, the CDR1, CDR2 and CDR3 regions of the VH are at least 80%, 85%, 90% or 95% identical to reference heavy chain CDR1, CDR2 and CDR3 amino acid sequences from monoclonal LINGO-1 antibodies disclosed herein. Thus, according to this embodiment a heavy chain variable region of the invention has CDR1, CDR2, and CDR3 polypeptide sequences related to the groups shown in Table 3, supra. In certain embodiments, an antibody or antigen-binding fragment comprising the VH polypeptide specifically or preferentially binds to LINGO-1.

In another embodiment, the present invention provides an isolated polypeptide comprising, consisting essentially of, or consisting of an immunoglobulin heavy chain vairable region (VH), wherein at least the CDR3 region is at least 80%, 85%, 90% or 95% identical to a reference CDR3 sequence selected from the group consisting of SEQ ID NOs: 4, 8 and 17-49. In further embodiments, the CDR3 region is identical to a reference CDR3 sequence selected from the group consisting of SEQ ID NOs: 4, 8 and 17-49. In still further embodiments, the invention provides an isolated polypeptide comprising, consisting essentially of, or consisting of an immunoglobulin heavy chain vairable region (VH), wherein, the CDR1 and CDR2 regions are at least 80%, 85%, 90%, 95% or 100% identical to the CDR1 and CDR2 amino acid sequences of SEQ ID NOs: 2 and 3, respectively, and the CDR3 region is at least 80%, 85%, 90%, 95% or 100% identical to a CDR3 amino acid sequence selected from the group consisting of SEQ ID NOs: 4 and 17-34. In other embodiments, the invention provides an isolated polypeptide comprising, consisting essentially of, or consisting of an immunoglobulin heavy chain vairable region (VH), wherein the CDR1 and CDR2 regions are at least 80%, 85%, 90%, 95% or 100% identical to the CDR1 and CDR2 amino acid sequences of SEQ ID NOs: 6 and 7, respectively, and the CDR3 region is at least 80%, 85%, 90%, 95% or 100% identical to a CDR3 amino acid sequence selected from the group consisting of SEQ ID NOs: 8 and 35-49.

In another embodiment, the present invention provides an isolated polypeptide comprising, consisting essentially of, or consisting of an immunoglobulin heavy chain variable region (VH) in which the CDR1, CDR2, and CDR3 regions have polypeptide sequences which are identical to the CDR1, CDR2, and CDR3 groups shown in Table 3. In certain embodiments, an antibody or antigen-binding fragment comprising the VH polypeptide specifically or preferentially binds to LINGO-1.

In a further embodiment, the present invention includes an isolated polypeptide comprising, consisting essentially of, or consisting of a VH polypeptide at least 80%, 85%, 90% 95% or 100% identical to a reference VH polypeptide sequence selected from SEQ ID NOs: 1, 5 and 53-85. In one particular embodiment, the VH polypeptide comprises a CDR3 amino acid sequence selected from the group consisting of SEQ ID NOs: 4, 8 and 17-49.

In certain embodiments, an antibody or antigen-binding fragment comprising the VH polypeptide specifically or preferentially binds to LINGO-1. In another aspect, the present invention includes an isolated polypeptide comprising, consisting essentially of, or consisting of a VH polypeptide selected from the group consisting of SEQ ID NOs: 1, 5 and 53-85. In certain embodiments, an antibody or antigen-binding fragment comprising the VH polypeptide specifically or preferentially binds to LINGO-1.

In certain embodiments, the present invention provides an isolated polypeptide, comprising, consisting essentially of, or consisting of an immunoglobulin heavy chain which is identical to the polypeptide of SEQ ID NO:146 except for a replacement of one or more of the following amino acids: W50, P53, I57 and/or W104. In some embodiments, W50 is replaced with an H, F, L, M, G, I, or D residue. In some embodiments, P53 is replaced with an L, S, T, W, or G residue. In some embodiments, I57 is replaced with a G, M, N, H, L, F, W, Y, S, P, V or T residue. In some embodiments, W104 is replaced with a V, H, S, Q, M, L, T, or I residue.

In certain embodiments, the present invention provides an isolated polypeptide, comprising, consisting essentially of, or consisting of an immunoglobulin heavy chain variable region which is identical to the polypeptide of SEQ ID NO:5 except for a replacement of amino acid P53. In some embodiments, P53 is replaced with an L, S, T, W, or G residue.

In certain embodiments, the present invention provides an isolated polypeptide, comprising, consisting essentially of, or consisting of an immunoglobulin heavy chain varible region which is identical to the polypeptide of SEQ ID NO:1 except for a replacement of one or more of the following amino acids: W50, P53, I57 and/or W104. In some embodiments, W50 is replaced with an H, F, L, M, G, I, or D residue. In some embodiments, P53 is replaced with an L, S, T, W, or G residue. In some embodiments, I57 is replaced with a G, M, N, H, L, F, W, Y, S, P, V or T residue. In some embodiments, W104 is replaced with a V, H, S, Q, M, L, T, or I residue.

In certain embodiments, the present invention provides an isolated polypeptide, comprising, consisting essentially of, or consisting of an immunoglobulin heavy chain variable region which is identical to the polypeptide of SEQ ID NO:66 except for a replacement of one or more of the following amino acids: W50, P53, I57 and/or W104. In some embodiments, W50 is replaced with an H, F, L, M, G, I, or D residue. In some embodiments, P53 is replaced with an L, S, T, W, or G residue. In some embodiments, I57 is replaced with a G, M, N, H, L, F, W, Y, S, P, V or T residue. In some embodiments, W104 is replaced with a V, H, S, Q, M, L, T, or I residue.

In certain embodiments, an antibody or antigen-binding fragment thereof comprising, consisting essentially of, or consisting of a one or more of the VH polypeptides described above specifically or preferentially binds to the same epitope as Li62, Li81 or a variant thereof as described in Table 3, or will competitively inhibit such an antibody from binding to LINGO-1.

In certain embodiments, an antibody or antigen-binding fragment thereof comprising, consisting essentially of, or consisting of one or more of the VH polypeptides described above specifically or preferentially binds to a LINGO-1 polypeptide or fragment thereof, or a LINGO-1 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10-11$ M, $10^{-11}$ M, $5 \times 10^{-12}$ M, $10^{-12}$ M $5 \times 10^{-13}$ M, $10^{-13}$ M, $5 \times 10^{-14}$ M, $10^{-14}$ M, $5 \times 10^{-15}$ M, or $10^{-15}$ M.

In another embodiment, the present invention provides an isolated polypeptide comprising, consisting essentially of, or consisting of an immunoglobulin light chain variable region (VL), where at least one of the CDRs of the light chain variable region or at least two of the CDRs of the light chain variable region are at least 80%, 85%, 90% or 95% identical to reference heavy chain CDR1, CDR2, or CDR3 amino acid sequences from monoclonal LINGO-1 antibodies disclosed herein. Alternatively, the CDR1, CDR2 and CDR3 regions of the VL are at least 80%, 85%, 90% or 95% identical to reference light chain CDR1, CDR2, and CDR3 amino acid sequences from monoclonal LINGO-1 antibodies disclosed herein. Thus, according to this embodiment a light chain variable region of the invention has CDR1, CDR2, and CDR3 polypeptide sequences related to the polypeptides shown in Table 4, supra. In certain embodiments, an antibody or antigen-binding fragment comprising the VL polypeptide specifically or preferentially binds to LINGO-1.

In another embodiment, the present invention provides an isolated polypeptide comprising, consisting essentially of, or consisting of an immunoglobulin light chain variable region (VL) in which the CDR1, CDR2, and CDR3 regions have polypeptide sequences which are identical to the CDR1, CDR2, and CDR3 groups shown in Table 4. In certain embodiments, an antibody or antigen-binding fragment comprising the VL polypeptide specifically or preferentially binds to LINGO-1.

In a further embodiment, the present invention includes an isolated polypeptide comprising, consisting essentially of, or consisting of a VL polypeptide at least 80%, 85%, 90% or 95% identical to a reference VL polypeptide sequence selected from SEQ ID NO: 9 or SEQ ID NO: 13, shown in Table 4. In certain embodiments, an antibody or antigen-binding fragment comprising the VL polypeptide specifically or preferentially binds to LINGO-1. In another aspect, the present invention includes an isolated polypeptide comprising, consisting essentially of, or consisting of a VL polypeptide selected from SEQ ID NO: 9 or SEQ ID NO: 13, shown in Table 4. In certain embodiments, an antibody or antigen-binding fragment comprising the VL polypeptide specifically or preferentially binds to LINGO-1.

In certain embodiments, the present invention provides an isolated polypeptide consisting essentially of, or consisting of an immunoglobulin light chain which is identical to the polypeptide of SEQ ID NO:145 except for a replacement of amino acid W94. In some embodiments, W94 is replaced with an A, D, L, N, G, Q, V, or S residue.

In certain embodiments, the present invention provides an isolated polypeptide, comprising, consisting essentially of, or consisting of an immunoglobulin light chain variable region which is identical to the polypeptide of SEQ ID NO:5 except for a replacement of amino acid W94. In some embodiments, W94 is replaced with an A, D, L, N, G, Q, V, or S residue.

In certain embodiments, an antibody or antigen-binding fragment thereof comprising, consisting essentially of, one or more of the VL polypeptides described above specifically or preferentially binds to the same epitope as Li62 or Li81, or will competitively inhibit such a monoclonal antibody from binding to LINGO-1.

In certain embodiments, an antibody or antigen-binding fragment thereof comprising, consisting essentially of, or consisting of a one or more of the VL polypeptides described above specifically or preferentially binds to a LINGO-1 polypeptide or fragment thereof, or a LINGO-1 variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-3}$ M, $10^{-13}$ M, $5 \times 10^{-14}$ M, $10^{-14}$ M, $5 \times 10^{-15}$ M, or $10^{-15}$ M.

In other embodiments, an antibody or antigen-binding fragment thereof comprises, consists essentially of or consists of a VH polypeptide, as shown in Table 3, and a VL polypeptide, as shown in Table 4, selected from the group consisting of:
  i) SEQ ID NO: 1 or SEQ ID NOs: 53-70 and SEQ ID NO: 9; and
  iii) SEQ ID NO: 5 or SEQ ID NOs: 71-85 and SEQ ID NO: 13.

Any of the polypeptides described above may further include additional polypeptides, e.g., a signal peptide to direct secretion of the encoded polypeptide, antibody constant regions as described herein, or other heterologous polypeptides as described herein. Additionally, polypeptides of the invention include polypeptide fragments as described elsewhere. Additionally polypeptides of the invention include fusion polypeptide, Fab fragments, and other derivatives, as described herein.

Also, as described in more detail elsewhere herein, the present invention includes compositions comprising the polypeptides described above.

It will also be understood by one of ordinary skill in the art that LINGO-1 antibody polypeptides as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, or 95% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

Certain LINGO-1 antibody polypeptides of the present invention comprise, consist essentially of, or consist of an amino acid sequence derived from a human amino acid sequence. However, certain LINGO-1 antibody polypeptides comprise one or more contiguous amino acids derived from another mammalian species. For example, a LINGO-1 antibody of the present invention may include a primate heavy chain portion, hinge portion, or antigen binding region. In another example, one or more murine-derived amino acids may be present in a non-murine antibody polypeptide, e.g., in an antigen binding site of a LINGO-1 antibody. In certain therapeutic applications, LINGO-1-specific antibodies, or antigen-binding fragments, variants, or analogs thereof are designed so as to not be immunogenic in the animal to which the antibody is administered.

In certain embodiments, a LINGO-1 antibody polypeptide comprises an amino acid sequence or one or more moieties not normally associated with an antibody. Exemplary modifications are described in more detail below. For example, a single-chain fv antibody fragment of the invention may comprise a flexible linker sequence, or may be modified to add a functional moiety (e.g., PEG, a drug, a toxin, or a label).

A LINGO-1 antibody polypeptide of the invention may comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to a LINGO-1 antibody, or an antigen-binding fragment, variant, or analog thereof is derived from a non-immunoglobulin polypeptide of the same species, or an immunoglobulin or non-immunoglobulin polypeptide of a different species.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence, such as by saturation mutagenesis, and the resultant mutants can be incorporated into LINGO-1 antibodies for use in the diagnostic and treatment methods disclosed herein and screened for their ability to bind to the desired antigen, e.g., LINGO-1.

VI. Fusion Proteins and Antibody Conjugates

As discussed in more detail elsewhere herein, LINGO-1 antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, LINGO-1-specific LINGO-1 antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387, which are incorporated herein by reference in their entireties.

LINGO-1 antibodies, or antigen-binding fragments, variants, or derivatives thereof of the invention include derivatives that are modified, i.e., by the covalent attachment of any type of molecule to the antibody such that covalent attachment does not prevent the antibody binding LINGO-1. For example, but not by way of limitation, the antibody derivatives include antibodies that have been modified, e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

LINGO-1 antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. LINGO-1-specific antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the LINGO-1-specific antibody, including the peptide backbone, the amino acid side-chains and the amino or carboxyl termini, or on moieties such as carbohydrates. It will be appreciated that the same type of modification may be present in the same or varying degrees at several sites in a given LINGO-1-specific antibody. Also, a given LINGO-1-specific antibody may contain many types of modifications. LINGO-1-specific antibodies may be branched, for example, as a result of ubiquitination, and they may be cyclic, with or without branching. Cyclic, branched, and branched cyclic LINGO-1-specific antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W.H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The present invention also provides for fusion proteins comprising a LINGO-1 antibody, or antigen-binding fragment, variant, or derivative thereof, and a heterologous polypeptide. The heterologous polypeptide to which the antibody is fused may be useful for function or is useful to target the LINGO-1 polypeptide expressing cells. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$ CDRs of a LINGO-1-specific antibody, or fragments, variants, or derivatives thereof, or the amino acid sequence of any one, two, three of the $V_L$ CDRs of a LINGO-1-specific antibody, or fragments, variants, or derivatives thereof, and a heterologous polypeptide sequence. In one embodiment, the fusion protein comprises a polypeptide having the amino acid sequence of a $V_H$ CDR3 of a LINGO-1-specific antibody of the present invention, or fragment, derivative, or variant thereof, and a heterologous polypeptide sequence, which fusion protein specifically binds to at least one epitope of LINGO-1. In another embodiment, a fusion protein comprises a polypeptide having the amino acid sequence of at least one $V_H$ region of a LINGO-1-specific antibody of the invention and the amino acid sequence of at least one $V_L$ region of a LINGO-1-specific antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds at least one epitope of LINGO-1. In yet another embodiment, a fusion protein for use in the diagnostic and treatment methods disclosed herein comprises a polypeptide having the amino acid sequence of any one, two, three or more of the $V_H$ CDRs of a LINGO-1-specific antibody and the amino acid sequence of any one, two, three or more of the $V_L$ CDRs of a LINGO-1-specific antibody, or fragments or variants thereof, and a heterologous polypeptide sequence. Preferably, two, three, four, five, six, or more of the $V_H$CDR(s) or $V_L$CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., *Proc. Natl. Acad. Sci. USA* 84:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 110:2221-2229 (1990); and Watson et al., *Nature* 349: 164-167 (1991)); CD44 (Aruffo et al., *Cell* 61:1303-1313 (1990)); CD28 and B7 (Linsley et al., *J. Exp. Med.* 173:721-730 (1991)); CTLA-4 (Lisley et al., *J. Exp. Med.* 174:561-569 (1991)); CD22 (Stamenkovic et al., *Cell* 66:1133-114 (1991)); TNF receptor (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med.* 174:1483-1489 (1991)); and IgE receptor a (Ridgway and Gorman, *J. Cell. Biol. Vol.* 115, Abstract No. 1448 (1991)).

In certain embodiments, LINGO-1 antibodies, antibody fragments, derivatives and variants thereof further comprise a targeting moiety. Targeting moieties include a protein or a peptide which directs localization to a certain part of the body, for example, to the brain or compartments therein. In certain embodiments, LINGO-1 antibodies, antibody fragments, derivatives and variants thereof are attached or fused to a brain targeting moiety. The brain targeting moieties are attached covalently (e.g., direct, translational fusion, or by chemical linkage either directly or through a spacer molecule, which can be optionally cleavable) or non-covalently attached (e.g., through reversible interactions such as avidin, biotin, protein A, IgG, etc.). In other embodiments, the LINGO-1 antibodies, antibody fragments, derivatives and variants thereof are attached to one more brain targeting moieties. In additional embodiments, the brain targeting moiety is attached to a plurality of LINGO-1 antibodies, antibody fragments, derivatives and variants thereof.

A brain targeting moiety associated with a LINGO-1 antibody, antibody fragment, derivative or variant thereof enhances brain delivery of such a LINGO-1 antibodies, antibody fragments, dervatives and variants thereof. A number of polypeptides have been described which, when fused to a protein or therapeutic agent, delivers the protein or therapeutic agent through the blood brain barrier (BBB). Non-limiting examples include the single domain antibody FC5 (Abulrob et al. (2005) *J. Neurochem.* 95, 1201-1214); mAB 83-14, a monoclonal antibody to the human insulin receptor (Pardridge et al. (1995) *Pharmacol. Res.* 12, 807-816); the B2, B6 and B8 peptides binding to the human transferrin receptor (hTfR) (Xia et al. (2000) *J. Virol.* 74, 11359-11366); the OX26 monoclonal antibody to the transferrin receptor (Pardridge et al. (1991) *J. Pharmacol. Exp. Ther.* 259, 66-70); and SEQ ID NOs: 1-18 of U.S. Pat. No. 6,306,365. The contents of the above references are incorporated herein by reference in their entirety.

Enhanced brain delivery of a LINGO-1 antibody, antibody fragment, derivative or variant thereof is determined by a number of means well established in the art. For example, administering to an animal a radioactively, enzymatically or fluorescently labeled LINGO-1 antibody, antibody fragment, derivative and variant thereof linked to a brain targeting moiety; determining brain localization; and comparing localization with an equivalent radioactively, enzymatically or fluorescently labeled LINGO-1 antibody, antibody fragment, deirvative or variant thereof that is not associated with a brain targeting moiety. Other means of determining enhanced targeting are described in the above references.

As discussed elsewhere herein, LINGO-1 antibodies, or antigen-binding fragments, variants, or derivatives thereof of the invention may be fused to heterologous polypeptides to increase the in vivo half life of the polypeptides or for use in immunoassays using methods known in the art. For example, in one embodiment, PEG can be conjugated to the LINGO-1 antibodies of the invention to increase their half-life in vivo. Leong, S. R., et al., *Cytokine* 16:106 (2001); *Adv. in Drug Deliv. Rev.* 54:531 (2002); or Weir et al., *Biochem. Soc. Transactions* 30:512 (2002).

Moreover, LINGO-1 antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Fusion proteins can be prepared using methods that are well known in the art (see for example U.S. Pat. Nos. 5,116, 964 and 5,225,538). The precise site at which the fusion is made may be selected empirically to optimize the secretion or binding characteristics of the fusion protein. DNA encoding the fusion protein is then transfected into a host cell for expression.

LINGO-1 antibodies or antigen-binding fragments, variants, or derivatives thereof of the present invention may be used in non-conjugated form or may be conjugated to at least one of a variety of molecules, e.g., to improve the therapeutic properties of the molecule, to facilitate target detection, or for imaging or therapy of the patient. LINGO-1 antibodies, or antigen-binding fragments, variants, or derivatives thereof of the invention can be labeled or conjugated either before or after purification, when purification is performed.

In particular, LINGO-1 antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared e.g. by reacting a binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the LINGO-1 antibodies, or antigen-binding fragments, variants, or derivatives thereof of the invention are prepared in an analogous manner.

The present invention further encompasses LINGO-1 antibodies, or antigen-binding fragments, variants, or derivatives thereof of the invention conjugated to a diagnostic or therapeutic agent. The LINGO-1 antibodies can be used diagnostically to, for example, monitor the development or progression of a neurological disease as part of a clinical testing procedure to, e.g., determine the efficacy of a given treatment and/or prevention regimen. Detection can be facilitated by coupling the LINGO-1 antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

A LINGO-1 antibody, or antigen-binding fragment, variant, or derivative thereof also can be detectably labeled by coupling it to a chemiluminescent compound. The presence of the chemiluminescent-tagged LINGO-1 antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which a LINGO-1 antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., *Diagnostic Horizons* 2:1-7 (1978)); Voller et al., *J. Clin. Pathol.* 31:507-520 (1978); Butler, J. E., *Meth. Enrymol.* 73:482-523 (1981); Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the LINGO-1 antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the LINGO-1 antibody, or antigen-binding fragment, variant, or derivative thereof, it is possible to detect the antibody through the use of a radioimmunoassay (RIA) (see, for example, Weintraub, B., *Principles of Radioimmunoassays, Seventh Training Course on Radioligand Assay Techniques*, The Endocrine Society, (March, 1986)), which is incorporated by reference herein). The radioactive isotope can be detected by means including, but not limited to, a gamma counter, a scintillation counter, or autoradiography.

A LINGO-1 antibody, or antigen-binding fragment, variant, or derivative thereof can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to a LINGO-1 antibody, or antigen-binding fragment, variant, or derivative thereof are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", *Immunol. Rev.* 62:119-58 (1982).

VII. Expression of Antibody Polypeptides

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide LINGO-1 antibodies, or antigen-binding fragments, variants, or derivatives thereof of the invention, the polynucleotides encoding the LINGO-1 antibodies are typically inserted in an expression vector for introduction into host cells that may be used to produce the desired quantity of LINGO-1 antibody.

Recombinant expression of an antibody, or fragment, derivative or analog thereof, e.g., a heavy or light chain of an antibody which binds to a target molecule described herein, e.g., LINGO-1, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthetic as discussed above. In one embodiment, this is effected using a proprietary expression vector of Biogen IDEC, Inc., referred to as NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the LINGO-1 antibodies, or antigen-binding fragments, variants, or derivatives thereof of the invention may be expressed using polycistronic constructs such as those disclosed in United States Patent Application Publication No. 2003-0157641 A1, filed Nov. 18, 2002 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of LINGO-1 antibodies, e.g., binding polypeptides, e.g., LINGO-1-specific antibodies or immunospecific fragments thereof in eukaryotic host cells. Compatible IRES sequences are disclosed in U.S. Pat. No. 6,193,980 which is also incorporated herein. Those skilled in the art will appreciate that such expression systems may be used to effectively produce the full range of LINGO-1 antibodies disclosed in the instant application.

More generally, once the vector or DNA sequence encoding a monomeric subunit of the LINGO-1 antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Vectors, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, W138, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527

(1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Prolocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding LINGO-1 antibodies, or antigen-binding fragments, variants, or derivatives thereof of the invention can also be expressed non-mammalian cells such as bacteria or yeast or plant cells. Bacteria which readily take up nucleic acids include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the heterologous polypeptides typically become part of inclusion bodies. The heterologous-polypeptides must be isolated, purified and then assembled into functional molecules. Where tetravalent forms of antibodies are desired, the subunits will then self-assemble into tetravalent antibodies (WO02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., Nature 282:39 (1979); Kingsman et al., *Gene* 7:141 (1979); Tschemper et al., *Gene* 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, *Genetics* 85:12 (1977)). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002 0123057 A1.

VIII. Treatment Methods Using Therapeutic LINGO-1 Antibodies

As described herein, LINGO-1 antibodies, or antigen-binding fragments, variants, or derivatives thereof of the invention can relieve NgR1-mediated inhibition of axonal extension that normally takes place in CNS neurons. This is beneficial in situations where axonal extension or neurite sprouting is needed in the brain or spinal cord. Spinal cord injury, including partial or complete crush or severance, exemplifies a situation in which axonal extension is needed, but is normally inhibited through operation of the Nogo pathway. Examples of diseases or disorders in which axonal extension and/or neurite sprouting in the brain would be beneficial include stroke, multiple sclerosis, and other neurodegenerative diseases or disorders such as multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, neuropathy, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, Bell's palsy, spinal cord injury and all neurological diseases related to neuronal cell death.

The inventors have further discovered that LINGO-1 is expressed in oligodendrocytes, and contributes to oligodendrocyte biology. Soluble derivatives of LINGO-1, certain polynucleotides (e.g. RNAi), as well as certain antibodies which specifically bind to LINGO-1, as described herein act as antagonists to LINGO-1 function in oligodendrocytes, promoting proliferation, differentiation and survival of oligodendrocytes and promoting myelination of neurons in vitro and in vivo. This is beneficial in for diseases, disorders or conditions involving demyelination and dysmyelination. Examples of diseases or disorders in which oligodendrocyte proliferation, differentiation and survival, and/or myelination or remyelination would be beneficial include multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, and Bell's palsy.

Accordingly, one embodiment of the present invention provides methods for treating spinal cord injury, diseases or disorders associated with inhibition of neuronal growth in the CNS, diseases or disorders associated with inhibition of oligodendrocyte growth or differentiation, and diseases involving demyelination or dysmyelination of CNS neurons in an animal suffering from such injury or disease or predisposed to contract such disease, the method comprising, consisting essentially of, or consisting of administering to the animal an effective amount of a LINGO-1 antibody, or antigen-binding fragment, variant, or derivative thereof.

A therapeutic LINGO-1 antibody to be used in treatment methods disclosed herein can be prepared and used as a therapeutic agent which promotes CNS neurite outgrowth, neuronal survival, axon guidance and axon regeneration, which promotes oligodendrocyte survival, growth, and/or differentiation, and which promotes myelination or remyelination of CNS neurons. Characteristics of suitable therapeutic LINGO-1 antibodies include: binding to LINGO-1 epitopes which result in blocking of LINGO-1 activity, binding to LINGO-1 with sufficient affinity to elicit a therapeutic effect, and binding to LINGO-1 preferentially to normal binding partners, e.g., Nogo Receptor.

Therapeutic LINGO-1 antibodies may be monoclonal, chimeric or humanized antibodies, or fragments of antibodies that bind specifically to LINGO-1. The antibodies may be monovalent, bivalent, polyvalent, or bifunctional antibodies. Antibody fragments include without limitation Fab F(ab')$_2$, and Fv fragments.

Therapeutic LINGO-1 antibodies, or antigen-binding fragments, variants or derivatives thereof according to the invention can be used in unlabeled or unconjugated form, or can be coupled or linked to drugs, labels or stabilization agents which may or may not exert additional therapeutic effects.

A specific dosage and treatment regimen for any particular patient will depend upon a variety of factors, including the particular LINGO-1 antibody, or antigen-binding fragment, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

In the methods of the invention the LINGO-1 antibodies, or antigen-binding fragments, variants or derivatives thereof may be administered directly to the nervous system, intracerebroventricularly, or intrathecally, e.g. into a chronic lesion of MS, as discussed in more detail below.

In various embodiments, a LINGO-1 antibody as described above is an antagonist of LINGO-1 activity. In certain embodiments, for example, binding of an antagonist LINGO-1 antibody to LINGO-1, as expressed on neurons, blocks myelin-associated neurite outgrowth inhibition or neuronal cell death. In other embodiments, binding of the LINGO-1 antibody to LINGO-1, as expressed on oligodendrocytes, blocks inhibition of oligodendrocyte growth or differentiation, or blocks demyelination or dysmyelination of CNS neurons.

In methods of the present invention, a LINGO-1 antibody, or an antigen-binding fragment, variant, or derivative thereof, in particular the LINGO-1 antibodies described herein, can be administered directly as a preformed polypeptide, or indirectly through a nucleic acid vector, to permit beneficial axonal outgrowth, promote oligodendrocyte proliferation, differentiation, and survival, and/or promote myelination or remyelination.

In certain embodiments, a subject may be treated with a nucleic acid molecule encoding a LINGO-1 antibody, or antigen-binding fragment, variant, or analog thereof, e.g., in a vector. Doses for nucleic acids encoding polypeptides range from about 10 ng to 1 g, 100 ng to 100 mg, 1 µg to 10 mg, or 30-300 µg DNA per patient. Doses for infectious viral vectors vary from 10-100, or more, virions per dose.

In some embodiments of the present invention a LINGO-1 antibody, or an antigen-binding fragment, variant, or derivative thereof is administered in a treatment method that includes: (1) transforming or transfecting an implantable host cell with a nucleic acid, e.g., a vector, that expresses a LINGO-1 antibody, or an antigen-binding fragment, variant, or derivative thereof; and (2) implanting the transformed host cell into a mammal, at the site of a disease, disorder or injury. For example, the transformed host cell can be implanted at the site of a spinal cord injury or at a site of dysmyelination. In some embodiments of the invention, the implantable host cell is removed from a mammal, temporarily cultured, transformed or transfected with an isolated nucleic acid encoding a LINGO-1 antibody, and implanted back into the same mammal from which it was removed. The cell can be, but is not required to be, removed from the same site at which it is implanted. Such embodiments, sometimes known as ex vivo gene therapy, can provide a continuous supply of the LINGO-1 polypeptide, localized at the site of site of action, for a limited period of time.

The methods for treating spinal cord injury, diseases or disorders associated with inhibition of neuronal growth in the CNS, diseases or disorders associated with inhibition of oligodendrocyte growth or differentiation, and diseases involving demyelination or dysmyelination of CNS neurons comprising administration of a LINGO-1 antibody, or antigen-binding fragment, variant, or derivative thereof of the invention are typically tested in vitro, and then in vivo in an acceptable animal model, for the desired therapeutic or prophylactic activity, prior to use in humans. Suitable animal models, including transgenic animals, are will known to those of ordinary skill in the art. For example, in vitro assays to demonstrate the therapeutic utility of LINGO-1 antibody described herein include the effect of a LINGO-1 antibody on a cell line or a patient tissue sample. The effect of the LINGO-1 antibody on the cell line and/or tissue sample can be determined utilizing techniques known to those of skill in the art, such as the assays disclosed elsewhere herein. In accordance with the invention, in vitro assays which can be used to determine whether administration of a specific LINGO-1 antibody is indicated, include in vitro cell culture assays in which a patient tissue sample is grown in culture, and exposed to or otherwise administered a compound, and the effect of such compound upon the tissue sample is observed.

Supplementary active compounds also can be incorporated into the compositions of the invention. For example, a LINGO-1 antibody, or antigen-binding fragment, variant, or derivative thereof of the invention may be coformulated with and/or coadministered with one or more additional therapeutic agents.

The invention encompasses any suitable delivery method for a LINGO-1 antibody, or antigen-binding fragment, variant, or derivative thereof of the invention to a selected target tissue, including bolus injection of an aqueous solution or implantation of a controlled-release system. Use of a controlled-release implant reduces the need for repeat injections.

IX. Pharmaceutical Compositions and Administration Methods

Methods of preparing and administering LINGO-1 antibodies, or antigen-binding fragments, variants, or derivatives thereof of the invention to a subject in need thereof are well known to or are readily determined by those skilled in the art. The route of administration of the LINGO-1 antibody, or antigen-binding fragment, variant, or derivative thereof may be, for example, oral, parenteral, by inhalation or topical. The term parenteral as used herein includes, e.g., intravenous, intraarterial, intraperitoneal, intramuscular, subcutaneous, rectal or vaginal administration. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, LINGO-1 antibodies, or antigen-binding fragments, variants, or derivatives thereof of the invention can be delivered directly to the site of the adverse cellular population thereby increasing the exposure of the diseased tissue to the therapeutic agent.

As previously discussed, LINGO-1 antibodies, or antigen-binding fragments, variants, or derivatives thereof of the invention may be administered in a pharmaceutically effective amount for the in vivo treatment of mammalian spinal cord injury, diseases or disorders associated with inhibition of neuronal growth in the CNS, diseases or disorders associated with inhibition of oligodendrocyte growth or differentiation, and diseases involving demyelination or dysmyelination of CNS. In this regard, it will be appreciated that the disclosed antibodies will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of a LINGO-1 antibody, or antigen-binding fragment, variant, or derivative thereof, conjugated or unconjugated, shall be held to mean an amount sufficient to achieve effective binding to a target and to achieve a benefit, e.g., to ameliorate symptoms of a disease or disorder or to detect a substance or a cell.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a LINGO-1 antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 (US-2002-0102208 A1), which is incorporated herein by reference in its entirety. Such articles of manufacture will preferably have labels or package inserts indicating that the associated compositions are useful for treating a subject suffering from, or predisposed to autoimmune or neoplastic disorders.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of a LINGO-1 antibody, or fragment, variant, or derivative thereof that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (e.g., a therapeutic or prophylactic response).

In keeping with the scope of the present disclosure, LINGO-1 antibodies, or antigen-binding fragments, variants, or derivatives thereof of the invention may be administered to a human or other animal in accordance with the aforementioned methods of treatment in an amount sufficient to produce a therapeutic effect. The LINGO-1 antibodies, or antigen-binding fragments, variants, or derivatives thereof of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of LINGO-1 antibodies, or antigen-binding fragments, variants, or derivatives thereof of the invention may prove to be particularly effective.

Effective doses of the compositions of the present invention, for treatment of spinal cord injury, diseases or disorders associated with inhibition of neuronal growth in the CNS, diseases or disorders associated with inhibition of oligodendrocyte growth or differentiation, and diseases involving demyelination or dysmyelination of CNS vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

For treatment of spinal cord injury, diseases or disorders associated with inhibition of neuronal growth in the CNS, diseases or disorders associated with inhibition of oligodendrocyte growth or differentiation, and diseases involving demyelination or dysmyelination of CNS with a LINGO-1 antibody, or antigen-binding fragment, variant, or derivative thereof, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

LINGO-1 antibodies, or antigen-binding fragments, variants, or derivatives thereof of the invention can be administered on multiple occasions. Intervals between single dosages can be daily, weekly, monthly or yearly. Intervals can also be irregular as indicated by measuring blood levels of target polypeptide or target molecule in the patient. In some methods, dosage is adjusted to achieve a plasma polypeptide concentration of 1-1000 µg/ml and in some methods 25-300 µg/ml. Alternatively, LINGO-1 antibodies, or antigen-binding fragments, variants, or derivatives thereof of the invention can be administered as a sustained release formulation, in which case less frequent administration is required. Dosage and frequency vary depending on the half-life of the antibody in the patient. The half-life of a LINGO-1 antibody can also be prolonged via fusion to a stable polypeptide or moeity, e.g., albumin or PEG. In general, humanized antibodies show the longest half-life, followed by chimeric antibodies and non-human antibodies. In one embodiment, the LINGO-1 antibodies, or antigen-binding fragments, variants, or derivatives thereof of the invention can be administered in unconjugated form, In another embodiment, the LINGO-1 antibodies, or antigen-binding fragments, variants, or derivatives thereof of the invention can be administered multiple times in conjugated form. In still another embodiment, LINGO-1 antibodies, or antigen-binding fragments, variants, or derivatives thereof of the invention can be administered in unconjugated form, then in conjugated form, or vice versa.

The compositions of the present invention may be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. As described previously, LINGO-1 antibodies, or antigen-binding fragments, variants, or derivatives thereof of the invention act in the nervous system to promote survival, proliferation and differentiation of oligodendrocytes and myelination of neurons and neuronal survival, axon regeneration and axon guidance. Accordingly, in the methods of the invention, the LINGO-1 antibodies, or antigen-binding fragments, variants, or derivatives thereof are administered in such a way that they cross the blood-brain barrier. This crossing can result from the physico-chemical properties inherent in the LINGO-1 antibody molecule itself, from other components in a pharmaceutical formulation, or from the use of a mechanical device such as a needle, cannula or surgical instruments to breach the blood-brain barrier. Where the LINGO-1 antibody is a molecule that does not inherently cross the blood-brain barrier, e.g., a fusion to a moiety that facilitates the crossing, suitable routes of administration are, e.g., intrathecal or intracranial, e.g., directly into a chronic lesion of MS. Where the LINGO-1 antibody is a molecule that inherently crosses the blood-brain barrier, the route of administration may be by one or more of the various routes described below. In some methods, antibodies are administered as a sustained release composition or device, such as a Medipad™ device. Delivery across the blood brain barrier can be enhanced by a carrying molecule, such as anti-Fc receptor, transferrin, anti-insulin receptor or a toxin conjugate or penetration enhancer.

The LINGO-1 antibodies, or antigen-binding fragments, variants, or derivatives thereof used in the methods of the invention may be directly infused into the brain. Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., "Direct brain infusion of glial cell line-derived neurotrophic factor in Parkinson disease," Nature Med. 9: 589-95 (2003); Scharfen et al., "High Activity Iodine-125 Interstitial Implant For Gliomas," Int. J. Radiation Oncology Biol. Phys. 24(4):583-91 (1992); Gaspar et al., "Permanent $^{125}$I Implants for Recurrent Malignant Gliomas," Int. J. Radiation Oncology Biol. Phys. 43(5):977-82 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," J. Neuro-Oncology 26:111-23 (1995).

The compositions may also comprise a LINGO-1 antibody dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., Biopolymers 22:547-56 (1985)); poly(2-hydroxyethyl-methacrylate), ethylene vinyl acetate (Langer et al., J. Biomed. Mater. Res. 15:167-277 (1981); Langer, Chem. Tech. 12:98-105 (1982)) or poly-D-(−)-3hydroxybutyric acid (EP 133,988).

In some embodiments of the invention, a LINGO-1 antibody, or antigen-binding fragment, variant, or derivative thereof of the invention is administered to a patient by direct infusion into an appropriate region of the brain. See, e.g., Gill et al., supra. Alternative techniques are available and may be applied to administer a LINGO-1 antibody according to the invention. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

LINGO-1 antibodies, or antigen-binding fragments, variants, or derivatives thereof of the invention can optionally be administered in combination with other agents that are effective in treating the disorder or condition in need of treatment (e.g., prophylactic or therapeutic).

X. Diagnostics

The invention further provides a diagnostic method useful during diagnosis of neronal disorders or injuries, which involves measuring the expression level of LINGO-1 protein or transcript in tissue or other cells or body fluid from an individual and comparing the measured expression level with a standard LINGO-1 expression levels in normal tissue or body fluid, whereby an increase in the expression level compared to the standard is indicative of a disorder.

LINGO-1-specific antibodies can be used to assay protein levels in a biological sample using classical immunohistological methods known to those of skill in the art (e.g., see Jalkanen, et al., *J. Cell. Biol.* 101:976-985 (1985); Jalkanen, et al., *J. Cell Biol.* 105:3087-3096 (1987)). Other antibody-based methods useful for detecting protein expression include immunoassays, such as the enzyme linked immunosorbent assay (ELISA), immunoprecipitation, or western blotting. Suitable assays are described in more detail elsewhere herein.

By "assaying the expression level of LINGO-1 polypeptide" is intended qualitatively or quantitatively measuring or estimating the level of LINGO-1 polypeptide in a first biological sample either directly (e.g., by determining or estimating absolute protein level) or relatively (e.g., by comparing to the cancer associated polypeptide level in a second biological sample). Preferably, LINGO-1 polypeptide expression level in the first biological sample is measured or estimated and compared to a standard LINGO-1 polypeptide level, the standard being taken from a second biological sample obtained from an individual not having the disorder or being determined by averaging levels from a population of individuals not having the disorder. As will be appreciated in the art, once the "standard" LINGO-1 polypeptide level is known, it can be used repeatedly as a standard for comparison.

By "biological sample" is intended any biological sample obtained from an individual, cell line, tissue culture, or other source of cells potentially expressing LINGO-1. Methods for obtaining tissue biopsies and body fluids from mammals are well known in the art.

LINGO-1 antibodies for use in the diagnostic methods described above include any LINGO-1 antibody which specifically binds to a LINGO-1 gene product, as described elsewhere herein.

XI. Immunoassays

LINGO-1 antibodies, or antigen-binding fragments, variants, or derivatives thereof of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, *Current Protocols in Molecular Biology*, John Wiley & Sons, Inc., New York, Vol. 1 (1994), which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, *Current Protocols in Molecular Biology*, John Wiley & Sons, Inc., New York, Vol. 1 (1994) at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, *Current Protocols in Molecular Biology*, John Wiley & Sons, Inc., New York Vol. 1 (1994) at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, *Current Protocols in Molecular Biology*, John Wiley & Sons, Inc., New York, Vol. 1 (1994) at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

LINGO-1 antibodies, or antigen-binding fragments, variants, or derivatives thereof of the invention, additionally, be employed histologically, as in immunofluorescence, immunoelectron microscopy or non-immunological assays, for in situ detection of cancer antigen gene products or conserved variants or peptide fragments thereof. In situ detection may be accomplished by removing a histological specimen from a patient, and applying thereto a labeled LINGO-1 antibody, or antigen-binding fragment, variant, or derivative thereof, preferably applied by overlaying the labeled antibody (or fragment) onto a biological sample. Through the use of such a procedure, it is possible to determine not only the presence of LINGO-1 protein, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for LINGO-1 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding to LINGO-1 or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled LINGO-1 antibody, or antigen-binding fragment, variant, or derivative thereof. The solid phase support may then be washed with the buffer a second time to remove unbound antibody. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of LINGO-1 antibody, or antigen-binding fragment, variant, or derivative thereof may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon reasonance (SPR) as performed on BIAcore offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE code No. BR-1001-86; BIAtechnology Handbook, version AB (reprinted 1998), BIACORE code No. BR-1001-84.

SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIAcore measurements monitor interactions directly as they happen. The technique is well suited to determination of kinetic parameters. Comparative affinity ranking is extremely simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIAcore investigations. The range of affinities measurable by this technique is very broad ranging from mM to pM.

Epitope specificity is an important characteristic of a monoclonal antibody. Epitope mapping with BIAcore, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIAcore are straightforward to carry out.

For example, one can use a capture molecule to bind the first Mab, followed by addition of antigen and second MAb sequentially. The sensorgrams will reveal: 1. how much of the antigen binds to first Mab, 2. to what extent the second MAb binds to the surface-attached antigen, 3. if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), *DNA Cloning*, D. N. Glover ed., Volumes I and II (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical-Immunology* (8th ed.), Appleton & Lange, Norwalk, Conn. (1994) and Mishell and Shiigi (eds), *Selected Methods in Cellular Immunology*, W.H. Freeman and Co., New York (1980).

Standard reference works setting forth general principles of immunology include *Current Protocols in Immunology*, John Wiley & Sons, New York; Klein, J., Immunology: *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunnology* 4$^{th}$ ed. Ed. Richard A. Goldsby, Thomas J. Kindt and Barbara A. Osborne, H. Freemand & Co. (2000); Roitt, I., Brostoff, J. and Male D., *Immunology* 6$^{th}$ ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, *Genes VIII*, Prentice Hall (2003); Harlow and Lane, Antibodies: *A Laboratory Manual*, Cold Spring Harbor Press (1988); Dieffenbach and Dveksler, *PCR Primer* Cold Spring Harbor Press (2003).

All of the references cited above, as well as all references cited herein, are incorporated herein by reference in their entireties.

EXAMPLES

Example 1

Identification of Anti-LINGO-1 Antibodies by Phage Display

Li13 and Li33 were identified as Fab-phages that specifically bound to LINGO-1 using phage display as described in PCT/US2006/026271, filed Jul. 7, 2006, which is herein incorporated by reference in its entirety. Li81 is derived from Li13 and Li33. It includes the Li13 light chain and an affinity matured heavy chain. The isolation of Li81 is described in more detail in PCT/US2008/000316, filed Jan. 9, 2008, which is incorporated herein by reference in its entirety. An aglycosylated fully human monoclonal antibody was created from the Li81 Fab, Li81 (agly), and its production is also detailed in PCT/US2008/000316. Li62 is derived from Li33. It includes the Li33 heavy chain and a light chain that was identified in a library screen.

The isolation of the Fab fragments is summarized briefly as follows. Fab fragments were isolated from phage display libraries as described in Hoet et al., *Nat. Biotech.* 23:34-348 (2005); Rauchenberger, et al., *J. Biol. Chem.* 278:194-205 (2003); and Knappik, et al., *J. Mol. Biol.* 296:57-86 (2000), all of which are incorporated herein by reference in their entireties.

Li62 and Li81 Fabs, as well as Li62 (agly) and Li8 (agly), have been purified and demonstrated to bind to specifically to LINGO-1 by both ELISA and FACS. Assays were performed as described in PCT/US2008/000316.

Example 2

Li62 and Li81 Promote Myelination In Vitro

The role of Li62 and Li81 in myelination was investigated in vitro by treating co-cultures of dorsal root ganglion (DRG)

neurons and oligodendrocytes with Li62 (agly) and Li81 (agly). The DRG nuerons were then tested for myelination using Western blotting. For these studies, it was necessary to first generate primary cultures of DRG neurons and of oligodendrocytes.

Female Long Evans rat E14-E17 embryonic dorsal root ganglia were cultured as described by Plant et al., *J. Neurosci.* 22:6083-91 (2002). Dissected DRGs were plated on poly-L-lysine-coated cover slips (100 μg/ml) for 2 weeks. The cells were incubated in the presence of fluorodeoxyuridine for days 2-6 and in NLA medium containing 1× B27, 100 ng/ml NGF (Gibco) for days 8-11.

Female Long Evans post-natal day 2 (P2) rat oligodendrocytes were cultured as described by Conn, *Meth. Neurosci.* 2:1-4 (Academic Press; 1990) with modifications as follows. Briefly, the forebrain was extirpated from P2 rats and placed in cold HBSS medium (Gibco). The tissue fragments were cut into 1 mm pieces and incubated at 37° C. for 15 min in 0.01% trypsin and 10 μg/ml DNase. Dissociated cells were plated on a poly-L-lysine coated T75 tissue culture flasks and grown in DMEM with 20% fetal bovine serum at 37° C. for 10 days. A2B5-positive oligodendrocytes were collected by shaking the flasks overnight at 200 rpm at 37° C. The A2B5 oligodendrocytes were cultured for 7 days in DMEM (Gibco) containing 25 mM D-glucose, 4 mM L-glutamine, 1 mM sodium pyruvate, 50 μg/ml human apo-transferrin, 5 μg/ml bovine pancreatic insulin, 30 nM sodium selenate, 10 nM hydrocortisone, 10 nM D-biotin, 1 mg/ml BSA, 10 ng/ml FGF and PDGF (Peprotech). The cells were then harvested by trypsinization. The cells then co-cultured with the DRG neurons in the presence or absence of 1.0, 0.30, 0.10, or 0.03 μg/ml of Li62 (agly) or Li81 (agly), or a negative control antibody (h5C8 Ctrl) in NLA medium containing 2% fetal bovine serum, 50 μg/ml ascorbic acid, 100 ng/ml NGF (Gibco). One of skill in the art would be able to determine an effective dose using assays described herein.

The culture medium was changed and the antibodies or antibody fragments were replenished every three days. After 3 weeks at 37° C., the co-cultured cells were lysed and subjected to Western blot analysis to quantify the MBP and MOG (FIG. 1). Based on Western blot analyses, co-cultured cells treated with Li62 (agly) and Li81 (agly) showed increased levels of both MBP and MOG compared to control-antibody treated co-cultures. Similar results were obtained using Li62 and Li81 Fabs. These data suggest that both Li62 and Li81 can promote myelination in vitro and can promote mature oligodendrocyte axon interactions and myelination compared to control-antibody treated co-cultures.

Example 3

Li62 and Li81 Variants

In order to identify antibodies with improved affinity, Li62 and Li81 variants were isolated by targeted phage display. The variants included alterations in the amino acid sequence of the VH CDR3 sequence in each of the Fabs. Eighteen Li62 variants had improved affinities as shown below in Table 5.

TABLE 5

| Li62 Variants | | | | | | | | | | | | | | |
|---|---|---|---|---|---|---|---|---|---|---|---|---|---|---|
| Li62 Variant | Fold-Improvement | SEQ ID NO | \multicolumn{10}{c}{Li62 Heavy Chain CDR3 Sequence} | ELISA Signal | Reps |
| | | | E | G | H | N | D | W | Y | F | D | L | | |
| B06 | 8 | 17 | | | | | | Y | Y | | | Q | 3 | |
| B12 | 8 | 18 | | | | | Q | | Y | | V | | 3 | |
| F06 | 12 | 19 | | | | | D | | Y | | | | 3 | 12 |
| B01 | 8 | 20 | | | | | Q | | Y | | | | 3 | |
| D09 | 15 | 21 | | | A | | D | I | | F | | | 3 | |
| D12 | 8 | 22 | | | | | | | Y | | | | 3 | 26 |
| F01 | 9 | 23 | | | | | R | | Y | | P | | 3 | |
| F02 | 8 | 24 | | | | | D | | Y | | | | 3 | |
| F06 | 8 | 25 | | | | | R | | Y | | | | 3 | 2 |
| F10 | 5 | 26 | | | S | | | I | R | | | | 3 | |
| G08 | 10 | 27 | | | | | Q | | Y | | V | | 3 | 4 |
| H08 | 6 | 28 | | | | | Y | N | G | | | | 0.5 | |
| C10 | 11 | 29 | | | | | Y | | Y | | | | 3 | 4 |
| C02 | 8 | 30 | | | | | T | | Y | | | L | 3 | |
| D05 | 10 | 31 | | | | | Y | | Y | | E | | 3 | 2 |
| F02 | 16 | 32 | | | | | L | I | | F | | Q | 3 | |
| C10 | 9 | 33 | | | | | Q | F | | | | | 3 | |
| H08 | 9 | 34 | | | | | T | | Y | | | | 3 | |

Additionally, fifteen Li81 variants had improved affinities as shown below in Table 6.

TABLE 6

Li81 Variants

| Li81 variant | Fold-Improvement | SEQ ID NO | Li81 Heavy Chain CDR3 Sequence | | | | | | | | | ELISA Signal | Reps |
|---|---|---|---|---|---|---|---|---|---|---|---|---|---|
| | | | E | G | D | N | D | A | F | D | I | | |
| F09 | 9 | 35 | E | | | | | | | | V | 2.5 | |
| G02 | 6 | 36 | | | | | | | Y | T | | 3 | |
| H03 | 9 | 37 | | | T | | | | | | | 3 | |
| A12 | 15.1 | 38 | | | | | | | | | S | 2.6 | |
| C02 | 6 | 39 | | | | | | | | | T | 2.8 | 2 |
| C11 | 15.1 | 40 | | | | | | | Y | R | | 2 | |
| D11 | 6 | 41 | | | | | | V | | S | | 2.1 | |
| E05 | 15 | 42 | | | | D | | V | | | M | 2.9 | |
| H04 | 6 | 43 | | | Y | | | | F | | | 3 | |
| B04 | 8 | 44 | | | D | | | Y | | | M | 3 | |
| A02 | 8 | 45 | Q | | Y | | T | Y | | | L | 3 | |
| B12 | 6 | 46 | | | D | | | | | T | | 3 | |
| H06 | 6 | 47 | A | | D | | | | | | | 3 | |
| H08 | 6 | 48 | E | | | | | | | | M | 3 | |
| E07 | 6 | 49 | E | | Y | | T | Y | | | | 3 | |

Example 4

Li81 Promotes Rat Oligodendrocyte Differentiation

The ability of Li81 to promote the differentiation of rat A2B5+ progenitor cells into mature MBP+ myelinating oligodendroctyes was tested. This process was studied in vitro by plating primary rat forebrain A2B5+ cells into 24-well culture plates, treating cultures for 72 hr with Li81 (agly), and staining cultures for myelin basic protein (MBP) expression by Western blotting. In Western blots, myelin oligodendrocyte glycoprotein (MOG) expression was also used as a marker for maturation.

Treatment with Li81 (agly) resulted in more highly differentiated, mature oligodendrocytes as evidenced by increases in the length of cell processes and the presence of abundant myelin sheet structures that are stained by the anti-MBP antibody. A dose-dependent increase in number of mature oligodendrocytes was observed. The lowest concentration of Li81 (agly) with a detectable effect on MBP production was 0.1 µg/mL. A small percentage of less differentiated oligodendrocytes was seen in the control antibody treated cells. By Western blotting, there was a dose-dependent increase in MBP and MOG expression in the Li81 (agly) treated samples (FIG. 2). No expression was observed with the isotype control antibody at any concentration. The complex pattern of MBP bands results from alternatively spliced forms of the MBP protein. Similar results were obtained using Li81 Fab. These results indicate that Li81 can promote differentiation of rat A2B5+ progenitor cells into mature MBP+ myelinating oligodendroctyes in vitro.

Example 5

Li81 Promotes Human Oligodendrocyte Differentiation

The ability of Li81 to promote differentiation of human oligodendrocyte precursor cells (OPC) was also evaluated. As with rat OPCs, Li81 Fab and Li81 (agly) had a dramatic effect on the human OPC cultures and resulted in the formation of highly differentiated, mature oligodendrocytes as evidenced by increases in the length of cell processes and the presence of abundant myelin sheet structures that are stained by the anti-MBP antibody. The number of human OPCs that were MBP+ after treatment with a control antibody (hIgG1) or Li81 (agly) is shown in FIG. 3. Only a small percentage of less differentiated oligodendrocytes was seen in the control antibody (hIgG1) treated cells (FIG. 3). Similar results were obtained using Li81 Fab.

Example 6

Li81 Promotes Remyelination in Lysolecithin-Treated Brains

The cerebellar slice culture system is an in vitro model for analyzing mechanisms of remyelination. Coronal cerebellar slices from P17 rats approximately 300 µm thick were placed in tissue culture medium for 4 days, then treated with lysolecithin for 24 hours to induce demyelination and incubated with medium containing Li81 (agly) (30, 10, 3, and 1 μg/ml) or an isotype-matched control antibody (5c8) for 3 days to allow remyelination to occur. Remyelination was visualized by black gold immunostaining, which selectively stains myelin in brain slices. In black gold stained sections, myelinated white matter appears dark brown and demyelinated lesions appear as pale brown or white.

Treatment of the brain slices with lysolecithin resulted in almost complete demyelination of the tissue as evidenced by loss of staining in the control antibody treated culture. Li81 (agly) treatment resulted in robust remyelination as evidenced from the reappearance of the staining. The immunohistochemistry data were quantified by measuring the intensity of the black gold staining as summarized in the bar graph of FIG. 4. Treatment with Li81 (agly) resulted in approximately a 30-fold increase in myelinated tissue over the level seen in the control treated brain slice. The overall level of remyelination following Li81 (agly) treatment was approximately half of that observed without any demyelination treatment. Similar results were obtained using Li81 Fab.

Example 7

Decreased Binding of Aglycosylated Anti-LINGO-1 Antibody to Fc(Gamma) Receptors

Relative binding affinities of IgG for human Fc receptors (CD16, CD32a and b, CD64) were measured using the Amplified Luminescent Proximity Homogeneous Assay (ALPHA) technology from Perkin Elmer. The assay was performed in a competitive format in which serial dilutions of test antibodies were incubated with the receptor-GST fusion proteins and anti-GST acceptor beads overnight at 40° C. in a 96-well plate. Streptavidin donor beads and biotinylated wild-type IgG1 were also incubated overnight at 40° C. in a separate tube and then added to the assay plate the next day. The plates were incubated at room temperature for 2 hours with gentle shaking and read in an Envision plate reader (Perkin Elmer). The data were plotted to a 4-parameter curve fit using Graphpad Prism software to calculate the $IC_{50}$ values in order to determine the relative binding affinities. The antibodies tested were Li81 (agly), an isotype-matched control antibody (5c8) and an aglycosylated version of the control antibody. The data are plotted in FIG. 5. The $IC_{50}$ values of Li81 (agly) were calculated as follows: CD32a: 365 μg/mL (down 60× from wt), CD32b: 350 μg/mL (down 15× from wt), CD16: 179 μg/mL (down 50× from wt), and CD64: >100 μg/mL (down >100× from wt).

The ability of Li81 (agly) to bind certain Fc(gamma) receptors was also evaluated in a cell bridging assay. For these studies, CHO cells expressing human LINGO-1 were plated into 96-well tissue culture plates, then incubated with serial dilutions of test samples, and with BCECF-AM labeled U937 cells that naturally express both CD64 (FcgR1) and CD32 (FcgRIIa). Bound U937 cells were quantified by fluorescence (ex485/em530) using a cytofluor plate reader. Anti-LINGO-1 monoclonal antibodies Li33 and Li13 that bind LINGO-1 with nM $EC_{50}$ values and contain wild type Ig1 frameworks showed typical sigmoidal binding curves with $EC_{50}$ values of 0.17 and 0.23 μg/mL, respectively (FIG. 6). In contrast, Li81 (agly) showed a very poor bridging response, consistent with a reduction in the affinity of the aglycosylated framework for CD64 and CD32. The shift in dose response is consistent with a >10 fold drop in binding. Control huIg1 showed no bridging activity.

Example 8

Aglycosylated Anti-LINGO-1 Antibody does not Promote Complement Activation

The effect of the aglycosylated variant of IgG1 antibodies on reducing C1q binding and activation of the complement pathway are well documented. To verify these effects on the Li81 (agly) antibody, the antibody was tested for C1q binding in an ELISA format and for complement-dependent cytotoxicity (CDC) in CHO cells expressing human LINGO-1. For the CDC assay LINGO-1 and Lt-beta (positive control) expressing CHO cells were treated with serial dilutions of anti-LINGO-1 antibodies or LtbetaR-Fc, low toxicity rabbit serum complement and propidium iodide and assayed for killing. Li81 (agly) did not elicit a cytotoxic response whereas the LtbetaR-Fc reagent promoted a robust killing response (FIG. 7). To date no measurable cytotoxic response in the CDC assay has been observed with any LINGO-1 targeted reagent including Li33 or Li13 as intact Ig1 anti-LINGO-1 Mabs (shown in FIG. 7) or aggregated 1A7 Ig1.

Example 9

Anti-LINGO-1 Antibodies Promote Myelination In Vivo in Lysolecithin Assay

The lysolecithin (LPC)-induced demyelination model is a simple in vivo system for investigating remyelination. LPC was injected into the dorsal column of 9 week old adult female Sprague Dawley rats (250 g) on day 0. Demyelination occurred within a few hours following LPC treatment. Li81 (agly) or a control antibody was administered IP on day 3. The animals were sacrificed on day 9, and the region of the spinal cord encompassing the lesion was excised and sectioned.

Sections from control antibody-treated animals showed large lesions with extensive areas of demyelination as evident from the absence of stain in the lesion area. Smaller lesions were apparent in Li81 (agly)-treated rats and the lesions contained lace-like structures representative of the remyelinated axons (FIG. 8). In subsequent studies, the model was run with Li81 (agly) at 2, 1, and 0.3 mg/kg. The 2 and 1 mg/kg doses of Li81 (agly) were highly efficacious, while effects from the 0.3 mg/kg treated animals were less efficient. These results demonstrate that anti-LINGO-1 antibodies promote myelination in vivo in a dose dependent manner.

In a similar experiment, lysolecithin-treated rats are administered 2, 1, and 0.3 mg/kg of Li62 (agly) antibody on day 3 instead of Li81 (agly). Animals are sacrificed on day 9, and the region of the spinal cord encompassing the lesion is excised and sectioned. Sections are analyzed to compare lesion size and myelination in animals treated with Li62 (agly) to lesion size and myelination in animals treated with a control antibody.

Example 10

Anti-LINGO-1 Antibodies Promote Myelination In Vivo in MOG-EAE Assay

Myelin oligodendrocyte glycoprotein (MOG)-induced murine experimental autoimmune encephalomyelitis (EAE) is a widely accepted model for studying the clinical and pathological features of multiple sclerosis and has been described in more detail in PCT/US2008/000316, filed Jan. 9, 2008, which is incorporated by reference herein. Li81 (agly)

was tested in the EAE model to determine if inhibition of endogenous LINGO-1 function promotes functional recovery.

Adult 9-week-old brown Norway female rats (150 g) were injected with 75 μg recombinant rat MOG (amino acids 1-125) in PBS. Animals developed signs of EAE at 15 days. Li81 (agly) treatment or isotype control (3 mg/kg) was injected IP at days 15, 18, 21, 24 and 27 (10 rats per group). The EAE clinical score was measured daily for 2 weeks. As shown in FIG. 9, Li81 (agly) promotes functional recovery in this model by improving hind limb and tail movement.

In a similar experiment, MOG-treated rats are injected with Li62 (agly) or an isotype control at days 15, 18, 21, 24 and 27. The EAE clinical score is measured daily for 2 weeks to assess hind limb paralysis, complete tail paralysis and distal tail paralysis, and the paralysis in animals treated with Li62 (agly) is compared to paralysis in animals treated with the control antibody.

Example 11

Testing the Effect of LINGO-1 Antibodies and Fragments Thereof on Oligodendrocytes in an In Vivo Cuprizone Model In order to determine if Li62, Li81, and variants thereof promote myelination in vivo adult mice are fed cuprizone (0.2% milled with ground mouse chow by weight) for 6 weeks to induce demyelination within the corpus callosum according to the method described by Morell P et al., *Mol Cell Neurosci.* 12:220-7 (1998) and in PCT/US2008/000316, filed Jan. 9, 2008, which is incorporated herein by reference in its entirety. Briefly, an anti-LINGO-1 Li62 or Li81 monoclonal antibody, Fab, or a variant thereof, is stereotactically injected into the demyelinating corpus callosum at weeks 2, 2.5, and 3 weeks of cuprizone feeding. Control mice are stereotactically injected at the same intervals with sterilized media containing control antibody. After the 6 weeks of cuprizone feeding is completed, the mice are returned to a normal diet for 2, 4 and 6 weeks to allow remyelination.

The animals receiving anti-LINGO-1 antibody treatment are evaluated for mature oligodendrocyte survival (based on CC1 antibody staining) and axon myelination by IHC using anti-MBP protein antibody or luxol fast blue. CC1 antibody-positive oligodendrocytes are quantitated at four weeks and six weeks. Increased CC1 and/or MBP levels indicate that the antibodies promote mature oligodendrocyte survival and axon myelination.

Example 12

Testing the Effect of LINGO-1 Antibodies and Fragments Thereof on Retinal Ganglion Cell Survival in the Optic Nerve Transection Model Anti-LINGO-1 antibodies are tested in an optic nerve transection model, which investigates factors that affect neuronal function. The right optic nerve of an adult rat is transected intraorbitally 1.5 mm from the optic disc. A piece of gelfoam soaked with 6% Fluoro-Gold (FG) is applied to the newly transected site right behind the optic disc to label the surviving retinal ganglion cells (RGCs). The animals are divided into three groups which receive Li81 or Li62 monoclonal antibodies, Fabs, variants thereof, a control antibody, or PBS, by intravitreal injection. The volume of each intravitreal injection is 4 μl while the dosage of each injection is 2 μg. The intravitreal injections are performed immediately after the optic nerve transection.

All animals are allowed to survive for 1 week. Two days before sacrificing the animals, the left optic nerve of each animal is transected and 6% FG is administered as described above to label the surviving RGCs, to serve as the internal control. Animals are sacrificed with an overdose of Nembutal and the retinas are dissected in 4% paraformaldehyde. Four radial cuts are made to divide the retinas into four quadrants (superior, inferior, nasal and temporal). The retinas are then post-fixed in the same fixative for 1 hour before they are flat-mounted with the mounting medium (Dako). The slides are examined under a fluorescence microscope using an ultraviolet filter (excitation wavelength=330-380 nm). Labeled RGCs are counted along the median line of each quadrants starting from the optic disc to the peripheral border of the retina at 500 μm intervals, under an eyepiece grid of 200×200 μm$^2$. The percentage of surviving RGCs resulting from each treatment is expressed by comparing the number of surviving RGCs in the injured eyes with their contra-lateral eyes. Effective antibodies show increased neuronal survival when compared to control-antibody or PBS treated animals.

Example 13

Testing LINGO-1 Antibodies for Remyelination in the Optic Nerve Crush Model

The right optic nerve is completely crushed by #5 forceps for 10 seconds around 1.5 mm behind the eyeball intraorbitally just before administration of 2 μl of Li62 or Li81 monoclonal antibody, Fab, or a variant thereof, in 2 ml by intravitreal injection.

The animals receive a second intravitreal injection of the same treatment one week after the surgery. Two weeks after the surgery, the animals are perfused with EM fixatives, postfixed and processed for semithin and ultrathin sections. The longitudinal optic nerve sections are stained and prepared for myelin observation. The myelination of the proximal and the distal parts of the crushed optic nerve are compared among different treatment groups. Animals treated with Li62 or Li81 monoclonal antibody, Fab, or variants thereof will be analyzed for remyelination in the distal part of the optic nerve compared to the controls.

Example 14

Testing LINGO-1 Antibodies for Axon Regeneration in the Optic Nerve Crush Model

The right optic nerve is crushed by #5 forceps for 10 seconds around 1.5-2 mm behind the eyeball intraorbitally just before administration of 2 μg of Li62 or Li81 monoclonal antibody, Fab, or a variant thereof in PBS via intravitreal injection. Control animals are administered a control antibody or PBS. The animals receive a second intravitreal injection of the same treatment one week after the surgery. Three days prior to sacrifice of the test animals (day 11 of the experiment), 2 ml of CTB-FITC is injected intravitreally to label, anterograde, the regenerative optic nerve axons. On the 14th day post surgery, the animals are perfused and postfixed. The crushed optic nerve is processed for frozen longitudinal sections. The CTB-FITC labeled axons, which cross the lesion site are counted as regenerative fibers at various distances beyond the crush site. The regeneration of axons in animals treated with Li62 or Li81 monoclonal antibody, Fab, or a variant thereof and compared to control animals.

Example 15

Identification and Characterization of Li113

Li62 variant C02, also called Li113, was elected for further study. A LINGO-1 ELISA assay demonstrated that the Li113 Fab bound to LINGO-1 with an EC50 of 0.09 nM. The EC50 measurements of the Li33 Fab, the Li62 Fab, and Li81 Fab were 0.30 nM, 0.26 nM and 0.11 nM, respectively in the same experiment (FIG. 10). The Li113 Fab was also tested in the oligodendrocyte differentiation assay. The assay was performed essentially as described above in Example 2, but MBP levels were measured by ELISA. The results for a control monoclonal antibody, the Li81 monoclonal antibody, the Li62 Fab, and the Li13 Fab are shown in FIG. 11. These data demonstrate that Li113 can effectively bind to LINGO-1 and promote oligodendrocyte differentiation.

Example 16

Isotype Switching to Improve Antibody Solubility A2B5+ progenitor cells into mature MBP+ myelinating oli The anti-LINGO-1 Li33 Fab was converted into a full human antibody and expressed in mammalian cells. Three different IgG frameworks (Ig1, Ig2, and Ig4) were evaluated both in wildtype and aglycosyl forms. For the Ig2 framework, the V234A/G237A mutation was also evaluated as an alternative to the glycosylation site mutation to eliminate FcRIIa binding. Native human kappa light chain and heavy chain signal peptides were used to direct secretion of Li33 light and heavy chains, respectively, in mammalian cell hosts. The variable domain fragment of the light chain was subcloned into a shuttle vector containing the intact signal peptide and light chain kappa chain constant region. The variable domain fragment of the heavy chain was subcloned into shuttle vectors containing the intact signal peptide and Ig1, Ig1agly, Ig4, Ig4agly, Ig2, Ig2agly, and Ig2 V234A/G237A heavy chain constant region.

Each of the generated antibodies showed typical antibody features by SDS-PAGE gel analysis under both reducing and non-reducing conditions. In addition, the ability of each of the isotypes to bind LINGO-1 was assessed in an ELISA format. ELISA plates were coated with LINGO-1, treated with serial dilutions of each antibody, and bound Li33 was detected with an alkaline phosphatase anti-human Fab conjugate. The seven Mabs showed similar EC50 values for binding to LINGO-1 (Table 7) with apparent affinities of 0.12 nM for the Ig1 wt and agly, ~0.24 nM for Ig2 and Ig2agly, and ~0.36 nM for Ig4 and Ig4agly.

TABLE 7

Impact of Li33 Ig frameworks on solubility.

| Li33 Isotype | Solubility (mg/mL) | LINGO-1 binding EC50 (nM) | Stability ° C. TM1 | Stability ° C. TM2 | SEC % monomer |
|---|---|---|---|---|---|
| Ig1 | 0.9 | 0.12 | 69 | 76 | 99 |
| Ig1agly | 0.3 | 0.12 | 60 | 77 | >99 |
| Ig4 | >30 | 0.35 | 64 | 72 | 98 |
| Ig4Pagly | 0.3 | 0.37 | 56 | 73 | 95 |
| Ig2 | >50 | 0.23 | 69 | 76 | 96 |
| Ig2agly | 0.2 | 0.26 | 59 | 76 | 98 |
| Ig2-V234A/G237A | 5.6 | 0.19 | 69 | 76 | 95 |
| Ig1 Fab2 | 0.3 | 0.10 | — | 77 | 98 |
| Ig2 Fab2 | >50 | 0.39 | — | 77 | 98 |
| Ig1 Fab | >50 | 0.68 | — | 76 | 95 |
| PEG-Fab | >50 | 1.9 | — | 77 | 98 |
| Ig1agly reduced | >40 | 0.12 | 55 | 75 | 98 |
| Ig1 reduced | >50 | 0.15 | 63 | 75 | 98 |
| Ig1 pH 7.0 | 0.9 | 0.08 | 68 | 77 | |

TABLE 7-continued

Impact of Li33 Ig frameworks on solubility.

| Li33 Isotype | Solubility (mg/mL) | LINGO-1 binding EC50 (nM) | Stability ° C. TM1 | Stability ° C. TM2 | SEC % monomer |
|---|---|---|---|---|---|
| Ig1 pH 6.5 | 1.7 | 0.10 | 69 | 77 | |
| Ig1 pH 6.0 | 2.4 | 0.10 | 69 | 78 | |
| Ig1 pH 5.5 | 30 | 0.16 | 66 | 81 | |
| Ig1 pH 5.0 | >50 | 0.45 | 66 | 81 | |
| Ig1 pH 4.5 | >50 | 2.1 | 62 | 82 | |
| Ig1 pH 4.0 | >50 | 16 | 54 | 78 | |
| Ig1 pH 3.5 | >50 | 34 | 46/66 | 74 | |
| Ig1 pH 3.0 | >50 | ND | 34/52 | 72 | |

The solubility of the isoforms was assayed as follows. Samples were buffer exchanged using multiples cycles of concentration and dilution in centrifugation YM30 filter devices. Protein concentration was determined immediately after concentration from absorbance scans and again after 5 days at 4° C. following filtration through a 0.45 μm filter. If the absorbance had decreased, samples continued to be monitored over time at 4° C. When possible, samples were concentrated to 50 mg/mL; however, some of the purified constructs were only concentrated to the amount indicated due to small sample size.

All three of the aglycosyl antibodies had poor solubility at pH 7.0 with extensive precipitation at concentrations greater than 0.3 mg/mL Mab. The solubility of the Ig1 wt Mab was slightly improved (0.9 mg/mL) while the Ig2 and Ig4 Mabs were soluble at the highest concentration tested. The solubility of the Ig2 Mab was >50 mg/mL, representing a >150 fold increase over the aglycosyl version of the same construct. The Ig2 V234A/G237A variant was intermediate in terms of its solubility. Below the solubility limits, the antibodies were stable to prolonged storage at 4° C. and to freeze-thaw.

Since the solubility of a protein can be significantly reduced at pH near its isoelectric point (pI), pI values for the Li33 Mabs were determined by isoelectric focusing. Samples were subjected to isoelectric focusing on a pH 3-10 IEF minigel (Invitrogen). Elecrophoresis was carried out at 100V for 1 hour, 200V for 1 hour and 500V for 30 minutes. The gel was fixed, stained with Coomassie brilliant blue R-250, and destained. All of the antibodies had basic isoelectric points with pI values >pH 8.2. The pI values for both the Ig1 and Ig1agly Li33 were ~9.0, for Ig4 and Ig4agly Li33 were 8.2, and for Ig2, Ig2agly, and Ig2 V234A/G237A were 8.5.

The aggregation state of the antibodies was studied by size exclusion chromatography (SEC). SEC was performed on a Superdex 200 FPLC column using 20 mM sodium phosphate pH 7.2 and 150 mM NaCl as the mobile phase. The column was run at 0.3 mL/min. The column effluent was monitored by UV detection at 280 nm, and purity was assessed by peak height. All constructs eluted as a single prominent peak with an apparent molecular mass of 150 kDa with >95% purity (Table 7). Selected profiles are shown in FIG. 12. The soluble fraction for the Ig1agly by SEC was >99% monomer with no evidence of soluble aggregates. In contrast, the Ig2 contained 2% dimer and 2% higher molecular mass aggregates. The aggregation state of Li33 Ig2 was further evaluated by analytical ultracentrifugation (FIG. 13), which revealed that the antibody actually formed reversible dimers at high concentrations. Thus, while the Ig2 framework prevented the transition to an insoluble aggregate, it had not ablated all protein-protein interactions.

The stability of a protein can also impact its solubility. The thermal stability of the constructs was measured by differential scanning fluorometry (DSF). Measurements were conducted on an Mx3005p real-time PCR system (Agilent Technologies) in a 96-well format using 10 μg of protein in 50-55 μL phosphate buffer (at neutral pH) supplemented with SYPRO orange fluorophor (Invitrogen) at a final concentration of 10×. Samples were heated from 25° C. to 95° C. at 1° C./min with fluorescence intensity measured 3 times every 1° C. Fluorescence intensities were plotted as a function of temperature. Melting temperatures (Tm) were derived from these curves by taking the negative derivative ("—R'(T)" in the Mx3005p software) and selecting the local minima of the derivative plots. For DSF measurements at various pH values, 10 mM sodium citrate was used as the buffering agent.

Tm values for the Fab region (TM2) were 76-77° C. for the Ig1 and Ig2 constructs and 72-73° C. for the Ig4 wt and agly. TM1 values for the CH2 region were variable. Transitions were 8-10° C. lower for each of the agly constructs. The Ig4 constructs were the least stable. The stability of Li33 Ig1 and Li33 Ig2 was also studied using guanidine denaturation as an alternative to thermal denaturation to assess stability. FIG. 14. The denaturation curve for the Ig1 was monophasic with a transition point of 3.1 M guanidine. The denaturation curve for the Ig1 Fab was similar to that for the intact Mab. Reduction of the Ig1 Fab shifted the transition point to 1.8 M guanidine. Li33 Ig2 denatures at a higher guanidine concentration than the Ig 1 with a 50% transition point of 4.1 M. The shape of the curve suggests there may be several transitions.

To further assess features of the antibodies that were affecting solubility a variety of conditions and fragmentation were tested (Table 7). Fab2 fragments of Ig1 and Ig2 were generated enzymatically with pepsin, and a Fab fragment of Ig1 was generated with papain. The solubility of the Ig2 Fab was >50 mg/mL, whereas the solubility of the Ig1 Fab2 was only 0.3 mg/mL. The solubility of the Ig1 Fab was >50 mg/mL.

A pegylated version of the Fab was also generated. For pegylation, Ig1 Fab2 at 1.2 mg/mL in 40 mM sodium borate pH 7.0 and 0.1 mM TCEP was incubated for 75 min at 37° C. The reduced sample was desalted on a G25M column that had been equilibrated in 5 mM MES pH 5.0 and 50 mM NaCl (final Fab concentration 0.5 mg/mL). After storage overnight at 4° C., over 90% of the disulfide bond holding the heavy and light chain together had reoxidized to a Fab' leaving the 2 hinge Cys residues free for conjugation. 10 kDa methoxypolyethyleneglycol maleimide (PEGmal) (Nektar) was added to 0.4 mg/mL, and MES pH 6.0 was added to 25 mM. The sample was incubated at room temperature for 2.5 hours and overnight at 4° C. The sample was then subjected to cation exchange chromatography on a Fractogel EMD sulfate column. The column was washed with 2 column volumes of 10 mM sodium phosphate pH 6.0, and the PEG-Fab was eluted with 10 mM sodium phosphate pH 6.0 and 50 mM NaCl. The pegylated version also had excellent solubility (Table 7).

Fragmentation had little impact on stability. No TM1 signal was observed for the Fab2 and Fab moieties as expected, since the TM1 transition is produced from the CH2 domain. Differences in LINGO-1 binding were consistent with the nature of the products as the three monvalent versions had reduced binding. Reduction of the interchain disulfides that link the heavy-heavy and heavy-light chains also had a very dramatic affect on solubility. After reduction, the Li33 Ig1 and Ig1agly Mabs were soluble at the highest concentration tested (Table 7). Reduction had only a slight effect on thermal stability and had no impact on aggregation state or LINGO-1 binding.

Finally, the effect of pH on solubility was tested. A dramatic transition in the solubility of Li33 Ig1 occurred between pH 6 and pH 5.5. Below pH 5.5 the protein was very soluble, and above pH 5.5, it had poor solubility. Thermal stability and LINGO-1 binding were reduced under the more acidic conditions that had improved solubility.

Example 17

Disulfide Bond Mapping

The disulfide structure of Li33 Ig2 was determined by peptide mapping. In these experiments, alkylation of Li33 Ig2 was done under denaturing and non-reducing conditions. 5 uL of 100 mM idoacetamide solution was added to 25 μL of the solution containing ~22.5 μg of the protein, and 25 mg of guanidine hydrochloride was immediately added to the solution. The solution was kept at room temperature in the dark for 30 minutes. The alkylated proteins were recovered by precipitation in cooled ethanol. The solution was stored at −20° C. for 1 hour and then centrifuged at 20,000 g for 12 min at 4° C. The alkylated and recovered proteins were digested with 20% (w/w) of endo-Lys-C in 2 M urea and 0.6 M Tris-HCl pH 6.5 for 8 hours at room temperature. Then 5% (w/w) of trypsin was added to the solution, and the solution was kept overnight at room temperature. Another aliquot of 5% of trypsin was added the second morning, and the solution was kept at room temperature for an additional 4 hours. Prior to analysis of the digests, 50 μL of freshly prepared 8 M urea was added to the digest, and the solution was split into two parts: one was analyzed after reduction, which was done by incubating the digest with 40 mM DTT at 37° C. for 1 hour; the other part was not reduced before analysis. The reduced and non-reduced digests were analyzed on an LC-MS system comprised of a reversed-phase HPLC (Alliance, Waters, Milford Mass.) and an LCT mass spectrometer (Waters Corp., Milford, Mass.). The separation was carried out on a 1.0 mm×15-cm Vydac C4 column (214TP5115) using a flow rate of 0.07 mL/min. The mobile phase A was water with 0.03% trifluoroacetic acid, and mobile phase B was acetonitrile with 0.024% trifluoroacetic acid. The gradient was running linearly from 0 to 15% B in 65 minutes, then to 26% B in 55 minutes, then to 39% B in 30 minutes. The ESI source voltage was set at 3,300 V, and the cone voltage was 30 V, with a desolvation temperature set to 200° C. Peaks on the maps were identified using MassLynx 4.1 software.

Unlike Ig1 and Ig4 Mabs, which each contain a distinct interchain disulfide pattern, the disulfide structure on an Ig2 antibody is complex and contains a mixture of different isoforms. The detected disulfide linked peptide clusters for Li33 Ig2 are listed in Table 8.

TABLE 8

Disulfide structure of Li33 IgG2.

| | Linkage | Calc. Mass (Da) | Detected Mass (Da) | RT (min) | Recovery (%)* |
|---|---|---|---|---|---|
| Non-hinge | | | | | |
| Intrachain | LT2(C1)1-LT6(C2) | 4204.89 | 4204.90 | 133.1 | 100% |
| | LT11(C3)-LT18(C4) | 3555.75 | 3555.73 | 123.1 | 100% |
| | HT2(C1)-HT10(C2) | 3442.55 | 3442.54 | 141.5 | 100% |
| | HT14(C4)-HT15(C5) | 8073.92* | 8073.78* | 142.3 | 90% |
| | HT21(C10)-HT26(C11) | 3986.85 | 3986.84 | 124.5 | 100% |
| | HT34(C12)-HT39(C13) | 3844.82 | 3844.77 | 110.7 | 100% |
| Interchain | LT20(C5)-HT13(C3) | 1535.69 | 1535.66 | 83.5 | 30% |

TABLE 8-continued

Disulfide structure of Li33 IgG2.

| | Linkage | Calc. Mass (Da) | Detected Mass (Da) | RT (min) | Recovery (%)* |
|---|---|---|---|---|---|
| Hinge | | | | | |
| Pattern A + A | HT19(C6-9)-HT19(C6-9) | 5350.56 | 5350.52 | 138.9 | 10 |
| | HT19(C6-9)-HT19'(C6-9) | 5125.40 | 5125.37 | 140.5 | |
| | HT19' (C6-9)-HT19'(C6-9) | 4900.26 | 4900.25 | 142.3 | |
| Pattern B + B | 2x(HT13(C3) + LT20(C5)) + 2xHT19(C6-9) | 8425.62* | 8425.46* | 138.2 | 20 |
| | 2x(HT13(C3) + LT20(C5)) + HT19(C6-9) + HT19'(C6-9) | 8200.33* | 8200.02* | 139.4 | |
| | 2x(HT13(C3) + LT20(C5)) + 2xHT19'(C6-9) | 7975.04* | 7975.05* | 140.8 | |
| Pattern A + B | HT13(C3) + LT20(C5) + 2xHT19(C6-9) | 6885.24 | 6885.47 | 138.8 | 15 |
| | HT13(C3) + LT20(C5) + HT19(C6-9) + HT19'(C6-9) | 6660.08 | 6660.29 | 140.1 | |
| | HT13(C3) + LT20(C5) + 2xHT19'(C6-9) | 6434.92 | 6434.95 | 141.5 | |
| Pattern C | HT13(C3) + LT20(C5) + HT19(C6-9) | 4209.97 | 4209.88 | 138.2 | 5 |
| | HT13(C3) + LT20(C5) + HT19'(C6-9) | 3984.82 | 3984.78 | 141.7 | |

*indicates average mass

All the predicted intrachain disulfides were detected with high recovery. The recovery percentage of the intrachain disulfide linkage between the 3rd cysteine on the heavy chain to the 5th cysteine on the light chain was 30%. Four different forms of disulfide linkage were detected for the hinge region. The first form is the classic four parallel linked disulfides in the hinge region. The second form is the 3rd cysteines in both heavy chains and the 5th cysteines in both light chains linked to cysteines in the dimer of the hinge peptide. The third form is a mixture of the first and second forms, on one arm, the 3rd cysteine in the heavy chain linked to the 5th cysteine in the light chain, whereas, one the other arm, the 3rd cysteine in the heavy chain and the 5th cysteine in the light chain are linked to cysteines in the dimer of the hinge peptide. The forth form is a half antibody with the 3rd Cys in the heavy chain and the 5th cysteine in the light chain forming disulfide bonds with cysteines in the hinge. Further heterogeneity in the Li33 Ig2 Mab resulted from glycosylation. Typical for a glycosylated protein, 15 different glycan structures were observed. Glycans were largely simple biantemary core structures (G0 55%, G1 24%, G2 3%). Six percent of the glycan structures were sialyated.

Example 18

Targeted Mutagenesis to Improve Solubility

The crystal structures of Li33 Ig1 Fab and Li33 Ig2 Fab2 were determined in order to identify contact points that could be altered to improve solubility.

The crystal structure of the Li33 Ig1 Fab was solved to 3.2 Å. Li33 Ig1 Fab at 5 mg/ml was mixed at a volumetric ratio of 1:1 with a reservoir solution consisting of 2 M ammonium sulfate, 0.1M sodium acetate pH 3.5, and 0.1 M TCEP. Football-shaped crystals were grown by vapor diffusion at 20° C. They were then cryoprotected by transferring them into 2M ammonium sulfate, 0.1 M citrate pH 3.5, 20% glycerol, 10% sucrose, and 10% xylitol for 2 minutes and freezing them by a quick transfer into liquid nitrogen. The crystals diffracted to 3.2 Å at the SGXcat beamline at the Advanced Photon Source (Argonne, Ill.). Data processing with the HKL program package v. 1.97 [1] revealed the crystals to belong to a P6(5)22 space group with approximate cell dimensions a, b=90.6 Å, c=215.0 Å, and a=b=90 o, g=120o. The crystal structure was solved by molecular replacement based on another IgG1 homology model (AQC2 mutant Fab PDBID: 2B2X) in PHASER (Otwinowski and Minor, *Methods in Enzymology* 276: 307-326 (1997)) with all possible arrangements of the screw access leading to a clear solution in space group P6(5) 22. Model building of the single Fab and 4 sulfates in Coot 0.5.2 (Vagin et al., *Acta Cystallogr D Biol Cystallogr* 60:2184-2195 (2004)) followed by refinement using Refmac5 (Emsley and Cowtan, *Acta Cystallogr D Biol Cystallogr* 60:2126-32 (2004)) to 3.2 Å resolution resulted in a final R-factor of 19.3% and Rfree of 28.9% with reasonable geometry (Table1).

For crystallization of the Li33 Ig2 Fab2, the sample at 7.2 mg/ml was mixed at a volumetric ratio of 1:1 with a reservoir solution consisting of 12% Peg3350, 0.1M phosphate citrate pH 4, and 0.2M NaCl. Rod-shaped crystals were grown by vapor diffusion at 20° C. They were then cryoprotected by transferring them into 20% Peg3350, 0.1M phosphate citrate pH 4, 0.2M NaCl, and 15% glycerol for 2 minutes and then freezing them by a quick transfer into liquid nitrogen. The crystals of the Li33 Ig2 Fab2 diffracted to 2.8 Å at the SGXcat beamline at the Advanced Photon Source (Argonne, Ill.). Data processing with the HKL program package v. 1.97 (Otwinowski and Minor, *Methods in Enzymology* 276: 307-326 (1997)) revealed the crystals to belong to a P1 space group with approximate cell dimensions α=91.7., β=109.5 A, c=118.4, and α=61.4o, β=74.3o, γ7=87.6o. The crystal structure was solved by molecular replacement based on another Ig2 homology model (3GIZ) in PHASER.

These crystal structure provided a unique opportunity to identify contact points and use rational design to address solubility issues. FIG. 15 shows structural interfaces from the crystal structure with CDR-CDR and CDR-framework contact points highlighted. Five residues were identified with intermolecular contacts, W50, W94, W104, I57, and P54 and are highlighted in the figure. Targeted site directed mutagenesis was performed on the key residues within the CDR sequences that contributed to contact points. Results from selected mutations are shown in Table 9.

TABLE 9

Impact of targeted mutagenesis on Li33 solubility.

| Li33 Isotype | Solubility (mg/mL) | LINGO-1 binding EC50 (nM) | Stability ° C. TM1 | TM2 | SEC % monomer |
|---|---|---|---|---|---|
| Ig1agly | 0.3 | 0.12 | 60 | 77 | >99 |
| Ig1aglyW94V/I57V | >10 | 0.15 | 59 | 74/82 | 99 |
| Ig1aglyW94V/I57S | >7 | 0.38 | 58 | 75/82 | 99 |
| Ig1aglyW94V/I57P | >8 | 0.07 | 58 | 75/83 | 99 |
| Ig1aglyW94V/I57T | >7 | 0.13 | 59 | 75/83 | 99 |
| Ig2 | >50 | 0.23 | 69 | 76 | 96 |
| Ig2agly | 0.3 | 0.26 | 59 | 76 | 98 |
| Ig2-V234A/G237A | 5.6 | 0.19 | 69 | 76 | 95 |
| +94V/104Q/57S | >50 | 2.9 | 67 | 74 | 95 |
| +94V/104Q/57A | >50 | 2.4 | 69 | 73 | 95 |

The series of Ig1agly W94VI57 mutations all improved solubility with no impact on LINGO-1 binding, stability, and level of aggregation detected by size exclusion chromatography. The Ig2-PDL W104QW94VI57 mutations also improved solubility with no impact on stability and aggregation, but the additional mutation caused a 10-fold loss in LINGO-1 binding affinity. The triple mutants were further characterized by analytical ultracentrifugation where there was no evidence for dimer formation.

Example 19

PeEGylated Li33 Fab

PEGylated Li33 Fab constructs were created both by enzymatic digestion of the Li33 Mab and by direct expression of the Fab.

In order to directly express a Li33 Fab, a Fab construct was genetically engineered from the Li33 Ig1 construct so that the heavy chain terminated at P231 in the hinge, thereby deleting the Fc moiety and providing a single, unpaired cysteine from the natural Ig1 hinge sequence that could be targeted for PEGylation. The light chain sequence was not altered. The amino acid sequence for the heavy chain of Li33 Fab', as predicted from the DNA sequence, is:

(SEQ ID NO: 146)
EVQLLESGGGLVQPGGSLRLSCAASGFTFSIYPMFWVRQAPGKGLEWVSW

IGPSGGITKYADSVKGRFTIISRDNSKNTLYLQMNSLRAEDTATYYCARE

GHNDWYFDLWGRGTLVTVSSASTKGPSVFPLAPSSKSTSGIGTAALGCLV

KDYFPEPVTVSWNSGALTSGVHTFPAVLQSSGLYSLSSVVTVPSSSLGTQ

TYICNVNHKPSINTKVDKKVEPKSCDKTHTCPP.

The amino acid sequence for the light chain as predicted from the DNA sequence is:

(SEQ ID NO: 145)
DIQMTQSPGTLSLSPGERATLSCRASQSVSSYLAWYQQKPGQAPRLLIYD

ASNRATGIPARFSGSGSGTEFITLTISSLQSEDFAVYYCQQYDKWPLTFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC.

The Li33 Fab construct was expressed in CHO cells. Cells expressing high levels of the Li33 Fab were selected by FACS sorting. The Li33 Fab contains 11 cysteines: 5 that form disulfides and a single free cysteine. Of these, only the disulfide that holds the heavy and light chains together and the free cysteine are surface exposed and potential targets for PEGylation. To verify the reactivity of these cysteines, the Li33 Fab was reduced with 0.1 mM TCEP, treated with an excess of PEGmaleimide (PEGmal) (0.2 mM), and analyzed by SDS-PAGE for rapid assessment of both the extent of reduction and PEGylation.

Reduction (step 1 in methods 1, 2, and 3 of FIG. 16) was performed as follows. To 1 mL of Protein A purified Fab' at 1.2 mg/mL, 40 μL of 1M sodium borate, pH 8.4, and 1 μL of 100 mM TCEP (final 0.1 mM) were added, and the sample was incubated for 75 minutes at 37° C. Under these conditions, greater than 90% of the product was routinely reduced to heavy and light chain when analyzed by non-reducing SDS-PAGE. The predominant products after reduction were free heavy and light chain that each migrated with an apparent mass of 25 kDa.

For PEGylation with 20 kDa methoxy-polyethyleneglycol maleimide (PEGmal) (Nektar) (step 2 in method 1 of FIG. 16), MES pH 6.0 was added to 25 mM from a 0.5 M stock solution and PEGmal was added to 0.4 mg/mL (2× molar excess) from a 20 mg/mL stock solution that was stored at −70° C. The sample was incubated at room temperature for 2.5 hours then overnight at 4° C. and then subjected to cation exchange chromatography on a Fractogel EMD sulfate (EM Merck) resin.

When the TCEP-reduced Fab was treated with PEGmal, a nearly complete loss of the free heavy and light chains was observed. This observation is consistent with modification of the three cysteines. Three new bands were detected under non-reducing conditions that correspond to heavy chain or light chain containing a single PEG, heavy chain containing two PEGs, and the PEGylated Fab with a single PEG attached (FIG. 17, method 1).

The experiment was repeated with 5 kDA, 10 kDA, and 40 kDA PEGmal, and the same three bands were present regardless of the size of the PEGmal that was utilized. However, their molecular weights varied in a manner that was consistent with the size of the attached PEG moiety. For example the mono-PEGylated heavy or light chain had apparent molecular weights of 35, 40, 50, and 100 kDa when the samples were treated with the 5, 10, 20, and 40 kDa PEGs, respectively, and the di-PEGylated heavy chain migrated at 45, 80, 100, and 250 kDa under the same conditions. The PEGylated Fab bands with a single 5, 10, 20, and 40 kDa PEG attached, migrated with masses of 70, 80, 90, and 150 kDa, respectively.

Under reducing conditions the prominent bands corresponding to heavy chain or light chain containing a single PEG or two PEGs were not affected, while the PEG-Fab bands disappeared. A new prominent band corresponding to free heavy or light chain was present after reduction. In all cases, the percent of product that was accounted for in the PEG-Fab band was only 20% of the starting material indicating that the predominant product was Fab with three PEGs attached. These results confirm that after reduction, all three of the reactive cysteines are accessible for modification. Subsequent studies have focused on 20 kDa PEG as the reactive group.

Follow-up studies was performed to optimize the PEGylation reaction in order to form the desired PEG-Fab product (methods 2 and 3 in FIG. 16). The results are shown in FIG. 17 (methods 2 and 3). In both studies the TCEP reductant was removed on a desalting column prior to reaction of the reduced Fab' with the PEG. In method 2, the PEG was added immediately after the removal of the TCEP, allowing both the PEGylation reaction and oxidation of the interchain disulfide to occur concurrently. In contrast, for method 3, oxidation of the interchain disulfide was allowed to occur prior to the addition of the PEG. Both methods resulted in a much higher percentage of the desired PEG-Fab product than when PEGylation was performed in the presence of TCEP (method 1). When oxidation and PEGylation occurred simultaneously (method 2), the major contaminants were PEGylated light chain and di-PEGylated heavy chain. When oxidation and PEGylation were performed sequentially (method 3), the major contaminants were unmodified Fab and Fab2. The PEG-Fab' was purified from the reaction mixture by cation exchange chromatography on a Fractogel EMD sulfate resin. The unpegylated reaction products from the later scheme can be more easily fractionated away from the PEG-Fab based on preliminary purification studies.

In order to create a PEGylated Li33 Fab construct by enzymatic digestion, Fab2 fragments of Li33 were first generated with pepsin. Samples were dialyzed overnight at 4° C. against 10 mM sodium acetate pH 3.6. Pepsin was added at an enzyme:protein ratio of 1:00 and incubated at 37° C. for 6 hours for complete conversion of the Mab to Fab2. The pH of the digest was adjusted to 7.5 with 200 mM Hepes and the sample was loaded onto a Protein A Sepharose column at 10 mg protein/mL resin. The column was washed with 5 column volumes of PBS, 4 column volumes of 25 mM sodium phosphate pH 5.5 and 100 mM NaCl, and the Fab2 was eluted from the resin with 10 mM sodium citrate pH 3.3 and 50 mM NaCl, collecting six 0.5 column volume steps. The pH of the samples was adjusted to 4.7 with NaOH. Peak fractions were pooled, filtered through 0.22µ units, aliquoted and stored at −70° C.

For PEGylation, Ig1 Fab2 at 1.2 mg/ml in 40 mM sodium borate pH 7.0 and 0.1 mM TCEP was incubated for 75 minutes at 37° C. The reduced sample was desalted on a G25M column that had been equilibrated in 5 mM MES pH 5.0 and 50 mM NaCl (final Fab concentration 0.5 mg/ml). After storage overnight at 4° C., over 90% of the disulfide bonds holding the heavy and light chains together had reoxidzed to a Fab' leaving the 2 hinge Cys residue free for conjugation. 10 kDa PEGmal (Nektar) was added to 0.4 mg/mL and MES ph 6.0 was added to 25 mM. The sample was incubated at room temperature for 2.5 hours, overnight at 4° C., and then subjected to cation exchange chromatography on a Fractogel EMD sulfate column. The column was washed with 2 column volumes of 10 mM sodium phosphate pH 6.0, and the PEG-Fab was eluted with 10 mM sodium phosphate pH 6.0 and 50 mM NaCl. The results are shown in FIG. 18.

When evaluated for function by ELISA, the PEG-Li33 Fab' product was fully active in its ability to bind LINGO-1.

Example 20

Pegylated Li81 and Li113

Li81 fragments were created by pepsin cleavage and subject to both C-terminal and N-terminal PEGylation.

For N-terminal PEGylation, a Fab was generated from the Li81 antibody by enzymatic digestion with papain and repurification. Li81 Fab at ~2 mg/mL in 10 mM sodium citrate pH 6.0, 5 mg/mL 20 kDa methoxy-polyethyleneglycol proprionaldehyde (Nektar), and 5 mM sodium cyanoborohydride were incubated at room temperature for 24 hours. The pH was adjusted to pH 4, and the samples were concentrated to 10 mg Fab/mL and subjected to cation exchange chromatography at room temperature on a Fractogel EMD sulfate column (Merck) at 10 mg Fab/mL resin. The columns were washed with 2.5 column volumes of 10 mM sodium citrate pH 4.7, and 1 column volume of 10 mM sodium citrate pH 4.7, 15 mM NaCl. The PEG-Fab was eluted with 10 mM sodium citrate pH 4.7, 50 mM NaCl, and 0.25 column volume fractions were collected. Fractions were analyzed by SDS-PAGE and peak fractions containing monopegylated Fab were pooled, filtered, aliquoted and stored at −70° C. Protein concentrations were estimated from absorbance at 280 nm using the theoretical extinction coefficients for the Fabs.

For C-terminal PEGylation, Fab2 fragments of Li81 Ig1agly were generated with pepsin. Samples were dialyzed overnight at 4° C. against 10 mM sodium acetate pH 3.6. Pepsin was added at an enzyme:protein ratio of 1:1000 and incubated at 37° C. for 3 hours to achieve complete conversion of the Mab to Fab2. The pH of the digest was adjusted to 7.5 with 200 mM Hepes, and the sample was loaded onto a Protein A Sepharose column at 10 mg protein/mL resin. The column was washed with 5 column volumes of PBS, 4 column volumes of 25 mM sodium phosphate pH 5.5 and 100 mM NaCl, and the Fab2 was eluted from the resin with 10 mM sodium citrate pH 3.3, 50 mM NaCl, collecting 6×0.5 column volume steps. The pH of the samples were adjusted to 4.7 with NaOH. Peak fractions were pooled, filtered through 0.22µ units, aliquoted, and stored at −70° C.

For pegylation, Li81 Ig1agly Fab2 at 2.6 mg/mL in 20 mM sodium borate pH 7.0, 0.2 mM TCEP was incubated for 90 minutes at 37° C. The reduced sample was diluted with 2 volumes of 10 mM sodium citrate pH 4.7 and loaded onto a Fractogel EMD sulfate column (10 mg Fab'/mL resin), pre-equilibrated in the citrate pH 4.7 buffer. The column was washed with 3 column volumes of 10 mM sodium citrate pH 4.7, 2.5 column volumes of 10 mM sodium phosphate pH 6.0, 50 mM NaCl, and the Fab' was eluted with 7×0.8 column volume steps of 10 mM sodium phosphate pH 6.0, 200 mM NaCl. The protein eluate was diluted with water to a final protein concentration of 1.4 mg/mL. After storage for 48 hours at 4° C., most of the disulfide bond holding the heavy and light chain together had reoxidized to a Fab' leaving the 2 hinge Cys residues free for conjugation. 10 kDa methoxy-polyethyleneglycol maleimide (PEGmal) (Nektar) was added to 1.0 mg/mL, and sodium citrate pH 6.5 was added to 10 mM. The sample was incubated at room temperature for 2.5 hours and then overnight at 4° C., concentrated and buffer exchanged in an Amicon Ultra-15 30K centrifugal filter device to 8 mg/mL with a final buffer concentration of 10 mM citrate pH 4.7, 6 mM NaCl, and then subjected to cation exchange chromatography on a Fractogel EMD sulfate column (8 mg protein/mL resin), pre-equilibrated in the citrate pH 4.7 buffer. The column was washed with 1 column volume of 10 mM sodium citrate pH 4.7 buffer, and the PEG-Fab' was eluted with 12 0.15 column volume steps of 10 mM sodium citrate pH 4.7, 50 mM NaCl, 2 0.15 column volume steps of 10 mM sodium citrate pH 4.7, 100 mM NaCl, and 7 0.15 column volume steps of 10 mM sodium citrate pH 4.7, 200 mM NaCl. Column fractions were analyzed by SDS-PAGE. Peak fractions were pooled and the buffer adjusted to 15 mM sodium citrate pH 6.5, 125 mM NaCl. Protein concentration was determined by absorbance at 280 nm. The sample was filtered through a 0.22µ unit, aliquoted and stored at −70° C.

The N-terminally PEGylated Li81 Fab2 demonstrated an EC50 of 0.15 ng/ml, while the C-terminally PEGylated Li81 Fab' demonstrated an EC50 of 0.054 ng/ml, but both showed equivalent activity in an oligodendrocyte proliferation assay (0.1 µg/ml).

Li113 was also N-terminally PEGylated by following the same protocol as described for Li81 N-terminal PEGylation.

The FACS results shown in FIG. 19 demonstrate that PEGylated Li81 and Li113 can bind to LINGO-1.

Example 21

Evaluation of Functional Properties of LINGO-1 Antibody Variants

The efficacy of Li81 antibodies and fragments thereof was evaluated in an ELISA assay to assess LINGO-1 binding (FIG. 20), in an oligodendrocyte proliferation assay ("OPC assay") (FIG. 21), and in a rat remyelination assay (FIG. 22). The results demonstrate that each of the Li81 Mab, Fab2, Fab, N-PEG-Fab, and C-PEG Fab binds to LINGO-1 and is functional in in vitro assays. The biochemical and in vitro properties of the molecules tested are summarized in Table 10.

TABLE 10

Biochemical and in vitro LINGO-1 antibody properties.

| Property | Mab | Fab2 | Fab | N-PEG | C-PEG |
|---|---|---|---|---|---|
| Valency | Bivalent | Bivalent | Monovalent | Monovalent | Monovalent |
| Fc fucntion | Low effector; Wt FcRn | None | None | None | None |
| Size SEC (kDa) | 140 | 100 | 50 | 250 | 250 |
| EC50 (nM) | 0.017 | 0.017 | 0.041 | 0.15 | 0.054 |
| OPC assay (µg/ml) | 0.1 | 0.1 | 0.1 | 0.1 | 0.1 |

Example 22

LINGO-1 Antibody and Antibody Fragment Thermal Stability

Thermal denaturation was carried out using a UV-visible spectrophotometer fitted with a computer-controlled, thermoelectrically-heated cuvette holder. Solutions were equilibrated at 25° C. for 15 minutes in a 200:1 microcuvette. The temperature of the cuvette holder was then ramped from 25° C. to 90° C. at a rate of 2° C./min, and the denaturation of the protein was followed by continuous monitoring of absorbance at 280 nm. The mid-point of the cooperative unfolding event, Tm, was obtained from the melting curves by determining the temperature at which the measured absorbance was mid-way between the values defined by lines extrapolated from the linear regions on each side of the cooperative unfolding transition. The results of denaturation experiments are shown in FIG. 23 and demonstrate that the Tm of the LINGO-1 antibodies and Fabs tested range from about 66° C. to about 76° C.

Example 23

Li33 Variants

In order to identify other Li33 variants with improved affinity, the variants listed in Tables 11 below, were constructed and tested. A direct binding ELISA assay was performed using LINGO-Fc coated plates. The half maximal concentration that gave 50% saturation of binding was measured and is reported as a ratio of the same measurement for Li33. In addition, the OD450 for maximal saturation value was measured and is reported as a ratio of the same measurement for Li33.

TABLE 11

Li33 Variants.

| Variant | Chain with Variant | SEQ ID NO | ELISA Ratio | Plateau Ratio |
|---|---|---|---|---|
| WT Li33 | NA (WT) | 145 and 146 | 1.0 | 0.91 |
| W50H | Heavy | 147 | 1.3 | 0.87 |
| W50F | Heavy | 148 | 1.2 | 0.86 |
| W50L | Heavy | 149 | 1.8 | 1.00 |
| W50M | Heavy | 150 | 2.0 | 0.93 |
| P53L | Heavy | 151 | 2.2 | 1.13 |
| P53S | Heavy | 152 | 2.5 | 1.43 |
| P53T | Heavy | 153 | 2.1 | 0.85 |
| P53W | Heavy | 154 | 3.9 | 0.55 |
| W104V | Heavy | 155 | 2.8 | 0.94 |
| W104H | Heavy | 156 | 0.1 | 0.91 |

TABLE 11-continued

Li33 Variants.

| Variant | Chain with Variant | SEQ ID NO | ELISA Ratio | Plateau Ratio |
|---|---|---|---|---|
| W104S | Heavy | 157 | 2.7 | 0.85 |
| W104Q | Heavy | 158 | 2.4 | 0.91 |
| I57G | Heavy | 159 | 2.3 | 0.91 |
| I57M | Heavy | 160 | 3.8 | 1.09 |
| I57N | Heavy | 161 | 2.9 | 1.10 |
| I57H | Heavy | 162 | 3.2 | 1.07 |
| I57L | Heavy | 163 | 0.7 | 1.00 |
| I57F | Heavy | 164 | 2.0 | 0.83 |
| W94A | Light | 165 | 1.6 | 0.91 |
| W94D | Light | 166 | 1.5 | 0.87 |
| W94L | Light | 167 | 0.6 | 0.97 |
| W94N | Light | 168 | 0.8 | 1.05 |
| W94G | Light | 169 | 0.9 | 1.03 |
| W94Q | Light | 170 | 0.9 | 1.05 |
| W94V | Light | 171 | 1.4 | 0.91 |
| W94S | Light | 172 | 1.3 | 0.99 |
| W50G | Heavy | 173 | 2041.4 | 21.79 |
| W50I | Heavy | 174 | 93.5 | 12.44 |
| W50D | Heavy | 175 | 4.0 | 0.71 |
| W104M | Heavy | 176 | 3.8 | 0.88 |
| W104L | Heavy | 177 | 2.5 | 0.69 |
| W104T | Heavy | 178 | 3.5 | 0.33 |
| W104I | Heavy | 179 | 6.5 | 0.62 |
| P53G | Heavy | 180 | 3.1 | 0.83 |
| I57W | Heavy | 181 | 0.0 | |
| I57Y | Heavy | 182 | 0.0 | |
| I57S | Heavy | 183 | 0.6 | 0.96 |
| I57P | Heavy | 184 | 0.6 | 1.27 |
| I57V | Heavy | 185 | 1.4 | 1.13 |
| I57T | Heavy | 186 | 1.1 | 1.01 |
| W104Q | Heavy | 187 | 1.1 | 0.67 |

Several variants with an affinity within 2 fold of Li33 and a plateau value of at least 85% of that of Li33 were identified: W50F, W50L, W50M, I57L, I57F, W94A, W94L, W94N, W94G, W94Q, W94V, W94S, I57S, I57P, I57V, and I57T.

Li62 Variants

Example 24

In order to identify other Li62 variants with improved affinity, the variants listed in Table 12 below, are constructed and tested. A direct binding ELISA assay is performed using LINGO-Fc coated plates. Variants that show an affinity within 2 fold of Li62 and a plateau value of at least 85% of that of Li62 are identified and analyzed in in vitro and in viro functional assays as described above.

TABLE 12

Li62 Variants

| Variant | Chain with Variant | SEQ ID NO |
|---|---|---|
| Li62 | NA (WT) | 1 and 9 |
| W50H | Heavy | 188 |
| W50F | Heavy | 189 |
| W50L | Heavy | 190 |
| W50M | Heavy | 191 |
| P53L | Heavy | 192 |
| P53S | Heavy | 193 |
| P53T | Heavy | 194 |
| P53W | Heavy | 195 |
| W104V | Heavy | 196 |
| W104H | Heavy | 197 |
| W104S | Heavy | 198 |
| W104Q | Heavy | 199 |
| I57G | Heavy | 200 |
| I57M | Heavy | 201 |
| I57N | Heavy | 202 |
| I57H | Heavy | 203 |
| I57L | Heavy | 204 |
| I57F | Heavy | 205 |
| W50G | Heavy | 206 |
| W50I | Heavy | 207 |
| W50D | Heavy | 208 |
| W104M | Heavy | 209 |
| W104L | Heavy | 210 |
| W104T | Heavy | 211 |
| W104I | Heavy | 212 |
| P53G | Heavy | 213 |
| I57W | Heavy | 214 |
| I57Y | Heavy | 215 |
| I57S | Heavy | 216 |
| I57P | Heavy | 217 |
| I57V | Heavy | 218 |
| I57T | Heavy | 219 |
| W104Q | Heavy | 220 |

Li81 Variants

Example 25

In order to identify other Li81 variants with improved affinity, the variants listed in Table 13 below, are constructed and tested. A direct binding ELISA assay is performed using LINGO-Fc coated plates. Variants that show an affinity within 2 fold of Li81 and a plateau value of at least 85% of that of Li81 are identified and analyzed in in vitro and in viro functional assays as described above.

TABLE 13

Li81 Variants

| Variant | Chain with Variant | SEQ ID NO |
|---|---|---|
| Li81 | NA (WT) | 5 and 13 |
| M96L | Light | 221 |
| M96I | Light | 222 |
| M96Q | Light | 223 |
| M96K | Light | 224 |
| M96A | Light | 225 |
| M96V | Light | 226 |
| M96Y | Light | 227 |
| M96F | Light | 228 |
| P53L | Heavy | 229 |
| P53S | Heavy | 230 |
| P53T | Heavy | 231 |
| P53W | Heavy | 232 |
| P53G | Heavy | 233 |
| W94A | Light | 234 |
| W94D | Light | 235 |
| W94L | Light | 236 |
| W94N | Light | 237 |
| W94G | Light | 238 |
| W94Q | Light | 239 |
| W94V | Light | 240 |
| W94S | Light | 241 |

Li113 Variants

Example 26

In order to identify other Li113 variants with improved affinity, the variants listed in Table 14 below, are constructed and tested. A direct binding ELISA assay is performed using LINGO-Fc coated plates. Variants that show an affinity within 2 fold of Li113 and a plateau value of at least 85% of that of Li113 are identified and analyzed in in vitro and in viro functional assays as described above.

TABLE 14

Li113 Variants

| Variant | Chain with Variant | SEQ ID NO |
|---|---|---|
| Li113 | NA (WT) | 66 and 9 |
| W50H | Heavy | 242 |
| W50F | Heavy | 243 |
| W50L | Heavy | 244 |
| W50M | Heavy | 245 |
| P53L | Heavy | 246 |
| P53S | Heavy | 247 |
| P53T | Heavy | 248 |
| P53W | Heavy | 249 |
| W104V | Heavy | 250 |
| W104H | Heavy | 251 |
| W104S | Heavy | 252 |
| W104Q | Heavy | 253 |
| I57G | Heavy | 254 |
| I57M | Heavy | 255 |
| I57N | Heavy | 256 |
| I57H | Heavy | 257 |
| I57L | Heavy | 258 |
| I57F | Heavy | 259 |
| W50G | Heavy | 260 |
| W50I | Heavy | 261 |
| W50D | Heavy | 262 |
| W104M | Heavy | 263 |
| W104L | Heavy | 264 |
| W104T | Heavy | 265 |
| W104I | Heavy | 266 |
| P53G | Heavy | 267 |
| I57W | Heavy | 268 |
| I57Y | Heavy | 269 |
| I57S | Heavy | 270 |

TABLE 14-continued

Li113 Variants

| Variant | Chain with Variant | SEQ ID NO |
|---------|--------------------|-----------|
| I57P    | Heavy              | 271       |
| I57V    | Heavy              | 272       |
| I57T    | Heavy              | 273       |
| W104Q   | Heavy              | 274       |

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. An isolated antibody or antigen-binding fragment thereof that can specifically bind to a LINGO-1 polypeptide, wherein the antibody or antigen-binding fragment thereof comprises an immunoglobulin heavy chain variable region (VH) wherein the VH CDR1, CDR2, and CDR3 comprise the amino acids of SEQ ID NOs: 2, 3, and 30, respectively.

2. The isolated antibody or antigen-binding fragment thereof of claim 1, wherein the VH comprises the sequence of SEQ ID NO: 66.

3. The isolated antibody or antigen-binding fragment thereof of claim 1 further comprising a VL polypeptide comprising VL CDR1, CDR2, and CDR3 regions, wherein the VL CDR1, CDR2, and CDR3 regions are identical, respectively, to the reference VL CDR1, CDR2, and CDR3 sequences SEQ ID NOs: 10, 11, and 12.

4. An isolated antibody or antigen-binding fragment thereof that can specifically bind to a LINGO-1 polypeptide, wherein the VL comprises VL CDR1, CDR2, and CDR3 regions identical, respectively, to SEQ ID NOs: 10, 11, and 12.

5. The isolated antibody or antigen-binding fragment thereof of claim 4, wherein the VL comprises the sequence of SEQ ID NO:9.

6. The isolated antibody or antigen-binding fragment thereof of claim 5, further comprising a VH polypeptide comprising VH CDR1, CDR2, and CDR3 regions, wherein the VH CDR1, CDR2, and CDR3 sequences are identical, respectively, to SEQ ID NOs: 2, 3, and 30.

7. The isolated antibody or antigen-binding fragment thereof of claim 6, wherein the VH comprises the sequence of SEQ ID NO:66.

8. The isolated antibody or antigen-binding fragment thereof of claim 4, further comprising a VH polypeptide comprising the sequence of SEQ ID NO: 66.

9. The antibody or fragment thereof of claim 4, which is an antagonist of LINGO-1 mediated neuronal cell death.

10. The antibody or fragment thereof of claim 4, which is an antagonist of LINGO-1-mediated myelination inhibition.

11. The antibody or fragment thereof of claim 4, which is an antagonist of LINGO-1 mediated oligodendrocyte differentiation inhibition.

12. The antibody or fragment thereof of claim 4, further comprising a heterologous polypeptide fused thereto.

13. The antibody or fragment thereof of claim 4, wherein the antibody is conjugated to an agent selected from the group consisting of a therapeutic agent, a prodrug, a peptide, a protein, an enzyme, a virus, a lipid, a biological response modifier, a pharmaceutical agent, or PEG.

14. A composition comprising the antibody or fragment thereof of claim 4 and a carrier.

15. An isolated anti-LINGO-1 antibody, or antigen-binding fragment thereof, produced by a method comprising
culturing a host cell comprising a composition comprising
a VH encoding polynucleotide and a VL encoding polynucleotide, wherein the VH encoding polynucleotide and the VL encoding polynucleotide, respectively, comprise polynucleotides encoding the amino acid sequences of reference polypeptides SEQ ID NO:66 and SEQ ID NO:9; and
recovering the antibody.

* * * * *

UNITED STATES PATENT AND TRADEMARK OFFICE
CERTIFICATE OF CORRECTION

| | |
|---|---|
| PATENT NO. | : 8,058,406 B2 |
| APPLICATION NO. | : 12/500472 |
| DATED | : November 15, 2011 |
| INVENTOR(S) | : Sha Mi, R. Blake Pepinsky and Christilyn Graff |

Page 1 of 1

It is certified that error appears in the above-identified patent and that said Letters Patent is hereby corrected as shown below:

In the Claims:

<u>Column 312, Claim 13</u>

Line 54, delete "or" and insert -- and --.

Signed and Sealed this
Twelfth Day of August, 2014

Michelle K. Lee
*Deputy Director of the United States Patent and Trademark Office*

```
                       SEQUENCE LISTING

<160> NUMBER OF SEQ ID NOS: 274

<210> SEQ ID NO 1
<211> LENGTH: 119
<212> TYPE: PRT
<213> ORGANISM: Artificial
<220> FEATURE:
<223> OTHER INFORMATION: VH sequence of Li62 antibody

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 2
<211> LENGTH: 5
<212> TYPE: PRT
<213> ORGANISM: Artificial
<220> FEATURE:
<223> OTHER INFORMATION: VH CDR1 sequence of Li62 antibody

<400> SEQUENCE: 2

Ile Tyr Pro Met Phe
1               5

<210> SEQ ID NO 3
<211> LENGTH: 17
<212> TYPE: PRT
<213> ORGANISM: Artificial
<220> FEATURE:
<223> OTHER INFORMATION: VH CDR2 sequence of Li62 antibody

<400> SEQUENCE: 3

Trp Ile Gly Pro Ser Gly Gly Ile Thr Lys Tyr Ala Asp Ser Val Lys
1               5                   10                  15
```

Gly

<210> SEQ ID NO 4
<211> LENGTH: 10
<212> TYPE: PRT
<213> ORGANISM: Artificial
<220> FEATURE:
<223> OTHER INFORMATION: VH CDR3 sequence of Li62 antibody

<400> SEQUENCE: 4

Glu Gly His Asn Asp Trp Tyr Phe Asp Leu
1               5                   10

<210> SEQ ID NO 5
<211> LENGTH: 118
<212> TYPE: PRT
<213> ORGANISM: Artificial
<220> FEATURE:
<223> OTHER INFORMATION: VH sequence of Li81 antibody

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser
        115

<210> SEQ ID NO 6
<211> LENGTH: 5
<212> TYPE: PRT
<213> ORGANISM: Artificial
<220> FEATURE:
<223> OTHER INFORMATION: VH CDR1 sequence of Li81 antibody

<400> SEQUENCE: 6

Ala Tyr Glu Met Lys
1               5

<210> SEQ ID NO 7
<211> LENGTH: 17
<212> TYPE: PRT
<213> ORGANISM: Artificial
<220> FEATURE:
<223> OTHER INFORMATION: VH CDR2 sequence of Li81 antibody

<400> SEQUENCE: 7

Val Ile Gly Pro Ser Gly Gly Phe Thr Phe Tyr Ala Asp Ser Val Lys
1               5                   10                  15

Gly

<210> SEQ ID NO 8

```
<211> LENGTH: 9
<212> TYPE: PRT
<213> ORGANISM: Artificial
<220> FEATURE:
<223> OTHER INFORMATION: VH CDR3 sequence of Li81 antibody

<400> SEQUENCE: 8

Glu Gly Asp Asn Asp Ala Phe Asp Ile
1               5

<210> SEQ ID NO 9
<211> LENGTH: 107
<212> TYPE: PRT
<213> ORGANISM: Artificial
<220> FEATURE:
<223> OTHER INFORMATION: VL sequence of Li62 antibody

<400> SEQUENCE: 9

Asp Ile Gln Met Thr Gln Ser Pro Ser Phe Leu Ser Ala Ser Val Gly
1               5                   10                  15

Asp Ser Val Ala Ile Thr Cys Arg Ala Ser Gln Asp Ile Ser Arg Tyr
            20                  25                  30

Leu Ala Trp Tyr Gln Gln Arg Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Thr Ser Leu Gln Pro
65                  70                  75                  80

Glu Asp Phe Gly Thr Tyr Tyr Cys Gln Gln Tyr Asp Thr Leu His Pro
                85                  90                  95

Ser Phe Gly Pro Gly Thr Thr Val Asp Ile Lys
            100                 105

<210> SEQ ID NO 10
<211> LENGTH: 11
<212> TYPE: PRT
<213> ORGANISM: Artificial
<220> FEATURE:
<223> OTHER INFORMATION: VL CDR1 sequence of Li62 antibody

<400> SEQUENCE: 10

Arg Ala Ser Gln Asp Ile Ser Arg Tyr Leu Ala
1               5                   10

<210> SEQ ID NO 11
<211> LENGTH: 7
<212> TYPE: PRT
<213> ORGANISM: Artificial
<220> FEATURE:
<223> OTHER INFORMATION: VL CDR2 sequence of Li62 antibody

<400> SEQUENCE: 11

Asp Ala Ser Asn Leu Gln Thr
1               5

<210> SEQ ID NO 12
<211> LENGTH: 9
<212> TYPE: PRT
<213> ORGANISM: Artificial
<220> FEATURE:
<223> OTHER INFORMATION: VL CDR3 sequence of Li62 antibody

<400> SEQUENCE: 12

Gln Gln Tyr Asp Thr Leu His Pro Ser
1               5
```

```
<210> SEQ ID NO 13
<211> LENGTH: 108
<212> TYPE: PRT
<213> ORGANISM: Artificial
<220> FEATURE:
<223> OTHER INFORMATION: VL sequence of Li81 antibody

<400> SEQUENCE: 13

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Met
                85                  90                  95

Tyr Thr Phe Gly Gln Gly Thr Lys Leu Glu Ile Lys
            100                 105

<210> SEQ ID NO 14
<211> LENGTH: 11
<212> TYPE: PRT
<213> ORGANISM: Artificial
<220> FEATURE:
<223> OTHER INFORMATION: VL CDR1 sequence of Li81 antibody

<400> SEQUENCE: 14

Arg Ala Ser Gln Ser Val Ser Ser Tyr Leu Ala
1               5                   10

<210> SEQ ID NO 15
<211> LENGTH: 7
<212> TYPE: PRT
<213> ORGANISM: Artificial
<220> FEATURE:
<223> OTHER INFORMATION: VL CDR2 sequence of Li81 antibody

<400> SEQUENCE: 15

Asp Ala Ser Asn Arg Ala Thr
1               5

<210> SEQ ID NO 16
<211> LENGTH: 10
<212> TYPE: PRT
<213> ORGANISM: Artificial
<220> FEATURE:
<223> OTHER INFORMATION: VL CDR3 sequence of Li81 antibody

<400> SEQUENCE: 16

Gln Gln Arg Ser Asn Trp Pro Met Tyr Thr
1               5                   10

<210> SEQ ID NO 17
<211> LENGTH: 10
<212> TYPE: PRT
<213> ORGANISM: Artificial
<220> FEATURE:
<223> OTHER INFORMATION: VH CDR3 sequence of Li62 variant B06 antibody

<400> SEQUENCE: 17
```

```
Glu Gly Tyr Tyr Asp Trp Tyr Phe Asp Gln
1               5                   10

<210> SEQ ID NO 18
<211> LENGTH: 10
<212> TYPE: PRT
<213> ORGANISM: Artificial
<220> FEATURE:
<223> OTHER INFORMATION: VH CDR3 sequence of Li62 variant B12 antibody

<400> SEQUENCE: 18

Glu Gly Gln Tyr Asp Trp Tyr Phe Asp Val
1               5                   10

<210> SEQ ID NO 19
<211> LENGTH: 10
<212> TYPE: PRT
<213> ORGANISM: Artificial
<220> FEATURE:
<223> OTHER INFORMATION: VH CDR3 sequence of Li62 variant F06 antibody

<400> SEQUENCE: 19

Glu Gly Asp Tyr Asp Trp Tyr Phe Asp Leu
1               5                   10

<210> SEQ ID NO 20
<211> LENGTH: 10
<212> TYPE: PRT
<213> ORGANISM: Artificial
<220> FEATURE:
<223> OTHER INFORMATION: VH CDR3 sequence of Li62 variant B01 antibody

<400> SEQUENCE: 20

Glu Gly Gln Tyr Asp Trp Tyr Phe Glu Leu
1               5                   10

<210> SEQ ID NO 21
<211> LENGTH: 10
<212> TYPE: PRT
<213> ORGANISM: Artificial
<220> FEATURE:
<223> OTHER INFORMATION: VH CDR3 sequence of Li62 variant D09 antibody

<400> SEQUENCE: 21

Glu Ala Asp Ile Asp Trp Phe Phe Asp Leu
1               5                   10

<210> SEQ ID NO 22
<211> LENGTH: 10
<212> TYPE: PRT
<213> ORGANISM: Artificial
<220> FEATURE:
<223> OTHER INFORMATION: VH CDR3 sequence of Li62 variant D12 antibody

<400> SEQUENCE: 22

Glu Gly His Tyr Asp Trp Tyr Phe Asp Leu
1               5                   10

<210> SEQ ID NO 23
<211> LENGTH: 10
<212> TYPE: PRT
<213> ORGANISM: Artificial
<220> FEATURE:
<223> OTHER INFORMATION: VH CDR3 sequence of Li62 variant F01 antibody

<400> SEQUENCE: 23

Glu Gly Arg Tyr Asp Trp Tyr Phe Asp Pro
```

```
<210> SEQ ID NO 24
<211> LENGTH: 10
<212> TYPE: PRT
<213> ORGANISM: Artificial
<220> FEATURE:
<223> OTHER INFORMATION: VH CDR3 sequence of Li62 variant F02 antibody

<400> SEQUENCE: 24

Glu Gly Asp Tyr Asp Trp Tyr Phe Gly Leu
1               5                   10

<210> SEQ ID NO 25
<211> LENGTH: 10
<212> TYPE: PRT
<213> ORGANISM: Artificial
<220> FEATURE:
<223> OTHER INFORMATION: VH CDR3 sequence of Li62 variant F06 antibody

<400> SEQUENCE: 25

Glu Gly Arg Tyr Asp Trp Tyr Phe Asp Leu
1               5                   10

<210> SEQ ID NO 26
<211> LENGTH: 10
<212> TYPE: PRT
<213> ORGANISM: Artificial
<220> FEATURE:
<223> OTHER INFORMATION: VH CDR3 sequence of Li62 variant F10 antibody

<400> SEQUENCE: 26

Glu Ser His Ile Asp Arg Tyr Phe Asp Leu
1               5                   10

<210> SEQ ID NO 27
<211> LENGTH: 10
<212> TYPE: PRT
<213> ORGANISM: Artificial
<220> FEATURE:
<223> OTHER INFORMATION: VH CDR3 sequence of Li62 variant G08 antibody

<400> SEQUENCE: 27

Glu Gly Gln Tyr Asp Trp Tyr Phe Asp Val
1               5                   10

<210> SEQ ID NO 28
<211> LENGTH: 10
<212> TYPE: PRT
<213> ORGANISM: Artificial
<220> FEATURE:
<223> OTHER INFORMATION: VH CDR3 sequence of Li62 variant H08 antibody

<400> SEQUENCE: 28

Glu Gly His Tyr Asn Gly Tyr Phe Asp Leu
1               5                   10

<210> SEQ ID NO 29
<211> LENGTH: 10
<212> TYPE: PRT
<213> ORGANISM: Artificial
<220> FEATURE:
<223> OTHER INFORMATION: VH CDR3 sequence of Li62 variant C10 antibody

<400> SEQUENCE: 29

Glu Gly Tyr Tyr Asp Trp Tyr Phe Asp Leu
1               5                   10
```

```
<210> SEQ ID NO 30
<211> LENGTH: 10
<212> TYPE: PRT
<213> ORGANISM: Artificial
<220> FEATURE:
<223> OTHER INFORMATION: VH CDR3 sequence of Li62 variant C02 antibody

<400> SEQUENCE: 30

Glu Gly Thr Tyr Asp Trp Tyr Leu Asp Leu
1               5                   10

<210> SEQ ID NO 31
<211> LENGTH: 10
<212> TYPE: PRT
<213> ORGANISM: Artificial
<220> FEATURE:
<223> OTHER INFORMATION: VH CDR3 sequence of Li62 variant D05 antibody

<400> SEQUENCE: 31

Glu Gly Tyr Tyr Asp Trp Tyr Phe Glu Leu
1               5                   10

<210> SEQ ID NO 32
<211> LENGTH: 10
<212> TYPE: PRT
<213> ORGANISM: Artificial
<220> FEATURE:
<223> OTHER INFORMATION: VH CDR3 sequence of Li62 variant F02 antibody

<400> SEQUENCE: 32

Glu Gly Leu Ile Asp Trp Phe Phe Asp Gln
1               5                   10

<210> SEQ ID NO 33
<211> LENGTH: 10
<212> TYPE: PRT
<213> ORGANISM: Artificial
<220> FEATURE:
<223> OTHER INFORMATION: VH CDR3 sequence of Li62 variant C10 antibody

<400> SEQUENCE: 33

Glu Gly Gln Phe Asp Trp Tyr Phe Asp Leu
1               5                   10

<210> SEQ ID NO 34
<211> LENGTH: 10
<212> TYPE: PRT
<213> ORGANISM: Artificial
<220> FEATURE:
<223> OTHER INFORMATION: VH CDR3 sequence of Li62 variant H08 antibody

<400> SEQUENCE: 34

Glu Gly Thr Tyr Asp Trp Tyr Phe Asp Leu
1               5                   10

<210> SEQ ID NO 35
<211> LENGTH: 9
<212> TYPE: PRT
<213> ORGANISM: Artificial
<220> FEATURE:
<223> OTHER INFORMATION: VH CDR3 sequence of Li81 variant F09 antibody

<400> SEQUENCE: 35

Glu Gly Glu Asn Asp Ala Phe Asp Val
1               5

<210> SEQ ID NO 36
```

```
<211> LENGTH: 9
<212> TYPE: PRT
<213> ORGANISM: Artificial
<220> FEATURE:
<223> OTHER INFORMATION: VH CDR3 sequence of Li81 variant G02 antibody

<400> SEQUENCE: 36

Glu Gly Asp Asn Asp Ala Tyr Asp Thr
1               5

<210> SEQ ID NO 37
<211> LENGTH: 9
<212> TYPE: PRT
<213> ORGANISM: Artificial
<220> FEATURE:
<223> OTHER INFORMATION: VH CDR3 sequence of Li81 variant H03 antibody

<400> SEQUENCE: 37

Glu Gly Thr Asn Asp Ala Phe Asp Ile
1               5

<210> SEQ ID NO 38
<211> LENGTH: 9
<212> TYPE: PRT
<213> ORGANISM: Artificial
<220> FEATURE:
<223> OTHER INFORMATION: VH CDR3 sequence of Li81 variant A12 antibody

<400> SEQUENCE: 38

Glu Gly Asp Asn Asp Ala Phe Asp Ser
1               5

<210> SEQ ID NO 39
<211> LENGTH: 9
<212> TYPE: PRT
<213> ORGANISM: Artificial
<220> FEATURE:
<223> OTHER INFORMATION: VH CDR3 sequence of Li81 variant C02 antibody

<400> SEQUENCE: 39

Glu Gly Asp Asn Asp Ala Phe Asp Thr
1               5

<210> SEQ ID NO 40
<211> LENGTH: 9
<212> TYPE: PRT
<213> ORGANISM: Artificial
<220> FEATURE:
<223> OTHER INFORMATION: VH CDR3 sequence of Li81 variant C11 antibody

<400> SEQUENCE: 40

Glu Gly Asp Asn Asp Ala Tyr Asp Arg
1               5

<210> SEQ ID NO 41
<211> LENGTH: 9
<212> TYPE: PRT
<213> ORGANISM: Artificial
<220> FEATURE:
<223> OTHER INFORMATION: VH CDR3 sequence of Li81 variant D11 antibody

<400> SEQUENCE: 41

Glu Gly Asp Asn Asp Val Phe Asp Ser
1               5

<210> SEQ ID NO 42
<211> LENGTH: 9
<212> TYPE: PRT
```

```
<213> ORGANISM: Artificial
<220> FEATURE:
<223> OTHER INFORMATION: VH CDR3 sequence of Li81 variant E05 antibody

<400> SEQUENCE: 42

Glu Gly Asp Asp Asp Val Phe Asp Met
1               5

<210> SEQ ID NO 43
<211> LENGTH: 9
<212> TYPE: PRT
<213> ORGANISM: Artificial
<220> FEATURE:
<223> OTHER INFORMATION: VH CDR3 sequence of Li81 variant H04 antibody

<400> SEQUENCE: 43

Glu Gly Tyr Asn Asp Ala Phe Asp Phe
1               5

<210> SEQ ID NO 44
<211> LENGTH: 9
<212> TYPE: PRT
<213> ORGANISM: Artificial
<220> FEATURE:
<223> OTHER INFORMATION: VH CDR3 sequence of Li81 variant B04 antibody

<400> SEQUENCE: 44

Glu Gly Asp Asp Asp Ala Tyr Asp Met
1               5

<210> SEQ ID NO 45
<211> LENGTH: 9
<212> TYPE: PRT
<213> ORGANISM: Artificial
<220> FEATURE:
<223> OTHER INFORMATION: VH CDR3 sequence of Li81 variant A02 antibody

<400> SEQUENCE: 45

Glu Gln Asp Tyr Asp Thr Tyr Asp Leu
1               5

<210> SEQ ID NO 46
<211> LENGTH: 9
<212> TYPE: PRT
<213> ORGANISM: Artificial
<220> FEATURE:
<223> OTHER INFORMATION: VH CDR3 sequence of Li81 variant B12 antibody

<400> SEQUENCE: 46

Glu Gly Asp Asp Asp Ala Phe Asp Thr
1               5

<210> SEQ ID NO 47
<211> LENGTH: 9
<212> TYPE: PRT
<213> ORGANISM: Artificial
<220> FEATURE:
<223> OTHER INFORMATION: VH CDR3 sequence of Li81 variant H06 antibody

<400> SEQUENCE: 47

Glu Ala Asp Asp Asp Ala Phe Asp Ile
1               5

<210> SEQ ID NO 48
<211> LENGTH: 9
<212> TYPE: PRT
<213> ORGANISM: Artificial
<220> FEATURE:
```

<223> OTHER INFORMATION: VH CDR3 sequence of Li81 variant H08 antibody

<400> SEQUENCE: 48

Glu Gly Glu Asn Asp Ala Phe Asp Met
1               5

<210> SEQ ID NO 49
<211> LENGTH: 9
<212> TYPE: PRT
<213> ORGANISM: Artificial
<220> FEATURE:
<223> OTHER INFORMATION: VH CDR3 sequence of Li81 variant E07 antibody

<400> SEQUENCE: 49

Glu Gly Glu Tyr Asp Thr Tyr Asp Ile
1               5

<210> SEQ ID NO 50
<211> LENGTH: 447
<212> TYPE: PRT
<213> ORGANISM: Artificial
<220> FEATURE:
<223> OTHER INFORMATION: Aglycosylated Li81 heavy chain

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Ala Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 51
<211> LENGTH: 614
<212> TYPE: PRT
<213> ORGANISM: Homo sapiens

<400> SEQUENCE: 51

Met Leu Ala Gly Gly Val Arg Ser Met Pro Ser Pro Leu Leu Ala Cys
1               5                   10                  15

Trp Gln Pro Ile Leu Leu Val Leu Gly Ser Val Leu Ser Gly Ser
            20                  25                  30

Ala Thr Gly Cys Pro Pro Arg Cys Glu Cys Ser Ala Gln Asp Arg Ala
        35                  40                  45

Val Leu Cys His Arg Lys Arg Phe Val Ala Val Pro Glu Gly Ile Pro
    50                  55                  60

Thr Glu Thr Arg Leu Leu Asp Leu Gly Lys Asn Arg Ile Lys Thr Leu
65                  70                  75                  80

Asn Gln Asp Glu Phe Ala Ser Phe Pro His Leu Glu Glu Leu Glu Leu
                85                  90                  95

Asn Glu Asn Ile Val Ser Ala Val Glu Pro Gly Ala Phe Asn Asn Leu
            100                 105                 110

Phe Asn Leu Arg Thr Leu Gly Leu Arg Ser Asn Arg Leu Lys Leu Ile
        115                 120                 125

Pro Leu Gly Val Phe Thr Gly Leu Ser Asn Leu Thr Lys Leu Asp Ile
    130                 135                 140

Ser Glu Asn Lys Ile Val Ile Leu Leu Asp Tyr Met Phe Gln Asp Leu
145                 150                 155                 160

Tyr Asn Leu Lys Ser Leu Glu Val Gly Asp Asn Asp Leu Val Tyr Ile
                165                 170                 175

Ser His Arg Ala Phe Ser Gly Leu Asn Ser Leu Glu Gln Leu Thr Leu
            180                 185                 190

Glu Lys Cys Asn Leu Thr Ser Ile Pro Thr Glu Ala Leu Ser His Leu
        195                 200                 205
```

```
His Gly Leu Ile Val Leu Arg Leu Arg His Leu Asn Ile Asn Ala Ile
    210                 215                 220
Arg Asp Tyr Ser Phe Lys Arg Leu Tyr Arg Leu Lys Val Leu Glu Ile
225                 230                 235                 240
Ser His Trp Pro Tyr Leu Asp Thr Met Thr Pro Asn Cys Leu Tyr Gly
                245                 250                 255
Leu Asn Leu Thr Ser Leu Ser Ile Thr His Cys Asn Leu Thr Ala Val
            260                 265                 270
Pro Tyr Leu Ala Val Arg His Leu Val Tyr Leu Arg Phe Leu Asn Leu
        275                 280                 285
Ser Tyr Asn Pro Ile Ser Thr Ile Glu Gly Ser Met Leu His Glu Leu
    290                 295                 300
Leu Arg Leu Gln Glu Ile Gln Leu Val Gly Gly Gln Leu Ala Val Val
305                 310                 315                 320
Glu Pro Tyr Ala Phe Arg Gly Leu Asn Tyr Leu Arg Val Leu Asn Val
                325                 330                 335
Ser Gly Asn Gln Leu Thr Thr Leu Glu Glu Ser Val Phe His Ser Val
            340                 345                 350
Gly Asn Leu Glu Thr Leu Ile Leu Asp Ser Asn Pro Leu Ala Cys Asp
        355                 360                 365
Cys Arg Leu Leu Trp Val Phe Arg Arg Trp Arg Leu Asn Phe Asn
370                 375                 380
Arg Gln Gln Pro Thr Cys Ala Thr Pro Glu Phe Val Gln Gly Lys Glu
385                 390                 395                 400
Phe Lys Asp Phe Pro Asp Val Leu Leu Pro Asn Tyr Phe Thr Cys Arg
                405                 410                 415
Arg Ala Arg Ile Arg Asp Arg Lys Ala Gln Gln Val Phe Val Asp Glu
            420                 425                 430
Gly His Thr Val Gln Phe Val Cys Arg Ala Asp Gly Asp Pro Pro Pro
        435                 440                 445
Ala Ile Leu Trp Leu Ser Pro Arg Lys His Leu Val Ser Ala Lys Ser
    450                 455                 460
Asn Gly Arg Leu Thr Val Phe Pro Asp Gly Thr Leu Glu Val Arg Tyr
465                 470                 475                 480
Ala Gln Val Gln Asp Asn Gly Thr Tyr Leu Cys Ile Ala Ala Asn Ala
                485                 490                 495
Gly Gly Asn Asp Ser Met Pro Ala His Leu His Val Arg Ser Tyr Ser
            500                 505                 510
Pro Asp Trp Pro His Gln Pro Asn Lys Thr Phe Ala Phe Ile Ser Asn
        515                 520                 525
Gln Pro Gly Glu Gly Glu Ala Asn Ser Thr Arg Ala Thr Val Pro Phe
    530                 535                 540
Pro Phe Asp Ile Lys Thr Leu Ile Ile Ala Thr Thr Met Gly Phe Ile
545                 550                 555                 560
Ser Phe Leu Gly Val Val Leu Phe Cys Leu Val Leu Leu Phe Leu Trp
                565                 570                 575
Ser Arg Gly Lys Gly Asn Thr Lys His Asn Ile Glu Ile Glu Tyr Val
            580                 585                 590
Pro Arg Lys Ser Asp Ala Gly Ile Ser Ser Ala Asp Ala Pro Arg Lys
        595                 600                 605
Phe Asn Met Lys Met Ile
    610
```

<210> SEQ ID NO 52
<211> LENGTH: 1845
<212> TYPE: DNA
<213> ORGANISM: Homo sapiens

<400> SEQUENCE: 52

| | | | | | |
|---|---|---|---|---|---|
| atgctggcgg | ggggcgtgag | gagcatgccc | agcccctcc | tggcctgctg | gcagcccatc | 60 |
| ctcctgctgg | tgctgggctc | agtgctgtca | ggctcggcca | cgggctgccc | gccccgctgc | 120 |
| gagtgctccg | cccaggaccg | cgctgtgctg | tgccaccgca | agcgctttgt | ggcagtcccc | 180 |
| gagggcatcc | ccaccgagac | cgcctgctg | gacctaggca | agaaccgcat | caaaacgctc | 240 |
| aaccaggacg | agttcgccag | cttcccgcac | ctggaggagc | tggagctcaa | cgagaacatc | 300 |
| gtgagcgccg | tggagcccgg | cgccttcaac | aacctcttca | acctccggac | gctgggtctc | 360 |
| cgcagcaacc | gcctgaagct | catcccgcta | ggcgtcttca | ctggcctcag | caacctgacc | 420 |
| aagctggaca | tcagcgagaa | caagattgtt | atcctgctgg | actacatgtt | tcaggacctg | 480 |
| tacaacctca | gtcactgga | ggttggcgac | aatgacctcg | tctacatctc | tcaccgcgcc | 540 |
| ttcagcggcc | tcaacagcct | ggagcagctg | acgctggaga | atgcaacct | gacctccatc | 600 |
| cccaccgagg | cgctgtccca | cctgcacggc | ctcatcgtcc | tgaggctccg | gcacctcaac | 660 |
| atcaatgcca | tccgggacta | ctccttcaag | aggctctacc | gactcaaggt | cttggagatc | 720 |
| tcccactggc | cctacttgga | caccatgaca | cccaactgcc | tctacggcct | caacctgacg | 780 |
| tccctgtcca | tcacacactg | caatctgacc | gctgtgccct | acctggccgt | ccgccaccta | 840 |
| gtctatctcc | gcttcctcaa | cctctcctac | aaccccatca | gcaccattga | gggctccatg | 900 |
| ttgcatgagc | tgctccggct | gcaggagatc | cagctggtgg | gcgggcagct | ggccgtggtg | 960 |
| gagccctatg | ccttccgcgg | cctcaactac | ctgcgcgtgc | tcaatgtctc | tggcaaccag | 1020 |
| ctgaccacac | tggaggaatc | agtcttccac | tcggtgggca | acctggagac | actcatcctg | 1080 |
| gactccaacc | cgctggcctg | cgactgtcgg | ctcctgtggg | tgttccggcg | ccgctggcgg | 1140 |
| ctcaacttca | accggcagca | gcccacgtgc | gccacgcccg | agtttgtcca | gggcaaggag | 1200 |
| ttcaaggact | ccctgatgt | gctactgccc | aactacttca | cctgccgccg | cgcccgcatc | 1260 |
| cgggaccgca | aggcccagca | ggtgtttgtg | gacgagggcc | acacggtgca | gtttgtgtgc | 1320 |
| cgggccgatg | gcgacccgcc | gcccgccatc | tctggctct | cccccgaaa | gcacctggtc | 1380 |
| tcagccaaga | gcaatgggcg | gctcacagtc | ttccctgatg | gcacgctgga | ggtgcgctac | 1440 |
| gcccaggtac | aggacaacgg | cacgtacctg | tgcatcgcgg | ccaacgcggg | cggcaacgac | 1500 |
| tccatgcccg | cccacctgca | tgtgcgcagc | tactcgcccg | actggcccca | tcagcccaac | 1560 |
| aagaccttcg | ctttcatctc | caaccagccc | ggcgagggag | aggccaacag | cacccgcgcc | 1620 |
| actgtgcctt | tccccttcga | catcaagacc | ctcatcatcg | ccaccaccat | gggcttcatc | 1680 |
| tcttcctgg | gcgtcgtcct | cttctgcctg | gtgctgctgt | ttctctggag | ccggggcaag | 1740 |
| ggcaacacaa | agcacaacat | cgagatcgag | tatgtgccc | gaaagtcgga | cgcaggcatc | 1800 |
| agctccgccg | acgcgccccg | caagttcaac | atgaagatga | tatga | | 1845 |

<210> SEQ ID NO 53
<211> LENGTH: 119
<212> TYPE: PRT
<213> ORGANISM: Artificial
<220> FEATURE:
<223> OTHER INFORMATION: VH sequence of Li62 variant B06 antibody

<400> SEQUENCE: 53

Glu Val Gln Leu Leu Glu Ser Gly Gly Gly Leu Val Gln Pro Gly Gly

```
                1               5              10              15
Ser Leu Arg Leu Ser Cys Ala Ala Ser Gly Phe Thr Phe Ser Ile Tyr
            20              25              30

Pro Met Phe Trp Val Arg Gln Ala Pro Gly Lys Gly Leu Glu Trp Val
            35              40              45

Ser Trp Ile Gly Pro Ser Gly Gly Ile Thr Lys Tyr Ala Asp Ser Val
 50              55              60

Lys Gly Arg Phe Thr Ile Ser Arg Asp Asn Ser Lys Asn Thr Leu Tyr
 65                  70              75                      80

Leu Gln Met Asn Ser Leu Arg Ala Glu Asp Thr Ala Thr Tyr Tyr Cys
                85              90              95

Ala Arg Glu Gly Tyr Tyr Asp Trp Tyr Phe Asp Gln Trp Gly Arg Gly
            100             105             110

Thr Leu Val Thr Val Ser Ser
            115

<210> SEQ ID NO 54
<211> LENGTH: 119
<212> TYPE: PRT
<213> ORGANISM: Artificial
<220> FEATURE:
<223> OTHER INFORMATION: VH sequence of Li62 variant B12 antibody

<400> SEQUENCE: 54

Glu Val Gln Leu Leu Glu Ser Gly Gly Gly Leu Val Gln Pro Gly Gly
 1               5              10              15

Ser Leu Arg Leu Ser Cys Ala Ala Ser Gly Phe Thr Phe Ser Ile Tyr
            20              25              30

Pro Met Phe Trp Val Arg Gln Ala Pro Gly Lys Gly Leu Glu Trp Val
            35              40              45

Ser Trp Ile Gly Pro Ser Gly Gly Ile Thr Lys Tyr Ala Asp Ser Val
 50              55              60

Lys Gly Arg Phe Thr Ile Ser Arg Asp Asn Ser Lys Asn Thr Leu Tyr
 65                  70              75                      80

Leu Gln Met Asn Ser Leu Arg Ala Glu Asp Thr Ala Thr Tyr Tyr Cys
                85              90              95

Ala Arg Glu Gly Gln Tyr Asp Trp Tyr Phe Asp Val Trp Gly Arg Gly
            100             105             110

Thr Leu Val Thr Val Ser Ser
            115

<210> SEQ ID NO 55
<211> LENGTH: 119
<212> TYPE: PRT
<213> ORGANISM: Artificial
<220> FEATURE:
<223> OTHER INFORMATION: VH sequence of Li62 variant F06 antibody

<400> SEQUENCE: 55

Glu Val Gln Leu Leu Glu Ser Gly Gly Gly Leu Val Gln Pro Gly Gly
 1               5              10              15

Ser Leu Arg Leu Ser Cys Ala Ala Ser Gly Phe Thr Phe Ser Ile Tyr
            20              25              30

Pro Met Phe Trp Val Arg Gln Ala Pro Gly Lys Gly Leu Glu Trp Val
            35              40              45

Ser Trp Ile Gly Pro Ser Gly Gly Ile Thr Lys Tyr Ala Asp Ser Val
 50              55              60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Thr Tyr Tyr Cys
                    85                  90                  95

Ala Arg Glu Gly Asp Tyr Asp Trp Tyr Phe Asp Leu Trp Gly Arg Gly
                100                 105                 110

Thr Leu Val Thr Val Ser Ser
        115

<210> SEQ ID NO 56
<211> LENGTH: 119
<212> TYPE: PRT
<213> ORGANISM: Artificial
<220> FEATURE:
<223> OTHER INFORMATION: VH sequence of Li62 variant B01 antibody

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
                35                  40                  45

Ser Trp Ile Gly Pro Ser Gly Gly Ile Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                    85                  90                  95

Ala Arg Glu Gly Gln Tyr Asp Trp Tyr Phe Glu Leu Trp Gly Arg Gly
                100                 105                 110

Thr Leu Val Thr Val Ser Ser
        115

<210> SEQ ID NO 57
<211> LENGTH: 119
<212> TYPE: PRT
<213> ORGANISM: Artificial
<220> FEATURE:
<223> OTHER INFORMATION: VH sequence of Li62 variant D09 antibody

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
                35                  40                  45

Ser Trp Ile Gly Pro Ser Gly Gly Ile Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                    85                  90                  95

Ala Arg Glu Ala Asp Ile Asp Trp Phe Phe Asp Leu Trp Gly Arg Gly
                100                 105                 110

Thr Leu Val Thr Val Ser Ser
        115
```

```
<210> SEQ ID NO 58
<211> LENGTH: 119
<212> TYPE: PRT
<213> ORGANISM: Artificial
<220> FEATURE:
<223> OTHER INFORMATION: VH sequence of Li62 variant D12 antibody

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Tyr Asp Trp Tyr Phe Asp Leu Trp Gly Arg Gly
            100                 105                 110

Thr Leu Val Thr Val Ser Ser
        115

<210> SEQ ID NO 59
<211> LENGTH: 119
<212> TYPE: PRT
<213> ORGANISM: Artificial
<220> FEATURE:
<223> OTHER INFORMATION: VH sequence of Li62 variant F01 antibody

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Arg Tyr Asp Trp Tyr Phe Asp Pro Trp Gly Arg Gly
            100                 105                 110

Thr Leu Val Thr Val Ser Ser
        115

<210> SEQ ID NO 60
<211> LENGTH: 119
<212> TYPE: PRT
<213> ORGANISM: Artificial
<220> FEATURE:
<223> OTHER INFORMATION: VH sequence of Li62 variant F02 antibody

<400> SEQUENCE: 60

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ile Tyr
        20                  25                  30

Pro Met Phe Trp Val Arg Gln Ala Pro Gly Lys Gly Leu Glu Trp Val
            35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Gly Asp Tyr Asp Trp Tyr Phe Gly Leu Trp Gly Arg Gly
            100                 105                 110

Thr Leu Val Thr Val Ser Ser
        115

<210> SEQ ID NO 61
<211> LENGTH: 119
<212> TYPE: PRT
<213> ORGANISM: Artificial
<220> FEATURE:
<223> OTHER INFORMATION: VH sequence of Li62 variant F06 antibody

<400> SEQUENCE: 61

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Gly Arg Tyr Asp Trp Tyr Phe Asp Leu Trp Gly Arg Gly
            100                 105                 110

Thr Leu Val Thr Val Ser Ser
        115

<210> SEQ ID NO 62
<211> LENGTH: 119
<212> TYPE: PRT
<213> ORGANISM: Artificial
<220> FEATURE:
<223> OTHER INFORMATION: VH sequence of Li62 variant F10 antibody

<400> SEQUENCE: 62

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Thr Tyr Tyr Cys
                85                  90                  95

Ala Arg Glu Ser His Ile Asp Arg Tyr Phe Asp Leu Trp Gly Arg Gly
            100                 105                 110

Thr Leu Val Thr Val Ser Ser
        115

<210> SEQ ID NO 63
<211> LENGTH: 119
<212> TYPE: PRT
<213> ORGANISM: Artificial
<220> FEATURE:
<223> OTHER INFORMATION: VH sequence of Li62 variant G08 antibody

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Gln Tyr Asp Trp Tyr Phe Asp Val Trp Gly Arg Gly
            100                 105                 110

Thr Leu Val Thr Val Ser Ser
        115

<210> SEQ ID NO 64
<211> LENGTH: 119
<212> TYPE: PRT
<213> ORGANISM: Artificial
<220> FEATURE:
<223> OTHER INFORMATION: VH sequence of Li62 variant H08 antibody

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Tyr Asn Gly Tyr Phe Asp Leu Trp Gly Arg Gly
            100                 105                 110

Thr Leu Val Thr Val Ser Ser
        115

<210> SEQ ID NO 65
<211> LENGTH: 119
```

```
<212> TYPE: PRT
<213> ORGANISM: Artificial
<220> FEATURE:
<223> OTHER INFORMATION: VH sequence of Li62 variant C10 antibody

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Tyr Tyr Asp Trp Tyr Phe Asp Leu Trp Gly Arg Gly
            100                 105                 110

Thr Leu Val Thr Val Ser Ser
        115

<210> SEQ ID NO 66
<211> LENGTH: 119
<212> TYPE: PRT
<213> ORGANISM: Artificial
<220> FEATURE:
<223> OTHER INFORMATION: VH sequence of Li62 variant C02 antibody

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 67
<211> LENGTH: 119
<212> TYPE: PRT
<213> ORGANISM: Artificial
<220> FEATURE:
<223> OTHER INFORMATION: VH sequence of Li62 variant D05 antibody

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30
```

```
Pro Met Phe Trp Val Arg Gln Ala Pro Gly Lys Gly Leu Glu Trp Val
        35                  40                  45

Ser Trp Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Tyr Tyr Asp Trp Tyr Phe Glu Leu Trp Gly Arg Gly
                100                 105                 110

Thr Leu Val Thr Val Ser Ser
        115

<210> SEQ ID NO 68
<211> LENGTH: 119
<212> TYPE: PRT
<213> ORGANISM: Artificial
<220> FEATURE:
<223> OTHER INFORMATION: VH sequence of Li62 variant F02 antibody

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Leu Ile Asp Trp Phe Phe Asp Gln Trp Gly Arg Gly
                100                 105                 110

Thr Leu Val Thr Val Ser Ser
        115

<210> SEQ ID NO 69
<211> LENGTH: 119
<212> TYPE: PRT
<213> ORGANISM: Artificial
<220> FEATURE:
<223> OTHER INFORMATION: VH sequence of Li62 variant C10 antibody

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95
```

-continued

```
Ala Arg Glu Gly Gln Phe Asp Trp Tyr Phe Asp Leu Trp Gly Arg Gly
            100                 105                 110

Thr Leu Val Thr Val Ser Ser
        115

<210> SEQ ID NO 70
<211> LENGTH: 119
<212> TYPE: PRT
<213> ORGANISM: Artificial
<220> FEATURE:
<223> OTHER INFORMATION: VH sequence of Li62 variant H08 antibody

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Phe Asp Leu Trp Gly Arg Gly
            100                 105                 110

Thr Leu Val Thr Val Ser Ser
        115

<210> SEQ ID NO 71
<211> LENGTH: 118
<212> TYPE: PRT
<213> ORGANISM: Artificial
<220> FEATURE:
<223> OTHER INFORMATION: VH sequence of Li81 variant F09 antibody

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Glu Asn Asp Ala Phe Asp Val Trp Gly Gln Gly Thr
            100                 105                 110

Thr Val Thr Val Ser Ser
        115

<210> SEQ ID NO 72
<211> LENGTH: 118
<212> TYPE: PRT
<213> ORGANISM: Artificial
```

<220> FEATURE:
<223> OTHER INFORMATION: VH sequence of Li81 variant G02 antibody

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Tyr Asp Thr Trp Gly Gln Gly Thr
            100                 105                 110

Thr Val Thr Val Ser Ser
        115

<210> SEQ ID NO 73
<211> LENGTH: 118
<212> TYPE: PRT
<213> ORGANISM: Artificial
<220> FEATURE:
<223> OTHER INFORMATION: VH sequence of Li81 variant H03 antibody

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Thr Asn Asp Ala Phe Asp Ile Trp Gly Gln Gly Thr
            100                 105                 110

Thr Val Thr Val Ser Ser
        115

<210> SEQ ID NO 74
<211> LENGTH: 118
<212> TYPE: PRT
<213> ORGANISM: Artificial
<220> FEATURE:
<223> OTHER INFORMATION: VH sequence of Li81 variant A12 antibody

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val

-continued

```
                35                  40                  45
Ser Val Ile Gly Pro Ser Gly Gly Phe Thr Phe Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Thr Glu Gly Asp Asn Asp Ala Phe Asp Ser Trp Gly Gln Gly Thr
                100                 105                 110
Thr Val Thr Val Ser Ser
                115

<210> SEQ ID NO 75
<211> LENGTH: 118
<212> TYPE: PRT
<213> ORGANISM: Artificial
<220> FEATURE:
<223> OTHER INFORMATION: VH sequence of Li81 variant C02 antibody

<400> SEQUENCE: 75

Glu Val Gln Leu Leu Glu Ser Gly Gly Gly Leu Val Gln Pro Gly Gly
 1                   5                  10                  15
Ser Leu Arg Leu Ser Cys Ala Ala Ser Gly Phe Thr Phe Ser Ala Tyr
                 20                  25                  30
Glu Met Lys Trp Val Arg Gln Ala Pro Gly Lys Gly Leu Glu Trp Val
                 35                  40                  45
Ser Val Ile Gly Pro Ser Gly Gly Phe Thr Phe Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Thr Glu Gly Asp Asn Asp Ala Phe Asp Thr Trp Gly Gln Gly Thr
                100                 105                 110
Thr Val Thr Val Ser Ser
                115

<210> SEQ ID NO 76
<211> LENGTH: 118
<212> TYPE: PRT
<213> ORGANISM: Artificial
<220> FEATURE:
<223> OTHER INFORMATION: VH sequence of Li81 variant C11 antibody

<400> SEQUENCE: 76

Glu Val Gln Leu Leu Glu Ser Gly Gly Gly Leu Val Gln Pro Gly Gly
 1                   5                  10                  15
Ser Leu Arg Leu Ser Cys Ala Ala Ser Gly Phe Thr Phe Ser Ala Tyr
                 20                  25                  30
Glu Met Lys Trp Val Arg Gln Ala Pro Gly Lys Gly Leu Glu Trp Val
                 35                  40                  45
Ser Val Ile Gly Pro Ser Gly Gly Phe Thr Phe Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Thr Glu Gly Asp Asn Asp Ala Tyr Asp Arg Trp Gly Gln Gly Thr
```

Thr Val Thr Val Ser Ser
        115

<210> SEQ ID NO 77
<211> LENGTH: 118
<212> TYPE: PRT
<213> ORGANISM: Artificial
<220> FEATURE:
<223> OTHER INFORMATION: VH sequence of Li81 variant D11 antibody

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Val Phe Asp Ser Trp Gly Gln Gly Thr
            100                 105                 110

Thr Val Thr Val Ser Ser
        115

<210> SEQ ID NO 78
<211> LENGTH: 118
<212> TYPE: PRT
<213> ORGANISM: Artificial
<220> FEATURE:
<223> OTHER INFORMATION: VH sequence of Li81 variant E05 antibody

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asp Asp Val Phe Asp Met Trp Gly Gln Gly Thr
            100                 105                 110

Thr Val Thr Val Ser Ser
        115

<210> SEQ ID NO 79
<211> LENGTH: 118
<212> TYPE: PRT
<213> ORGANISM: Artificial
<220> FEATURE:
<223> OTHER INFORMATION: VH sequence of Li81 variant H04 antibody -continued

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Tyr Asn Asp Ala Phe Asp Phe Trp Gly Gln Gly Thr
            100                 105                 110

Thr Val Thr Val Ser Ser
        115

<210> SEQ ID NO 80
<211> LENGTH: 118
<212> TYPE: PRT
<213> ORGANISM: Artificial
<220> FEATURE:
<223> OTHER INFORMATION: VH sequence of Li81 variant B04 antibody

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asp Asp Ala Tyr Asp Met Trp Gly Gln Gly Thr
            100                 105                 110

Thr Val Thr Val Ser Ser
        115

<210> SEQ ID NO 81
<211> LENGTH: 118
<212> TYPE: PRT
<213> ORGANISM: Artificial
<220> FEATURE:
<223> OTHER INFORMATION: VH sequence of Li81 variant A02 antibody

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

```
Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Gln Asp Tyr Asp Thr Tyr Asp Leu Trp Gly Gln Gly Thr
            100                 105                 110

Thr Val Thr Val Ser Ser
            115

<210> SEQ ID NO 82
<211> LENGTH: 118
<212> TYPE: PRT
<213> ORGANISM: Artificial
<220> FEATURE:
<223> OTHER INFORMATION: VH sequence of Li81 variant B12 antibody

<400> SEQUENCE: 82

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
             20                  25                  30

Glu Met Lys Trp Val Arg Gln Ala Pro Gly Lys Gly Leu Glu Trp Val
         35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Gly Asp Asp Asp Ala Phe Asp Thr Trp Gly Gln Gly Thr
            100                 105                 110

Thr Val Thr Val Ser Ser
            115

<210> SEQ ID NO 83
<211> LENGTH: 118
<212> TYPE: PRT
<213> ORGANISM: Artificial
<220> FEATURE:
<223> OTHER INFORMATION: VH sequence of Li81 variant H06 antibody

<400> SEQUENCE: 83

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
             20                  25                  30

Glu Met Lys Trp Val Arg Gln Ala Pro Gly Lys Gly Leu Glu Trp Val
         35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Ala Asp Asp Asp Ala Phe Asp Ile Trp Gly Gln Gly Thr
            100                 105                 110
```

-continued

Thr Val Thr Val Ser Ser
        115

<210> SEQ ID NO 84
<211> LENGTH: 118
<212> TYPE: PRT
<213> ORGANISM: Artificial
<220> FEATURE:
<223> OTHER INFORMATION: VH sequence of Li81 variant H08 antibody

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Glu Asn Asp Ala Phe Asp Met Trp Gly Gln Gly Thr
            100                 105                 110

Thr Val Thr Val Ser Ser
        115

<210> SEQ ID NO 85
<211> LENGTH: 118
<212> TYPE: PRT
<213> ORGANISM: Artificial
<220> FEATURE:
<223> OTHER INFORMATION: VH sequence of Li81 variant E07 antibody

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Pro Ser Gly Gly Phe Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Glu Tyr Asp Thr Tyr Asp Ile Trp Gly Gln Gly Thr
            100                 105                 110

Thr Val Thr Val Ser Ser
        115

<210> SEQ ID NO 86
<211> LENGTH: 447
<212> TYPE: PRT
<213> ORGANISM: Artificial
<220> FEATURE:
<223> OTHER INFORMATION: Li81 heavy chain

<400> SEQUENCE: 86

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ala Tyr
             20                  25                  30

Glu Met Lys Trp Val Arg Gln Ala Pro Gly Lys Gly Leu Glu Trp Val
         35                  40                  45

Ser Val Ile Gly Pro Ser Gly Gly Phe Thr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Gly Asp Asn Asp Ala Phe Asp Ile Trp Gly Gln Gly Thr
             100                 105                 110

Thr Val Thr Val Ser Ser Ala Ser Thr Lys Gly Pro Ser Val Phe Pro
             115                 120                 125

Leu Ala Pro Ser Ser Lys Ser Thr Ser Gly Gly Thr Ala Ala Leu Gly
         130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                 165                 170                 175

Ser Ser Gly Leu Tyr Ser Leu Ser Ser Val Val Thr Val Pro Ser Ser
             180                 185                 190

Ser Leu Gly Thr Gln Thr Tyr Ile Cys Asn Val Asn His Lys Pro Ser
         195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Val Asp Val Ser His Glu Asp Pro
             260                 265                 270

Glu Val Lys Phe Asn Trp Tyr Val Asp Gly Val Glu Val His Asn Ala
         275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                 325                 330                 335

Ile Ser Lys Ala Lys Gly Gln Pro Arg Glu Pro Gln Val Tyr Thr Leu
             340                 345                 350

Pro Pro Ser Arg Asp Glu Leu Thr Lys Asn Gln Val Ser Leu Thr Cys
         355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                 405                 410                 415

Arg Trp Gln Gln Gly Asn Val Phe Ser Cys Ser Val Met His Glu Ala
```

420                 425                 430
Leu His Asn His Tyr Thr Gln Lys Ser Leu Ser Leu Ser Pro Gly
        435                 440                 445

<210> SEQ ID NO 87
<211> LENGTH: 6
<212> TYPE: PRT
<213> ORGANISM: Artificial
<220> FEATURE:
<223> OTHER INFORMATION: N-terminus of LINGO-1 polypeptide

<400> SEQUENCE: 87

Met Gln Val Ser Lys Arg
1               5

<210> SEQ ID NO 88
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(5)
<223> OTHER INFORMATION: X can be lysine, arginine, histidine,
      glutamine, asparagine

<400> SEQUENCE: 88

Ile Thr Xaa Xaa Xaa
1               5

<210> SEQ ID NO 89
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(5)
<223> OTHER INFORMATION: X can be lysine, arginine, histidine,
      glutamine, asparagine

<400> SEQUENCE: 89

Ala Cys Xaa Xaa Xaa
1               5

<210> SEQ ID NO 90
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(5)
<223> OTHER INFORMATION: X can be lysine, arginine, histidine,
      glutamine, asparagine

<400> SEQUENCE: 90

Val Cys Xaa Xaa Xaa
1               5

<210> SEQ ID NO 91
<211> LENGTH: 5
<212> TYPE: PRT
<213> ORGANISM: Artificial
<220> FEATURE:
<223> OTHER INFORMATION: LINGO-1 polypeptide
<220> FEATURE:

```
<221> NAME/KEY: MISC_FEATURE
<222> LOCATION: (3)..(5)
<223> OTHER INFORMATION: X can be lysine, arginine, histidine,
      glutamine, asparagine

<400> SEQUENCE: 91

Ser Pro Xaa Xaa Xaa
1               5

<210> SEQ ID NO 92
<211> LENGTH: 5
<212> TYPE: PRT
<213> ORGANISM: Artificial
<220> FEATURE:
<223> OTHER INFORMATION: LINGO-1 polypeptide

<400> SEQUENCE: 92

Ser Pro Arg Lys His
1               5

<210> SEQ ID NO 93
<211> LENGTH: 5
<212> TYPE: PRT
<213> ORGANISM: Artificial
<220> FEATURE:
<223> OTHER INFORMATION: LINGO-1 polypeptide

<400> SEQUENCE: 93

Ser Pro Arg Lys Lys
1               5

<210> SEQ ID NO 94
<211> LENGTH: 5
<212> TYPE: PRT
<213> ORGANISM: Artificial
<220> FEATURE:
<223> OTHER INFORMATION: LINGO-1 polypeptide

<400> SEQUENCE: 94

Ser Pro Arg Lys Arg
1               5

<210> SEQ ID NO 95
<211> LENGTH: 5
<212> TYPE: PRT
<213> ORGANISM: Artificial
<220> FEATURE:
<223> OTHER INFORMATION: LINGO-1 polypeptide

<400> SEQUENCE: 95

Ser Pro Lys Lys His
1               5

<210> SEQ ID NO 96
<211> LENGTH: 5
<212> TYPE: PRT
<213> ORGANISM: Artificial
<220> FEATURE:
<223> OTHER INFORMATION: LINGO-1 polypeptide

<400> SEQUENCE: 96

Ser Pro His Lys His
1               5

<210> SEQ ID NO 97
<211> LENGTH: 5
<212> TYPE: PRT
<213> ORGANISM: Artificial
```

<220> FEATURE:
<223> OTHER INFORMATION: LINGO-1 polypeptide

<400> SEQUENCE: 97

Ser Pro Arg Arg His
1               5

<210> SEQ ID NO 98
<211> LENGTH: 5
<212> TYPE: PRT
<213> ORGANISM: Artificial
<220> FEATURE:
<223> OTHER INFORMATION: LINGO-1 polypeptide

<400> SEQUENCE: 98

Ser Pro Arg His His
1               5

<210> SEQ ID NO 99
<211> LENGTH: 5
<212> TYPE: PRT
<213> ORGANISM: Artificial
<220> FEATURE:
<223> OTHER INFORMATION: LINGO-1 polypeptide

<400> SEQUENCE: 99

Ser Pro Arg Arg Arg
1               5

<210> SEQ ID NO 100
<211> LENGTH: 5
<212> TYPE: PRT
<213> ORGANISM: Artificial
<220> FEATURE:
<223> OTHER INFORMATION: LINGO-1 polypeptide

<400> SEQUENCE: 100

Ser Pro His His His
1               5

<210> SEQ ID NO 101
<211> LENGTH: 5
<212> TYPE: PRT
<213> ORGANISM: Artificial
<220> FEATURE:
<223> OTHER INFORMATION: LINGO-1 polypeptide

<400> SEQUENCE: 101

Ser Pro Lys Lys Lys
1               5

<210> SEQ ID NO 102
<211> LENGTH: 6
<212> TYPE: PRT
<213> ORGANISM: Artificial
<220> FEATURE:
<223> OTHER INFORMATION: LINGO-1 polypeptide

<400> SEQUENCE: 102

Leu Ser Pro Arg Lys His
1               5

<210> SEQ ID NO 103
<211> LENGTH: 6
<212> TYPE: PRT
<213> ORGANISM: Artificial
<220> FEATURE:
<223> OTHER INFORMATION: LINGO-1 polypeptide

```
<400> SEQUENCE: 103

Leu Ser Pro Arg Lys Lys
1               5

<210> SEQ ID NO 104
<211> LENGTH: 6
<212> TYPE: PRT
<213> ORGANISM: Artificial
<220> FEATURE:
<223> OTHER INFORMATION: LINGO-1 polypeptide

<400> SEQUENCE: 104

Leu Ser Pro Arg Lys Arg
1               5

<210> SEQ ID NO 105
<211> LENGTH: 6
<212> TYPE: PRT
<213> ORGANISM: Artificial
<220> FEATURE:
<223> OTHER INFORMATION: LINGO-1 polypeptide

<400> SEQUENCE: 105

Leu Ser Pro Lys Lys His
1               5

<210> SEQ ID NO 106
<211> LENGTH: 6
<212> TYPE: PRT
<213> ORGANISM: Artificial
<220> FEATURE:
<223> OTHER INFORMATION: LINGO-1 polypeptide

<400> SEQUENCE: 106

Leu Ser Pro His Lys His
1               5

<210> SEQ ID NO 107
<211> LENGTH: 6
<212> TYPE: PRT
<213> ORGANISM: Artificial
<220> FEATURE:
<223> OTHER INFORMATION: LINGO-1 polypeptide

<400> SEQUENCE: 107

Leu Ser Pro Arg Arg His
1               5

<210> SEQ ID NO 108
<211> LENGTH: 6
<212> TYPE: PRT
<213> ORGANISM: Artificial
<220> FEATURE:
<223> OTHER INFORMATION: LINGO-1 polypeptide

<400> SEQUENCE: 108

Leu Ser Pro Arg His His
1               5

<210> SEQ ID NO 109
<211> LENGTH: 6
<212> TYPE: PRT
<213> ORGANISM: Artificial
<220> FEATURE:
<223> OTHER INFORMATION: LINGO-1 polypeptide

<400> SEQUENCE: 109
```

```
Leu Ser Pro Arg Arg Arg
1               5

<210> SEQ ID NO 110
<211> LENGTH: 6
<212> TYPE: PRT
<213> ORGANISM: Artificial
<220> FEATURE:
<223> OTHER INFORMATION: LINGO-1 polypeptide

<400> SEQUENCE: 110

Leu Ser Pro His His His
1               5

<210> SEQ ID NO 111
<211> LENGTH: 6
<212> TYPE: PRT
<213> ORGANISM: Artificial
<220> FEATURE:
<223> OTHER INFORMATION: LINGO-1 polypeptide

<400> SEQUENCE: 111

Leu Ser Pro Lys Lys Lys
1               5

<210> SEQ ID NO 112
<211> LENGTH: 7
<212> TYPE: PRT
<213> ORGANISM: Artificial
<220> FEATURE:
<223> OTHER INFORMATION: LINGO-1 polypeptide

<400> SEQUENCE: 112

Trp Leu Ser Pro Arg Lys His
1               5

<210> SEQ ID NO 113
<211> LENGTH: 7
<212> TYPE: PRT
<213> ORGANISM: Artificial
<220> FEATURE:
<223> OTHER INFORMATION: LINGO-1 polypeptide

<400> SEQUENCE: 113

Trp Leu Ser Pro Arg Lys Lys
1               5

<210> SEQ ID NO 114
<211> LENGTH: 7
<212> TYPE: PRT
<213> ORGANISM: Artificial
<220> FEATURE:
<223> OTHER INFORMATION: LINGO-1 polypeptide

<400> SEQUENCE: 114

Trp Leu Ser Pro Arg Lys Arg
1               5

<210> SEQ ID NO 115
<211> LENGTH: 7
<212> TYPE: PRT
<213> ORGANISM: Artificial
<220> FEATURE:
<223> OTHER INFORMATION: LINGO-1 polypeptide

<400> SEQUENCE: 115

Trp Leu Ser Pro Lys Lys His
```

-continued

```
<210> SEQ ID NO 116
<211> LENGTH: 7
<212> TYPE: PRT
<213> ORGANISM: Artificial
<220> FEATURE:
<223> OTHER INFORMATION: LINGO-1 polypeptide

<400> SEQUENCE: 116

Trp Leu Ser Pro His Lys His
1               5

<210> SEQ ID NO 117
<211> LENGTH: 7
<212> TYPE: PRT
<213> ORGANISM: Artificial
<220> FEATURE:
<223> OTHER INFORMATION: LINGO-1 polypeptide

<400> SEQUENCE: 117

Trp Leu Ser Pro Arg Arg His
1               5

<210> SEQ ID NO 118
<211> LENGTH: 7
<212> TYPE: PRT
<213> ORGANISM: Artificial
<220> FEATURE:
<223> OTHER INFORMATION: LINGO-1 polypeptide

<400> SEQUENCE: 118

Trp Leu Ser Pro Arg His His
1               5

<210> SEQ ID NO 119
<211> LENGTH: 7
<212> TYPE: PRT
<213> ORGANISM: Artificial
<220> FEATURE:
<223> OTHER INFORMATION: LINGO-1 polypeptide

<400> SEQUENCE: 119

Trp Leu Ser Pro Arg Arg Arg
1               5

<210> SEQ ID NO 120
<211> LENGTH: 7
<212> TYPE: PRT
<213> ORGANISM: Artificial
<220> FEATURE:
<223> OTHER INFORMATION: LINGO-1 polypeptide

<400> SEQUENCE: 120

Trp Leu Ser Pro His His His
1               5

<210> SEQ ID NO 121
<211> LENGTH: 7
<212> TYPE: PRT
<213> ORGANISM: Artificial
<220> FEATURE:
<223> OTHER INFORMATION: LINGO-1 polypeptide

<400> SEQUENCE: 121

Trp Leu Ser Pro Lys Lys Lys
1               5
```

<210> SEQ ID NO 122
<211> LENGTH: 6
<212> TYPE: PRT
<213> ORGANISM: Artificial
<220> FEATURE:
<223> OTHER INFORMATION: LINGO-1 polypeptide

<400> SEQUENCE: 122

Ile Thr Pro Lys Arg Arg
1               5

<210> SEQ ID NO 123
<211> LENGTH: 5
<212> TYPE: PRT
<213> ORGANISM: Artificial
<220> FEATURE:
<223> OTHER INFORMATION: LINGO-1 polypeptide

<400> SEQUENCE: 123

Ala Cys His His Lys
1               5

<210> SEQ ID NO 124
<211> LENGTH: 5
<212> TYPE: PRT
<213> ORGANISM: Artificial
<220> FEATURE:
<223> OTHER INFORMATION: LINGO-1 polypeptide

<400> SEQUENCE: 124

Val Cys His His Lys
1               5

<210> SEQ ID NO 125
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 125

Xaa Xaa Arg Lys His
1               5

<210> SEQ ID NO 126
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 126

Xaa Xaa Arg Arg Arg
1               5

<210> SEQ ID NO 127
<211> LENGTH: 5
<212> TYPE: PRT
<213> ORGANISM: Artificial
<220> FEATURE:
<223> OTHER INFORMATION: LINGO-1 polypeptide

```
<220> FEATURE:
<221> NAME/KEY: misc_feature
<222> LOCATION: (1)..(2)
<223> OTHER INFORMATION: Xaa can be any naturally occurring amino acid

<400> SEQUENCE: 127

Xaa Xaa Lys Lys Lys
1               5

<210> SEQ ID NO 128
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 128

Xaa Xaa His His His
1               5

<210> SEQ ID NO 129
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 129

Xaa Xaa Arg Lys Lys
1               5

<210> SEQ ID NO 130
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 130

Xaa Xaa Arg Lys Arg
1               5

<210> SEQ ID NO 131
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 131

Xaa Xaa Lys Lys His
1               5

<210> SEQ ID NO 132
```

```
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 132

Xaa Xaa His Lys His
1               5

<210> SEQ ID NO 133
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 133

Xaa Xaa Arg Arg His
1               5

<210> SEQ ID NO 134
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 134

Xaa Xaa Arg His His
1               5

<210> SEQ ID NO 135
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(3)
<223> OTHER INFORMATION: X can be lysine, arginine, histidine,
      glutamine, asparagine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X can be lysine, arginine, histidine,
      glutamine, asparagine

<400> SEQUENCE: 135

Ile Thr Xaa Xaa Xaa
1               5

<210> SEQ ID NO 136
<211> LENGTH: 5
<212> TYPE: PRT
```

```
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(3)
<223> OTHER INFORMATION: X can be lysine, arginine, histidine,
      glutamine, asparagine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X can be lysine, arginine, histidine,
      glutamine, asparagine

<400> SEQUENCE: 136

Ala Cys Xaa Xaa Xaa
1               5

<210> SEQ ID NO 137
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(3)
<223> OTHER INFORMATION: X can be lysine, arginine, histidine,
      glutamine, asparagine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X can be lysine, arginine, histidine,
      glutamine, asparagine

<400> SEQUENCE: 137

Val Cys Xaa Xaa Xaa
1               5

<210> SEQ ID NO 138
<211> LENGTH: 5
<212> TYPE: PRT
<213> ORGANISM: Artificial
<220> FEATURE:
<223> OTHER INFORMATION: LINGO-1 polypeptide
<220> FEATURE:
<221> NAME/KEY: MISC_FEATURE
<222> LOCATION: (3)..(3)
<223> OTHER INFORMATION: X can be lysine, arginine, histidine,
      glutamine, asparagine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X can be lysine, arginine, histidine,
      glutamine, asparagine

<400> SEQUENCE: 138

Ser Pro Xaa Xaa Xaa
1               5

<210> SEQ ID NO 139
<211> LENGTH: 5
```

```
<212> TYPE: PRT
<213> ORGANISM: Artificial
<220> FEATURE:
<223> OTHER INFORMATION: LINGO-1 polypeptide

<400> SEQUENCE: 139

Ser Pro Arg Leu His
1               5

<210> SEQ ID NO 140
<211> LENGTH: 9
<212> TYPE: PRT
<213> ORGANISM: Artificial
<220> FEATURE:
<223> OTHER INFORMATION: LINGO-1 polypeptide

<400> SEQUENCE: 140

Arg Arg Ala Arg Ile Arg Asp Arg Lys
1               5

<210> SEQ ID NO 141
<211> LENGTH: 9
<212> TYPE: PRT
<213> ORGANISM: Artificial
<220> FEATURE:
<223> OTHER INFORMATION: LINGO-1 polypeptide

<400> SEQUENCE: 141

Lys Lys Val Lys Val Lys Glu Lys Arg
1               5

<210> SEQ ID NO 142
<211> LENGTH: 9
<212> TYPE: PRT
<213> ORGANISM: Artificial
<220> FEATURE:
<223> OTHER INFORMATION: LINGO-1 polypeptide

<400> SEQUENCE: 142

Arg Arg Leu Arg Leu Arg Asp Arg Lys
1               5

<210> SEQ ID NO 143
<211> LENGTH: 9
<212> TYPE: PRT
<213> ORGANISM: Artificial
<220> FEATURE:
<223> OTHER INFORMATION: LINGO-1 polypeptide

<400> SEQUENCE: 143

Arg Arg Gly Arg Gly Arg Asp Arg Lys
1               5

<210> SEQ ID NO 144
<211> LENGTH: 9
<212> TYPE: PRT
<213> ORGANISM: Artificial
<220> FEATURE:
<223> OTHER INFORMATION: LINGO-1 polypeptide

<400> SEQUENCE: 144

Arg Arg Ile Arg Ala Arg Asp Arg Lys
1               5

<210> SEQ ID NO 145
<211> LENGTH: 214
<212> TYPE: PRT
<213> ORGANISM: Artificial
```

```
<220> FEATURE:
<223> OTHER INFORMATION: Li33 Fab' light chain

<400> SEQUENCE: 145

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Trp Pro Leu
            85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 146
<211> LENGTH: 230
<212> TYPE: PRT
<213> ORGANISM: Artificial
<220> FEATURE:
<223> OTHER INFORMATION: Li33 Fab' heavy chain

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
        100                 105                 110

Thr Leu Val Thr Val Ser Ser Ala Ser Thr Lys Gly Pro Ser Val Phe
    115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro
225                 230

<210> SEQ ID NO 147
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser His Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro
225                 230

<210> SEQ ID NO 148
<211> LENGTH: 230
```

```
<212> TYPE: PRT
<213> ORGANISM: Artificial
<220> FEATURE:
<223> OTHER INFORMATION: Li33 Heavy Chain Variant

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Phe Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 149
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Leu Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95
```

```
Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225             230

<210> SEQ ID NO 150
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Met Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
```

<210> SEQ ID NO 151
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 151

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Leu Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230
```

<210> SEQ ID NO 152
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 152

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Ser Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
```

```
                    65                  70                  75                  80
Leu Gln Met Asn Ser Leu Arg Ala Glu Asp Thr Ala Thr Tyr Tyr Cys
                    85                  90                  95

Ala Arg Glu Gly His Asn Asp Trp Tyr Phe Asp Leu Trp Gly Arg Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro
225             230

<210> SEQ ID NO 153
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 153

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Thr Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 154
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 154

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Trp Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 155
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 155

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45
```

```
Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Val Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 156
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 156

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Pro Met Phe Trp Val Arg Gln Ala Pro Gly Lys Gly Leu Glu Trp Val
         35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp His Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro
225                 230

<210> SEQ ID NO 157
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Ser Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro
225                 230

<210> SEQ ID NO 158
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 158

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ile Tyr
             20                  25                  30

Pro Met Phe Trp Val Arg Gln Ala Pro Gly Lys Gly Leu Glu Trp Val
         35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Gln Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 159
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 159

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ile Tyr
             20                  25                  30

Pro Met Phe Trp Val Arg Gln Ala Pro Gly Lys Gly Leu Glu Trp Val
         35                  40                  45

Ser Trp Ile Gly Pro Ser Gly Gly Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
145                 150                 155                 160
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 160
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Met Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 161
<211> LENGTH: 230
<212> TYPE: PRT
<213> ORGANISM: Artificial
<220> FEATURE:
<223> OTHER INFORMATION: Li33 Heavy Chain Variant
```

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Asn Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 162
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly His Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
                165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
        195             200             205

Ser Asn Thr Lys Val Asp Lys Lys Val Glu Pro Lys Ser Cys Asp Lys
    210             215             220

Thr His Thr Cys Pro Pro
225             230

<210> SEQ ID NO 163
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Leu Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
                165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
        195             200             205

Ser Asn Thr Lys Val Asp Lys Lys Val Glu Pro Lys Ser Cys Asp Lys
    210             215             220

Thr His Thr Cys Pro Pro
225             230

<210> SEQ ID NO 164
<211> LENGTH: 230

```
<212> TYPE: PRT
<213> ORGANISM: Artificial
<220> FEATURE:
<223> OTHER INFORMATION: Li33 Heavy Chain Variant

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 165
<211> LENGTH: 214
<212> TYPE: PRT
<213> ORGANISM: Artificial
<220> FEATURE:
<223> OTHER INFORMATION: Li33 Light Chain Variant

<400> SEQUENCE: 165

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Ala Pro Leu
                85                  90                  95
```

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 166
<211> LENGTH: 214
<212> TYPE: PRT
<213> ORGANISM: Artificial
<220> FEATURE:
<223> OTHER INFORMATION: Li33 Light Chain Variant

<400> SEQUENCE: 166

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Asp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 167
<211> LENGTH: 214
<212> TYPE: PRT
```

<213> ORGANISM: Artificial
<220> FEATURE:
<223> OTHER INFORMATION: Li33 Light Chain Variant

<400> SEQUENCE: 167

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 168
<211> LENGTH: 214
<212> TYPE: PRT
<213> ORGANISM: Artificial
<220> FEATURE:
<223> OTHER INFORMATION: Li33 Light Chain Variant

<400> SEQUENCE: 168

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Asn Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
                115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 169
<211> LENGTH: 214
<212> TYPE: PRT
<213> ORGANISM: Artificial
<220> FEATURE:
<223> OTHER INFORMATION: Li33 Light Chain Variant

<400> SEQUENCE: 169

Asp Ile Gln Met Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asp Lys Gly Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 170
<211> LENGTH: 214
<212> TYPE: PRT
<213> ORGANISM: Artificial
<220> FEATURE:
<223> OTHER INFORMATION: Li33 Light Chain Variant
```

```
<400> SEQUENCE: 170

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Gln Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 171
<211> LENGTH: 214
<212> TYPE: PRT
<213> ORGANISM: Artificial
<220> FEATURE:
<223> OTHER INFORMATION: Li33 Light Chain Variant

<400> SEQUENCE: 171

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Val Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 172
<211> LENGTH: 214
<212> TYPE: PRT
<213> ORGANISM: Artificial
<220> FEATURE:
<223> OTHER INFORMATION: Li33 Light Chain Variant

<400> SEQUENCE: 172

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 173
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 173

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Gly Ile Gly Pro Ser Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

```
<210> SEQ ID NO 174
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 174
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Ile Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro
225                 230

<210> SEQ ID NO 175
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Asp Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro
225                 230

<210> SEQ ID NO 176
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Met Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro
225                 230

<210> SEQ ID NO 177
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Leu Tyr Phe Asp Leu Trp Gly Arg Gly
            100                 105                 110

Thr Leu Val Thr Val Ser Ser Ala Ser Thr Lys Gly Pro Ser Val Phe

-continued

```
                115                 120                 125
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
        210                 215                 220

Thr His Thr Cys Pro Pro
225                 230
```

<210> SEQ ID NO 178
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 178

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
                35                  40                  45

Ser Trp Ile Gly Pro Ser Gly Gly Ile Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Thr Tyr Phe Asp Leu Trp Gly Arg Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
        210                 215                 220

Thr His Thr Cys Pro Pro
225                 230
```

<210> SEQ ID NO 179

```
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 179

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Ile Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 180
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Gly Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95
```

```
Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225             230

<210> SEQ ID NO 181
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 181

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Trp Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro
225              230

<210> SEQ ID NO 182
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 182

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Tyr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225              230

<210> SEQ ID NO 183
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 183

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ser Thr Lys Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 184
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 184

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ile Tyr
             20                  25                  30

Pro Met Phe Trp Val Arg Gln Ala Pro Gly Lys Gly Leu Glu Trp Val
         35                  40                  45

Ser Trp Ile Gly Pro Ser Gly Gly Pro Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

```
                195                 200                 205
Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 185
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 185

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Val Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 186
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
```

```
                    35                  40                  45
Ser Trp Ile Gly Pro Ser Gly Thr Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro
225                 230

<210> SEQ ID NO 187
<211> LENGTH: 230
<212> TYPE: PRT
<213> ORGANISM: Artificial
<220> FEATURE:
<223> OTHER INFORMATION: Li33 Heavy Chain Variant

<400> SEQUENCE: 187

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
            35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Gln Tyr Phe Asp Leu Trp Gly Arg Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro
225             230

<210> SEQ ID NO 188
<211> LENGTH: 119
<212> TYPE: PRT
<213> ORGANISM: Artificial
<220> FEATURE:
<223> OTHER INFORMATION: Li62 VH Variant

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser His Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 189
<211> LENGTH: 119
<212> TYPE: PRT
<213> ORGANISM: Artificial
<220> FEATURE:
<223> OTHER INFORMATION: Li62 VH Variant

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Phe Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser
        115

```
<210> SEQ ID NO 190
<211> LENGTH: 119
<212> TYPE: PRT
<213> ORGANISM: Artificial
<220> FEATURE:
<223> OTHER INFORMATION: Li62 VH Variant

<400> SEQUENCE: 190

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Leu Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 191
<211> LENGTH: 119
<212> TYPE: PRT
<213> ORGANISM: Artificial
<220> FEATURE:
<223> OTHER INFORMATION: Li62 VH Variant

<400> SEQUENCE: 191

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Met Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 192
<211> LENGTH: 119
<212> TYPE: PRT
<213> ORGANISM: Artificial
<220> FEATURE:
<223> OTHER INFORMATION: Li62 VH Variant

<400> SEQUENCE: 192

Glu Val Gln Leu Leu Glu Ser Gly Gly Gly Leu Val Gln Pro Gly Gly
```

-continued

```
                1               5                  10                 15
Ser Leu Arg Leu Ser Cys Ala Ala Ser Gly Phe Thr Phe Ser Ile Tyr
            20                  25                 30

Pro Met Phe Trp Val Arg Gln Ala Pro Gly Lys Gly Leu Glu Trp Val
            35                  40                 45

Ser Trp Ile Gly Leu Ser Gly Gly Ile Thr Lys Tyr Ala Asp Ser Val
    50                  55                 60

Lys Gly Arg Phe Thr Ile Ser Arg Asp Asn Ser Lys Asn Thr Leu Tyr
65                  70                  75                     80

Leu Gln Met Asn Ser Leu Arg Ala Glu Asp Thr Ala Thr Tyr Tyr Cys
                85                  90                 95

Ala Arg Glu Gly His Asn Asp Trp Tyr Phe Asp Leu Trp Gly Arg Gly
            100                 105                110

Thr Leu Val Thr Val Ser Ser
            115

<210> SEQ ID NO 193
<211> LENGTH: 119
<212> TYPE: PRT
<213> ORGANISM: Artificial
<220> FEATURE:
<223> OTHER INFORMATION: Li62 VH Variant

<400> SEQUENCE: 193

Glu Val Gln Leu Leu Glu Ser Gly Gly Gly Leu Val Gln Pro Gly Gly
1               5                  10                 15

Ser Leu Arg Leu Ser Cys Ala Ala Ser Gly Phe Thr Phe Ser Ile Tyr
            20                  25                 30

Pro Met Phe Trp Val Arg Gln Ala Pro Gly Lys Gly Leu Glu Trp Val
            35                  40                 45

Ser Trp Ile Gly Ser Ser Gly Gly Ile Thr Lys Tyr Ala Asp Ser Val
    50                  55                 60

Lys Gly Arg Phe Thr Ile Ser Arg Asp Asn Ser Lys Asn Thr Leu Tyr
65                  70                  75                     80

Leu Gln Met Asn Ser Leu Arg Ala Glu Asp Thr Ala Thr Tyr Tyr Cys
                85                  90                 95

Ala Arg Glu Gly His Asn Asp Trp Tyr Phe Asp Leu Trp Gly Arg Gly
            100                 105                110

Thr Leu Val Thr Val Ser Ser
            115

<210> SEQ ID NO 194
<211> LENGTH: 119
<212> TYPE: PRT
<213> ORGANISM: Artificial
<220> FEATURE:
<223> OTHER INFORMATION: Li62 VH Variant

<400> SEQUENCE: 194

Glu Val Gln Leu Leu Glu Ser Gly Gly Gly Leu Val Gln Pro Gly Gly
1               5                  10                 15

Ser Leu Arg Leu Ser Cys Ala Ala Ser Gly Phe Thr Phe Ser Ile Tyr
            20                  25                 30

Pro Met Phe Trp Val Arg Gln Ala Pro Gly Lys Gly Leu Glu Trp Val
            35                  40                 45

Ser Trp Ile Gly Thr Ser Gly Gly Ile Thr Lys Tyr Ala Asp Ser Val
    50                  55                 60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Thr Tyr Tyr Cys
                    85                  90                  95

Ala Arg Glu Gly His Asn Asp Trp Tyr Phe Asp Leu Trp Gly Arg Gly
                100                 105                 110

Thr Leu Val Thr Val Ser Ser
            115

<210> SEQ ID NO 195
<211> LENGTH: 119
<212> TYPE: PRT
<213> ORGANISM: Artificial
<220> FEATURE:
<223> OTHER INFORMATION: Li62 VH Variant

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
            35                  40                  45

Ser Trp Ile Gly Trp Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                    85                  90                  95

Ala Arg Glu Gly His Asn Asp Trp Tyr Phe Asp Leu Trp Gly Arg Gly
                100                 105                 110

Thr Leu Val Thr Val Ser Ser
            115

<210> SEQ ID NO 196
<211> LENGTH: 119
<212> TYPE: PRT
<213> ORGANISM: Artificial
<220> FEATURE:
<223> OTHER INFORMATION: Li62 VH Variant

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
            35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                    85                  90                  95

Ala Arg Glu Gly His Asn Asp Val Tyr Phe Asp Leu Trp Gly Arg Gly
                100                 105                 110

Thr Leu Val Thr Val Ser Ser
            115
```

<210> SEQ ID NO 197
<211> LENGTH: 119
<212> TYPE: PRT
<213> ORGANISM: Artificial
<220> FEATURE:
<223> OTHER INFORMATION: Li62 VH Variant

<400> SEQUENCE: 197

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp His Tyr Phe Asp Leu Trp Gly Arg Gly
            100                 105                 110

Thr Leu Val Thr Val Ser Ser
        115

<210> SEQ ID NO 198
<211> LENGTH: 119
<212> TYPE: PRT
<213> ORGANISM: Artificial
<220> FEATURE:
<223> OTHER INFORMATION: Li62 VH Variant

<400> SEQUENCE: 198

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Ser Tyr Phe Asp Leu Trp Gly Arg Gly
            100                 105                 110

Thr Leu Val Thr Val Ser Ser
        115

<210> SEQ ID NO 199
<211> LENGTH: 119
<212> TYPE: PRT
<213> ORGANISM: Artificial
<220> FEATURE:
<223> OTHER INFORMATION: Li62 VH Variant

<400> SEQUENCE: 199

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Gln Tyr Phe Asp Leu Trp Gly Arg Gly
            100                 105                 110

Thr Leu Val Thr Val Ser Ser
            115
```

<210> SEQ ID NO 200
<211> LENGTH: 119
<212> TYPE: PRT
<213> ORGANISM: Artificial
<220> FEATURE:
<223> OTHER INFORMATION: Li62 VH Variant

<400> SEQUENCE: 200

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
            115
```

<210> SEQ ID NO 201
<211> LENGTH: 119
<212> TYPE: PRT
<213> ORGANISM: Artificial
<220> FEATURE:
<223> OTHER INFORMATION: Li62 VH Variant

<400> SEQUENCE: 201

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Met Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 202
<211> LENGTH: 119
<212> TYPE: PRT
<213> ORGANISM: Artificial
<220> FEATURE:
<223> OTHER INFORMATION: Li62 VH Variant

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Asn Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 203
<211> LENGTH: 119
<212> TYPE: PRT
<213> ORGANISM: Artificial
<220> FEATURE:
<223> OTHER INFORMATION: Li62 VH Variant

<400> SEQUENCE: 203

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly His Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 204
<211> LENGTH: 119
```

```
<212> TYPE: PRT
<213> ORGANISM: Artificial
<220> FEATURE:
<223> OTHER INFORMATION: Li62 VH Variant

<400> SEQUENCE: 204

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Leu Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 205
<211> LENGTH: 119
<212> TYPE: PRT
<213> ORGANISM: Artificial
<220> FEATURE:
<223> OTHER INFORMATION: Li62 VH Variant

<400> SEQUENCE: 205

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 206
<211> LENGTH: 119
<212> TYPE: PRT
<213> ORGANISM: Artificial
<220> FEATURE:
<223> OTHER INFORMATION: Li62 VH Variant

<400> SEQUENCE: 206

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30
```

```
Pro Met Phe Trp Val Arg Gln Ala Pro Gly Lys Gly Leu Glu Trp Val
            35                  40                  45

Ser Gly Ile Gly Pro Ser Gly Gly Ile Thr Lys Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
                100                 105                 110

Thr Leu Val Thr Val Ser Ser
            115
```

```
<210> SEQ ID NO 207
<211> LENGTH: 119
<212> TYPE: PRT
<213> ORGANISM: Artificial
<220> FEATURE:
<223> OTHER INFORMATION: Li62 VH Variant

<400> SEQUENCE: 207

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Ile Ile Gly Pro Ser Gly Gly Ile Thr Lys Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
                100                 105                 110

Thr Leu Val Thr Val Ser Ser
            115
```

```
<210> SEQ ID NO 208
<211> LENGTH: 119
<212> TYPE: PRT
<213> ORGANISM: Artificial
<220> FEATURE:
<223> OTHER INFORMATION: Li62 VH Variant

<400> SEQUENCE: 208

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Asp Ile Gly Pro Ser Gly Gly Ile Thr Lys Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95
```

```
Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 209
<211> LENGTH: 119
<212> TYPE: PRT
<213> ORGANISM: Artificial
<220> FEATURE:
<223> OTHER INFORMATION: Li62 VH Variant

<400> SEQUENCE: 209

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Met Tyr Phe Asp Leu Trp Gly Arg Gly
            100                 105                 110

Thr Leu Val Thr Val Ser Ser
            115

<210> SEQ ID NO 210
<211> LENGTH: 119
<212> TYPE: PRT
<213> ORGANISM: Artificial
<220> FEATURE:
<223> OTHER INFORMATION: Li62 VH Variant

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Leu Tyr Phe Asp Leu Trp Gly Arg Gly
            100                 105                 110

Thr Leu Val Thr Val Ser Ser
            115

<210> SEQ ID NO 211
<211> LENGTH: 119
<212> TYPE: PRT
<213> ORGANISM: Artificial
```

<220> FEATURE:
<223> OTHER INFORMATION: Li62 VH Variant

<400> SEQUENCE: 211

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Thr Tyr Phe Asp Leu Trp Gly Arg Gly
            100                 105                 110

Thr Leu Val Thr Val Ser Ser
        115

<210> SEQ ID NO 212
<211> LENGTH: 119
<212> TYPE: PRT
<213> ORGANISM: Artificial
<220> FEATURE:
<223> OTHER INFORMATION: Li62 VH Variant

<400> SEQUENCE: 212

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Ile Tyr Phe Asp Leu Trp Gly Arg Gly
            100                 105                 110

Thr Leu Val Thr Val Ser Ser
        115

<210> SEQ ID NO 213
<211> LENGTH: 119
<212> TYPE: PRT
<213> ORGANISM: Artificial
<220> FEATURE:
<223> OTHER INFORMATION: Li62 VH Variant

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val

```
                   35                  40                  45
Ser Trp Ile Gly Gly Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
                100                 105                 110

Thr Leu Val Thr Val Ser Ser
            115

<210> SEQ ID NO 214
<211> LENGTH: 119
<212> TYPE: PRT
<213> ORGANISM: Artificial
<220> FEATURE:
<223> OTHER INFORMATION: Li62 VH Variant

<400> SEQUENCE: 214

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser Trp Ile Gly Pro Ser Gly Gly Trp Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
                100                 105                 110

Thr Leu Val Thr Val Ser Ser
            115

<210> SEQ ID NO 215
<211> LENGTH: 119
<212> TYPE: PRT
<213> ORGANISM: Artificial
<220> FEATURE:
<223> OTHER INFORMATION: Li62 VH Variant

<400> SEQUENCE: 215

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser Trp Ile Gly Pro Ser Gly Gly Tyr Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Trp Tyr Phe Asp Leu Trp Gly Arg Gly
```

```
              100                 105                 110
Thr Leu Val Thr Val Ser Ser
            115

<210> SEQ ID NO 216
<211> LENGTH: 119
<212> TYPE: PRT
<213> ORGANISM: Artificial
<220> FEATURE:
<223> OTHER INFORMATION: Li62 VH Variant

<400> SEQUENCE: 216

Glu Val Gln Leu Leu Glu Ser Gly Gly Gly Leu Val Gln Pro Gly Gly
1               5                  10                   15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ser Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 217
<211> LENGTH: 119
<212> TYPE: PRT
<213> ORGANISM: Artificial
<220> FEATURE:
<223> OTHER INFORMATION: Li62 VH Variant

<400> SEQUENCE: 217

Glu Val Gln Leu Leu Glu Ser Gly Gly Gly Leu Val Gln Pro Gly Gly
1               5                  10                   15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Pro Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
            115

<210> SEQ ID NO 218
<211> LENGTH: 119
<212> TYPE: PRT
<213> ORGANISM: Artificial
<220> FEATURE:
<223> OTHER INFORMATION: Li62 VH Variant
```

<400> SEQUENCE: 218

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Val Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 219
<211> LENGTH: 119
<212> TYPE: PRT
<213> ORGANISM: Artificial
<220> FEATURE:
<223> OTHER INFORMATION: Li62 VH Variant

<400> SEQUENCE: 219

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Thr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 220
<211> LENGTH: 119
<212> TYPE: PRT
<213> ORGANISM: Artificial
<220> FEATURE:
<223> OTHER INFORMATION: Li62 VH Variant

<400> SEQUENCE: 220

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

```
Ser Trp Ile Gly Pro Ser Gly Ile Thr Lys Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly His Asn Asp Gln Tyr Phe Asp Leu Trp Gly Arg Gly
            100                 105                 110

Thr Leu Val Thr Val Ser Ser
            115

<210> SEQ ID NO 221
<211> LENGTH: 108
<212> TYPE: PRT
<213> ORGANISM: Artificial
<220> FEATURE:
<223> OTHER INFORMATION: Li81 VL Variant

<400> SEQUENCE: 221

Asp Ile Gln Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Tyr Thr Phe Gly Gln Gly Thr Lys Leu Glu Ile Lys
            100                 105

<210> SEQ ID NO 222
<211> LENGTH: 108
<212> TYPE: PRT
<213> ORGANISM: Artificial
<220> FEATURE:
<223> OTHER INFORMATION: Li81 VL Variant

<400> SEQUENCE: 222

Asp Ile Gln Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Ile
                 85                  90                  95

Tyr Thr Phe Gly Gln Gly Thr Lys Leu Glu Ile Lys
            100                 105

<210> SEQ ID NO 223
<211> LENGTH: 108
```

```
<212> TYPE: PRT
<213> ORGANISM: Artificial
<220> FEATURE:
<223> OTHER INFORMATION: Li81 VL Variant

<400> SEQUENCE: 223

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Gln
                85                  90                  95

Tyr Thr Phe Gly Gln Gly Thr Lys Leu Glu Ile Lys
            100                 105

<210> SEQ ID NO 224
<211> LENGTH: 108
<212> TYPE: PRT
<213> ORGANISM: Artificial
<220> FEATURE:
<223> OTHER INFORMATION: Li81 VL Variant

<400> SEQUENCE: 224

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Lys
                85                  90                  95

Tyr Thr Phe Gly Gln Gly Thr Lys Leu Glu Ile Lys
            100                 105

<210> SEQ ID NO 225
<211> LENGTH: 108
<212> TYPE: PRT
<213> ORGANISM: Artificial
<220> FEATURE:
<223> OTHER INFORMATION: Li81 VL Variant

<400> SEQUENCE: 225

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Ala
                 85                  90                  95

Tyr Thr Phe Gly Gln Gly Thr Lys Leu Glu Ile Lys
            100                 105

<210> SEQ ID NO 226
<211> LENGTH: 108
<212> TYPE: PRT
<213> ORGANISM: Artificial
<220> FEATURE:
<223> OTHER INFORMATION: Li81 VL Variant

<400> SEQUENCE: 226

Asp Ile Gln Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Val
                 85                  90                  95

Tyr Thr Phe Gly Gln Gly Thr Lys Leu Glu Ile Lys
            100                 105

<210> SEQ ID NO 227
<211> LENGTH: 108
<212> TYPE: PRT
<213> ORGANISM: Artificial
<220> FEATURE:
<223> OTHER INFORMATION: Li81 VL Variant

<400> SEQUENCE: 227

Asp Ile Gln Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Tyr
                 85                  90                  95

Tyr Thr Phe Gly Gln Gly Thr Lys Leu Glu Ile Lys
            100                 105

<210> SEQ ID NO 228
<211> LENGTH: 108
<212> TYPE: PRT
<213> ORGANISM: Artificial
<220> FEATURE:
<223> OTHER INFORMATION: Li81 VL Variant
```

<400> SEQUENCE: 228

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Phe
                85                  90                  95

Tyr Thr Phe Gly Gln Gly Thr Lys Leu Glu Ile Lys
            100                 105

<210> SEQ ID NO 229
<211> LENGTH: 118
<212> TYPE: PRT
<213> ORGANISM: Artificial
<220> FEATURE:
<223> OTHER INFORMATION: Li81 VH Variant

<400> SEQUENCE: 229

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Leu Ser Gly Gly Phe Thr Phe Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser
        115

<210> SEQ ID NO 230
<211> LENGTH: 118
<212> TYPE: PRT
<213> ORGANISM: Artificial
<220> FEATURE:
<223> OTHER INFORMATION: Li81 VH Variant

<400> SEQUENCE: 230

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Ser Ser Gly Gly Phe Thr Phe Tyr Ala Asp Ser Val
50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Thr Glu Gly Asp Asn Asp Ala Phe Asp Ile Trp Gly Gln Gly Thr
                100                 105                 110

Thr Val Thr Val Ser Ser
        115

<210> SEQ ID NO 231
<211> LENGTH: 118
<212> TYPE: PRT
<213> ORGANISM: Artificial
<220> FEATURE:
<223> OTHER INFORMATION: Li81 VH Variant

<400> SEQUENCE: 231

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
                20                  25                  30

Glu Met Lys Trp Val Arg Gln Ala Pro Gly Lys Gly Leu Glu Trp Val
            35                  40                  45

Ser Val Ile Gly Thr Ser Gly Gly Phe Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
                100                 105                 110

Thr Val Thr Val Ser Ser
        115

<210> SEQ ID NO 232
<211> LENGTH: 118
<212> TYPE: PRT
<213> ORGANISM: Artificial
<220> FEATURE:
<223> OTHER INFORMATION: Li81 VH Variant

<400> SEQUENCE: 232

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
                20                  25                  30

Glu Met Lys Trp Val Arg Gln Ala Pro Gly Lys Gly Leu Glu Trp Val
            35                  40                  45

Ser Val Ile Gly Trp Ser Gly Gly Phe Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
                100                 105                 110

Thr Val Thr Val Ser Ser
        115
```

-continued

<210> SEQ ID NO 233
<211> LENGTH: 118
<212> TYPE: PRT
<213> ORGANISM: Artificial
<220> FEATURE:
<223> OTHER INFORMATION: Li81 VH Variant

<400> SEQUENCE: 233

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Glu Met Lys Trp Val Arg Gln Ala Pro Gly Lys Gly Leu Glu Trp Val
        35                  40                  45

Ser Val Ile Gly Gly Ser Gly Gly Phe Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Asn Asp Ala Phe Asp Ile Trp Gly Gln Gly Thr
            100                 105                 110

Thr Val Thr Val Ser Ser
        115

<210> SEQ ID NO 234
<211> LENGTH: 108
<212> TYPE: PRT
<213> ORGANISM: Artificial
<220> FEATURE:
<223> OTHER INFORMATION: Li81 VL Variant

<400> SEQUENCE: 234

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Ala Pro Met
                85                  90                  95

Tyr Thr Phe Gly Gln Gly Thr Lys Leu Glu Ile Lys
            100                 105

<210> SEQ ID NO 235
<211> LENGTH: 108
<212> TYPE: PRT
<213> ORGANISM: Artificial
<220> FEATURE:
<223> OTHER INFORMATION: Li81 VL Variant

<400> SEQUENCE: 235

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Asp Pro Met
                85                  90                  95

Tyr Thr Phe Gly Gln Gly Thr Lys Leu Glu Ile Lys
            100                 105

<210> SEQ ID NO 236
<211> LENGTH: 108
<212> TYPE: PRT
<213> ORGANISM: Artificial
<220> FEATURE:
<223> OTHER INFORMATION: Li81 VL Variant

<400> SEQUENCE: 236

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Leu Pro Met
                85                  90                  95

Tyr Thr Phe Gly Gln Gly Thr Lys Leu Glu Ile Lys
            100                 105

<210> SEQ ID NO 237
<211> LENGTH: 108
<212> TYPE: PRT
<213> ORGANISM: Artificial
<220> FEATURE:
<223> OTHER INFORMATION: Li81 VL Variant

<400> SEQUENCE: 237

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Asn Pro Met
                85                  90                  95

Tyr Thr Phe Gly Gln Gly Thr Lys Leu Glu Ile Lys
            100                 105

<210> SEQ ID NO 238
<211> LENGTH: 108

<212> TYPE: PRT
<213> ORGANISM: Artificial
<220> FEATURE:
<223> OTHER INFORMATION: Li81 VL Variant

<400> SEQUENCE: 238

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Gly Pro Met
                85                  90                  95

Tyr Thr Phe Gly Gln Gly Thr Lys Leu Glu Ile Lys
            100                 105

<210> SEQ ID NO 239
<211> LENGTH: 108
<212> TYPE: PRT
<213> ORGANISM: Artificial
<220> FEATURE:
<223> OTHER INFORMATION: Li81 VL Variant

<400> SEQUENCE: 239

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Gln Pro Met
                85                  90                  95

Tyr Thr Phe Gly Gln Gly Thr Lys Leu Glu Ile Lys
            100                 105

<210> SEQ ID NO 240
<211> LENGTH: 108
<212> TYPE: PRT
<213> ORGANISM: Artificial
<220> FEATURE:
<223> OTHER INFORMATION: Li81 VL Variant

<400> SEQUENCE: 240

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Val Pro Met
                 85                  90                  95

Tyr Thr Phe Gly Gln Gly Thr Lys Leu Glu Ile Lys
            100                 105

<210> SEQ ID NO 241
<211> LENGTH: 108
<212> TYPE: PRT
<213> ORGANISM: Artificial
<220> FEATURE:
<223> OTHER INFORMATION: Li81 VL Variant

<400> SEQUENCE: 241

Asp Ile Gln Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Ser Pro Met
                 85                  90                  95

Tyr Thr Phe Gly Gln Gly Thr Lys Leu Glu Ile Lys
            100                 105

<210> SEQ ID NO 242
<211> LENGTH: 119
<212> TYPE: PRT
<213> ORGANISM: Artificial
<220> FEATURE:
<223> OTHER INFORMATION: Li113 VH Variant

<400> SEQUENCE: 242

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
             35                  40                  45

Ser His Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 243
<211> LENGTH: 119
<212> TYPE: PRT
<213> ORGANISM: Artificial
```

```
<220> FEATURE:
<223> OTHER INFORMATION: Li113 VH Variant

<400> SEQUENCE: 243

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Phe Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 244
<211> LENGTH: 119
<212> TYPE: PRT
<213> ORGANISM: Artificial
<220> FEATURE:
<223> OTHER INFORMATION: Li113 VH Variant

<400> SEQUENCE: 244

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Leu Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 245
<211> LENGTH: 119
<212> TYPE: PRT
<213> ORGANISM: Artificial
<220> FEATURE:
<223> OTHER INFORMATION: Li113 VH Variant

<400> SEQUENCE: 245

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
```

```
                35                  40                  45
Ser Met Ile Gly Pro Ser Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Trp Tyr Leu Asp Leu Trp Gly Arg Gly
                100                 105                 110

Thr Leu Val Thr Val Ser Ser
        115

<210> SEQ ID NO 246
<211> LENGTH: 119
<212> TYPE: PRT
<213> ORGANISM: Artificial
<220> FEATURE:
<223> OTHER INFORMATION: Li113 VH Variant

<400> SEQUENCE: 246

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
                 35                  40                  45

Ser Trp Ile Gly Leu Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Trp Tyr Leu Asp Leu Trp Gly Arg Gly
                100                 105                 110

Thr Leu Val Thr Val Ser Ser
        115

<210> SEQ ID NO 247
<211> LENGTH: 119
<212> TYPE: PRT
<213> ORGANISM: Artificial
<220> FEATURE:
<223> OTHER INFORMATION: Li113 VH Variant

<400> SEQUENCE: 247

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
                 20                  25                  30

Pro Met Phe Trp Val Arg Gln Ala Pro Gly Lys Gly Leu Glu Trp Val
                 35                  40                  45

Ser Trp Ile Gly Ser Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Trp Tyr Leu Asp Leu Trp Gly Arg Gly
```

```
                    100                 105                 110
Thr Leu Val Thr Val Ser Ser
            115

<210> SEQ ID NO 248
<211> LENGTH: 119
<212> TYPE: PRT
<213> ORGANISM: Artificial
<220> FEATURE:
<223> OTHER INFORMATION: Li113 VH Variant

<400> SEQUENCE: 248

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Thr Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
            115

<210> SEQ ID NO 249
<211> LENGTH: 119
<212> TYPE: PRT
<213> ORGANISM: Artificial
<220> FEATURE:
<223> OTHER INFORMATION: Li113 VH Variant

<400> SEQUENCE: 249

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Trp Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
            115

<210> SEQ ID NO 250
<211> LENGTH: 119
<212> TYPE: PRT
<213> ORGANISM: Artificial
<220> FEATURE:
<223> OTHER INFORMATION: Li113 VH Variant
```

<400> SEQUENCE: 250

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Val Tyr Leu Asp Leu Trp Gly Arg Gly
            100                 105                 110

Thr Leu Val Thr Val Ser Ser
        115

<210> SEQ ID NO 251
<211> LENGTH: 119
<212> TYPE: PRT
<213> ORGANISM: Artificial
<220> FEATURE:
<223> OTHER INFORMATION: Li113 VH Variant

<400> SEQUENCE: 251

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp His Tyr Leu Asp Leu Trp Gly Arg Gly
            100                 105                 110

Thr Leu Val Thr Val Ser Ser
        115

<210> SEQ ID NO 252
<211> LENGTH: 119
<212> TYPE: PRT
<213> ORGANISM: Artificial
<220> FEATURE:
<223> OTHER INFORMATION: Li113 VH Variant

<400> SEQUENCE: 252

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Ser Tyr Leu Asp Leu Trp Gly Arg Gly
            100                 105                 110

Thr Leu Val Thr Val Ser Ser
        115

<210> SEQ ID NO 253
<211> LENGTH: 119
<212> TYPE: PRT
<213> ORGANISM: Artificial
<220> FEATURE:
<223> OTHER INFORMATION: Li113 VH Variant

<400> SEQUENCE: 253

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Gln Tyr Leu Asp Leu Trp Gly Arg Gly
            100                 105                 110

Thr Leu Val Thr Val Ser Ser
        115

<210> SEQ ID NO 254
<211> LENGTH: 119
<212> TYPE: PRT
<213> ORGANISM: Artificial
<220> FEATURE:
<223> OTHER INFORMATION: Li113 VH Variant

<400> SEQUENCE: 254

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Tyr Leu Asp Leu Trp Gly Arg Gly
            100                 105                 110

Thr Leu Val Thr Val Ser Ser
        115

<210> SEQ ID NO 255
<211> LENGTH: 119
<212> TYPE: PRT
<213> ORGANISM: Artificial
<220> FEATURE:
<223> OTHER INFORMATION: Li113 VH Variant

<400> SEQUENCE: 255

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Met Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 256
<211> LENGTH: 119
<212> TYPE: PRT
<213> ORGANISM: Artificial
<220> FEATURE:
<223> OTHER INFORMATION: Li113 VH Variant

<400> SEQUENCE: 256

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Asn Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 257
<211> LENGTH: 119
<212> TYPE: PRT
<213> ORGANISM: Artificial
<220> FEATURE:
<223> OTHER INFORMATION: Li113 VH Variant

<400> SEQUENCE: 257

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly His Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
                100                 105                 110

Thr Leu Val Thr Val Ser Ser
        115
```

<210> SEQ ID NO 258
<211> LENGTH: 119
<212> TYPE: PRT
<213> ORGANISM: Artificial
<220> FEATURE:
<223> OTHER INFORMATION: Li113 VH Variant

<400> SEQUENCE: 258

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Leu Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
                100                 105                 110

Thr Leu Val Thr Val Ser Ser
        115
```

<210> SEQ ID NO 259
<211> LENGTH: 119
<212> TYPE: PRT
<213> ORGANISM: Artificial
<220> FEATURE:
<223> OTHER INFORMATION: Li113 VH Variant

<400> SEQUENCE: 259

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
            35                  40                  45

Ser Trp Ile Gly Pro Ser Gly Gly Phe Thr Lys Tyr Ala Asp Ser Val
        50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115
```

<210> SEQ ID NO 260
<211> LENGTH: 119
<212> TYPE: PRT
<213> ORGANISM: Artificial
<220> FEATURE:
<223> OTHER INFORMATION: Li113 VH Variant

<400> SEQUENCE: 260

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Pro Met Phe Trp Val Arg Gln Ala Pro Gly Lys Gly Leu Glu Trp Val
         35                  40                  45

Ser Gly Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115
```

<210> SEQ ID NO 261
<211> LENGTH: 119
<212> TYPE: PRT
<213> ORGANISM: Artificial
<220> FEATURE:
<223> OTHER INFORMATION: Li113 VH Variant

<400> SEQUENCE: 261

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Pro Met Phe Trp Val Arg Gln Ala Pro Gly Lys Gly Leu Glu Trp Val
         35                  40                  45

Ser Ile Ile Gly Pro Ser Gly Gly Ile Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115
```

<210> SEQ ID NO 262
<211> LENGTH: 119
<212> TYPE: PRT
<213> ORGANISM: Artificial
<220> FEATURE:
<223> OTHER INFORMATION: Li113 VH Variant

<400> SEQUENCE: 262

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Asp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 263
<211> LENGTH: 119
<212> TYPE: PRT
<213> ORGANISM: Artificial
<220> FEATURE:
<223> OTHER INFORMATION: Li113 VH Variant

<400> SEQUENCE: 263

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Met Tyr Leu Asp Leu Trp Gly Arg Gly
            100                 105                 110

Thr Leu Val Thr Val Ser Ser
        115

<210> SEQ ID NO 264
<211> LENGTH: 119
<212> TYPE: PRT
<213> ORGANISM: Artificial
<220> FEATURE:
<223> OTHER INFORMATION: Li113 VH Variant

<400> SEQUENCE: 264

Glu Val Gln Leu Leu Glu Ser Gly Gly Gly Leu Val Gln Pro Gly Gly

```
                    1               5                  10                 15
Ser Leu Arg Leu Ser Cys Ala Ala Ser Gly Phe Thr Phe Ser Ile Tyr
                20                 25                 30

Pro Met Phe Trp Val Arg Gln Ala Pro Gly Lys Gly Leu Glu Trp Val
            35                 40                 45

Ser Trp Ile Gly Pro Ser Gly Gly Ile Thr Lys Tyr Ala Asp Ser Val
 50                 55                 60

Lys Gly Arg Phe Thr Ile Ser Arg Asp Asn Ser Lys Asn Thr Leu Tyr
 65                 70                 75                 80

Leu Gln Met Asn Ser Leu Arg Ala Glu Asp Thr Ala Thr Tyr Tyr Cys
                85                 90                 95

Ala Arg Glu Gly Thr Tyr Asp Leu Tyr Leu Asp Leu Trp Gly Arg Gly
            100                105                110

Thr Leu Val Thr Val Ser Ser
        115

<210> SEQ ID NO 265
<211> LENGTH: 119
<212> TYPE: PRT
<213> ORGANISM: Artificial
<220> FEATURE:
<223> OTHER INFORMATION: Li113 VH Variant

<400> SEQUENCE: 265

Glu Val Gln Leu Leu Glu Ser Gly Gly Gly Leu Val Gln Pro Gly Gly
 1               5                  10                 15

Ser Leu Arg Leu Ser Cys Ala Ala Ser Gly Phe Thr Phe Ser Ile Tyr
                20                 25                 30

Pro Met Phe Trp Val Arg Gln Ala Pro Gly Lys Gly Leu Glu Trp Val
            35                 40                 45

Ser Trp Ile Gly Pro Ser Gly Gly Ile Thr Lys Tyr Ala Asp Ser Val
 50                 55                 60

Lys Gly Arg Phe Thr Ile Ser Arg Asp Asn Ser Lys Asn Thr Leu Tyr
 65                 70                 75                 80

Leu Gln Met Asn Ser Leu Arg Ala Glu Asp Thr Ala Thr Tyr Tyr Cys
                85                 90                 95

Ala Arg Glu Gly Thr Tyr Asp Thr Tyr Leu Asp Leu Trp Gly Arg Gly
            100                105                110

Thr Leu Val Thr Val Ser Ser
        115

<210> SEQ ID NO 266
<211> LENGTH: 119
<212> TYPE: PRT
<213> ORGANISM: Artificial
<220> FEATURE:
<223> OTHER INFORMATION: Li113 VH Variant

<400> SEQUENCE: 266

Glu Val Gln Leu Leu Glu Ser Gly Gly Gly Leu Val Gln Pro Gly Gly
 1               5                  10                 15

Ser Leu Arg Leu Ser Cys Ala Ala Ser Gly Phe Thr Phe Ser Ile Tyr
                20                 25                 30

Pro Met Phe Trp Val Arg Gln Ala Pro Gly Lys Gly Leu Glu Trp Val
            35                 40                 45

Ser Trp Ile Gly Pro Ser Gly Gly Ile Thr Lys Tyr Ala Asp Ser Val
 50                 55                 60

Lys Gly Arg Phe Thr Ile Ser Arg Asp Asn Ser Lys Asn Thr Leu Tyr
```

```
                  65                  70                  75                  80
Leu Gln Met Asn Ser Leu Arg Ala Glu Asp Thr Ala Thr Tyr Tyr Cys
                85                  90                  95

Ala Arg Glu Gly Thr Tyr Asp Ile Tyr Leu Asp Leu Trp Gly Arg Gly
            100                 105                 110

Thr Leu Val Thr Val Ser Ser
        115

<210> SEQ ID NO 267
<211> LENGTH: 119
<212> TYPE: PRT
<213> ORGANISM: Artificial
<220> FEATURE:
<223> OTHER INFORMATION: Li113 VH Variant

<400> SEQUENCE: 267

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
            35                  40                  45

Ser Trp Ile Gly Gly Ser Gly Gly Ile Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 268
<211> LENGTH: 119
<212> TYPE: PRT
<213> ORGANISM: Artificial
<220> FEATURE:
<223> OTHER INFORMATION: Li113 VH Variant

<400> SEQUENCE: 268

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
                20                  25                  30

Pro Met Phe Trp Val Arg Gln Ala Pro Gly Lys Gly Leu Glu Trp Val
            35                  40                  45

Ser Trp Ile Gly Pro Ser Gly Gly Trp Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115
```

```
<210> SEQ ID NO 269
<211> LENGTH: 119
<212> TYPE: PRT
<213> ORGANISM: Artificial
<220> FEATURE:
<223> OTHER INFORMATION: Li113 VH Variant

<400> SEQUENCE: 269

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Tyr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 270
<211> LENGTH: 119
<212> TYPE: PRT
<213> ORGANISM: Artificial
<220> FEATURE:
<223> OTHER INFORMATION: Li113 VH Variant

<400> SEQUENCE: 270

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Ser Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 271
<211> LENGTH: 119
<212> TYPE: PRT
<213> ORGANISM: Artificial
<220> FEATURE:
<223> OTHER INFORMATION: Li113 VH Variant

<400> SEQUENCE: 271

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ile Tyr
        20                  25                  30

Pro Met Phe Trp Val Arg Gln Ala Pro Gly Lys Gly Leu Glu Trp Val
        35                  40                  45

Ser Trp Ile Gly Pro Ser Gly Gly Pro Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 272
<211> LENGTH: 119
<212> TYPE: PRT
<213> ORGANISM: Artificial
<220> FEATURE:
<223> OTHER INFORMATION: Li113 VH Variant

<400> SEQUENCE: 272

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
        20                  25                  30

Pro Met Phe Trp Val Arg Gln Ala Pro Gly Lys Gly Leu Glu Trp Val
        35                  40                  45

Ser Trp Ile Gly Pro Ser Gly Gly Val Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 273
<211> LENGTH: 119
<212> TYPE: PRT
<213> ORGANISM: Artificial
<220> FEATURE:
<223> OTHER INFORMATION: Li113 VH Variant

<400> SEQUENCE: 273

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
        20                  25                  30

Pro Met Phe Trp Val Arg Gln Ala Pro Gly Lys Gly Leu Glu Trp Val
        35                  40                  45

Ser Trp Ile Gly Pro Ser Gly Gly Thr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

-continued

```
Leu Gln Met Asn Ser Leu Arg Ala Glu Asp Thr Ala Thr Tyr Tyr Cys
                85                  90                  95

Ala Arg Glu Gly Thr Tyr Asp Trp Tyr Leu Asp Leu Trp Gly Arg Gly
            100                 105                 110

Thr Leu Val Thr Val Ser Ser
        115

<210> SEQ ID NO 274
<211> LENGTH: 119
<212> TYPE: PRT
<213> ORGANISM: Artificial
<220> FEATURE:
<223> OTHER INFORMATION: Li113 VH Variant

<400> SEQUENCE: 274

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly Thr Tyr Asp Gln Tyr Leu Asp Leu Trp Gly Arg Gly
            100                 105                 110

Thr Leu Val Thr Val Ser Ser
        115
```